(12) United States Patent
Blaschuk et al.

(10) Patent No.: US 6,967,238 B2
(45) Date of Patent: Nov. 22, 2005

(54) COMPOUNDS AND METHODS FOR MODULATING CELL ADHESION

(75) Inventors: Orest W. Blaschuk, Westmount (CA); Barbara J. Gour, Kemptville (CA); Riaz Farookhi, Montreal (CA); Anmar Ali, Ottawa (CA)

(73) Assignee: McGill University, Montreal (CA)

( * ) Notice: Subject to any disclaimer, the term of this patent is extended or adjusted under 35 U.S.C. 154(b) by 338 days.

(21) Appl. No.: 10/105,008

(22) Filed: Mar. 22, 2002

(65) Prior Publication Data

US 2003/0065136 A1 Apr. 3, 2003

Related U.S. Application Data

(60) Division of application No. 09/458,870, filed on Dec. 10, 1999, now Pat. No. 6,465,427, which is a continuation-in-part of application No. 09/357,717, filed on Jul. 20, 1999, now Pat. No. 6,417,325, which is a continuation-in-part of application No. 09/248,074, filed on Feb. 10, 1999, now Pat. No. 6,346,512, which is a continuation-in-part of application No. 08/996,679, filed on Dec. 23, 1997, now Pat. No. 6,169,071, which is a continuation-in-part of application No. 08/893,534, filed on Jul. 11, 1997, now Pat. No. 6,031,072.

(60) Provisional application No. 60/021,612, filed on Jul. 12, 1996.

(51) Int. Cl.[7] ............................................. A61K 38/00
(52) U.S. Cl. ......................... 530/317; 514/9; 514/11
(58) Field of Search .......................... 530/317; 514/9, 514/11

(56) References Cited

U.S. PATENT DOCUMENTS

| 5,231,082 | A | 7/1993 | Schasteen ................. 514/11 |
|---|---|---|---|
| 5,352,667 | A | 10/1994 | Lider et al. ................ 514/19 |
| 5,510,628 | A | 4/1996 | Georger, Jr. et al. .......... 257/32 |
| 5,585,351 | A | 12/1996 | Ranscht .................... 514/12 |
| 5,591,432 | A | 1/1997 | Bronson et al. ......... 424/130.1 |
| 5,646,250 | A | 7/1997 | Suzuki ..................... 530/350 |
| 5,665,590 | A | 9/1997 | Yang ........................... 435/6 |
| 6,031,072 | A | * 2/2000 | Blaschuk et al. ........... 530/317 |
| 6,169,071 | B1 | 1/2001 | Blaschuk et al. ............ 514/15 |
| 6,207,639 | B1 | 3/2001 | Blaschuk et al. ............ 514/11 |

FOREIGN PATENT DOCUMENTS

| EP | 406 428 B1 | 1/1991 |
|---|---|---|
| WO | WO 91/04745 | 4/1991 |
| WO | WO 92/08731 | 5/1992 |
| WO | WO 94/11401 | 5/1994 |
| WO | WO 96/40781 | 12/1996 |
| WO | WO 97/07209 | 2/1997 |
| WO | WO 98/02452 | 1/1998 |
| WO | WO 98/45319 | 10/1998 |

OTHER PUBLICATIONS

Alexander et al., "N–Cadherin–Like Protein Contributes to Solute Barrier Maintenance in Cultured Endothelium," *Journal of Cellular Physiology* 156:610–618, 1993.

(Continued)

*Primary Examiner*—Christopher Tate
*Assistant Examiner*—Roy Teller
(74) *Attorney, Agent, or Firm*—Seed IP Law Group PLLC

(57) ABSTRACT

Cyclic peptides comprising a cadherin cell adhesion recognition sequence HAV, and compositions comprising such cyclic peptides, are provided. Methods for using such peptides for modulating cadherin-mediated cell adhesion in a variety of contexts are also provided.

13 Claims, 56 Drawing Sheets

OTHER PUBLICATIONS

Ali et al., "Conformationally Constrained Peptides and Semipeptides Derived from RGD as Potent Inhibitors of the Platelet Fibrinogen Receptor and Platelet Aggregation," *J. Med. Chem.* 37(6):769–780, 1994.

Beesley et al., "The post–synaptic density: putative involvement in synapse stabilization via cahderins and covalent modification by ubiquitination," *Biochemical Society Transactions* 23:59–64, 1995.

Blakemore, "Remyelination of CNS axons by Schwann cells transplanted from the sciatic nerve," *Nature* 266:68–69, 1977.

Blaschuk and Farookhi, "Estradiol Stimulates Cadherin Expression in Rat Granulosa Cells," *Developmental Biology* 136:564–567, 1989.

Blaschuk et al., "E–Cadherin, estrogens and cancer: is there a connection?" *The Canadian Journal of Oncology* 4(4):291–301, 1994.

Blaschuk et al., "Identification of a Cadherin Cell Adhesion Recognition Sequence," *Developmental Biology* 139:227–229, 1990.

Blaschuk et al., "Identification of a Conserved Region Common to Cadherins and Influenza Strain A Hemagglutinins," *J. Mol. Biol.* 211:679–682, 1990.

Bottenstein and Sato, "Growth of a rat neuroblastoma cell line in serum–free supplemented medium," *Proc.Natl. Acad. Sci. USA* 76(1):514–517, 1979.

Brecknell et al., "Bridge grafts of Fibroblast Growth Factor–4–Secreting Schwannoma Cells Promote Functional Axonal Regeneration in the Nigrostriatal Pathway of the Adult Rat," *Neuroscience* 74(3):775–784 1996.

Brockes et al., "Studies on Cultured Rat Schwann Cells. I. Establishment of Purified Populations from Cultures of Peripheral Nerve," *Brain Research* 165:104–118, 1979.

Brook et al., "Morphology and Migration of Cultured Schwann Cells Transplanted Into the Fimbria and Hippocampus in Adult Rats," *GLIA* 9:292–304, 1993.

Byers et al., "Fibroblast Growth Factor Receptors Contain a Conserved HAV Region Common to Cadherins and Influenza Strain A Hemagglutinins: A Role in Protein–Protein Interactions?, " *Developmental Biology* 152:411–414, 1992.

Cardarelli et al., "The Collagen Receptor$\alpha 3\beta 1$, from MG–63 and HT1080 Cells, Interacts with a Cyclic RGD Peptide," *The Journal of Biological Chemistry* 267(32):23159–23164, 1992.

Carlstedt et al., "Nerve Fibre Regeneration Across the PNS–CNS Interface at the Root–Spinal Cord Junction," *Brain Research Bulletin* 22:93–102, 1989.

Cepek et al., "Expression of a candidate cadherin in T lymphocytes," *Proc. Natl. Acad. Sci. USA* 93:6567–6571, 1996.

Chuah et al., "Differentiation and survival of rat olfactory epithelial neurons in dissociated cell culture," *Developmental Brain Research* 60: 123–132, 1991.

Craig et al., "Concept and Progress in Development of RGD–Containing Peptide Pharmaceuticals, " *Biopolymers (Peptide Science)* 37:157–175, 1995.

Doherty and Walsh, "CAM–FGF Receptor Interactions: A Model for Axonal Growth," *Molecular and Cellular Neuroscience* 8(Article No. 0049):99–111, 1996.

Doherty and Walsh, "Signal transduction events underlying neurite outgrowth stimulated by cell adhesion molecules," *Current Opinion in Neurobiology* 4:49–55, 1994.

Doherty and Walsh, "Neurite Outgrowth in Response to Transfected N–CAM and N–Cadherin Reveals Fundamental Differences in Neuronal Responsiveness to CAMS," *Neuron* 6:247–258, 1991.

Duncan et al., "Transplantation of oligodendrocytes and Schwann cells into the spinal cord of the myelin–deficient rat," *Journal of Neurocytology* 17:351–361, 1988.

Fok–Seang et al., "An analysis of astrocytic cell lines with different abilities to promote axon growth," *Brain Research* 1689:207–223, 1995.

Fok–Seang et al., "Migration of Oligodendrocyte Precursors on Astrocytes and Meningeal Cells," *Developmental Biology* 171:1–15, 1995.

Franz, "Percutaneous Absorption. On The Relevance Of In Vitro Data," *The Journal of Investigative Dermatology* 64(3):190–195, 1975.

Franz, "The Finite Dose Technique as a Valid in Vitro Model for the Study of Percutaneous Absorption in Man," *Curr. Probl. Dermatol.* 7:58–68, 1978.

Ghimikar and Eng, "Astrocyte–Schwann Cell Interactions in Culture," *GLIA* 11:367–377, 1994.

Gumbiner et al., "The Role of the Cell Adhesion Molecule Uvomorulin in the Formation and Maintenance of the Epithelial Junctional Complex," *The Journal of Cell Biology* 107:1575–1587, 1988.

Iruela–Arispe et al., "Expression of SPARC during Development of the Chicken Chorioallantoic Membrane: Evidence for Regulated Proteolysis in Vivo," *Molecular Biology of the Cell* 6: 327–343, 1995.

Laird et al., "Gap Junction Turnover, Intracellular Trafficking, and Phosphorylation of Connexcin43 in Brefeldin A–treated Rat Mammary Tumor Cells," *The Journal of Cell Biology* 131(5):1193–1203, 1995.

Lee et al., "Expression of the Homotypic Adhesion Molecule E–Cadherin by Immature Murine Thymocytes and Thymic Epithelial Cells," *Journal of Immunology* 152:5653–5659, 1994.

Letourneaur et al., "Interactions of Schwann Cells with Neurites and with Other Schwann Cells Involve the Calcium–dependent Adhesion Molecule, N–cadherin," *Journal of Neurobiology* 22(7):707–720, 1991.

Liuzzi and Lasek , "Astrocytes Block Axonal Regeneration in Mammals by Activating the Physiological Stop Pathway," *Science* 237:642–645, 1987.

Lutz et al., "Secondary Structure of the HAV Peptide Which Regulates Cadherin–Cadherin Interaction," *Journal of Biomolecular Structure & Dynamics* 13(3):447–455, 1995.

Matsuzaki et al., "cDNAs of Cell Adhesion Molecules of Different Specificity Induce Changes in Cell Shape and Border Formation in Cultured S180 Cells," *The Journal of Cell Biology* 110:1239–1252, 1990.

McCarthy and Vellis, "Preparation of Separate Astroglial and Oligodendroglial Cell Cultures from Rat Cerebral Tissue," *J. Cell Biology* 85:890–902, 1980.

Mege et al., "Construction of epithelioid sheets by transfection of mouse sarcoma cells with cDNAs for chicken cell adhesion molecules," *Proc. Natl. Acad. Sci. USA* 85:7274–7278, 1988.

Moran, "The Protein Delivery Service. Advances in technologies for delivering proteins and peptides in therapeutically useful forms," *Pharmaceutical Forum Issue* 6:4–7, 1996.

Munro and Blaschuk, *Cell Adhesion and Invasion in Cancer Metastasis*, R.G. Landes Company, Austin, TX, 1996, Chapter 3, "The Structure, Function and Regulation of Cadherins," pp. 17–34.

Munro et al., "Characterization of Cadherins Expressed by Murine Thymocytes," *Cellular Immunology* 169(Article No. 0123):309–312, 1996.

Newton et al., "N–Cadherin Mediates Sertoli Cell–Spermatogenic Cell Adhesion," *Developmental Dynamics* 197:1–13, 1993.

Nose et al., "Localization of Specificity Determining Sites in Cadherin Cell Adhesion Molecules," *Cell* 61:147–155, 1990.

Orr, "Angiogenesis Research Offers New Approaches to Treatment of Disease," *Genetic Engineering News*, pp. 15–16, 42, May 1, 1996.

Overduin et al., "Solution Structure of the Epithelial Cadherin Domain Responsible for Selective Cell Adhesion," *Science* 267:386–389, 1995.

Redies and Takeichi, "Cadherins in the Developing Central Nervous System: An Adhesive Code for Segmental and Functional Subdivisions," *Developmental Biology* 180:413–423, 1996.

Saffell et al., "Expression of a Dominant Negative FGF Receptor Inhibits Axonal Growth and FGF Receptor Phosphorylation Stimulated by CAMs," *Neuron*, pp. 231–242, Feb. 1997.

Samanen et al., "Development of a Small RGD Peptide Fibrinogen Receptor Antagonist with Potent Antiaggregatory Activity in Vitro," *J. Med. Chem*. 34(10):3114–3125, 1991.

Shapiro et al., "Structural basis of cell–cell adhesion by cadherins,") *Nature* 374:327–337, 1995.

Tsutsui et al., "Expression of Cadherin–Catenin Complexes in Human Leukemia Cell Lines," *J. Biochem*. 120:1034–1039, 1996.

Wickelgren, "Breaking the Skin Barrier," *PS* 12:86–88, 1996.

Willems et al., "Cadherin–dependent cell aggregation is affected by decapeptide derived from rat extracellular super–oxide dismutase," *FEBS Letters* 363:289–292, 1995.

Williams et al., "Activation of the FGF Receptor Underlies Neurite Outgrowth Stimulated by L1, N–CAM, and N–Cadherin," *Neuron* 12:583–594, 1994.

Williams et al., "The Primary Structure of Hen Ovotransferrin," *Eur. J. Biochem*. 122:297–303, 1982.

* cited by examiner

```
human N-cad   DWVIPPINLPENSRGPFPQELVRIRSDRDKNLSLRYSVTGPGADQPPTGIFILNPISGQLSVTKPLDREQ
mouse N-cad   DWVIPPINLPENSRGPFPQELVRIRSDRDKNLSLRYSVTGPGADQPPTGIFILNPISGQLSVTKPLDREL
cow N-cad     DWVIPPINLPENSRGPFPQELVRIRSDRDKNLSLRYSVTGPGADQPPTGIFILNPISGQLSVTKPLDREL
human P-cad   DWVVAPISVPENGKGPFPQRLNQLKSNKDRDTKIFYSITGPGADSPPEGVFAVEKETGWLLLNKPLDREE
mouse P-cad   EWVMPPIFVPENGKGPFPQRLNQLKSNKDRGTKIFYSITGPGADSPPEGVFTIEKESGWLLLHMPLDREK
human E-cad   DWVIPPISCPENEKGPFPKNLVQIKSNKDKEGKVFYSITGQGADTPPVGVFIIERETGWLKVTEPLDRER
mouse E-cad   DWVIPPISCPENEKGEFPKNLVQIKSNRDKETKVFYSITGQGADKPPVGVFIIERETGWLKVTQPLDREA human N-cad   IARFHLRAHAVDINGNQVENPIDIVINVIDMNDNRPEF
mouse N-cad   IARFHLRAHAVDINGNQVENPIDIVINVIDMNDNRPEF
cow N-cad     IARFHLRAHAVDINGNQVENPIDIVINVIDMNDNRPEF
human P-cad   IAKYELFGHAVSENGASVEDPMNISIIVTDQNDHKPKF
mouse P-cad   IVKYELYGHAVSENGASVEEPMNISIIVTDQNDNKPKF
human E-cad   IATYTLFSHAVSSNGNAVEDPMEILITVTDQNDNKPEF
mouse E-cad   IAKYILYSHAVSSNGEAVEDPMEIVITVTDQNDNRPEF
```

Fig. 2

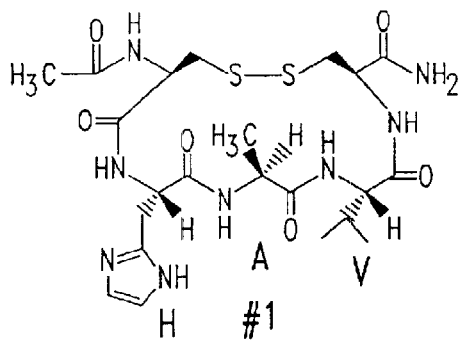
N-Ac-CHAVC-NH₂
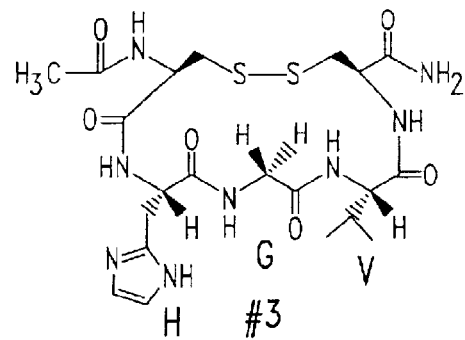
N-Ac-CHGVC-NH₂
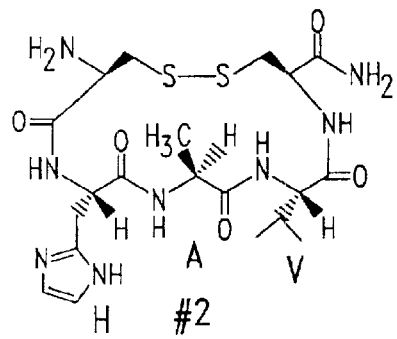
H-CHAVC-NH₂
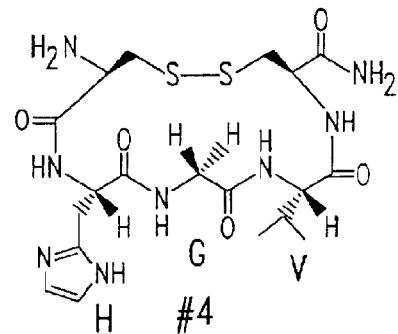
H-CHGVC-NH₂
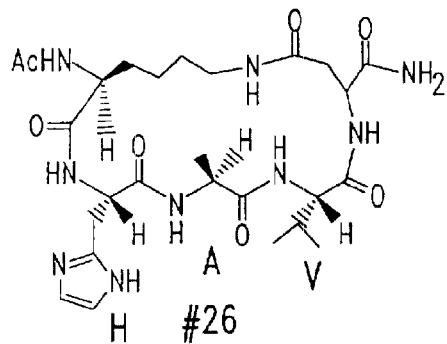
N-Ac-KHAVD-NH₂
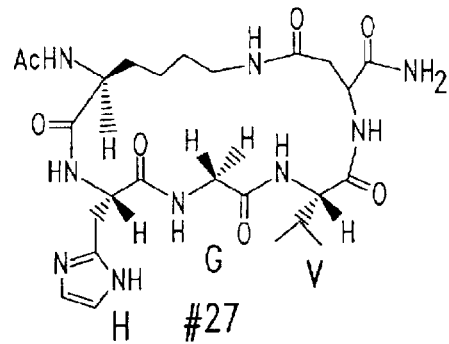
N-Ac-KHGVD-NH₂
Fig. 3A

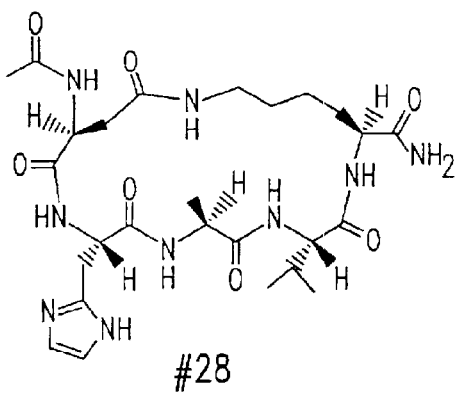
28
N-Ac-DHAVK-NH₂
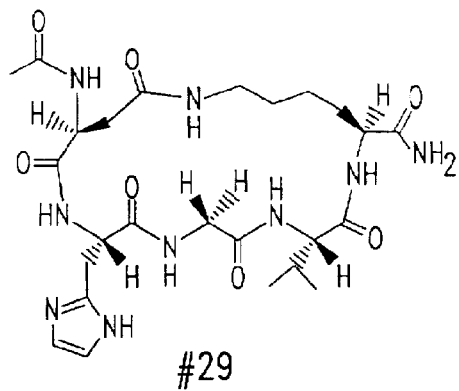
29
N-Ac-DHGVK-NH₂
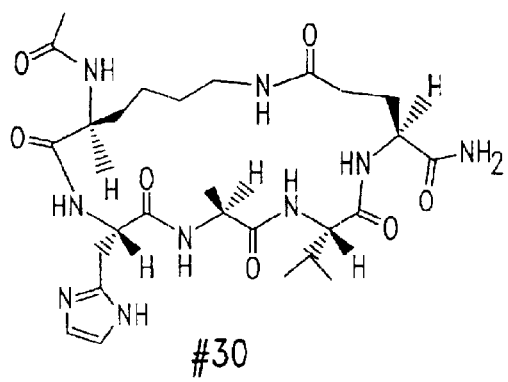
30
N-Ac-KHAVE-NH₂
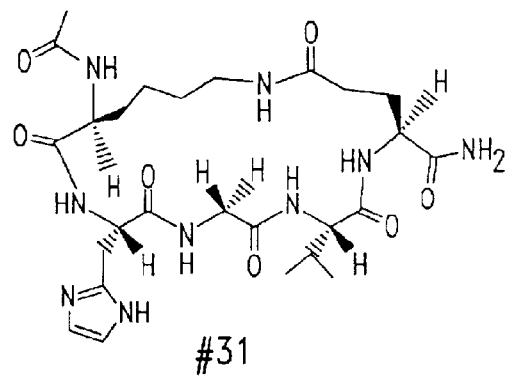
31
N-Ac-KHGVE-NH₂
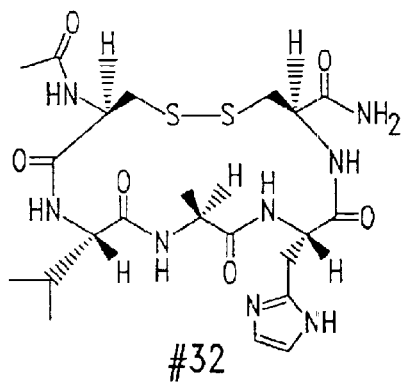
32
N-Ac-CVAHC-NH₂
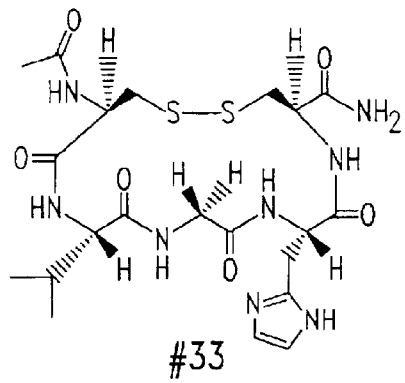
33
N-Ac-CVGHC-NH₂
*Fig. 3B*

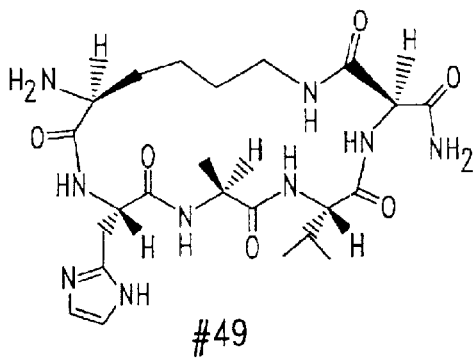
49
H-KHAVD-NH$_2$
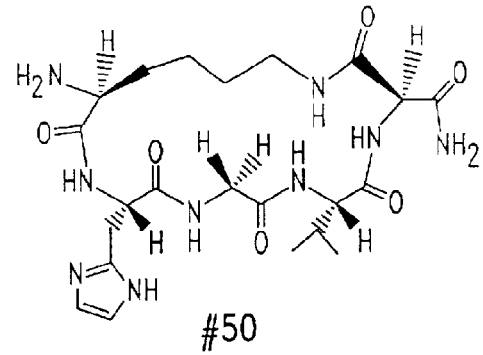
50
H-KHGVD-NH$_2$
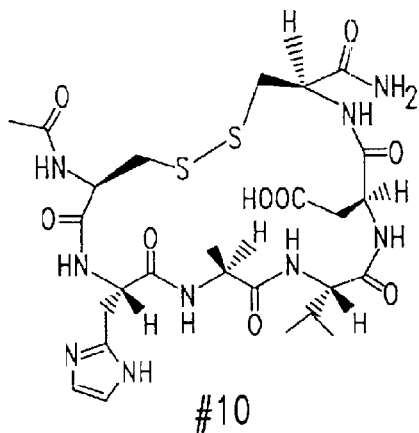
10
N-Ac-CHAVDC-NH$_2$
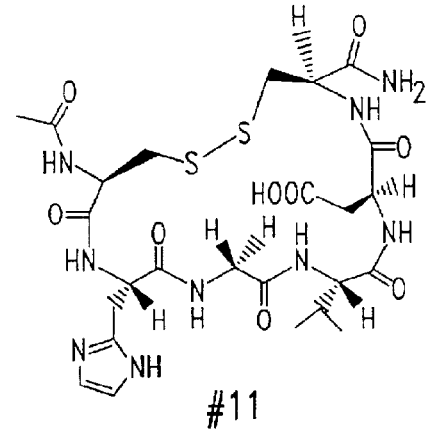
11
N-Ac-CHGVDC-NH$_2$
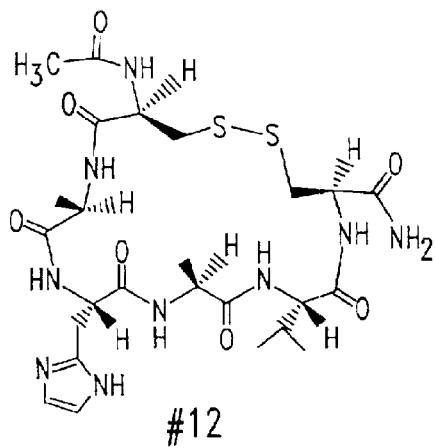
12
N-Ac-CAHAVC-NH$_2$
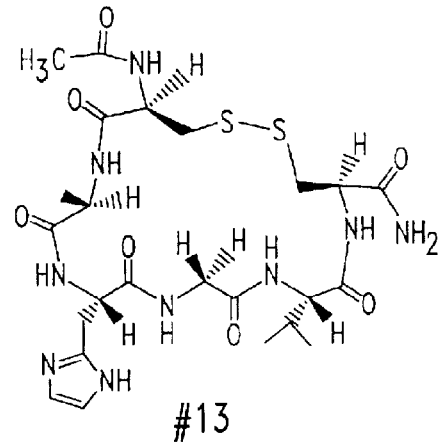
13
N-Ac-CAHGVC-NH$_2$
*Fig. 3C*

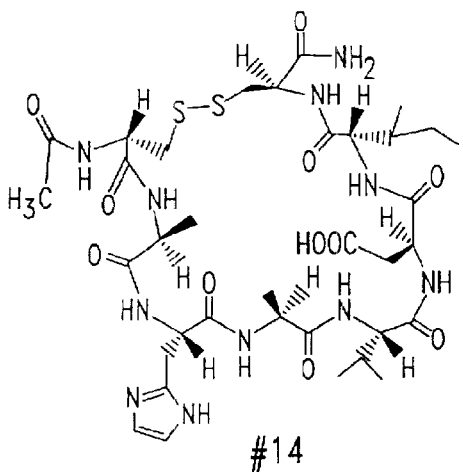
14
N-Ac-CAHAVDIC-NH₂
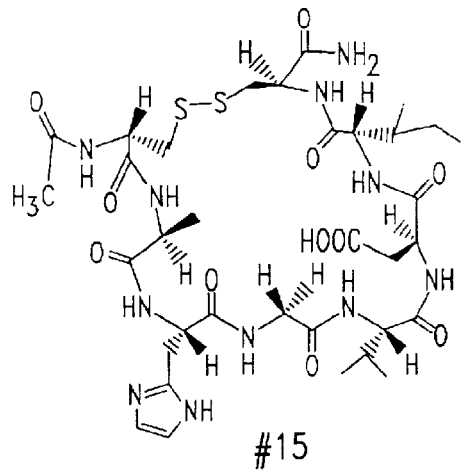
15
N-Ac-CAHGVDIC-NH₂
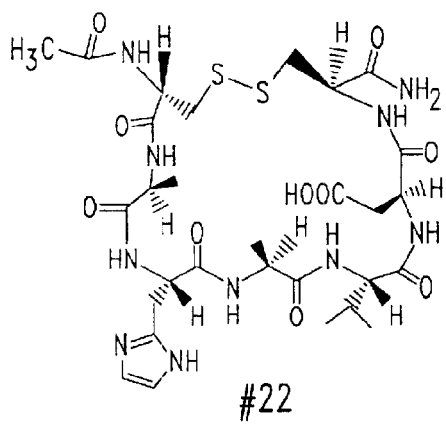
22
N-Ac-CAHAVDC-NH₂
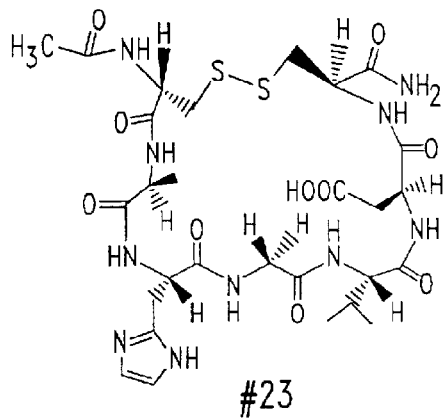
23
N-Ac-CAHGVDC-NH₂
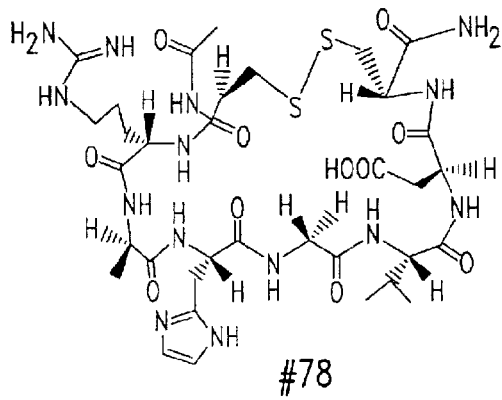
78
N-Ac-CRAHAVDC-NH₂
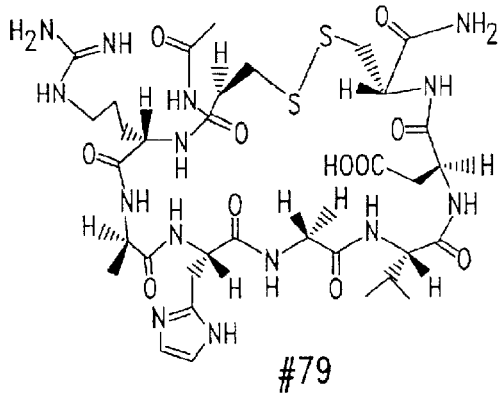
79
N-Ac-CRAHGVDC-NH₂
*Fig. 3D*

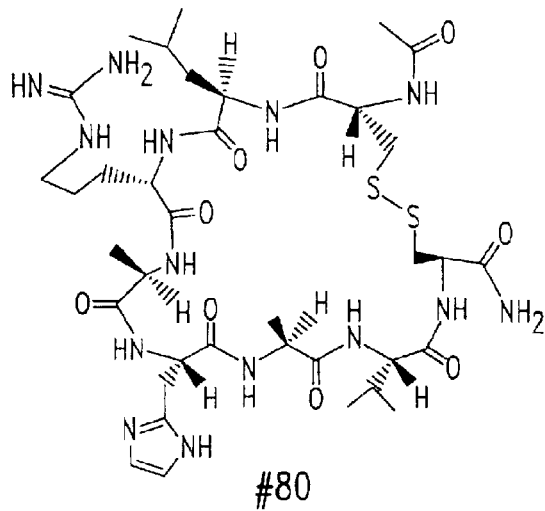
80
N-Ac-CLRAHAVC-NH₂
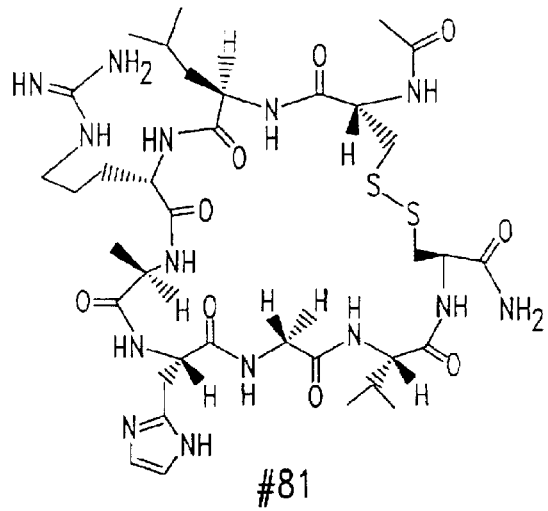
81
N-Ac-CLRAHGVC-NH₂
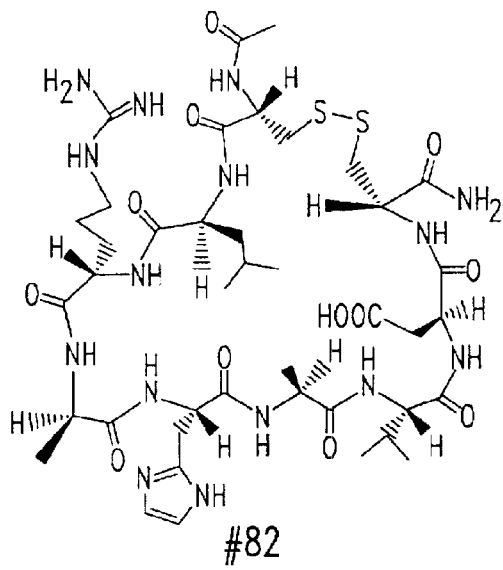
82
N-Ac-CLRAHAVDC-NH₂
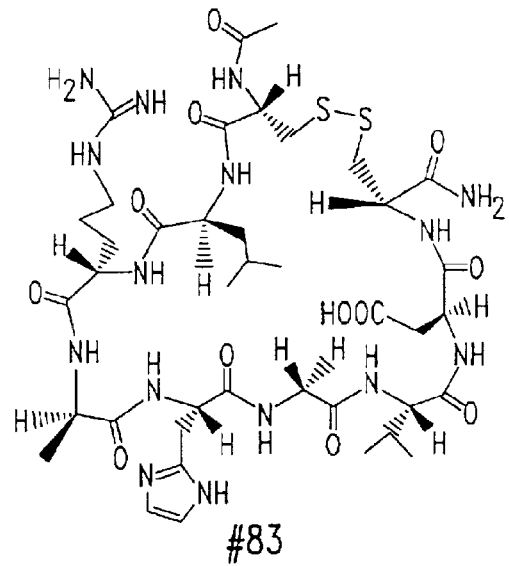
83
N-Ac-CLRAHGVDC-NH₂
Fig. 3E

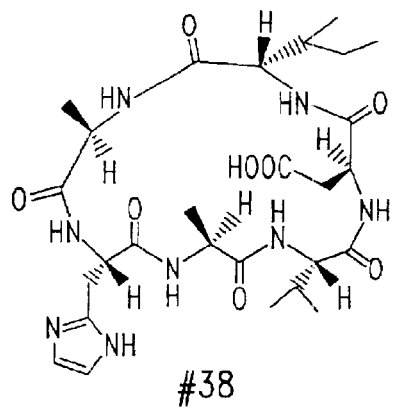
38
AHAVDI
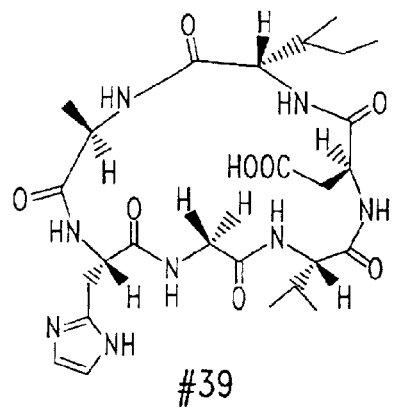
39
AHGVDI
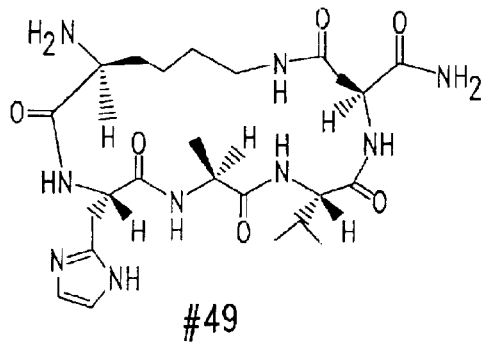
49
H-KHAVD-NH₂
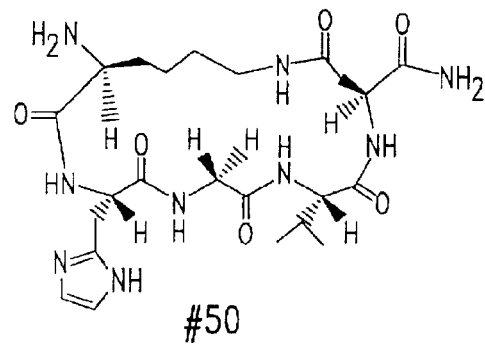
50
H-KHGVD-NH₂
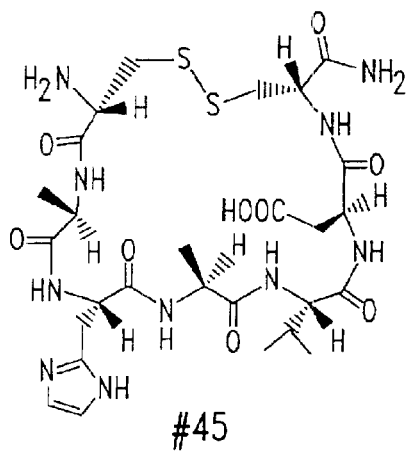
45
H-CAHAVDC-NH₂
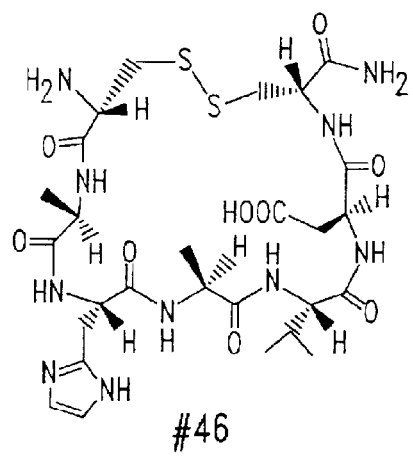
46
H-CAHGVDC-NH₂
*Fig. 3F*

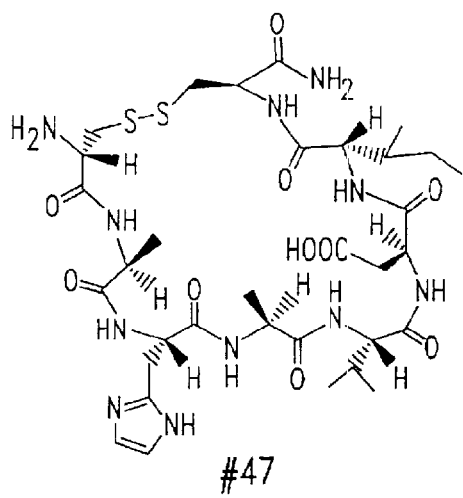
47
H-CAHAVDIC-NH2
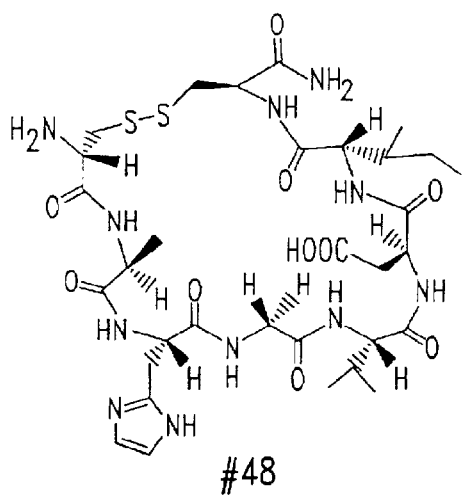
48
H-CAHGVDIC-NH2
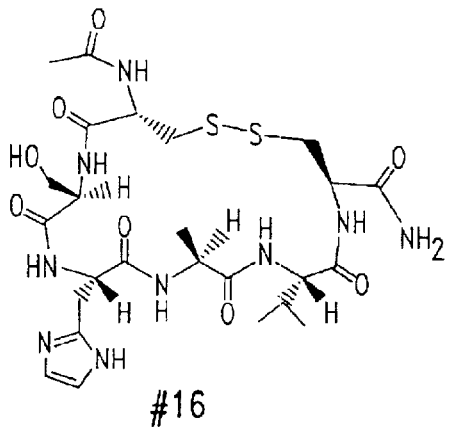
16
N-Ac-CSHAVC-NH2
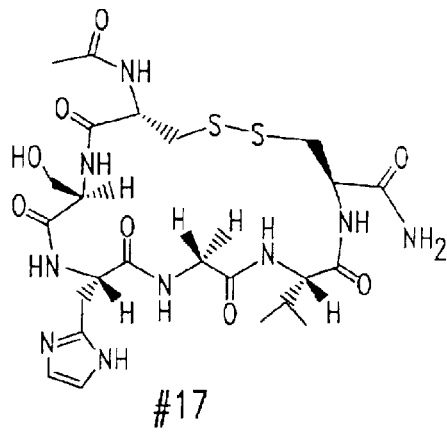
17
N-Ac-CSHGVC-NH2
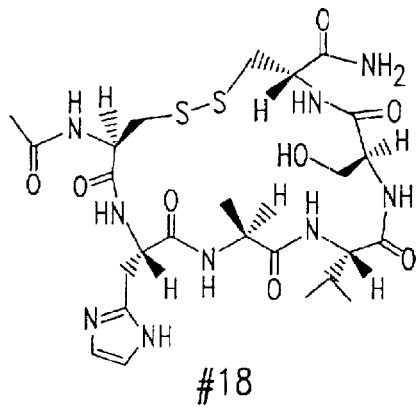
18
N-Ac-CHAVSC-NH2
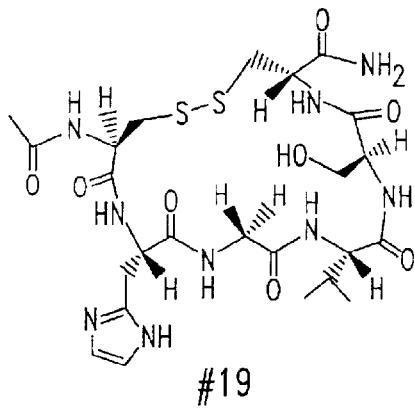
19
N-Ac-CHGVSC-NH2
*Fig. 3G*

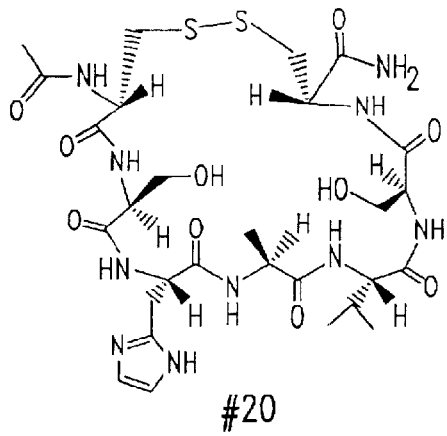
20
N-Ac-CSHAVSC-NH₂
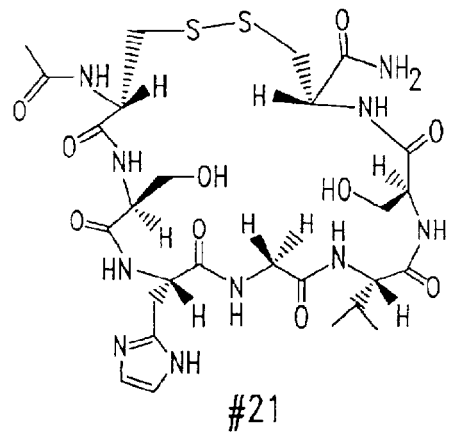
21
N-Ac-CSHGVSC-NH₂
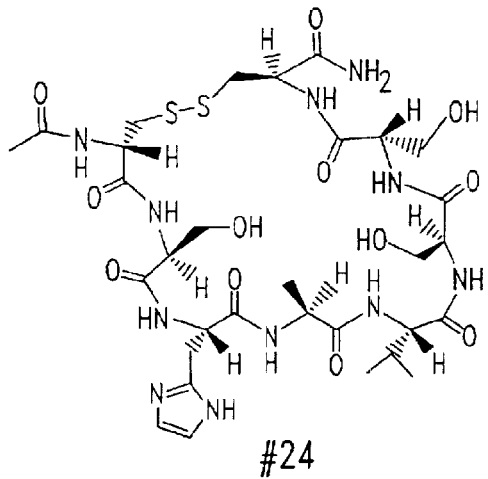
24
N-Ac-CSHAVSSC-NH₂
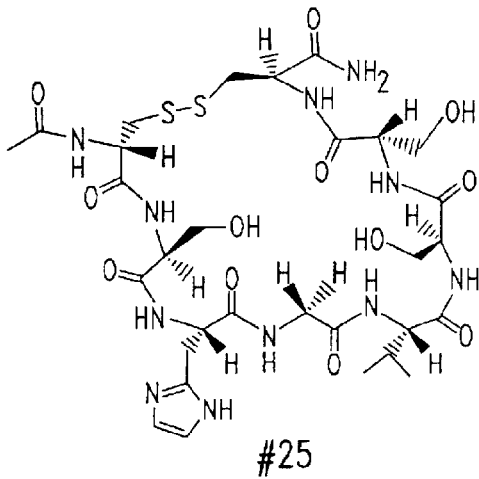
25
N-Ac-CSHGVSSC-NH₂
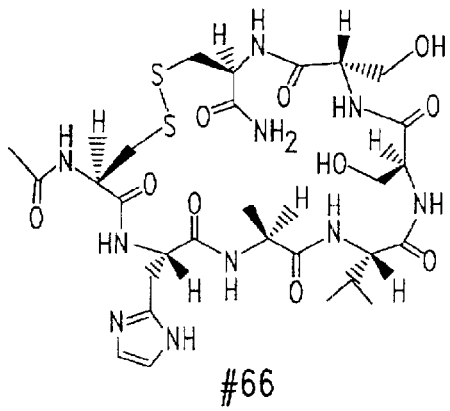
66
N-Ac-CHAVSSC-NH₂
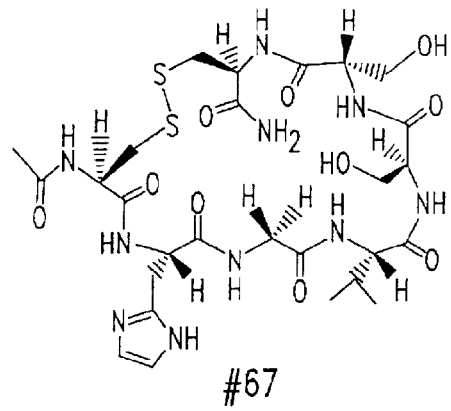
67
N-Ac-CHGVSSC-NH₂
Fig. 3H

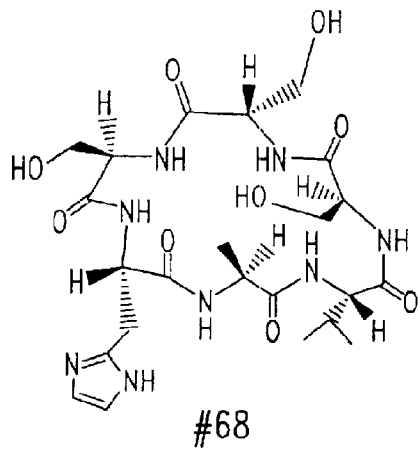
68
SHAVSS
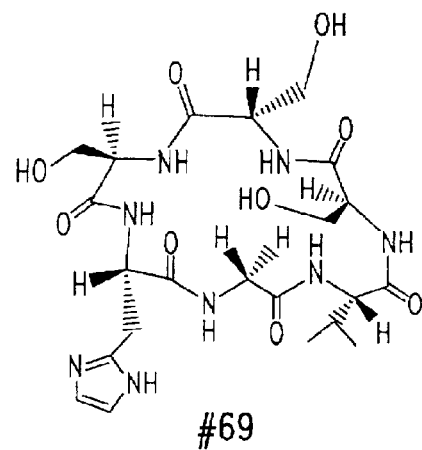
69
SHGVSS
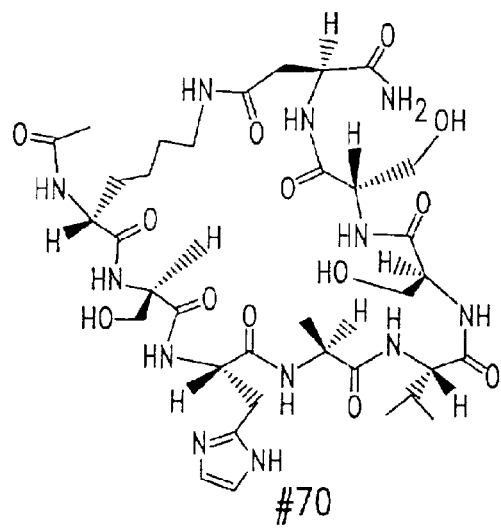
70
N-Ac-KSHAVSSD-NH$_2$
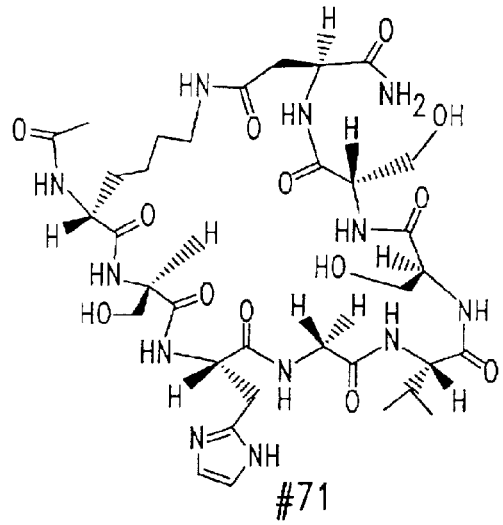
71
N-Ac-KSHGVSSD-NH$_2$
*Fig. 31*

ADH1 (2mg/kg) killed after 5 days control

ADH1 (2mg/kg) killed after 5 days

Control

ADH148 1mg/ml

SEQUENCE LISTING

<160> NUMBER OF SEQ ID NOS: 99

<210> SEQ ID NO 1
<211> LENGTH: 108
<212> TYPE: PRT
<213> ORGANISM: Homo sapiens

<400> SEQUENCE: 1

```
Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Leu Asn Pro Ile Ser Gly Gln Leu Ser Val Thr Lys
    50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105
```

<210> SEQ ID NO 2
<211> LENGTH: 108
<212> TYPE: PRT
<213> ORGANISM: Mus musculus

<400> SEQUENCE: 2

```
Asp Trp Val Ile Pro Pro Ile Asn Leu Pro Glu Asn Ser Arg Gly Pro
 1               5                  10                  15
```

-continued

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Ile Asn Pro Ile Ser Gly Gln Leu Ser Val Thr Lys
    50                  55                  60

Pro Leu Asp Arg Glu Leu Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

<210> SEQ ID NO 3
<211> LENGTH: 108
<212> TYPE: PRT
<213> ORGANISM: Bos taurus

<400> SEQUENCE: 3

Asp Trp Val Ile Pro Pro Ile Asn Leu Pro Glu Asn Ser Arg Gly Pro
1               5                   10                  15

Phe Pro Gln Glu Leu Val Arg Ile Arg Ser Asp Arg Asp Lys Asn Leu
            20                  25                  30

Ser Leu Arg Tyr Ser Val Thr Gly Pro Gly Ala Asp Gln Pro Pro Thr
        35                  40                  45

Gly Ile Phe Ile Ile Asn Pro Ile Ser Gly Gln Leu Ser Val Thr Lys
    50                  55                  60

Pro Leu Asp Arg Glu Leu Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

<210> SEQ ID NO 4
<211> LENGTH: 108
<212> TYPE: PRT
<213> ORGANISM: Homo sapiens

<400> SEQUENCE: 4

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
            20                  25                  30

Lys Ile Phe Tyr Ser Ile Thr Gly Pro Gly Ala Asp Ser Pro Pro Glu
        35                  40                  45

Gly Val Phe Ala Val Glu Lys Glu Thr Gly Trp Leu Leu Leu Asn Lys
    50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe
            100                 105

<210> SEQ ID NO 5

```
<211> LENGTH: 108
<212> TYPE: PRT
<213> ORGANISM: Mus musculus

<400> SEQUENCE: 5

Glu Trp Val Met Pro Pro Ile Phe Val Pro Glu Asn Gly Lys Gly Pro
 1               5                  10                  15

Phe Pro Gln Arg Leu Asn Gln Leu Lys Ser Asn Lys Asp Arg Gly Thr
                20                  25                  30

Lys Ile Phe Tyr Ser Ile Thr Gly Pro Gly Ala Asp Ser Pro Pro Glu
            35                  40                  45

Gly Val Phe Thr Ile Glu Lys Glu Ser Gly Trp Leu Leu His Met
     50                  55                  60

Pro Leu Asp Arg Glu Lys Ile Val Lys Tyr Glu Leu Tyr Gly His Ala
65                  70                  75                  80

Val Ser Glu Asn Gly Ala Ser Val Glu Glu Pro Met Asn Ile Ser Ile
                85                  90                  95

Ile Val Thr Asp Gln Asn Asp Asn Lys Pro Lys Phe
            100                 105

<210> SEQ ID NO 6
<211> LENGTH: 108
<212> TYPE: PRT
<213> ORGANISM: Homo sapiens

<400> SEQUENCE: 6

Asp Trp Val Ile Pro Pro Ile Ser Cys Pro Glu Asn Glu Lys Gly Pro
 1               5                  10                  15

Phe Pro Lys Asn Leu Val Gln Ile Lys Ser Asn Lys Asp Lys Glu Gly
                20                  25                  30

Lys Val Phe Tyr Ser Ile Thr Gly Gln Gly Ala Asp Thr Pro Pro Val
            35                  40                  45

Gly Val Phe Ile Ile Glu Arg Glu Thr Gly Trp Leu Lys Val Thr Glu
     50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
                85                  90                  95

Thr Val Thr Asp Gln Asn Asp Asn Lys Pro Glu Phe
            100                 105

<210> SEQ ID NO 7
<211> LENGTH: 108
<212> TYPE: PRT
<213> ORGANISM: Mus musculus

<400> SEQUENCE: 7

Asp Trp Val Ile Pro Pro Ile Ser Cys Pro Glu Asn Glu Lys Gly Glu
 1               5                  10                  15

Phe Pro Lys Asn Leu Val Gln Ile Lys Ser Asn Arg Asp Lys Glu Thr
                20                  25                  30

Lys Val Phe Tyr Ser Ile Thr Gly Gln Gly Ala Asp Lys Pro Pro Val
            35                  40                  45

Gly Val Phe Ile Ile Glu Arg Glu Thr Gly Trp Leu Lys Val Thr Gln
     50                  55                  60

Pro Leu Asp Arg Glu Ala Ile Ala Lys Tyr Ile Leu Tyr Ser His Ala
65                  70                  75                  80
```

-continued

```
Val Ser Ser Asn Gly Glu Ala Val Glu Asp Pro Met Glu Ile Val Ile
                85                  90                  95
Thr Val Thr Asp Gln Asn Asp Asn Arg Pro Glu Phe
            100                 105

<210> SEQ ID NO 8
<211> LENGTH: 5
<212> TYPE: PRT
<213> ORGANISM: Unknown
<220> FEATURE:
<221> NAME/KEY: MOD_RES
<222> LOCATION: (2)
<223> OTHER INFORMATION: Where Xaa is any amino acid
<223> OTHER INFORMATION: Description of Unknown Organism:  Cadherin
      Calcium Binding Motif

<400> SEQUENCE: 8

Asp Xaa Asn Asp Asn
 1               5

<210> SEQ ID NO 9
<211> LENGTH: 4
<212> TYPE: PRT
<213> ORGANISM: Unknown
<220> FEATURE:
<223> OTHER INFORMATION: Description of Unknown Organism:  Cadherin
      Calcium Binding Motif

<400> SEQUENCE: 9

Leu Asp Arg Glu
 1

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group and/or
      C-terminal modifications such as amide or ester group

<400> SEQUENCE: 10

Tyr Cys His Ala Val Cys
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 11

Cys His Gly Val Cys
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:  Cyclic
``` peptide with cadherin cell adhesion recognition
      sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 12

Lys His Ala Val Asp
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 13

Lys His Gly Val Asp
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with cadherin cell adhesion recognition
      sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 14

Asp His Ala Val Lys
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 15

Asp His Gly Val Lys
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or

```
        ester group

<400> SEQUENCE: 16

Lys His Ala Val Glu
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 17

Lys His Gly Val Glu
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 18

Cys Val Ala His Cys
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 19

Cys Val Gly His Cys
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 20

Cys His Ala Val Asp Cys
```

1            5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 21

Cys His Gly Val Asp Cys
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 22

Cys Ala His Ala Val Cys
  1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 23

Cys Ala His Gly Val Cys
  1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 24

Cys Ala His Ala Val Asp Ile Cys
  1               5

<210> SEQ ID NO 25
<211> LENGTH: 8

```
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 25

Cys Ala His Gly Val Asp Ile Cys
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 26

Cys Ala His Ala Val Asp Cys
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 27

Cys Ala His Gly Val Asp Cys
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 28

Cys Arg Ala His Ala Val Asp Cys
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
```

```
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 29

Cys Arg Ala His Gly Val Asp Cys
  1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 30

Cys Leu Arg Ala His Ala Val Cys
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 31

Cys Leu Arg Ala His Gly Val Cys
  1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 32

Cys Leu Arg Ala His Ala Val Asp Cys
  1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group
```

```
<400> SEQUENCE: 33

Cys Leu Arg Ala His Gly Val Asp Cys
 1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 34

Ala His Ala Val Asp Ile
 1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 35

Ala His Gly Val Asp Ile
 1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 36

Cys Ser His Ala Val Cys
 1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 37

Cys Ser His Gly Val Cys
 1               5
```

```
<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 38

Cys His Ala Val Ser Cys
 1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 39

Cys His Gly Val Ser Cys
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 40

Cys Ser His Ala Val Ser Cys
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 41

Cys Ser His Gly Val Ser Cys
 1               5

<210> SEQ ID NO 42
<211> LENGTH: 8
<212> TYPE: PRT
<213> ORGANISM: Artificial Sequence
```

-continued

```
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 42

Cys Ser His Ala Val Ser Ser Cys
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 43

Cys Ser His Gly Val Ser Ser Cys
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 44

Cys His Ala Val Ser Ser Cys
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 45

Cys His Gly Val Ser Ser Cys
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
```

```
        modification such as acetyl or alkoxybenzyl group
        and/or C-terminal modifications such as amide or
        ester group

<400> SEQUENCE: 46

Ser His Ala Val Ser Ser
  1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:  Cyclic
        control peptide
<223> OTHER INFORMATION: Cyclic Peptide may comprise N-terminal
        modification such as acetyl or alkoxybenzyl group
        and/or C-terminal modifications such as amide or
        ester group

<400> SEQUENCE: 47

Ser His Gly Val Ser Ser
  1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence:  Cyclic
        peptide with classical cadherin cell adhesion
        recognition sequence
<223> OTHER INFORMATION: Cyclic Peptide may comprise N-terminal
        modification such as acetyl or alkoxybenzyl group
        and/or C-terminal modifications such as amide or
        ester group

<400> SEQUENCE: 48

Lys Ser His Ala Val Ser Ser Asp
  1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence:  Cyclic
        control peptide
<223> OTHER INFORMATION: Cyclic Peptide may comprise N-terminal
        modification such as acetyl or alkoxybenzyl group
        and/or C-terminal modifications such as amide or
        ester group

<400> SEQUENCE: 49

Lys Ser His Gly Val Ser Ser Asp
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:  Cyclic
        peptide with classical cadherin cell adhesion
        recognition sequence
<223> OTHER INFORMATION: Cyclic Peptide may comprise N-terminal
        modification such as acetyl or alkoxybenzyl group
        and/or C-terminal modifications such as amide or
        ester group

<400> SEQUENCE: 50
```

Cys His Ala Val Asp Ile Cys
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 51

Cys His Ala Val Asp Ile Asn Cys
1               5

<210> SEQ ID NO 52
<211> LENGTH: 5
<212> TYPE: PRT
<213> ORGANISM: Unknown
<220> FEATURE:
<223> OTHER INFORMATION: Description of Unknown Organism: Cadherin cell
      adhesion recognition sequencebound by
      alpha-6-beta-1 integrin

<400> SEQUENCE: 52

Tyr Ile Gly Ser Arg
1               5

<210> SEQ ID NO 53
<211> LENGTH: 10
<212> TYPE: PRT
<213> ORGANISM: Unknown
<220> FEATURE:
<223> OTHER INFORMATION: Description of Unknown Organism: Cadherin cell
      adhesion recognition sequence bound by N-CAM

<400> SEQUENCE: 53

Lys Tyr Ser Phe Asn Tyr Asp Gly Ser Glu
1               5                   10

<210> SEQ ID NO 54
<211> LENGTH: 17
<212> TYPE: PRT
<213> ORGANISM: Unknown
<220> FEATURE:
<223> OTHER INFORMATION: Description of Unknown Organism: N-CAM
      heparin sulfate binding site

<400> SEQUENCE: 54

Ile Trp Lys His Lys Gly Arg Asp Val Ile Leu Lys Lys Asp Val Arg
1               5                   10                  15

Phe

<210> SEQ ID NO 55
<211> LENGTH: 4
<212> TYPE: PRT
<213> ORGANISM: Unknown
<220> FEATURE:
<223> OTHER INFORMATION: Description of Unknown Organism: Occluding
      cell adhesion recognition sequence

<400> SEQUENCE: 55

-continued

```
Leu Tyr His Tyr
  1

<210> SEQ ID NO 56
<211> LENGTH: 8
<212> TYPE: PRT
<213> ORGANISM: Unknown
<220> FEATURE:
<223> OTHER INFORMATION: Description of Unknown Organism:  Claudin cell
      adhesion recognition sequence
<221> NAME/KEY: MOD_RES
<222> LOCATION: (2)
<223> OTHER INFORMATION: Where Xaa is either Lysine or arginine
<221> NAME/KEY: MOD_RES
<222> LOCATION: (3)..(4)
<223> OTHER INFORMATION: Where Xaa is an independently selected amino
      acid residue
<221> NAME/KEY: MOD_RES
<222> LOCATION: (5)
<223> OTHER INFORMATION: Where Xaa is either Serine or Alanine
<221> NAME/KEY: MOD_RES
<222> LOCATION: (6)
<223> OTHER INFORMATION: Where Xaa is either Tyrosine or Phenylalanine
<221> NAME/KEY: MOD_RES
<222> LOCATION: (7)
<223> OTHER INFORMATION: Where Xaa is an independently selected amino
      acid residue

<400> SEQUENCE: 56

Trp Xaa Xaa Xaa Xaa Xaa Xaa Gly
  1               5

<210> SEQ ID NO 57
<211> LENGTH: 9
<212> TYPE: PRT
<213> ORGANISM: Unknown
<220> FEATURE:
<223> OTHER INFORMATION: Description of Unknown Organism:  Nonclassical
      cadherin cell adhesion recognition sequence
<221> NAME/KEY: MOD_RES
<222> LOCATION: (1)
<223> OTHER INFORMATION: Where Xaa is an independently selected amino
      acid residue
<221> NAME/KEY: MOD_RES
<222> LOCATION: (3)
<223> OTHER INFORMATION: Where Xaa is an independently selected amin
      acid residue
<221> NAME/KEY: MOD_RES
<222> LOCATION: (4)
<223> OTHER INFORMATION: Where Xaa is Isoleucine, Leucine or Valine
<221> NAME/KEY: MOD_RES
<222> LOCATION: (5)
<223> OTHER INFORMATION: Where Xaa is Aspartic Acid, Asparagine or
      Glutamic Acid
<221> NAME/KEY: MOD_RES
<222> LOCATION: (6)..(7)
<223> OTHER INFORMATION: Where Xaa is an independently selected amino
      acid residue
<221> NAME/KEY: MOD_RES
<222> LOCATION: (8)
<223> OTHER INFORMATION: Where Xaa is Serine, Threonine or Asparagine

<400> SEQUENCE: 57

Xaa Phe Xaa Xaa Xaa Xaa Xaa Xaa Gly
  1               5

<210> SEQ ID NO 58
<211> LENGTH: 4
<212> TYPE: PRT
<213> ORGANISM: Unknown
<220> FEATURE:
<223> OTHER INFORMATION: Description of Unknown Organism:  Representative
      claudin cell adhesion recognition sequence
```

```
<400> SEQUENCE: 58

Ile Tyr Ser Tyr
 1

<210> SEQ ID NO 59
<211> LENGTH: 4
<212> TYPE: PRT
<213> ORGANISM: Unknown
<220> FEATURE:
<223> OTHER INFORMATION: Description of Unknown Organism:  Representative
      claudin cell adhesion recognition sequence

<400> SEQUENCE: 59

Thr Ser Ser Tyr
 1

<210> SEQ ID NO 60
<211> LENGTH: 4
<212> TYPE: PRT
<213> ORGANISM: Unknown
<220> FEATURE:
<223> OTHER INFORMATION: Description of Unknown Organism:  Representative
      claudin cell adhesion recognition sequence

<400> SEQUENCE: 60

Val Thr Ala Phe
 1

<210> SEQ ID NO 61
<211> LENGTH: 4
<212> TYPE: PRT
<213> ORGANISM: Unknown
<220> FEATURE:
<223> OTHER INFORMATION: Description of Unknown Organism:  Representative
      claudin cell adhesion recognition sequence

<400> SEQUENCE: 61

Val Ser Ala Phe
 1

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence:  Synthesized
      Peptide
<221> NAME/KEY: MOD_RES
<222> LOCATION: (1)
<223> OTHER INFORMATION: BLOCKED by 9-fluorenymethyloxycarbonyl
<221> NAME/KEY: MOD_RES
<222> LOCATION: (2)
<223> OTHER INFORMATION: tert-butyl protecting group
<221> NAME/KEY: MOD_RES
<222> LOCATION: (4)
<223> OTHER INFORMATION: tert-butyl protecting group
<221> NAME/KEY: MOD_RES
<222> LOCATION: (6)
<223> OTHER INFORMATION: t-Butoxycarbonyl protecting group
<221> NAME/KEY: MOD_RES
<222> LOCATION: (7)
<223> OTHER INFORMATION: tert-butyl protecting group
<221> NAME/KEY: MOD_RES
<222> LOCATION: (9)
<223> OTHER INFORMATION: tert-butyl protecting group
<221> NAME/KEY: MOD_RES
<222> LOCATION: (10)
<223> OTHER INFORMATION: Methoxy terminal group

<400> SEQUENCE: 62
```

-continued

```
Cys Asp Gly Tyr Pro Lys Asp Cys Lys Gly
 1               5                  10
```

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthesized
      Cyclic Peptide
<221> NAME/KEY: MOD_RES
<222> LOCATION: (1)
<223> OTHER INFORMATION: 9-fluorenylmethoxycarbonyl protecting group
<221> NAME/KEY: MOD_RES
<222> LOCATION: (2)
<223> OTHER INFORMATION: tert-butyl protecting group
<221> NAME/KEY: MOD_RES
<222> LOCATION: (4)
<223> OTHER INFORMATION: tert-butyl protecting group
<221> NAME/KEY: MOD_RES
<222> LOCATION: (6)
<223> OTHER INFORMATION: t-butoxycarbonyl protecting group
<221> NAME/KEY: MOD_RES
<222> LOCATION: (7)
<223> OTHER INFORMATION: tert-butyl protecting group
<221> NAME/KEY: MOD_RES
<222> LOCATION: (9)
<223> OTHER INFORMATION: tert-butyl protecting group
<221> NAME/KEY: MOD_RES
<222> LOCATION: (10)
<223> OTHER INFORMATION: Methoxy terminal group

<400> SEQUENCE: 63

```
Cys Asp Gly Tyr Pro Lys Asp Cys Lys Gly
 1               5                  10
```

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthesized
      peptide
<221> NAME/KEY: MOD_RES
<222> LOCATION: (1)
<223> OTHER INFORMATION: Residue has t-butoxycarbonyl, and Trityl or
      Acetamidomethyl protecting groups
<221> NAME/KEY: MOD_RES
<222> LOCATION: (5)..(6)
<223> OTHER INFORMATION: tert-butyl protecting group
<221> NAME/KEY: MOD_RES
<222> LOCATION: (7)
<223> OTHER INFORMATION: Trityl or acetaminomethly protecting group

<400> SEQUENCE: 64

```
Cys Gly Asn Leu Ser Thr Cys Met Leu Gly
 1               5                  10
```

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthesized
      cyclic peptide
<221> NAME/KEY: MOD_RES
<222> LOCATION: (1)
<223> OTHER INFORMATION: t-butoxycarbonyl protecting group
<221> NAME/KEY: MOD_RES
<222> LOCATION: (5)..(6)
<223> OTHER INFORMATION: tert-butyl protecting group

<400> SEQUENCE: 65

```
Cys Gly Asn Leu Ser Thr Cys Met Leu Gly
 1               5                  10

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence:  Synthesized
      peptide
<221> NAME/KEY: MOD_RES
<222> LOCATION: (2)
<223> OTHER INFORMATION: Residue has Acetamidomethyl or
      tert-Acetaminomethyl or tert-butyl protecting
      group
<221> NAME/KEY: MOD_RES
<222> LOCATION: (6)
<223> OTHER INFORMATION: Residue has Acetamidomethyl,
      tert-Acetamidomethyl or tert-butyl protecting group
<221> NAME/KEY: MOD_RES
<222> LOCATION: (9)
<223> OTHER INFORMATION: AMIDATION

<400> SEQUENCE: 66

Cys Tyr Ile Gln Asn Cys Pro Leu Gly
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:  Synthesized
      cyclic peptide
<221> NAME/KEY: MOD_RES
<222> LOCATION: (9)
<223> OTHER INFORMATION: AMIDATION

<400> SEQUENCE: 67

Cys Tyr Ile Gln Asn Cys Pro Leu Gly
 1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group
<221> NAME/KEY: MOD_RES
<222> LOCATION: (5)
<223> OTHER INFORMATION: Where Xaa is beta,beta-dimethyl cysteine

<400> SEQUENCE: 68

Cys His Ala Val Xaa
 1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion
      recognition sequence
<223> OTHER INFORMATION: Cyclic Peptide may comprise N-terminal
      modification such as acetyl or alkoxybenzyl group
```

```
      and/or C-terminal modifications such as amide or
      ester group
<221> NAME/KEY: MOD_RES
<222> LOCATION: (2)
<223> OTHER INFORMATION: Where Xaa is beta,beta-tetramethylene cysteine

<400> SEQUENCE: 69

Ile Xaa Tyr Ser His Ala Val Ser Cys Glu
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group
<221> NAME/KEY: MOD_RES
<222> LOCATION: (2)
<223> OTHER INFORMATION: Where Xaa is beta,beta-pentamethylene cysteine

<400> SEQUENCE: 70

Ile Xaa Tyr Ser His Ala Val Ser Ser Cys
 1               5                  10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group
<221> NAME/KEY: MOD_RES
<222> LOCATION: (1)
<223> OTHER INFORMATION: Where Xaa is beta-mercaptopropionic acid

<400> SEQUENCE: 71

Xaa Tyr Ser His Ala Val Ser Ser Cys
 1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group
<221> NAME/KEY: MOD_RES
<222> LOCATION: (1)
<223> OTHER INFORMATION: Where Xaa is
      beta,beta-pentamethylene-beta-mercaptopropionic
      acid

<400> SEQUENCE: 72

Xaa Tyr Ser His Ala Val Ser Ser Cys
 1               5
```

-continued

```
<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<221> NAME/KEY: MOD_RES
<222> LOCATION: (4)
<223> OTHER INFORMATION: Where Serine is D-Serine

<400> SEQUENCE: 73

His Ala Val Ser Ser
  1               5

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence:  Synthesized
      cyclic peptide

<400> SEQUENCE: 74

Trp Gly Gly Trp
  1

<210> SEQ ID NO 75
<211> LENGTH: 15
<212> TYPE: PRT
<213> ORGANISM: Homo sapiens
<220> FEATURE:
<223> OTHER INFORMATION: Description of Artificial Sequence:
      Representative immunogen containing the HAV
      classical cadherin cell adhesion recognition
      sequence
<223> OTHER INFORMATION: N-cadherin with HAV cell adhesion recognition
      sequence and flanking amino acids

<400> SEQUENCE: 75

Phe His Leu Arg Ala His Ala Val Asp Ile Asn Gly Asn Gln Val
  1               5                  10                  15

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 76

Cys His Ala Val Asp Ile Asn Gly Cys
  1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<223> OTHER INFORMATION: Cyclic Peptide may comprise N-terminal
```

```
        modification such as acetyl or alkoxybenzyl group
        and/or C-terminal modifications such as amide or
        ester group

<400> SEQUENCE: 77

Ser His Ala Val Asp Ser Ser
 1               5

<210> SEQ ID NO 78
<211> LENGTH: 48
<212> TYPE: PRT
<213> ORGANISM: Unknown
<220> FEATURE:
<223> OTHER INFORMATION: Description of Unknown Organism:  Occludin cell
      adhesion recognition sequnce and flanking amino
      acids

<400> SEQUENCE: 78

Gly Val Asn Pro Thr Ala Gln Ser Ser Gly Ser Leu Tyr Gly Ser Gln
 1               5                  10                  15

Ile Tyr Ala Leu Cys Asn Gln Phe Tyr Thr Pro Ala Ala Thr Gly Leu
             20                  25                  30

Tyr Val Asp Gln Tyr Leu Tyr His Tyr Cys Val Val Asp Pro Gln Glu
         35                  40                  45

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence:  Peptide
      with classica 1 cadherin cell adhesion recognition sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 79

Leu Arg Ala His Ala Val Asp Ile Asn Gly
 1               5                  10

<210> SEQ ID NO 80
<211> LENGTH: 14
<212> TYPE: PRT
<213> ORGANISM: Homo sapiens
<220> FEATURE:
<223> OTHER INFORMATION: N-cadherin with HAV cell adhesion recognition
      sequence and flanking amino acids

<400> SEQUENCE: 80

Arg Phe His Leu Arg Ala His Ala Val Asp Ile Asn Gly Asn
 1               5                  10

<210> SEQ ID NO 81
<211> LENGTH: 12
<212> TYPE: PRT
<213> ORGANISM: Homo sapiens
<220> FEATURE:
<223> OTHER INFORMATION: E-cadherin with HAV cell adhesion recognition
      sequence and flanking amino acids

<400> SEQUENCE: 81

Thr Leu Phe Ser His Ala Val Ser Ser Asn Gly Asn
 1               5                  10

<210> SEQ ID NO 82
<211> LENGTH: 4
```

```
<212> TYPE: PRT
<213> ORGANISM: Unknown
<220> FEATURE:
<223> OTHER INFORMATION: Description of Unknown Organism: Cadherin
      Calcium Binding Motif
<221> NAME/KEY: VARIANT
<222> LOCATION: (1)...(4)
<223> OTHER INFORMATION: Xaa is any amino acid

<400> SEQUENCE: 82

Xaa Asp Xaa Glu
  1

<210> SEQ ID NO 83
<211> LENGTH: 4
<212> TYPE: PRT
<213> ORGANISM: Unknown
<220> FEATURE:
<223> OTHER INFORMATION: Description of Unknown Organism: Cadherin
      Calcium Binding Motif

<400> SEQUENCE: 83

Asp Val Asn Glu
  1

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 84

Cys His Ala Val Cys Tyr
  1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 85

Cys Phe Ser His Ala Val Cys
  1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 86
```

Cys Leu Phe Ser His Ala Val Cys
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 87

Cys His Ala Val Cys Ser
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 88

Ser Cys His Ala Val Cys
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 89

Cys His Ala Val Cys Ser Ser
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 90

Ser Cys His Ala Val Cys Ser
1               5

<210> SEQ ID NO 91
<211> LENGTH: 6
<212> TYPE: PRT

```
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 91

Cys His Ala Val Cys Thr
 1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 92

Cys His Ala Val Cys Glu
 1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 93

Cys His Ala Val Cys Asp
 1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 94

Cys His Ala Val Tyr Cys
 1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
```

```
            ester group

<400> SEQUENCE: 95

Cys His Ala Val Cys Tyr
 1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 96

Cys His Ala Val Cys
 1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group
<221> NAME/KEY: MOD_RES
<222> LOCATION: (5)
<223> OTHER INFORMATION: Where Xaa is beta,beta-dimethyl cysteine

<400> SEQUENCE: 97

Cys His Ala Val Xaa
 1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group
<221> NAME/KEY: MOD_RES
<222> LOCATION: (1)
<223> OTHER INFORMATION: Where Xaa is beta,beta-dimethyl cysteine

<400> SEQUENCE: 98

Xaa His Ala Val Cys
 1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<223> OTHER INFORMATION: Cyclic Peptide may comprise N-terminal
      modification such as acetyl or alkoxybenzyl group
      and/or C-terminal modifications such as amide or
      ester group
```

-continued

<400> SEQUENCE: 99

Cys His Ala Val Pro Cys
1 5

COMPOUNDS AND METHODS FOR MODULATING CELL ADHESION

CROSS-REFERENCE TO RELATED APPLICATIONS

This application is a division of U.S. Ser. No. 09/458,870, filed Dec. 10, 1999 (now U.S. Pat. No. 6,465,427); which is a continuation-in-part of U.S. Ser. No. 09/357,717, filed Jul. 20, 1999 (now U.S. Pat. No. 6,417,325); which is a continuation-in-part of U.S. Ser. No. 09/248,074, filed Feb. 10, 1999 and issued as U.S. Pat. No. 6,346,512 on Feb. 12, 2002; which is a continuation-in-part of U.S. Ser. No. 08/996,679, filed Dec. 23, 1997 and issued as U.S. Pat. No. 6,169,071 on Jan. 2, 2001; which is a continuation-in-part of U.S. Ser. No. 08/893,534, filed Jul. 11, 1997 and issued as U.S. Pat. No. 6,031,072 on Feb. 24, 2000; which claims the benefit of U.S. Provisional Application No. 60/021,612, filed on Jul. 12, 1996, wherein these six applications are incorporated herein by reference in their entireties.

TECHNICAL FIELD

The present invention relates generally to methods for modulating cell adhesion, and more particularly to cyclic peptides comprising a cadherin cell adhesion recognition sequence, and to the use of such cyclic peptides for inhibiting or enhancing cadherin-mediated cell adhesion.

BACKGROUND OF THE INVENTION

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins are a rapidly expanding family of calcium-dependent CAMs (Munro et al., *In: Cell Adhesion and Invasion in Cancer Metastasis*, P. Brodt, ed., pp. 17–34, RG Landes Co.(Austin Tex., 1996). The classical cadherins (abbreviated CADs) are integral membrane glycoproteins that generally promote cell adhesion through homophilic interactions (a CAD on the surface of one cell binds to an identical CAD on the surface of another cell), although CADs also appear to be capable of forming heterotypic complexes with one another under certain circumstances and with lower affinity. Cadherins have been shown to regulate epithelial, endothelial, neural and cancer cell adhesion, with different CADs expressed on different cell types. N (neural)—cadherin is predominantly expressed by neural cells, endothelial cells and a variety of cancer cell types. E (epithelial)—cadherin is predominantly expressed by epithelial cells. Other CADs are P (placental)—cadherin, which is found in human skin and R (retinal)—cadherin. A detailed discussion of the classical cadherins is provided in Munro SB et al., 1996, *In: Cell Adhesion and Invasion in Cancer Metastasis*, P. Brodt, ed., pp.17–34 (RG Landes Company, Austin Tex.).

The structures of the CADs are generally similar. As illustrated in FIG. 1, CADs are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:8), DXD and LDRE (SEQ ID NO:9) are interspersed throughout the extracellular domains. The first extracellular domain (EC1) contains the classical cadherin cell adhesion recognition (CAR) sequence, HAV (His-Ala-Val), along with flanking sequences on either side of the CAR sequence that may play a role in conferring specificity. Synthetic peptides containing the CAR sequence and antibodies directed against the CAR sequence have been shown to inhibit CAD-dependent processes (Munro et al., supra; Blaschuk et al., *J. Mol. Biol.* 211:679–82, 1990; Blaschuk et al., *Develop. Biol.* 139:227–29, 1990; Alexander et al., *J. Cell. Physiol.* 156:610–18, 1993). The three-dimensional solution and crystal structures of the EC1 domain have been determined (Overduin et al., *Science* 267:386–389, 1995; Shapiro et al., *Nature* 374:327–337, 1995).

Although cell adhesion is required for certain normal physiological functions, there are situations in which cell adhesion is undesirable. For example, many pathologies (such as autoimmune and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects. It has been suggested that linear synthetic peptides containing a cadherin CAR sequence may be employed for drug transport (WO 91/04745), but such peptides are often metabolically unstable and are generally considered to be poor therapeutic agents.

Accordingly, there is a need in the art for compounds that modulate cell adhesion and improve drug delivery across permeability barriers without such disadvantages. The present invention fulfills this need and further provides other related advantages.

SUMMARY OF THE INVENTION

The present invention provides modulating agents comprising cyclic peptides, and methods for using such agents to inhibit or enhance cadherin-mediated cell adhesion. Such cyclic peptides generally comprise the sequence His-Ala-Val. Within certain aspects, such cyclic peptides have the formula:

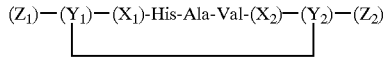

wherein $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. Such cyclic peptides may comprise modifications such as an N-acetyl or N-alkoxybenzyl group and/or a C-terminal amide or ester group. Cyclic peptides may be cyclized via, for example, a disulfide bond; an amide bond between terminal functional groups, between residue side-chains or between one terminal functional group and one residue side chain; a thioether bond or $\delta_1\delta_1$-ditryptophan, or a derivative thereof.

Within certain embodiments, a cyclic peptide has the formula:

wherein $Y_1$ and $Y_2$ are optional and, if present are independently selected from the group consisting of amino acid residues and combinations thereof in which the residues are linked by peptide bonds, and wherein $Y_1$ and $Y_2$ range in size from 0 to 10 residues; and wherein X and Z are independently selected from the group consisting of amino acid residues, wherein a disulfide bond is formed between residues X and Z; and wherein X has a terminal modification (e.g., an N-acetyl group).

Within further embodiments, a cyclic peptide has the formula:

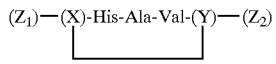

wherein $Z_1$ and $Z_2$ are selected from the group consisting of amino acid residues and combinations thereof in which the residues are linked by peptide bonds, and wherein $Z_1$ and $Z_2$ range in size from 1 to 10 residues; and wherein X and Y are independently selected from the group consisting of amino acid residues, wherein a disulfide bond is formed between residues X and Y; and wherein X has a terminal modification (e.g., an N-acetyl group).

Certain specific cyclic peptides provided by the present invention include N—Ac—CHAVC—NH₂ (SEQ ID NO:96), N—Ac—CHAVC—Y—NH₂ (SEQ ID NO:84), N—Ac—CHAVDC—NH₂ (SEQ ID NO:20), N—Ac—CHAVDIC—NH₂ (SEQ ID NO:50), N—Ac—CHAVDINC—NH₂ (SEQ ID NO:51), N—Ac—CHAVDINGC—NH₂ (SEQ ID NO:76), N—Ac—CAHAVC—NH₂ (SEQ ID NO:22), N—Ac—CAHAVDC—NH₂ (SEQ ID NO:26), N—Ac—CAHAVDIC—NH₂ (SEQ ID NO:24), N—Ac—CRAHVDC—NH₂ (SEQ ID NO:28), N—Ac—CLRAHAVC—NH₂ (SEQ ID NO:30), N—Ac—CLRAHAVDC—NH₂ (SEQ ID NO:32), N—Ac—CSHAVC—NH₂ (SEQ ID NO:36), N—Ac—CFSHAVC—NH₂ (SEQ ID NO:85), N—Ac—CLFSHAVC—NH₂ (SEQ ID NO: 86), N—Ac—CHAVSC—NH₂ (SEQ ID NO:38), N—Ac—CSHAVSC—NH₂ (SEQ ID NO:40), N—Ac—CSHAVSSC—NH₂ (SEQ ID NO:42), N—Ac—CHAVSSC—NH₂ (SEQ ID NO:44), N—Ac—KHAVD—NH₂ (SEQ ID NO:12), N—Ac—KHAVK—NH₂ (SEQ ID NO: 14), N—Ac—KHAVE—NH₂ (SEQ ID NO:16), N—Ac—AHAVDI—NH₂ (SEQ ID NO:34), N—Ac—SHAVDSS—NH₂ (SEQ ID NO:77), N—Ac—KSHAVSSD—NH₂ (SEQ ID NO:48), N—Ac—CHAVC—S—NH₂ (SEQ ID NO:87), N—Ac—S—CHAVC—NH₂ (SEQ ID NO:88), N—Ac—CHAVC—SS—NH₂ (SEQ ID NO:89), N—Ac—S—CHAVC—S—NH₂ (SEQ ID NO:90), N—Ac—CHAVC—T—NH₂ (SEQ ID NO:91), N—Ac—CHAVC—E—NH₂ (SEQ ID NO:92), N—Ac—CHAVC—D—NH₂ (SEQ ID NO:93), N—Ac—CHAVYC—NH₂ (SEQ ID NO:94), CH₃—SO₂—HN—CHAVC—Y—NH₂ (SEQ ID NO:95), CH₃—SO₂—HN—CHAVC—NH₂ (SEQ ID NO:96), HC(O)—HN—CHAVC—NH₂ (SEQ ID NO:96), N—Ac—CHAVPen—NH₂ (SEQ ID NO:97), N—Ac—PenHAVC—NH₂ (SEQ ID NO:98) and N—Ac—CHAVPC—NH₂. (SEQ ID NO:99), as well as derivatives thereof in which the N—Ac group is replaced by a different terminal group.

Within further aspects, the present invention provides cell adhesion modulating agents that comprise a cyclic peptide as described above. Within specific embodiments, such modulating agents may be linked to one or more of a targeting agent, a drug, a solid support or support molecule, or a detectable marker. In addition, or alternatively, a cell adhesion modulating agent may further comprising one or more of: (a) a cell adhesion recognition sequence that is bound by an adhesion molecule other than a cadherin, wherein the cell adhesion recognition sequence is separated from any HAV sequence(s) by a linker; and/or (b) an antibody or antigen-binding fragment thereof that specifically binds to a cell adhesion recognition sequence bound by an adhesion molecule other than a cadherin.

The present invention further provides pharmaceutical compositions comprising a cell adhesion modulating agent as described above, in combination with a pharmaceutically acceptable carrier. Such compositions may further comprise a drug. Alternatively, or in addition, such compositions may comprise: (a) a peptide comprising a cell adhesion recognition sequence that is bound by an adhesion molecule other than a cadherin; and/or (b) an antibody or antigen-binding fragment thereof that specifically binds to a cell adhesion recognition sequence bound by an adhesion molecule other than a cadherin.

Within further aspects, methods are provided for modulating cell adhesion, comprising contacting a cadherin-expressing cell with a cell adhesion modulating agent as described above.

Within a further aspect, methods are provided for reducing unwanted cellular adhesion in a mammal, comprising administering to a mammal a cell adhesion modulating agent as described above, wherein the modulating agent inhibits cadherin-mediated cell adhesion.

In a further aspect, a method is provided for enhancing the delivery of a drug to a tumor in a mammal, comprising administering to a mammal a cell adhesion modulating agent as described above and a drug, wherein the modulating agent inhibits cadherin-mediated cell adhesion.

Within related aspects, methods for treating cancer and/or inhibiting metastasis of tumor cells in a mammal are provided, comprising administering to a mammal afflicted with cancer a cell adhesion modulating agent as described above, wherein the modulating agent inhibits cadherin-mediated cell adhesion.

In a further aspect, methods are provided for inducing apoptosis in a cadherin-expressing cell, comprising contacting a cadherin-expressing cell with a cell adhesion modulating agent as described above, wherein the modulating agent inhibits cadherin-mediated cell adhesion.

The present invention also provides, within other aspects, methods for inhibiting angiogenesis in a mammal, comprising administering to a mammal a cell adhesion modulating agent as described above, wherein the modulating agent inhibits cadherin-mediated cell adhesion.

Methods are further provided, within other aspects, for stimulating blood vessel regression, comprising administering to a mammal a cell adhesion modulating agent as described above, wherein the cyclic peptide modulates cadherin-mediated cell adhesion.

Within a further embodiment, the present invention provides methods for enhancing drug delivery to the central nervous system of a mammal, comprising administering to a mammal a cell adhesion modulating agent as described above, wherein the modulating agent inhibits cadherin-mediated cell adhesion.

In still further aspects, methods are provided for enhancing cell adhesion. Within one such aspect, methods for enhancing wound healing in a mammal are provided, comprising contacting a wound in a mammal with a cell adhesion modulating agent as described above, wherein the modulating agent enhances cadherin-mediated cell adhesion.

Within a related aspect, the present invention provides methods for enhancing adhesion of foreign tissue implanted within a mammal, comprising contacting a site of implantation of foreign tissue in a mammal with a cell adhesion modulating agent as described above, wherein the modulating agent enhances cadherin-mediated cell adhesion.

In a further aspect, the present invention provides methods for treating a demyelinating neurological disease in a mammal, comprising administering to a mammal a cell adhesion modulating agent as described above, wherein the modulating agent inhibits cadherin-mediated cell adhesion.

Within a related aspect, the present invention provides methods for facilitating migration of an N-cadherin expressing cell on astrocytes, comprising contacting an N-cadherin expressing cell with (a) a cell adhesion modulating agent that inhibits cadherin-mediated cell adhesion, wherein the modulating agent comprises a cyclic peptide that comprises the sequence HAV; and (b) one or more astrocytes; and thereby facilitating migration of the N-cadherin expressing cell on the astrocytes.

The present invention also provides methods for modulating the immune system of a mammal, comprising administering to a mammal a cell adhesion modulating agent as described above, wherein the modulating agent inhibits cadherin-mediated cell adhesion.

In yet another aspect, methods for preventing pregnancy in a mammal are provided, comprising administering to a mammal a cell adhesion modulating agent as described above, wherein the modulating agent inhibits cadherin-mediated cell adhesion.

Within a further aspect, methods are provided for increasing vasopermeability in a mammal, comprising administering to a mammal a cell adhesion modulating agent as described above, wherein the modulating agent inhibits cadherin-mediated cell adhesion.

The present invention further provides methods for inhibiting synaptic stability in a mammal, comprising administering to a mammal a cell adhesion modulating agent as described above, wherein the modulating agent inhibits cadherin-mediated cell adhesion.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 2 provides the amino acid sequences of mammalian classical cadherin EC1 domains: human N-cadherin (SEQ ID NO:1), mouse N-cadherin (SEQ ID NO:2), cow N-cadherin (SEQ ID NO:3), human P-cadherin (SEQ ID NO:4), mouse P-cadherin (SEQ ID NO:5), human E-cadherin (SEQ ID NO:6) and mouse E-cadherin (SEQ ID NO:7).

FIGS. 3A–3I provides the structures of representative cyclic peptides of the present invention (structures on the left hand side; SEQ ID Nos. 96,12,14,16,18,20,22,24,26,28, 30,32,34,36,38,40,42,44,46,48), along with similar, but inactive, structures (on the right; SEQ ID Nos. 11,13,15,17, 19,21,23,25,27,29,31,33,35,37,39,41,43,45,47,49).

and absence (FIG. 5C) of a representative cyclic peptide or in the presence of an inactive control peptide (FIG. 5B). FIG. 5A shows the cells 30 minutes after exposure to 500 μg/mL N—Ac—CHAVC—NH$_2$ (SEQ ID NO:96). FIG. 5B shows the cells 30 minutes after exposure to the control peptide N—Ac—CHGVC—NH$_2$ (SEQ ID NO:11). FIG. 5C shows the cells in the absence of cyclic peptide. Note that the endothelial cells retracted from one another in the presence of N—Ac—CHAVC—NH$_2$ (SEQ ID NO:96).

FIG. 6A shows the cells 30 minutes after exposure to 500 μg/mL N—Ac—CAHAVDIC—NH$_2$ (SEQ ID NO:24). FIG. 6B shows the cells 30 minutes after exposure to the control peptide N—Ac—CAHGVDIC—NH$_2$ (SEQ ID NO:25). FIG. 6C shows the cells in the absence of cyclic peptide. In this case, neither of the cyclic peptides show activity.

FIG. 7A shows the cells 30 minutes after exposure to 500 μg/mL N—Ac—CAHAVDC—NH$_2$ (SEQ ID NO:26). FIG. 7B shows the cells 30 minutes after exposure to the control peptide N—Ac—CAHGVDC—NH$_2$ (SEQ ID NO:27). FIG. 7C shows the cells in the absence of cyclic peptide. Note that the endothelial cells retracted from one another in the presence of N—Ac—CAHAVDC—NH$_2$ (SEQ ID NO:26).

FIG. 8A shows the cells 30 minutes after exposure to 500 μg/mL N—Ac—CSHAVSSC—NH$_2$ (SEQ ID NO:42). FIG. 8B shows the cells 30 minutes after exposure to the control peptide N—Ac—CSHGVSSC—NH$_2$ (SEQ ID NO:43). FIG. 8C shows the cells in the absence of cyclic peptide. Note that the endothelial cells retracted from one another and round up in the presence of N—Ac—CSHAVSSC—NH$_2$ (SEQ ID NO:42).

FIG. 9A shows the cells 24 hours after being cultured in the presence of 500 μg/mL N—Ac—CHAVC—NH$_2$ (SEQ ID NO:96; 10× magnification). FIG. 9B shows the cells (10× magnification) 24 hours after being cultured in the presence of the control peptide N—Ac—CHGVC—NH$_2$ (SEQ ID NO:11). FIG. 9C shows the cells (10× magnification) in the absence of cyclic peptide. FIGS. 9D–F show the cells (20× magnification) 48 hours after exposure to N—Ac—CHAVC—NH$_2$ (SEQ ID NO:96) at concentrations of 1 μg/mL, 100 μg/mL and 10 μg/mL, respectively. Note that the SKOV3 cells retract from one another and round-up when cultured in the presence of either 0.5 or 1 mg/ml N—Ac—CHAVC—NH$_2$ (SEQ ID NO:96).

FIG. 12A shows untreated cells and FIGS. 12B–D show cells after 48 hours of exposure to either 1 mg/mL H—CHAVSC—OH (SEQ ID NO:38) (FIG. 12B), the control peptide N—Ac—CHGVC—NH$_2$ (SEQ ID NO:11), (FIG. 12C) or the representative cyclic peptide N—Ac—CHAVC—NH$_2$ (SEQ ID NO:96), (FIG. 12D). Note that E-cadherin expression is greatly reduced in the cells treated with N—Ac—CHAVC—NH$_2$ (SEQ ID NO:96), as compared to the E-cadherin levels expressed by untreated cells and cells treated with the other two cyclic peptides FIG. 13A shows the cells 24 hours after being cultured in the presence of 1 mg/ml of N—Ac—CHAVSC—NH$_2$ (SEQ ID NO:38). FIG. 13B shows the cells 24 hours after being cultured in the presence of 100 μg/ml of N—Ac—CHAVSC—NH$_2$ (SEQ ID NO:38). FIG. 13C shows the cells 24 hours after being cultured in the presence of 10 μg/ml of N—Ac—CHAVSC—NH$_2$ (SEQ ID NO:38). Note that the cells retract form one another in the presence of 100 μg/ml of N—Ac—CHAVSC—NH$_2$ (SEQ ID NO:38), whereas they round up in the presence of 1 mg/ml of this peptide. FIG. 14B shows the cells 48 hours after being cultured in the presence of 500 μg/ml of N—Ac—CHAVC—NH$_2$ (SEQ ID NO:96). FIG. 14A shows untreated cultures of human melanoma ME115 cells. Note that cadherin is localized in intracellular vesicles in cells treated with peptide, whereas it is present at the surface in the untreated cells.

FIG. 15B shows the cells 48 hours after being cultured in the presence of 500 μg/ml of N—Ac—CHAVC—NH$_2$ (SEQ ID NO:96). FIG. 15A shows untreated monolayer cultures of A1N4 human breast epithelial cells. Note that the distribution of E-cadherin is non-contiguous in cells treated with the cyclic peptide. Furthermore, gaps have appeared in the monolayer of cells treated with the peptide.

FIGS. 35A and 35B show SKOV3 cells treated for 48 hours with the control peptide N—Ac—CHGVC—NH$_2$ (SEQ ID NO:11) at a concentration of 0.5 mg/mL (FIG. 35A) or 0.25 mg/mL (FIG. 35B). FIGS. 35C and 35D show SKOV3 cells treated for 48 hours with N—Ac—CHAVC—NH$_2$ (SEQ ID NO:96) at a concentration of 0.5 mg/mL (FIG. 35C) or 0.25 mg/mL (FIG. 35D). The fluorescent green nuclei in FIGS. 35C and 35D indicate cell death.

FIG. 37A shows the results for the control cells, and FIG. 37B shows the results for 1 mg/mL N—Ac—CHAVC—Y—NH$_2$ (SEQ ID NO:84).

FIGS. 40B, 40D and 40F show tumor sections obtained from mice treated with N—Ac—CHAVC—NH$_2$ (SEQ ID NO:96) at 20 mg/kg once daily for four days, and sacrificed 11 days after the last treatment. FIGS. 40A, 40C and 40E show saline controls. The magnification was 4× in FIGS. 40A–40B, 10× in FIGS. 40C–40D and 40× in FIGS. 40E–40F.

DETAILED DESCRIPTION OF THE INVENTION

Figure 1:
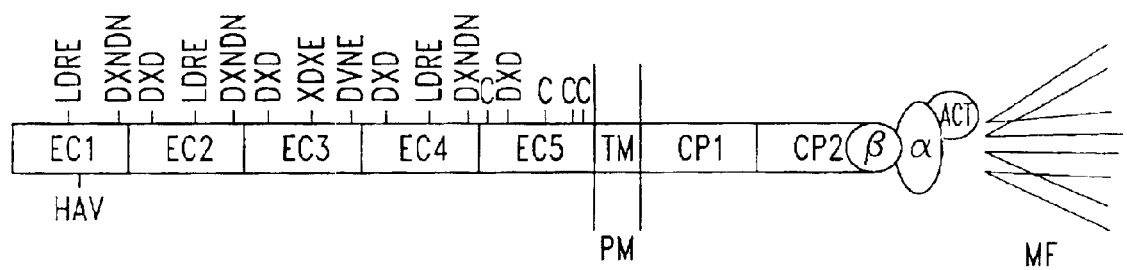
FIG. 1 is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:8), DXD, LDRE (SEQ ID NO:9), XDXE (SEQ ID NO:82) and DVNE (SEQ ID NO:83). The CAR sequence, HAV, is shown within EC1. Cytoplasmic proteins β-catenin (β), α-catenin (α) and α-actinin (ACT), which mediate the interaction between CADs and microfilaments (MF) are also shown.

As noted above, the present invention provides cell adhesion modulating agents comprising cyclic peptides that are capable of modulating classical cadherin-mediated processes, such as cell adhesion. Cyclic peptides provided herein generally contain the classical cadherin cell adhesion recognition (CAR) sequence HAV (i.e., His-Ala-Val) within the cyclized portion of the peptide (i.e., within the peptide ring). Certain modulating agents described herein inhibit cell adhesion. Such modulating agents may generally be used, for example, to treat diseases or other conditions characterized by undesirable cell adhesion or to facilitate drug delivery to a specific tissue or tumor. Alternatively, certain modulating agents may be used to enhance cell adhesion (e.g., to supplement or replace stitches or to facilitate wound healing) or to enhance or direct neurite outgrowth.

Cyclic Peptides

The term "cyclic peptide," as used herein, refers to a peptide or salt thereof that comprises (1) an intramolecular covalent bond between two non-adjacent residues and (2) at least one classical cadherin cell adhesion recognition (CAR) sequence HAV (His-Ala-Val). The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. In addition to the classical cadherin CAR sequence HAV, a modulating agent may comprise additional CAR sequences, which may or may not be cadherin CAR sequences, and/or antibodies or fragments thereof that specifically recognize a CAR sequence. Additional CAR sequences may be present within the cyclic peptide containing the HAV sequence, within a separate cyclic peptide component of the modulating agent and/or in a non-cyclic portion of the modulating agent. Antibodies and antigen-binding fragments thereof are typically present in a non-cyclic portion of the modulating agent.

Certain preferred cyclic peptides satisfy the formula:

$$(Y_1)-(X_1)\text{-His-Ala-Val-}(X_2)-(Y_2)$$

wherein $X_1$, and $X_2$ are independently selected from the group consisting of amino acid residues, with a covalent bond formed between residues $X_1$ and $X_2$; and wherein $Y_1$ and $Y_2$ are optional and, if present, are independently selected from the group consisting of amino acid residues and combinations thereof in which the residues are linked by peptide bonds.

Certain specific cyclic peptides also satisfy the formula:

$$(X)-(Y_1)\text{-His-Ala-Val-}(Y_2)-(Z)$$

wherein $Y_1$ and $Y_2$ are optional and, if present are independently selected from the group consisting of amino acid residues and combinations thereof in which the residues are linked by peptide bonds, and wherein $Y_1$ and $Y_2$ range in size from 0 to 10 residues; and wherein X and Z are independently selected from the group consisting of amino acid residues, wherein a disulfide bond is formed between residues X and Z; and wherein X has a terminal modification (e.g., an N-acetyl group).

Other cyclic peptides have the formula:

$$(Z_1)-(X)\text{-His-Ala-Val-}(Y)-(Z_2)$$

wherein $Z_1$ and $Z_2$ are selected from the group consisting of amino acid residues and combinations thereof in which the residues are linked by peptide bonds, and wherein $Z_1$ and $Z_2$ range in size from 1 to 10 residues; and wherein X and Y are independently selected from the group consisting of amino acid residues, wherein a disulfide bond is formed between residues X and Y; and wherein X has a terminal modification (e.g., an N-acetyl group).

Within certain embodiments, a cyclic peptide preferably comprises an N-acetyl group (i.e., the amino group present on the amino terminal residue of the peptide prior to cyclization is acetylated) or an N-formyl group (i.e., the amino group present on the amino terminal residue of the peptide prior to cyclization is formylated), or the amino group present on the amino terminal residue of the peptide prior to cyclization is mesylated. It has been found, within the context of the present invention, that the presence of such terminal groups may enhance cyclic peptide activity for certain applications. One particularly preferred cyclic peptide is N—Ac—CHAVC—NH$_2$ (SEQ ID NO:96). Another preferred cyclic peptide is N—Ac—CHAVC—Y—NH$_2$ (SEQ ID NO:84). Other cyclic peptides include, but are not limited to: N—Ac—CHAVDC—NH$_2$ (SEQ ID NO:20), N—Ac—CHAVDIC—NH$_2$ (SEQ ID NO:50), N—Ac—CHAVDINC—NH$_2$ (SEQ ID NO:51), N—Ac—CHAVDINGC—NH$_2$ (SEQ ID NO:76), N—Ac—CAHAVC—NH$_2$ (SEQ ID NO:22), N—Ac—CAHAVDC—NH$_2$ (SEQ ID NO:26), N—Ac—CAHAVDIC—NH$_2$ (SEQ ID NO:24), N—Ac—CRAHAVDC—NH$_2$ (SEQ ID NO:28), N—Ac—CLRAHAVC—NH$_2$ (SEQ ID NO:30), N—Ac—CLRAHAVDC—NH$_2$ (SEQ ID NO:32), N—Ac—CSHAVC—NH$_2$ (SEQ ID NO:36), N—Ac—CFSHAVC—NH$_2$ (SEQ ID NO:85), N—Ac—CLFSHAVC—NH$_2$ (SEQ ID NO:86), N—Ac—CHAVSC—NH$_2$ (SEQ ID NO:38), N—Ac—CSHAVSC—NH$_2$ (SEQ ID NO:40), N—Ac—CSHAVSSC—NH$_2$ (SEQ ID NO:42), N—Ac—CHAVSSC—NH$_2$ (SEQ ID NO:44), N—Ac—KHAVD—NH$_2$ (SEQ ID NO:12), N—Ac—KHAVK—NH$_2$ (SEQ ID NO:14), N—Ac—KHAVE—NH$_2$ (SEQ ID NO:16), N—Ac—AHAVDI—NH$_2$ (SEQ ID NO:34), N—Ac—SHAVDSS—NH$_2$ (SEQ ID NO:77), N—Ac—KSHAVSSD—NH$_2$ (SEQ ID NO:48), N—Ac—CHAVC—S—NH$_2$ (SEQ ID NO:87), N—Ac—S—CHAVC—NH$_2$ (SEQ ID NO:88), N—Ac—CHAVC—SS—NH$_2$ (SEQ ID NO:89), N—Ac—S—CHAVC—S—NH$_2$ (SEQ ID NO:90), N—Ac—CHAVC—T—NH$_2$ (SEQ ID NO:91), N—Ac—CHAVC—E—NH$_2$ (SEQ ID NO:92), N—Ac—CHAVC—D—NH$_2$ (SEQ ID NO:93), N—Ac—CHAVYC—NH$_2$ (SEQ ID NO:94), CH$_3$—SO$_2$—HN—CHAVC—Y—NH$_2$ (SEQ ID NO:95), CH$_3$—SO$_2$—HN—CHAVC—NH$_2$ (SEQ ID NO:96), HC(O)—HN—CHAVC—NH$_2$ (SEQ ID NO:96), N—Ac—CHAVPen—NH$_2$ (SEQ ID NO:97), N—Ac—PenHAVC—NH$_2$ (SEQ ID NO:98) and N—Ac—CHAVPC—NH$_2$ (SEQ ID NO:99).

In addition to the CAR sequence(s), cyclic peptides generally comprise at least one additional residue, such that the size of the cyclic peptide ring ranges from 4 to about 15 residues, preferably from 5 to 10 residues. Such additional residue(s) may be present on the N-terminal and/or C-terminal side of a CAR sequence, and may be derived from sequences that flank the HAV sequence within one or more naturally occurring cadherins (e.g., N-cadherin, E-cadherin, P-cadherin, R-cadherin or other cadherins containing the HAV sequence) with or without amino acid substitutions and/or other modifications. Flanking sequences for endogenous N-, E-, P- and R-cadherin are shown in FIG. 2, and in SEQ ID NOs: 1 to 7. Database accession numbers for representative naturally occurring cadherins are as follows: human N-cadherin M34064, mouse N-cadherin M31131 and M22556, cow N-cadherin X53615, human P-cadherin X63629, mouse P-cadherin X06340, human E-cadherin Z13009, mouse E-cadherin X06115. Alternatively, additional residues present on one or both sides of the CAR sequence(s) may be unrelated to an endogenous sequence (e.g., residues that facilitate cyclization).

Within certain preferred embodiments, as discussed below, relatively small cyclic peptides that do not contain significant sequences flanking the HAV sequence are preferred for modulating N-cadherin and E-cadherin mediated cell adhesion. Such peptides may contain an N-acetyl group and a C-amide group (e.g., the 5-residue rings N—Ac—CHAVC—$NH_2$ (SEQ ID NO:96), N—Ac—KHAVD—$NH_2$ (SEQ ID NO:12), H—C(O)—CHAVC—$NH_2$ (SEQ ID NO:96) or $CH_3$—$SO_2$—HN—CHAVC—$NH_2$ (SEQ ID NO:96)). The finding, within the present invention, that such relatively small cyclic peptides may be effective and all-purpose inhibitors of cell adhesion represents a unexpected discovery. Such cyclic peptides can be thought of as "master keys" that fit into peptide binding sites of each of the different classical cadherins, and are capable of disrupting cell adhesion of neural cells, endothelial cells, epithelial cells and/or certain cancer cells. Small cyclic peptides may generally be used to specifically modulate cell adhesion of neural and/or other cell types by topical administration or by systemic administration, with or without linking a targeting agent to the peptide, as discussed below.

Within other preferred embodiments, a cyclic peptide may contain sequences that flank the HAV sequence on one or both sides that are designed to confer specificity for cell adhesion mediated by one or more specific cadherins, resulting in tissue and/or cell-type specificity. Suitable flanking sequences for conferring specificity include, but are not limited to, endogenous sequences present in one or more naturally occurring cadherins, and cyclic peptides having specificity may be identified using the representative screens provided herein. For example, it has been found, within the context of the present invention, that cyclic peptides that contain additional residues derived from the native E-cadherin sequence on the N-terminal side of the CAR sequence are specific for epithelial cells (i.e., such peptides disrupt E-cadherin mediated cell adhesion to a greater extent than they disrupt N-cadherin expression). The addition of appropriate endogenous sequences may similarly result in peptides that disrupt N-cadherin mediated cell adhesion. For example, it has been found within the context of the present invention that the addition of one or more amino acid residues on the C-terminal side of the HAV sequence in an endogenous N-cadherin results in cyclic peptides that are potent inhibitors of neurite outgrowth.

To facilitate the preparation of cyclic peptides having a desired specificity, nuclear magnetic resonance (NMR) and computational techniques may be used to determine the conformation of a peptide that confers a known specificity. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space and across the ring of the cyclic peptide. This information may be used to facilitate calculation of the low energy conformations for the HAV sequence. Conformation may then be correlated with tissue specificity to permit the identification of peptides that are similarly tissue specific or have enhanced tissue specificity.

Cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations indicated in Table 1, and the corresponding D-amino acids are designated by a lower case one letter symbol. Modulating agents and cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

TABLE 1

| Amino acid one-letter and three-letter abbreviations | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

Cyclic peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solid phase and solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthogonal systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. By way of example, strong oxidizing agents can be used to perform the cyclization shown below (SEQ ID NOs: 62 and 63), in which the underlined portion is cyclized:

FmocCysAsp(t-Bu)GlyTyr(t-Bu)ProLys(Boc)Asp(t-Bu)CysLys(t-Bu)Gly-OMe→Fmoc
<u>Cys</u>Asp(t-Bu)GlyTyr(t-Bu)ProLys(Boc)Asp(t-Bu)<u>Cys</u>Lys(t-Bu)Gly-OMe Oxidizing agents also allow concurrent deprotection/oxidation of suitable S-protected linear precursors to avoid premature, nonspecific oxidation of free cysteine, as shown below (SEQ ID NOs: 64 and 65), where X and Y=S-Trt or S-Acm:

BocCys(X)GlyAsnLeuSer(t-Bu)Thr(t-Bu)Cys(Y)MetLeuGlyOH→
Boc<u>Cys</u>GlyAsnLeuSer(t-Bu)Thr(t-Bu)<u>Cys</u>MetLeuGlyOH

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. In the example below (SEQ ID NOs: 66 and 67), X is Acm, Tacm or t-Bu:

H-Cys(X)TyrIleGlnAsnCys(X)ProLeuGly-NH$_2$→H-<u>Cys</u>TyrIleGlnAsn<u>Cys</u>ProLeuGly-NH$_2$

Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N—Ac and C-terminal amide groups are represented by —NH$_2$:

i) N—Ac-<u>Cys-His-Ala-Val-Cys</u>-NH$_2$ (SEQ ID NO:96)
ii) N—Ac-<u>Cys-Ala-His-Ala-Val-Asp-Ile-Cys</u>-NH$_2$ (SEQ ID NO:24)
iii) N—Ac-<u>Cys-Ser-His-Ala-Val-Cys</u>-NH$_2$ (SEQ ID NO:36)
iv) N—Ac-<u>Cys-His-Ala-Val-Ser-Cys</u>-NH$_2$ (SEQ ID NO:38)
v) N—Ac-<u>Cys-Ala-His-Ala-Val-Asp-Cys</u>-NH$_2$ (SEQ ID NO:26)

vi) N—Ac-<u>Cys</u>-Ser-His-Ala-Val-Ser-Ser-<u>Cys</u>-NH₂ (SEQ ID NO:42)

vii) N—Ac-<u>Cys</u>-His-Ala-Val-Ser-<u>Cys</u>-OH (SEQ ID NO:38)

viii) H-<u>Cys</u>-Ala-His-Ala-Val-Asp-<u>Cys</u>-NH₂ (SEQ ID NO:26)

ix) N—Ac-<u>Cys</u>-His-Ala-Val-<u>Pen</u>-NH₂ (SEQ ID NO:68)

x) N—Ac-Ile-<u>Tmc</u>-<u>Tmc</u>-Ser-His-Ala-Val-Ser-<u>Cys</u>-Glu-NH₂ (SEQ ID NO:69)

xi) N—Ac-Ile-<u>Pmc</u>-Tyr-Ser-His-Ala-Val-Ser-Ser-<u>Cys</u>-NH₂ (SEQ ID NO:70)

xii) <u>Mpr</u>-Tyr-Ser-His-Ala-Val-Ser-Ser-<u>Cys</u>-NH₂ (SEQ ID NO:71)

xiii) <u>Pmp</u>-Tyr-Ser-His-Ala-Val-Ser-Ser-<u>Cys</u>-NH₂ (SEQ ID NO:72)

xii)

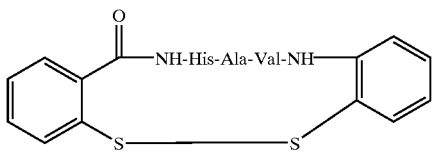

xiii)

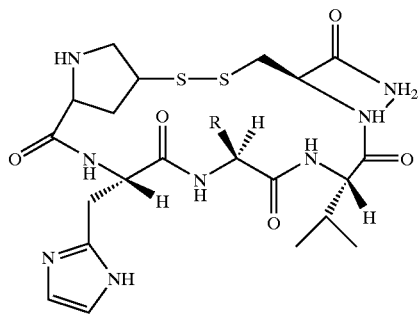

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization). Two such cyclic peptides are <u>AHAVDI</u> (SEQ ID NO:34) and <u>SHAVSS</u> (SEQ ID NO:46), with or without an N-terminal acetyl group and/or a C-terminal amide. Within another such embodiment, the linear peptide comprises a D-amino acid (e.g., <u>HAVsS</u>; SEQ ID NO:73). Alternatively, cyclization may be accomplished by linking one terminus and a residue side chain or using two side chains, as in <u>KHAVD</u> (SEQ ID NO:12) or <u>KSHAVSSD</u> (SEQ ID NO:48), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

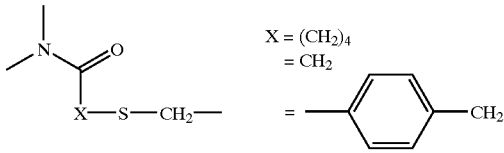

ii.

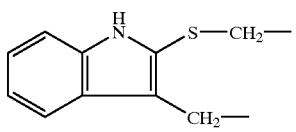

Cyclization may also be achieved using δ₁, δ₁'-Ditryptophan (i.e., Ac-<u>Trp-Gly-Gly-Trp</u>-OMe) (SEQ ID NO:74), as shown below:

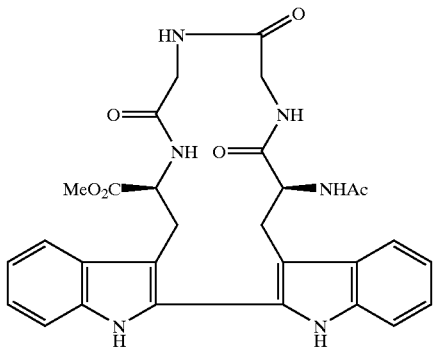

Representative structures of cyclic peptides are provided in FIG. 3. Within FIG. 3, certain cyclic peptides having the ability to modulate cell adhesion (shown on the left) are paired with similar inactive structures (on the right). The structures and formulas recited herein are provided solely for the purpose of illustration, and are not intended to limit the scope of the cyclic peptides described herein.

Cell Adhesion Modulating Agents

The term "cell adhesion modulating agent," as used herein, refers to a molecule comprising at least one cyclic peptide that contains the classical cadherin cell adhesion recognition (CAR) sequence HAV (His-Ala-Val), as described above. As noted above, multiple CAR sequences may be present within a modulating agent. Further, additional CAR sequences (i.e., any sequences specifically bound by an adhesion molecule) may be included within a modulating agent. As used herein, an "adhesion molecule" is any molecule that mediates cell adhesion via a receptor on the cell's surface. Adhesion molecules include members of the cadherin gene superfamily that are not classical cadherins (e.g., proteins that do not contain an HAV sequence and/or one or more of the other characteristics recited above for classical cadherins), such as desmogleins (Dsg) and desmocollins (Dsc); integrins; members of the immunoglobulin supergene family, such as N-CAM; and other uncategorized transmembrane proteins, such as occludin, as well as extracellular matrix proteins such as laminin, fibronectin, collagens, vitronectin, entactin and tenascin. Preferred CAR sequences for inclusion within a modulating agent include (a) Arg-Gly-Asp (RGD), which is bound by integrins (see Cardarelli et al., J. Biol. Chem. 267:23159–64, 1992); (b) Tyr-Ile-Gly-Ser-Arg (YIGSR; SEQ ID NO:52), which is bound by α6β1 integrin; (c) KYSFNYDGSE (SEQ ID NO:53), which is bound by N-CAM; (d) the N-CAM heparin sulfate-binding site IWKHKGRDVILKKDVRF (SEQ ID NO:54); (e) the occludin CAR sequence LYHY (SEQ ID NO:55); (f) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO:56), wherein Aaa, Baa and Caa indicate independently selected amino acid residues; Lys/Arg is an amino acid that is lysine or arginine; Ser/Ala is an amino acid that is serine or alanine; and Tyr/Phe is an amino acid that is tyrosine or phenylalanine; and (g) nonclassical cadherin CAR sequences comprising at least three consecutive amino acids present within a nonclassical cadherin region that has the formula: Aaa-Phe-Baa-Ile/Leu/Val-Asp/Asn/Glu-Caa-Daa-Ser/Thr/Asn-Gly (SEQ ID NO:57), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO:58), TSSY (SEQ ID NO:59), VTAF (SEQ ID NO:60) and VSAF (SEQ ID NO:61). Representative nonclassical cadherin CAR sequences include the VE-cadherin (cadherin-5) CAR sequence DAE; the cadherin-6 CAR sequences EEY, NEN, ESE and DSG; the cadherin-7 CAR sequences DEN, EPK and DAN; the cadherin-8 CAR sequences EEF and NDV; the OB-cadherin (cadherin-11) CAR sequences DDK, EEY and EAQ; the cadherin-12 CAR sequences DET and DPK; the cadherin-14 CAR sequences DDT, DPK and DAN; the cadherin-15 CAR sequences DKF and DEL; the PB-cadherin CAR sequences EEY, DEL, DPK and DAD; the protocadherin CAR sequences DLV, NRD, DPK and DPS; the dsg CAR sequences NQK, NRN and NKD; the dsc CAR sequences EKD and ERD and the cadherin-related neuronal receptor CAR sequences DPV, DAD, DSV, DSN, DSS, DEK and NEK.

Linkers may, but need not, be used to separate CAR sequences and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences. Using a linker, HAV-containing cyclic peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, YIGSR (SEQ ID NO:52) and HAV, one or more of which are present within a cyclic peptide. Within another embodiment, modulating agents having a branched structure comprise RGD, YIGSR (SEQ ID NO:52), HAV and KYSFNYDGSE (SEQ ID NO:53). In a third embodiment, modulating agents having a branched structure comprise HAV and LYHY (SEQ ID NO:55), along with one or more of NQK, NRN, NKD, EKD and ERD. Bi-functional modulating agents that comprise an FIAV sequence with flanking E-cadherin-specific sequences joined via a linker to an HAV sequence with flanking N-cadherin-specific sequences are also preferred for certain embodiments.

Linkers preferably produce a distance between CAR sequences between 0.1 to 10,000 nm, more preferably about 0.1–400 nm. A separation distance between recognition sites may generally be determined according to the desired function of the modulating agent. For inhibitors of cell adhesion, the linker distance should be small (0.1–400 nm). For enhancers of cell adhesion, the linker distance should be 400–10,000 nm. One linker that can be used for such purposes is $(H_2N(CH_2)_nCO_2H)_m$, or derivatives thereof, where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

Modulating agents that inhibit cell adhesion may contain one or more HAV sequences, provided that such sequences are adjacent to one another (i.e., without intervening sequences) or in close proximity (i.e., separated by peptide and/or non-peptide linkers to give a distance between the CAR sequences that ranges from about 0.1 to 400 nm). It will be apparent that other CAR sequences, as discussed above, may also be include. Such modulating agents may generally be used within methods in which it is desirable to simultaneously disrupt cell adhesion mediated by multiple adhesion molecules. Within certain preferred embodiments, an additional CAR sequence is derived from fibronectin and is recognized by an integrin (i.e., RGD; see Cardarelli et al., *J. Biol. Chem.* 267:23159–23164, 1992), or is an occludin CAR sequence (e.g., LYHY; SEQ ID NO:55). One or more antibodies, or fragments thereof, may similarly be used within such embodiments.

Modulating agents that enhance cell adhesion may contain multiple HAV sequences and/or antibodies that specifically bind to an HAV sequence, joined by linkers as described above. Enhancement of cell adhesion may also be achieved by attachment of multiple modulating agents to a support molecule or material, as discussed further below. Such modulating agents may additionally comprise one or more CAR sequence for one or more different adhesion molecules (including, but not limited to, other CAMs) and/or one or more antibodies or fragments thereof that bind to such sequences, to enhance cell adhesion mediated by multiple adhesion molecules.

As noted above, a modulating agent may consist entirely of one or more cyclic peptides, or may contain additional peptide and/or non-peptide sequences. Peptide portions may be synthesized as described above or may be prepared using recombinant methods. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., *J. Mol. Biol.* 211:679–682, 1990), or from sequences isolated by screening an appropriate library with probes designed based on the sequences of known cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a peptide portion of a modulating agent, an endogenous sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding a portion of the modulating agent.

As noted above, portions of a modulating agent may comprise an antibody, or antigen-binding fragment thereof, that specifically binds to a CAR sequence. As used herein, an antibody, or antigen-binding fragment thereof, is said to "specifically bind" to a CAR sequence (with or without flanking amino acids) if it reacts at a detectable level (within, for example, an ELISA, as described by Newton et al., *Develop. Dynamics* 197:1–13, 1993) with a peptide containing that sequence, and does not react detectably with peptides containing a different CAR sequence or a sequence in which the order of amino acid residues in the cadherin CAR sequence and/or flanking sequence is altered.

Antibodies and fragments thereof may be prepared using standard techniques. See, e.g., Harlow and Lane, *Antibodies: A Laboratory Manual*, Cold Spring Harbor Laboratory, 1988. In one such technique, an immunogen comprising a CAR sequence is initially injected into any of a wide variety of mammals (e.g. mice, rats, rabbits, sheep or goats). Small immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for a CAR sequence may be prepared, for example, using the technique of Kohler and Milstein, Eur. *J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Within certain embodiments, monoclonal antibodies may be specific for particular cadherins (e.g., the antibodies bind to E-cadherin, but do not bind significantly to N-cadherin, or vise versa). Such antibodies may be prepared as described above, using an immunogen that comprises (in addition to the HAV sequence) sufficient flanking sequence to generate the desired specificity (e.g., 5 amino acids on each side is generally sufficient). One representative immunogen is the 15-mer FHLRAHAVDINGNQV—$NH_2$ (SEQ ID NO:75), linked to KLH (see Newton et al., *Dev. Dynamics* 197:1–13, 1993). To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell, such as a leukemic cell in the blood.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Evaluation of Modulating Agent Activity

As noted above, cyclic peptides and other modulating agents as described herein are capable of modulating (i.e., enhancing or inhibiting) cadherin-mediated cell adhesion. The ability of a modulating agent to modulate cell adhesion may generally be evaluated in vitro by assaying the effect on one or more of the following: (1) neurite outgrowth, (2) adhesion between endothelial cells, (3) adhesion between epithelial cells (e.g., normal rat kidney cells and/or human skin) and/or (4) adhesion between cancer cells. In general, a modulating agent is an inhibitor of cell adhesion if, within one or more of these representative assays, contact of the test cells with the modulating agent results in a discernible disruption of cell adhesion. Modulating agents that enhance cell adhesion are considered to be modulators of cell adhesion if they are capable of enhancing neurite outgrowth as described below and/or are capable of promoting cell adhesion, as judged by plating assays to assess epithelial cell adhesion to a modulating agent attached to a support material, such as tissue culture plastic. For modulating agents that affect N-cadherin mediated functions, assays involving endothelial or cancer cell adhesion or neurite outgrowth are preferred.

Within a representative neurite outgrowth assay, neurons may be cultured on a monolayer of cells (e.g., 3T3) that express N-cadherin. Neurons grown on such cells (under suitable conditions and for a sufficient period of time) extend longer neurites than neurons cultured on cells that do not express N-cadherin. For example, neurons may be cultured on monolayers of 3T3 cells transfected with cDNA encoding N-cadherin essentially as described by Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell. Neurosci.* 8:99–111, 1994; and Safell et al., *Neuron* 18:231–242, 1997.

Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2% FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent that modulates N-cadherin-mediated cell adhesion may inhibit or enhance such neurite outgrowth. Under the conditions described above, the presence of 500 µg/mL of a modulating agent that disrupts neural cell adhesion should result in a decrease in the mean neurite length by at least 50%, relative to the length in the absence of modulating agent or in the presence of a negative control peptide. Alternatively, the presence of 500 µg/mL of a modulating agent that enhances neural cell adhesion should result in an increase in the mean neurite length by at least 50%.

Within one representative cell adhesion assay, the addition of a modulating agent to cells that express a cadherin results in disruption of cell adhesion. A "cadherin-expressing cell," as used herein, may be any type of cell that expresses at least one cadherin on the cell surface at a detectable level, using standard techniques such as immunocytochemical protocols (Blaschuk and Farookhi, *Dev. Biol.* 136:564–567, 1989). Cadherin-expressing cells include endothelial (e.g., bovine pulmonary artery endothelial cells), epithelial and/or cancer cells (e.g., the human ovarian cancer cell line SKOV3 (ATCC #HTB-77)). For example, such cells may be plated under standard conditions that permit cell adhesion in the presence and absence of modulating agent (e.g., 500 µg/mL). Disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/$cm^2$. Endothelial cultures may be used at 1 week in culture, which is approximately 3 days after culture confluency is established. The cells may be seeded onto coverslips and treated (e.g. for 30 minutes) with modulating agent or a control compound at, for example, 500 µg/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC #1571-CRL) may be plated at 10–20,000 cells per 35 mm tissue culture flasks containing DMEM with 10% FCS and sub-cultured periodically (Laird et al., *J. Cell Biol.* 131:1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition, 1 mg/mL of such a modulating agent reproducibly induces a readily apparent reduction in cell surface staining of E-cadherin, as judged by immunofluorescence microscopy (Laird et al., *J. Cell Biol.* 131:1193–1203, 1995), of at least 75% within 48 hours.

A third cell adhesion assay involves evaluating the effect of a modulating agent on permeability of adherent epithelial and/or endothelial cell layers. For example, the effect on permeability of human skin may be evaluated. Such skin may be derived from a natural source or may be synthetic. Human abdominal skin for use in such assays may generally be obtained from humans at autopsy within 24 hours of death. Briefly, a cyclic peptide and a test marker (e.g., the fluorescent markers Oregon Green™ and Rhodamine Green™ Dextran) may be dissolved in a sterile buffer, and the ability of the marker to penetrate through the skin and into a receptor fluid may be measured using a Franz Cell apparatus (Franz, *Curr. Prob. Dermatol.* 7:58–68, 1978; Franz, *J. Invest. Dermatol.* 64:190–195, 1975). In general, a modulating agent that enhances the permeability of human skin results in a statistically significant increase in the amount of marker in the receptor compartment after 6–48 hours in the presence of 500 µg/mL modulating agent. This assay evaluates the effect of a modulating agent on E-cadherin mediated cell adhesion.

Yet another assay evaluates the effect of a modulating agent on the electrical resistance across a monolayer of cells. For example, Madin Darby canine kidney (MDCK) cells can be exposed to the modulating agent dissolved in medium (e.g., at a final concentration of 0.5 mg/ml for a period of 24 hours). The effect on electrical resistance can be measured using standard techniques. This assay evaluates the effect of a modulating agent on tight junction formation in epithelial cells. In general, the presence of 500 µg/mL modulating agent should result in a statistically significant decrease in electrical resistance after 24 hours.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an RGD and/or LYHY (SEQ ID NO:55) sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent or linker). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')$_2$, -Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A modulating agent (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

For certain embodiments, as discussed below, a pharmaceutical composition may further comprise a modulator of cell adhesion that is mediated by one or more molecules other than cadherins. Such modulators may generally be prepared as described above, incorporating one or more non-cadherin CAR sequences and/or antibodies thereto in place of the cadherin CAR sequences and antibodies. Such compositions are particularly useful for situations in which it is desirable to inhibit cell adhesion mediated by multiple cell-adhesion molecules, such as other members of the cadherin gene superfamily that are not classical cadherins (e.g., Dsg and Dsc); claudins; integrins; members of the immunoglobulin supergene family, such as N-CAM; and other uncategorized transmembrane proteins, such as occludin, as well as extracellular matrix proteins such as laminin, fibronectin, collagens, vitronectin, entactin and tenascin. Preferred CAR sequences for use are as described above.

A pharmaceutical composition may also contain one or more drugs, which may be linked to a modulating agent or may be free within the composition. Virtually any drug may be administered in combination with a cyclic peptide as described herein, for a variety of purposes as described below. Examples of types of drugs that may be administered with a cyclic peptide include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a calorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of cyclic peptide following administration). Such formulations may generally be prepared using well known technology and administered by, for example, oral, rectal or subcutaneous implantation, or by implantation at the desired target site. Sustained-release formulations may contain a cyclic peptide dispersed in a carrier matrix and/or contained within a reservoir surrounded by a rate controlling membrane (see, e.g., European Patent Application 710,491A). Carriers for use within such formulations are biocompatible, and may also be biodegradable; preferably the formulation provides a relatively constant level of cyclic peptide release. The amount of cyclic peptide contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and the duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit.

Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.2%, and more preferably from 0.0001% to 0.002%. Fluid compositions typically contain about 10 ng/ml to 5 mg/ml, preferably from about 10 μg to 2 mg/mL cyclic peptide. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of classical cadherin-expressing cells (i.e., cells that express one or more of E-cadherin, N-cadherin, P-cadherin, R-cadherin and/or other cadherin(s) containing the HAV sequence, including as yet undiscovered classical cadherins) in vitro and/or in vivo. To modulate classical cadherin-mediated cell adhesion, a cadherin-expressing cell is contacted with a modulating agent either in vivo or in vitro. As noted above, modulating agents for purposes that involve the disruption of cadherin-mediated cell adhesion may comprise a cyclic peptide containing a single HAV sequence or multiple HAV sequences in close proximity, and/or an antibody (or an antigen-binding fragment thereof) that recognizes a cadherin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated by linkers. As noted above, such linkers may or may not comprise one or more amino acids. For enhancing cell adhesion, a modulating agent may contain multiple HAV sequences or antibodies (or fragments), preferably separated by linkers, and/or may be linked to a single molecule or to a support material as described above.

Certain methods involving the disruption of cell adhesion as described herein have an advantage over prior techniques in that they permit the passage of molecules that are large and/or charged across barriers of cadherin-expressing cells. As discussed in greater detail below, modulating agents as described herein may also be used to disrupt or enhance cell adhesion in a variety of other contexts. Within the methods described herein, one or more modulating agents may generally be administered alone, or within a pharmaceutical composition. In each specific method described herein, as noted above, a targeting agent may be employed to increase the local concentration of modulating agent at the target site.

In one such aspect, the present invention provides methods for reducing unwanted cellular adhesion by administering a modulating agent as described herein. Unwanted cellular adhesion can occur between tumor cells, between tumor cells and normal cells or between normal cells as a result of surgery, injury, chemotherapy, disease, inflammation or other condition jeopardizing cell viability or function. Preferred modulating agents for use within such methods comprise one or more cyclic peptides such as N—Ac—CHAVC—NH$_2$ (SEQ ID NO:96), CHAVC—Y—NH$_2$ (SEQ ID NO:84), N—Ac—CHAVDC—NH$_2$ (SEQ ID NO:20), N—Ac—CHAVDIC—NH$_2$ (SEQ ID NO:50), N—Ac—CHAVDINC—NH$_2$ (SEQ ID NO:51), N—Ac—CHAVDINGC—NH$_2$ (SEQ ID NO:76), N—Ac—CAHAVC—NH$_2$ (SEQ ID NO:22), N—Ac—CAHAVDC—NH$_2$ (SEQ ID NO:26), N—Ac—CAHAVDIC—NH$_2$ (SEQ ID NO:24), N—Ac—CRAHAVDC—NH$_2$ (SEQ ID NO:28), N—Ac—CLRAHAVC—NH$_2$ (SEQ ID NO:30), N—Ac—CLRAHAVDC—NH$_2$ (SEQ ID NO:32), N—Ac—CSHAVC—NH$_2$ (SEQ ID NO:36), N—Ac—CFSHAVC—NH$_2$ (SEQ ID NO:85), N—Ac—CLFSHAVC—NH$_2$ (SEQ ID NO:86), N—Ac—CHAVSC—NH$_2$ (SEQ ID NO:38), N—Ac—CSHAVSC—NH$_2$ (SEQ ID NO:40), N—Ac—CSHAVSSC—NH$_2$ (SEQ ID NO:42), N—Ac—CHAVSSC—NH$_2$ (SEQ ID NO:44), N—Ac—KHAVD-NH$_2$ (SEQ ID NO:12), N—Ac—DHAVK—NH$_2$ (SEQ ID NO:14), N—Ac—KHAVE-NH$_2$ (SEQ ID NO:16), N—Ac-AHAVDI—NH$_2$ (SEQ ID NO:34), N—Ac—SHAVDSS—NH$_2$ (SEQ ID NO:77), N—Ac—KSHAVSSD-NH$_2$ (SEQ ID NO:48), N—Ac—CHAVC—S—NH$_2$ (SEQ ID NO:87), N—Ac—S—CHAVC—NH$_2$ (SEQ ID NO:88), N—Ac—CHAVC—SS—NH$_2$ (SEQ ID NO:89), N—Ac—S—CHAVC—S—NH$_2$ (SEQ ID NO:90), N—Ac—CHAVC-T-NH$_2$ (SEQ ID NO:91), N—Ac—CHAVC-E-NH$_2$ (SEQ ID NO:92), N—Ac—CHAVC-D-NH$_2$ (SEQ ID NO:93), N—Ac—CHAVYC—NH$_2$ (SEQ ID NO:94), CH$_3$—SO$_2$—HN—CHAVC—Y—NH$_2$ (SEQ ID NO:95), CH$_3$—SO$_2$—HN—CHAVC—NH$_2$ (SEQ ID NO:96), HC(O)—HN—CHAVC—NH$_2$ (SEQ ID NO:96), N—Ac—CHAVPen-NH$_2$ (SEQ ID NO:97), N—Ac-PenHAVC—NH$_2$ (SEQ ID NO:98), N—Ac—CHAVPC—NH$_2$ (SEQ ID NO:99) and derivatives thereof (e.g., in which terminal modifications are varied). In addition, a modulating agent may comprise the sequence RGD, which is bound by integrins, and/or the sequence LYHY (SEQ ID NO:55), which is bound by occludin, separated from the HAV sequence via a linker. Other CAR sequences that may be present include OB-cadherin, dsg and dsc CAR sequences as described above. Alternatively, a separate modulator of integrin, occludin-, OB-cadherin-, dsc- and/or dsg-mediated cell adhesion may be administered in conjunction with the modulating agent(s), either within the same pharmaceutical composition or separately. Topical administration of the modulating agent(s) is generally preferred, but other means may also be employed. Preferably, a fluid composition for topical administration (comprising, for example, physiological saline) comprises an amount of cyclic peptide as described above, and more preferably an amount ranging from 10 μg/mL to 1 mg/mL. Creams may generally be formulated as described above. Topical administration in the surgical field may be given once at the end of surgery by irrigation of the wound, as an intermittent or continuous irrigation with use of surgical drains in the post operative period, or by the use of drains specifically inserted in an area of inflammation, injury or disease in cases where surgery does not need to be performed. Alternatively, parenteral or transcutaneous administration may be used to achieve similar results.

In another aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Preferred modulating agents for use within such methods comprise one or more cyclic peptides such as NAc—CHAVC—$NH_2$ (SEQ ID NO:96), CHAVC—Y—$NH_2$ (SEQ ID NO:84), N—Ac—CHAVDC—$NH_2$ (SEQ ID NO:20), N—Ac—CHAVDIC—$NH_2$ (SEQ ID NO:50), N—Ac—CHAVDINC—$NH_2$ (SEQ ID NO:51), N—Ac—CHAVDINGC—$NH_2$ (SEQ ID NO:76), N—Ac—CAHAVC—$NH_2$ (SEQ ID NO:22), N—Ac—CAHAVDC—$NH_2$ (SEQ ID NO:26), N—Ac—CAHAVDIC—$NH_2$ (SEQ ID NO:24), N—Ac—CRAHAVDC—$NH_2$ (SEQ ID NO:28), N—Ac—CLRAHAVC—$NH_2$ (SEQ ID NO:30), N—Ac—CLRAHAVDC—$NH_2$ (SEQ ID NO:32), N—Ac—CSHAVC—$NH_2$ (SEQ ID NO:36), N—Ac—CFSHAVC—$NH_2$ (SEQ ID NO:85), N—Ac—CLFSHAVC—$NH_2$ (SEQ ID NO:86), N—Ac—CHAVSC—$NH_2$ (SEQ ID NO:38), N—Ac—CSHAVSC—$NH_2$ (SEQ ID NO:40), N—Ac—CSHAVSSC—$NH_2$ (SEQ ID NO:42), N—Ac—CHAVSSC—$NH_2$ (SEQ ID NO:44), N—Ac—KHAVD-$NH_2$ (SEQ ID NO:12), N—Ac—DHAVK—$NH_2$ (SEQ ID NO:14), N—Ac—KHAVE-$NH_2$ (SEQ ID NO:16), N—Ac-AHAVDI—$NH_2$ (SEQ ID NO:34), N—Ac—SHAVDSS—$NH_2$ (SEQ ID NO:77), N—Ac—KSHAVSSD-$NH_2$ (SEQ ID NO:48), N—Ac—CHAVC—S—$NH_2$ (SEQ ID NO:87), N—Ac—S—CHAVC—$NH_2$ (SEQ ID NO:88), N—Ac—CHAVC—SS—$NH_2$ (SEQ ID NO:89), N—Ac—S—CHAVC—S—$NH_2$ (SEQ ID NO:90), N—Ac—CHAVC-T-$NH_2$ (SEQ ID NO:91), N—Ac—CHAVC-E-$NH_2$ (SEQ ID NO:92), N—Ac—CHAVC-D-$NH_2$ (SEQ ID NO:93), N—Ac—CHAVYC—$NH_2$ (SEQ ID NO:94), $CH_3$—$SO_2$—HN—CHAVC—Y—$NH_2$ (SEQ ID NO:95), $CH_3$—$SO_2$—HN—CHAVC—$NH_2$ (SEQ ID NO:96), HC(O)—HN—CHAVC—$NH_2$ (SEQ ID NO:96), N—Ac—CHAVPen-$NH_2$ (SEQ ID NO:97), N—Ac-PenHAVC—$NH_2$ (SEQ ID NO:98), N—Ac—CHAVPC—$NH_2$ (SEQ ID NO:99) and derivatives thereof (e.g., in which terminal modifications are varied). Multifunctional modulating agents comprising the cadherin CAR sequence HAV linked to one or more of the Dsc and/or the Dsg CAR sequences may also be used to disrupt epithelial cell adhesion. Such modulating agents may also, or alternatively, comprise the fibronectin CAR sequence RGD, which is recognized by integrins, the occludin CAR sequence LYHY (SEQ ID NO:55) and/or a claudin CAR sequences as described above. Alternatively, a separate modulator of non-classical cadherin-mediated cell adhesion may be administered in conjunction with the modulating agent(s), either within the same pharmaceutical composition or separately.

Contact may be achieved by direct application of the modulating agent, generally within a composition formulated as a cream or gel, or using any of a variety of skin contact devices for transdermal application (such as those described in European Patent Application No. 566,816 A; U.S. Pat. No. 5,613,958; U.S. Pat. No. 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides a convenient measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g., every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and interferons may be delivered via the skin.

Kits for administering a drug via the skin of a mammal are also provided within the present invention. Such kits generally comprise a device for transdermal application (i.e., skin patch) in combination with, or impregnated with, one or more modulating agents. A drug may additionally be included within such kits.

Within a related embodiment, the use of modulating agents as described herein to increase skin permeability may also facilitate sampling of the blood compartment by passive diffusion, permitting detection and/or measurement of the levels of specific molecules circulating in the blood. For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

Within a further aspect, methods are provided for enhancing delivery of a drug to a tumor in a mammal, comprising administering a modulating agent in combination with a drug to a tumor-bearing mammal. Modulating agents for use within such methods include those designed to disrupt E-cadherin and/or N-cadherin mediated cell adhesion, and may comprise one or more cyclic peptides such as NAc—CHAVC—NH$_2$ (SEQ ID NO:96), CHAVC—Y—NH$_2$ (SEQ ID NO:84), N—Ac—CHAVDC—NH$_2$ (SEQ ID NO:20), N—Ac—CHAVDIC—NH$_2$ (SEQ ID NO:50), N—Ac—CHAVDINC—NH$_2$ (SEQ ID NO:51), N—Ac—CHAVDINGC—NH$_2$ (SEQ ID NO:76), N—Ac—CAHAVC—NH$_2$ (SEQ ID NO:22), N—Ac—CAHAVDC—NH$_2$ (SEQ ID NO:26), N—Ac—CAHAVDIC—NH$_2$ (SEQ ID NO:24), N—Ac—CRAHAVDC—NH$_2$ (SEQ ID NO:28), N—Ac—CLRAHAVC—NH$_2$ (SEQ ID NO:30), N—Ac—CLRAHAVDC—NH$_2$ (SEQ ID NO:32), N—Ac—CSHAVC—NH$_2$ (SEQ ID NO:36), N—Ac—CFSHAVC—NH$_2$ (SEQ ID NO:85), N—Ac—CLFSHAVC—NH$_2$ (SEQ ID NO:86), N—Ac—CHAVSC—NH$_2$ (SEQ ID NO:38), N—Ac—CSHAVSC—NH$_2$ (SEQ ID NO:40), N—Ac—CSHAVSSC—NH$_2$ (SEQ ID NO:42), N—Ac—CHAVSSC—NH$_2$ (SEQ ID NO:44), N—Ac—KHAVD-NH$_2$ (SEQ ID NO:12), N—Ac—DHAVK—NH$_2$ (SEQ ID NO:14), N—Ac—KHAVE-NH$_2$ (SEQ ID NO:16), N—Ac-AHAVDI—NH$_2$ (SEQ ID NO:34), N—Ac—SHAVDSS—NH$_2$ (SEQ ID NO:77), N—Ac—KSHAVSSD-NH$_2$ (SEQ ID NO:48), N—Ac—CHAVC—S—NH$_2$ (SEQ ID NO:87), N—Ac—S—CHAVC—NH$_2$ (SEQ ID NO:88), N—Ac—CHAVC—SS—NH$_2$ (SEQ ID NO:89), N—Ac—S—CHAVC—S—NH$_2$ (SEQ ID NO:90), N—Ac—CHAVC-T-NH$_2$ (SEQ ID NO:91), N—Ac—CHAVC-E-NH$_2$ (SEQ ID NO:92), N—Ac—CHAVC-D-NH$_2$ (SEQ ID NO:93), N—Ac—CHAVYC—NH$_2$ (SEQ ID NO:94), CH$_3$—SO$_2$—HN—CHAVC—Y—NH$_2$ (SEQ ID NO:95), CH$_3$—SO$_2$—HN—CHAVC—NH$_2$ (SEQ ID NO:96), HC(O)—HN—CHAVC—NH$_2$ (SEQ ID NO:96), N—Ac—CHAVPen-NH$_2$ (SEQ ID NO:97), N—Ac-PenHAVC—NH$_2$ (SEQ ID NO:98), N—Ac—CHAVPC—NH$_2$ (SEQ ID NO:99) and derivatives thereof (e.g., in which terminal modifications are varied). Bi-functional modulating agents that comprise an HAV sequence with flanking E-cadherin-specific sequences and an HAV sequence with flanking N-cadherin-specific sequences are also preferred.

In one particularly preferred embodiment, a modulating agent is capable of disrupting cell adhesion mediated by multiple adhesion molecules. For example, a single branched modulating agent (or multiple agents linked to a single molecule or support material) may disrupt E-cadherin, N-cadherin, occludin, Dsc and Dsg mediated cell adhesion, thereby disrupting adherens junctions, tight junctions and desmosomes Such an agent may comprise the cadherin CAR sequence (HAV), as well as one or more of the fibronectin CAR sequence RGD, which is recognized by integrins; a dsg CAR sequence; a dsc CAR sequence; a claudin CAR sequence; an occludin CAR sequence and/or an OB-cadherin CAR sequence. Such agents serve as multifunctional disrupters of cell adhesion. Alternatively, a separate modulator of non-classical cadherin-mediated cell adhesion may be administered in conjunction with the modulating agent(s), either within the same pharmaceutical composition or separately. Antibodies or Fab fragments directed against a cadherin CAR sequence and/or an occludin CAR sequence may also be employed, either incorporated into a modulating agent or within a separate modulator that is administered concurrently.

Preferably, the cyclic peptide and the drug are formulated within the same composition or drug delivery device prior to administration. In general, a cyclic peptide may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the cyclic peptide and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of cyclic peptide administered varies with the method of administration and the nature of the tumor, within the typical ranges provided above, preferably ranging from about 1 µg/mL to about 2 mg/mL, and more preferably from about 10 µg/mL to 100 µg/mL. Transfer of the drug to the target tumor may be evaluated by appropriate means that will be apparent to those of ordinary skill in the art, such as a reduction in tumor size. Drugs may also be labeled (e.g., using radionuclides) to permit direct observation of transfer to the target tumor using standard imaging techniques.

Within a related aspect, the present invention provides methods for inhibiting the development of a cancer (i.e., for treating or preventing cancer and/or inhibiting metastasis) in a mammal. Cancer tumors are solid masses of cells, growing out of control, which require nourishment via blood vessels. The formation of new capillaries is a prerequisite for tumor growth and the emergence of metastases. Administration of a modulating agent as described herein may disrupt the growth of such blood vessels, thereby providing effective therapy for the cancer and/or inhibiting metastasis. Modulating agents comprising cyclic peptides may also be used to treat leukemias. Preferred modulating agents for use within such methods include those that disrupt N-cadherin mediated cell adhesion, and comprise one or more cyclic peptides such as NAc—CHAVC—NH$_2$ (SEQ ID NO:96), CHAVC—Y—NH$_2$ (SEQ ID NO:84), N—Ac—CHAVDC—NH$_2$ (SEQ ID NO:20), N—Ac—CHAVDIC—NH$_2$ (SEQ ID NO:50), N—Ac—CHAVDINC—NH$_2$ (SEQ ID NO:51), N—Ac—CHAVDINGC—NH$_2$ (SEQ ID NO:76), N—Ac—CAHAVC—NH$_2$ (SEQ ID NO:22), N—Ac—CAHAVDC—NH$_2$ (SEQ ID NO:26), N—Ac—CAHAVDIC—NH$_2$ (SEQ ID NO:24), N—Ac—CRAHAVDC—NH$_2$ (SEQ ID NO:28), N—Ac—CLRAHAVC—NH$_2$ (SEQ ID NO:30), N—Ac—CLRAHAVDC—NH2 (SEQ ID NO:32), N—Ac—CSHAVC—NH$_2$ (SEQ ID NO:36), N—Ac—CFSHAVC—NH$_2$ (SEQ ID NO:85), N—Ac—CLFSHAVC—NH$_2$ (SEQ ID NO:86), N—Ac—CHAVSC—NH$_2$ (SEQ ID NO:38), N—Ac—CSHAVSC—NH$_2$ (SEQ ID NO:40), N—Ac—CSHAVSSC—NH$_2$ (SEQ ID NO:42), N—Ac—CHAVSSC—NH$_2$ (SEQ ID NO:44), N—Ac—KHAVD-NH$_2$ (SEQ ID NO:12), N—Ac—DHAVK—NH$_2$ (SEQ ID NO:14), N—Ac—KHAVE-NH$_2$ (SEQ ID NO:16), N—Ac-AHAVDI—NH$_2$ (SEQ ID NO:34), N—Ac—SHAVDSS—NH$_2$ (SEQ ID NO:77), N—Ac—KSHAVSSD-NH$_2$ (SEQ ID NO:48), N—Ac—CHAVC—S—NH$_2$ (SEQ ID NO:87), N—Ac—S—CHAVC—NH$_2$ (SEQ ID NO:88), N—Ac—CHAVC—SS—NH$_2$ (SEQ ID NO:89), N—Ac—S—CHAVC—S—NH$_2$ (SEQ ID NO:90), N—Ac—CHAVC-T-NH$_2$ (SEQ ID NO:91), N—Ac—CHAVC-E-NH$_2$ (SEQ ID NO:92), N—Ac—CHAVC-D-NH$_2$ (SEQ ID NO:93), N—Ac—CHAVYC—NH$_2$ (SEQ ID NO:94), CH$_3$—SO$_2$—HN—CHAVC—Y—NH$_2$ (SEQ ID NO:95), CH$_3$—SO$_2$—HN—CHAVC—NH$_2$ (SEQ ID NO:96), HC(O)—HN—CHAVC—NH$_2$ (SEQ ID NO:96), N—Ac—CHAVPen-NH$_{12}$ (SEQ ID NO:97), N—Ac-PenHAVC—NH$_2$ (SEQ ID NO:98), N—Ac—CHAVPC—NH$_2$ (SEQ ID NO:99) and derivatives thereof (e.g., in which terminal modifications are varied). In addition, a modulating agent may comprise the sequence RGD, which is recognized by integrins, and/or the occludin CAR sequence LYHY (SEQ ID NO:55) separated via a linker. Other CAR sequences that may be present include an OB-cadherin CAR sequence; dse CAR sequence. dsg CAR sequence and/or claudin CAR sequence. Alternatively, a separate modulator of integrin- OB-cadherin-, dsc-, dsg-, claudin- and/or occludin-mediated cell adhesion may be administered in conjunction with the modulating agent(s), either within the same pharmaceutical composition or separately.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations such as the level of serum markers (e.g., CEA or PSA).

Within a further related aspect, a modulating agent may be used to inhibit angiogenesis (i.e., the growth of blood vessels from pre-existing blood vessels) in a mammal. In general, inhibition of angiogenesis may be beneficial in patients afflicted with diseases such as cancer or arthritis. Preferred modulating agents for inhibition of angiogenesis include those comprising one or more of NAc—CHAVC—NH₂ (SEQ ID NO:96), CHAVC—Y—NH₂ (SEQ ID NO:84), N—Ac—CHAVDC—NH₂ (SEQ ID NO:20), N—Ac—CHAVDIC—NH₂ (SEQ ID NO:50), N—Ac—CHAVDINC—NH₂ (SEQ ID NO:51), N—Ac—CHAVDINGC—NH₂ (SEQ ID NO:76), N—Ac—CAHAVC—NH2 (SEQ ID NO:22), N—Ac—CAHAVDC—NH? (SE ID NO:26), N—Ac—CAHAVDIC—NH₂ (SEQ ID NO:24), N—Ac—CRAHAVDC—NH₂ (SEQ ID NO:28), N—Ac—CLRAHAVC—NH₂ (SEQ ID NO:30), N—Ac—CLRAHAVDC—NH₂ (SEQ ID NO:32), N—Ac—KHAVD-NH₂ (SEQ ID NO:12), N—Ac—DHAVK—NH2 (SEQ ID NO:14), N—Ac—KHAVE-NH₂ (SEQ ID NO: 16), N—Ac-AHAVDI—NH₂ (SEQ ID NO:34), N—Ac—CHAVC—S—NH₂ (SEQ ID NO:87). N—Ac—S—CHAVC—NH₂ (SEQ ID NO:88), N—Ac—CHAVC—SS—NH₂ (SEQ ID NO:89), N—Ac—S—CHAVC—S—NH₂ (SEQ ID NO:90), N—Ac—CHAVC-T-NH₂ (SEQ ID NO:91), N—Ac—CHAVC-E-NH₂ (SEQ ID NO:92), N—Ac—CHAVC-D-NH₂ (SEQ ID NO:93), N—Ac—CHAVYC—NH₂ (SEQ ID NO:94), CH₃—SO₂—HN—CHAVC—Y—NH₂ (SEQ ID NO:95), CH₃—SO₂—HN—CHAVC—NH₂ (SEQ ID NO:96), HC(O)—HN—CHAVC—NH₂ (SEQ ID NO:96), N—Ac—CHAVPen-NH₂ (SEQ ID NO:97), N—Ac-PenHAVC—NH₂ (SEQ ID NO:98), N—Ac—CHAVPC—NH₂ (SEQ ID NO:99) and derivatives thereof (e.g., in which terminal modifications are varied). In addition, a modulating agent for use in inhibiting angiogenesis may comprise the sequence RGD, which is recognized by integrins, the occludin CAR sequence LYHY (SEQ ID NO:55) and/or a claudin CAR sequence, separated from the HAV sequence via a linker. Alternatively, a separate modulator of integrin- and/or occludin-mediated cell adhesion may be administered in conjunction with the modulating agent(s), either within the same pharmaceutical composition or separately.

The effect of a particular modulating agent on angiogenesis may generally be determined by evaluating the effect of the peptide on blood vessel formation. Such a determination may generally be performed, for example, using a chick chorioallantoic membrane assay (Iruela-Arispe et al., *Molecular Biology of the Cell* 6:327–343, 1995). Briefly, a modulating agent may be embedded in a mesh composed of vitrogen at one or more concentrations (e.g., ranging from about 1 to 100 μg/mesh). The mesh(es) may then be applied to chick chorioallantoic membranes. After 24 hours, the effect of the peptide may be determined using computer assisted morphometric analysis. A modulating agent should inhibit angiogenesis by at least 25% at a concentration of 33 μg/mesh.

The addition of a targeting agent may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumor to maintain growth and microscopically by an absence of nerves at the periphery of the tumor.

In another embodiment, methods are provided for causing the regression of blood vessels for the treatment of conditions such as cancer, psoriasis, arthritis, and age-related macular degeneration. Cancer tumors are solid masses of cells, growing out of control, which require nourishment via blood vessels. The formation of new capillaries is a prerequisite for tumor growth and the emergence of metastases. Administration of the modulating agents described herein may disrupt blood vessels and cause them to regress, thereby providing effective therapy for patients afflicted with diseases such as cancer. Certain preferred modulating agents for use within such methods comprise, in addition to an HAV sequence, a nonclassical cadherin CAR sequence (preferably an OB-cadherin or cadherin-5 CAR sequence) or RGD. Preferably, the peptide portion(s) of such modulating agents comprise 6–16 amino acids. Administration may be topical, via injection or by other means, and the addition of a targeting agent may be beneficial, particularly when the administration is systemic. Suitable modes of administration and dosages depend upon the location and nature of the endothelial cells and/or pericytes for which disruption of cell adhesion is desired but, in general, dosages may vary as described above. The addition of a targeting agent may be beneficial, particularly when the administration is systemic. Suitable modes of administration and dosages depend upon the condition to be prevented or treated but, in general, administration by injection is appropriate. Dosages may vary as described above.

In yet another related aspect, the present invention provides methods for inducing apoptosis in a cadherin-expressing cell. In general, patients afflicted with cancer may benefit from such treatment. Preferred modulating agents for use within such methods include those that comprise one or more cyclic peptides such as NAc—CHAVC—NH₂ (SEQ ID NO:96), CHAVC—Y—NH₂ (SEQ ID NO:84), N—Ac—CHAVDC—NH₂ (SEQ ID NO:20), N—Ac—CHAVDIC—NH₂ (SEQ ID NO:50), N—Ac—CHAVDINC—NH₂ (SEQ ID NO:51), N—Ac—CHAVDINGC—NH₂ (SEQ ID NO:76), N—Ac—CAHAVC—NH₂ (SEQ ID NO:22), N—Ac—CHAVDC—NH₂ (SEQ ID NO:26), N—Ac—CAHAVDIC—NH₂ (SEQ ID NO:24), N—Ac—CRAHAVDC—NH₂ (SEQ ID NO:28), N—Ac—CLRAHAVC—NH₂ (SEQ ID NO:30), N—Ac—CLRAHAVDC—NH₂ (SEQ ID NO:32), N—Ac—CSHAVC—NH₂ (SEQ ID NO:36), N—Ac—CFSHAVC—NH₂ (SEQ ID NO:85), N—Ac—CLFSHAVC—NH₂ (SEQ ID NO:86), N—Ac—CHAVSC—NH₂ (SEQ ID NO:38), N—Ac—CSHAVSC—NH₂ (SEQ ID NO:40), N—Ac—

CSHAVSSC—$NH_2$ (SEQ ID NO:42), N—Ac—CHAVSSC—$NH_2$ (SEQ ID NO:44), N—Ac—KHAVD-$NH_2$ (SEQ ID NO:12), N—Ac—DHAVK—$NH_2$ (SEQ ID NO:14), N—Ac—KHAVE-$NH_2$ (SEQ ID NO:16), N—Ac-AHAVDI—$NH_2$ (SEQ ID NO:34), N—Ac—SHAVDSS—$NH_2$ (SEQ ID NO:77), N—Ac—KSHAVSSD-$NH_2$ (SEQ ID NO:48), N—Ac—CHAVC—S—$NH_2$ (SEQ ID NO:87), N—Ac—S—CHAVC—$NH_2$ (SEQ ID NO:88), N—Ac—CHAVC—SS—$NH_2$ (SEQ ID NO:89), N—Ac—S—CHAVC—S—NH2 (SEQ ID NO:90), N—Ac—CHAVC-T-NH? (SEQ ID NO:91), N—Ac—CHAVC-E-$NH_2$ (SEQ ID NO:92), N—Ac—CHAVC-D-$NH_2$ (SEQ ID NO:93), N—Ac—CHAVYC—$NH_2$ (SEQ ID NO:94), $CH_3$—$SO_2$—HN—CHAVC—Y—$NH_2$ (SEQ ID NO:95), $CH_3$—$SO_2$—HN—CHAVC—$NH_2$ (SEQ ID NO:96), HC(O)—HN—CHAVC—$NH_2$ (SEQ ID NO:96), N—Ac—CHAVPen-$NH_2$ (SEQ ID NO:97), N—Ac-PenHAVC—$NH_2$ (SEQ ID NO:98), N—Ac—CHAVPC—$NH_2$ (SEQ ID NO:99) and derivatives thereof (e.g., in which terminal modifications are varied). Modulating agents comprising a CAR sequence for a second adhesion molecule (e.g., RGD, LYHY (SEQ ID NO:55) or a CAR sequence for OB-cadherin, a desmoglein, a desmocollin or claudin) are also preferred. Alternatively, a separate modulator of cell adhesion mediated by an adhesion molecule that is not a cadherin may be administered in conjunction with the modulating agent(s), either within the same pharmaceutical composition or separately. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a cyclic peptide-drug-targeting agent combination, injection of a cyclic peptide (alone or in combination with a drug and/or targeting agent) into the carotid artery or application of a skin patch comprising a modulating agent to the head of the patient. Certain preferred cyclic peptides for use within such methods are relatively small (e.g., a ring size of 4–10 residues; preferably 5–7 residues) and include peptides comprising a 5-residue ring such as N—Ac—CHAVC—$NH_2$ (SEQ ID NO:96) and N—Ac—KHAVD-$NH_2$ (SEQ ID NO:12). Other preferred modulating agents comprise one or more cyclic peptides such as NAc—CHAVC—$NH_2$ (SEQ ID NO:96), CHAVC—Y—$NH_2$ (SEQ ID NO:84), N—Ac—CHAVDC—$NH_2$ (SEQ ID NO:20), N—Ac—CHAVDIC—$NH_2$ (SEQ ID NO:50), N—Ac—CHAVDINC—$NH_2$ (SEQ ID NO:51), N—Ac—CHAVDINGC—$NH_2$ (SEQ ID NO:76), N—Ac—CAHAVC—$NH_2$ (SEQ ID NO:22), N—Ac—CAHAVDC—$NH_2$ (SEQ ID NO:26), N—Ac—CAHAVDIC—$NH_2$ (SEQ ID NO:24), N—Ac—CRAHAVDC—$NH_2$ (SEQ ID NO:28), N—Ac—CLRAHAVC—$NH_2$ (SEQ ID NO:30), N—Ac—CLRAHAVDC—$NH_2$ (SEQ ID NO:32), N—Ac—CSHAVC—$NH_2$ (SEQ ID NO:36), N—Ac—CFSHAVC—$NH_2$ (SEQ ID NO:85), N—Ac—CLFSHAVC—$NH_2$ (SEQ ID NO:86), N—Ac—CHAVSC—$NH_2$ (SEQ ID NO:38), N—Ac—CSHAVSC—$NH_2$ (SEQ ID NO:40), N—Ac—CSHAVSSC—$NH_2$ (SEQ ID NO:42), N—Ac—CHAVSSC—$NH_2$ (SEQ ID NO:44), N—Ac—KHAVD-$NH_2$ (SEQ ID NO:12), N—Ac—DHAVK—$NH_2$ (SEQ ID NO:14), N—Ac—KHAVE-$NH_2$ (SEQ ID NO:16), N—Ac-AHAVDI—$NH_2$ (SEQ ID NO:34), N—Ac—SHAVDSS—$NH_2$ (SEQ ID NO:77), N—Ac—KSHAVSSD-$NH_2$ (SEQ ID NO:48), N—Ac—CHAVC—S—$NH_2$ (SEQ ID NO:87), N—Ac—S—CHAVC—$NH_2$ (SEQ ID NO:88), N—Ac—CHAVC—SS—$NH_2$ (SEQ ID NO:89), N—Ac—S—CHAVC—S—$NH_2$ (SEQ ID NO:90), N—Ac—CHAVC-T-$NH_2$ (SEQ ID NO:91), N—Ac—CHAVC-E-$NH_2$ (SEQ ID NO:92), N—Ac—CHAVC-D-$NH_2$ (SEQ ID NO:93), N—Ac—CHAVYC—$NH_2$ (SEQ ID NO:94), $CH_3$—$SO_2$—NH—CHAVC—Y—$NH_2$ (SEQ ID NO:95), $CH_3$—$SO_2$—HN—CHAVC—$NH_2$ (SEQ ID NO:96), HC(O)—HN—CHAVC—$NH_2$ (SEQ ID NO:96), N—Ac—CHAVPen-$NH_2$ (SEQ ID NO:97), N—Ac-PenHAVC—$NH_2$ (SEQ ID NO:98), N—Ac—CHAVPC—$NH_2$ (SEQ ID NO:99) and derivatives thereof (e.g., in which terminal modifications are varied). Also preferred are bi-functional modulating agents comprising an occludin CAR sequence LYHY (SEQ ID NO:55) and/or claudin CAR sequence, preferably joined by a linker. Alternatively, a separate modulator of occludin-mediated cell adhesion may be administered in conjunction with the modulating agent(s), either within the same pharmaceutical composition or separately. Modulating agents may further comprise antibodies or Fab fragments directed against the N-cadherin CAR sequence FHLRAHAVDINGNQV—$NH_2$ (SEQ ID NO:75). Fab fragments directed against the occludin CAR sequence GVNPTAQSSGSLYGSQIYALCNQFYTPAATGLYVDQYLYHYCVVDPQE (SEQ ID NO:78) may also be employed, either incorporated into the modulating agent or administered concurrently as a separate modulator.

In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

In still further aspects, the present invention provides methods for enhancing adhesion of cadherin-expressing cells. Within certain embodiments, a modulating agent may be linked to a support molecule or to a solid support as described above, resulting in a matrix that comprises multiple modulating agents. Within one such embodiment, the support is a polymeric matrix to which modulating agents and molecules comprising other CAR sequence(s) are attached (e.g., modulating agents and molecules comprising RGD, LYHY (SEQ ID NO:55) or a CAR sequence for OB-cadherin, a desmoglein, a desmocollin or claudin, may be attached to the same matrix, preferably in an alternating pattern). Such matrices may be used in contexts in which it is desirable to enhance adhesion mediated by multiple cell adhesion molecules. Alternatively, the modulating agent itself may comprise multiple HAV sequences and/or antibodies (or fragments thereof), separated by linkers as described above. Either way, the modulating agent(s) function as a “biological glue” to bind multiple cadherin-expressing cells within a variety of contexts.

Within one embodiment, such modulating agents may be used to enhance wound healing and/or reduce scar tissue in a mammal. Preferred modulating agents for use within such methods include those that comprise one or more cyclic peptides such as NAc—CHAVC—NH₂ (SEQ ID NO:96), CHAVC—Y—NH₂ (SEQ ID NO:84), N—Ac—CHAVDC—NH₂ (SEQ ID NO:20), N—Ac—CHAVDIC—NH₂ (SEQ ID NO:50), N—Ac—CHAVDINC—NH₂ (SEQ ID NO:51), N—Ac—CHAVDINGC—NH₂ (SEQ ID NO:76), N—Ac—CAHAVC—NH₂ (SEQ ID NO:22), N—Ac—CAHAVDC—NH₂ (SEQ ID NO:26), N—Ac—CAHAVDIC—NH₂ (SEQ ID NO:24), N—Ac—CRAHAVDC—NH₂ (SEQ ID NO:28), N—Ac—CLRAHAVC—NH₂ (SEQ ID NO:30), N—Ac—CLRAHAVDC—NH₂ (SEQ ID NO:32), N—Ac—CSHAVC—NH₂ (SEQ ID NO:36), N—Ac—CFSHAVC—NH₂ (SEQ ID NO:85), N—Ac—CLFSHAVC—NH₂ (SEQ ID NO:86), N—Ac—CHAVSC—NH₂ (SEQ ID NO:38), N—Ac—CSHAVSC—NH₂ (SEQ ID NO:40), N—Ac—CSHAVSSC—NH₂ (SEQ ID NO:42), N—Ac—CHAVSSC—NH₂ (SEQ ID NO:44), N—Ac—KHAVD-NH₂ (SEQ ID NO:12), N—Ac—DHAVK—NH₂ (SEQ ID NO: 14), N—Ac—KHAVE-NH₂ (SEQ ID NO: 16), N—Ac-AHAVDI—NH₂ (SEQ ID NO:34), N—Ac—SHAVDSS—NH₂ (SEQ ID NO:77), N—Ac—KSHAVSSD-NH₂ (SEQ ID NO:48), N—Ac—CHAVC—S—NH₂ (SEQ ID NO:87), N—Ac—S—CHAVC—NH₂ (SEQ ID NO:88), N—Ac—CHAVC—SS—NH₂ (SEQ ID NO:89), N—Ac—S—CHAVC—S—NH₂ (SEQ ID NO:90), N—Ac—CHAVC-T-NH₂ (SEQ ID NO:91), N—Ac—CHAVC-E-NH₂ (SEQ ID NO:92), N—Ac—CHAVC-D-NH₂ (SEQ ID NO:93), N—Ac—CHAVYC—NH₂ (SEQ ID NO:94), CH₃—SO₂—HN—CHAVC—Y—NH₂ (SEQ ID NO:95), CH₃—SO₂—HN—CHAVC—NH₂ (SEQ ID NO:96), HC(O)—HN—CHAVC—NH₂ (SEQ ID NO:96), N—Ac—CHAVPen-NH₂ (SEQ ID NO:97), N—Ac-PenHAVC—NH₂ (SEQ ID NO:98), N—Ac—CHAVPC—NH₂ (SEQ ID NO:99) and derivatives thereof (e.g., in which terminal modifications are varied). Modulating agents that are linked to a biocompatible and biodegradable matrix such as cellulose or collagen are particularly preferred. For use within such methods, a modulating agent should have a free amino or hydroxyl group. Multi-functional modulating agents further comprising the fibronectin CAR sequence RGD, which is recognized by integrins, as well CAR sequences for OB-cadherin, claudin, dsc and/or dsg, may also be used as potent stimulators of wound healing and/or to reduce scar tissue. Such agents may also, or alternatively, comprise the occludin CAR sequence LYHY (SEQ ID NO:55). Alternatively, one or more separate modulators of integrin-, Dsc-, Dsg-, claudin-, OB-cadherin- and/or occludin-mediated cell adhesion may be administered in conjunction with the modulating agent(s), either within the same pharmaceutical composition or separately.

The modulating agents are generally administered topically to the wound, where they may facilitate closure of the wound and may augment, or even replace, stitches. Similarly, administration of matrix-linked modulating agents may facilitate cell adhesion in foreign tissue implants (e.g., skin grafting and prosthetic implants) and may prolong the duration and usefulness of collagen injection. In general, the amount of matrix-linked cyclic peptide administered to a wound, graft or implant site varies with the severity of the wound and/or the nature of the wound, graft, or implant, but may vary as discussed above.

Within another embodiment, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for larger scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of cyclic peptide(s) may also be used to facilitate the production of specific proteins.

Modulating agents as described herein may be used within a variety of bioreactor configurations. In general, a bioreactor is designed with an interior surface area sufficient to support larger numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Modulating agents may also be used, within other aspects of the present invention, to enhance and/or direct neurological growth. In one aspect, neurite outgrowth may be enhanced and/or directed by contacting a neuron with one or more modulating agents. Preferred modulating agents for use within such methods are linked to a polymeric matrix or other support and include those peptides without substantial flanking sequences, as described above. In particularly preferred embodiments, the modulating agent comprises one or more cyclic peptides such as NAc—CHAVC—NH₂ (SEQ ID NO:96), CHAVC—Y—NH₂ (SEQ ID NO:84), N—Ac—CHAVDC—NH₂ (SEQ ID NO:20), N—Ac—CHAVDIC—NH₂ (SEQ ID NO:50), N—Ac—CHAVDINC—NH₂ (SEQ ID NO:51), N—Ac—CHAVDINGC—NH₂ (SEQ ID NO:76), N—Ac—CAHAVC—NH₂ (SEQ ID NO:22), N—Ac—CAHAVDC—NH₂ (SEQ ID NO:26), N—Ac—CAHAVDIC—NH₂ (SEQ ID NO:24), N—Ac—CRAHAVDC—NH₂ (SEQ ID NO:28), N—Ac—CLRAHAVC—NH₂ (SEQ ID NO:30), N—Ac—CLRAHAVDC—NH₂ (SEQ ID NO:32), N—Ac—CSHAVC—NH₂ (SEQ ID NO:36), N—Ac—CFSHAVC—NH₂ (SEQ ID NO:85), N—Ac—CLFSHAVC—NH₂ (SEQ ID NO:86), N—Ac—CHAVSC—NH₂ (SEQ ID NO:38), N—Ac—CSHAVSC—NH₂ (SEQ ID NO:40), N—Ac—CSHAVSSC—NH₂ (SEQ ID NO:42), N—Ac—CHAVSSC—NH₂ (SEQ ID NO:44), N—Ac—KHAVD-NH₂ (SEQ ID NO:12), N—Ac—DHAVK—NH₂ (SEQ ID NO:14), N—Ac—KHAVE-NH₂ (SEQ ID NO:16), N—Ac-AHAVDI—NH₂ (SEQ ID NO:34), N—Ac—SHAVDSS—NH₂ (SEQ ID NO:77), N—Ac—

KSHAVSSD-NH₂ (SEQ ID NO:48), N—Ac—CHAVC—S—NH₂ (SEQ ID NO:87), N—Ac—S—CHAVC—NH₂ (SEQ ID NO:88), N—Ac—CHAVC—SS—NH₂ (SEQ ID NO:89), N—Ac—S—CHAVC—S—NH₂ (SEQ ID NO:90), N—Ac—CHAVC-T-NH₂ (SEQ ID NO:91), N—Ac—CHAVC-E-NH₂ (SEQ ID NO:92), N—Ac—CHAVC-D-NH₂ (SEQ ID NO:93), N—Ac—CHAVYC—NH₂ (SEQ ID NO:94), CH₃—SO₂—NH—CHAVC—Y—NH₂ (SEQ ID NO:95), CH₃—SO₂—HN—CHAVC—NH₂ (SEQ ID NO:96), HC(O)—HN—CHAVC—NH₂ (SEQ ID NO:96), N—Ac—CHAVPen-NH₂ (SEQ ID NO:97), N—Ac-PenHAVC—NH₂ (SEQ ID NO:98), N—Ac—CHAVPC—NH₂ (SEQ ID NO:99) and derivatives thereof (e.g., in which terminal modifications are varied). In addition, a modulating agent further comprising RGD and/or YIGSR (SEQ ID NO:52), which are bound by integrins, and/or the N-CAM CAR sequence KYS-FNYDGSE (SEQ ID NO:53) may further facilitate neurite outgrowth. Other CAR sequences that may also, or alternatively, be included are CAR sequences for cadherin-7, cadherin-8, cadherin-12, cadherin-14, cadherin-15, PB-cadherin, protocadherins and cadherin-related neuronal receptors. Modulating agents comprising antibodies, or fragments thereof, may be used within this aspect of the present invention without the use of linkers or support materials. Preferred antibody modulating agents include Fab fragments directed against the N-cadherin CAR sequence FHLRAHAVDINGNQV—NH₂ (SEQ ID NO:75). Fab fragments directed against the N-CAM CAR sequence KYS-FNYDGSE (SEQ ID NO:53) may also be employed, either incorporated into the modulating agent or administered concurrently as a separate modulator.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

Within another such aspect, one or more modulating agents may be used for therapy of a demyelinating neurological disease in a mammal. There are a number of demyelinating diseases, such as multiple sclerosis, characterized by oligodendrocyte death. It has been found, within the context of the present invention, that Schwann cell migration on astrocytes is inhibited by N-cadherin. Modulating agents that disrupt N-cadherin mediated cell adhesion as described herein may be implanted into the central nervous system with cells capable of replenishing an oligodendrocyte population, such as Schwann cells, oligodendrocytes or oligodendrocyte precursor cells. Such therapy may facilitate the function of the cell capable of replenishing an oligodendrocyte population and permit the practice of Schwann cell or oligodendrocyte replacement therapy.

Multiple sclerosis patients suitable for treatment may be identified by criteria that establish a diagnosis of clinically definite or clinically probable MS (see Poser et al., Ann. Neurol. 13:227, 1983). Candidate patients for preventive therapy may be identified by the presence of genetic factors, such as HLA-type DR2a and DR2b, or by the presence of early disease of the relapsing remitting type.

Schwann cell grafts may be implanted directly into the brain along with the modulating agent(s) using standard techniques. Preferred modulating agents for use within such methods include those that comprise one or more cyclic peptides such as NAc—CHAVC—NH₂ (SEQ ID NO:96), CHAVC—Y—NH₂ (SEQ ID NO:84), N—Ac—CHAVDC—NH₂ (SEQ ID NO:20), N—Ac—CHAVDIC—NH₂ (SEQ ID NO:50), N—Ac—CHAVDINC—NH₂ (SEQ ID NO:51), N—Ac—CHAVDINGC—NH₂ (SEQ ID NO:76), N—Ac—CAHAVC—NH₂ (SEQ ID NO:22), N—Ac—CAHAVDC—NH₂ (SEQ ID NO:26), N—Ac—CAHAVDIC—NH₂ (SEQ ID NO:24), N—Ac—CRAHAVDC—NH₂ (SEQ ID NO:28), N—Ac—CLRAHAVC—NH₂ (SEQ ID NO:30), N—Ac—CLRAHAVDC—NH₂ (SEQ ID NO:32), N—Ac—CSHAVC—NH₂ (SEQ ID NO:36), N—Ac—CFSHAVC—NH₂ (SEQ ID NO:85), N—Ac—CLFSHAVC—NH₂ (SEQ ID NO:86), N—Ac—CHAVSC—NH₂ (SEQ ID NO:38), N—Ac—CSHAVSC—NH₂ (SEQ ID NO:40), N—Ac—CSHAVSSC—NH₂ (SEQ ID NO:42), N—Ac—CHAVSSC—NH₂ (SEQ ID NO:44), N—Ac—KHAVD-NH₂ (SEQ ID NO:12), N—Ac—DHAVK—NH₂ (SEQ ID NO:14), N—Ac—KHAVE-NH₂ (SEQ ID NO:16), N—Ac-AHAVDI—NH₂ (SEQ ID NO:34), N—Ac—SHAVDSS—NH₂ (SEQ ID NO:77), N—Ac—KSHAVSSD-NH₂ (SEQ ID NO:48), N—Ac—CHAVC—S—NH₂ (SEQ ID NO:87), N—Ac—S—CHAVC—NH₂ (SEQ ID NO:88), N—Ac—CHAVC—SS—NH₂ (SEQ ID NO:89), N—Ac—S—CHAVC—S—NH₂ (SEQ ID NO:90), N—Ac—CHAVC-T-NH₂ (SEQ ID NO:91), N—Ac—CHAVC-E-NH₂ (SEQ ID NO:92), N—Ac—CHAVC-D-NH₂ (SEQ ID NO:93), N—Ac—CHAVYC—NH₂ (SEQ ID NO:94), CH₃—SO₂—HN—CHAVC—Y—NH₂ (SEQ ID NO:95), CH₃—SO₂—HN—CHAVC—NH₂ (SEQ ID NO:96), HC(O)—HN—CHAVC—NH₂ (SEQ ID NO:96), N—Ac—CHAVPen-NH₂ (SEQ ID NO:97), N—Ac-PenHAVC—NH₂ (SEQ ID NO:98), N—Ac—CHAVPC—NH₂ (SEQ ID NO:99) and derivatives thereof (e.g., in which terminal modifications are varied). Modulating agents comprising antibodies, or fragments thereof, may also be used within this aspect of the present invention. Preferred antibody modulating agents include Fab fragments directed against the N-cadherin CAR sequence FHLRAHAVDINGNQV—NH₂ (SEQ ID NO:75). Suitable amounts of cyclic peptide generally range as described above, preferably from about 10 μg/mL to about 1 mg/mL.

Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelin-forming oligodendrocytes and contribute to repair of demyelinated axons (see e.g., Groves et al., *Nature* 362:453–55, 1993; Baron-Van Evercooren et al., *Glia* 16:147–64, 1996). OPs can be isolated using routine techniques known in the art (see e.g., Milner and French-Constant, *Development* 120:3497–3506, 1994), from many regions of the CNS including brain, cerebellum, spinal cord, optic nerve and olfactory bulb. Substantially greater yields of OP's are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyelinating diseases such as MS.

OPs can be expanded in vitro if cultured as "homotypic aggregates" or "spheres" (Avellana-Adalid et al, *J. Neurosci. Res.* 45:558–70, 1996). Spheres (sometimes called "oligospheres" or "neurospheres") are formed when OPs are grown in suspension in the presence of growth factors such as PDGF and FGF. OPs can be harvested from spheres by mechanical dissociation and used for subsequent transplantation or establishment of new spheres in culture. Alternatively, the spheres themselves may be transplanted, providing a "focal reservoir" of OPs (Avellana-Adalid et al, *J. Neurosci. Res.* 45:558–70, 1996).

An alternative source of OP may be spheres derived from CNS stem cells. Recently, Reynolds and Weiss, *Dev. Biol.* 165:1–13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1–13, 1996). Spheres derived from CNS stem cells provide an alternative source of OP which may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt N-cadherin mediated cell adhesion as described herein, when injected with neurospheres into the central nervous system, may improve cell migration and increase the efficacy of OP replacement therapy. Neurosphere grafts may be implanted directly into the central nervous system along with the modulating agent(s) using standard techniques.

Alternatively, a modulating agent may be administered alone or within a pharmaceutical composition. The duration and frequency of administration will be determined by such factors as the condition of the patient, and the type and severity of the patient's disease. Within particularly preferred embodiments of the invention, the cyclic peptide or pharmaceutical composition may be administered at a dosage ranging from 0.1 mg/kg to 20 mg/kg, although appropriate dosages may be determined by clinical trials. Methods of administration include injection, intravenous or intrathecal (i.e., directly in cerebrospinal fluid).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one full step defines an effective treatment in the context of the present invention (Kurtzke, *Ann. Neurol.* 36:573–79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium-DTPA-enhanced imaging (McDonald et al. *Ann. Neurol.* 36:14, 1994) or the location and extent of lesions using $T_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by gadolinium enhanced images.

Within a related aspect, the present invention provides methods for facilitating migration of an N-cadherin expressing cell on astrocytes, comprising contacting an N-cadherin expressing cell with (a) a cell adhesion modulating agent that inhibits cadherin-mediated cell adhesion, wherein the modulating agent comprises a cyclic peptide that comprises the sequence HAV; and (b) one or more astrocytes; and thereby facilitating migration of the N-cadherin expressing cell on the astrocytes. Preferred N-cadherin expressing cells include Schwann cells, oligodendrocytes and oligodendrocyte progenitor cells.

Within another aspect, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies (see Lee et al., *J. Immunol.* 152:5653–5659, 1994; Munro et al., *Cellular Immunol.* 169:309–312, 1996; Tsutsui et al., *J. Biochem.* 120:1034–1039, 1996; Cepek et al., *Proc. Natl. Acad. Sci. USA* 93:6567–6571, 1996). Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-T cells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a cyclic peptide. Such treatment may also benefit patients undergoing transplantation with peripheral blood stem cells.

Preferred modulating agents for use within such methods include those that disrupt E-cadherin and/or N-cadherin mediated cell adhesion, and comprise one or more cyclic peptides such as NAc—CHAVC—$NH_2$ (SEQ ID NO:96), CHAVC—Y—$NH_2$ (SEQ ID NO:84), N—Ac—CHAVDC—$NH_2$ (SEQ ID NO:20), N—Ac—CHAVDIC—$NH_2$ (SEQ ID NO:50), N—Ac—CHAVDINC—$NH_2$ (SEQ ID NO:51), N—Ac—CHAVDINGC—$NH_2$ (SEQ ID NO:76), N—Ac—CAHAVC—$NH_2$ (SEQ ID NO:22), N—Ac—CAHAVDC—$NH_2$ (SEQ ID NO:26), N—Ac—CAHAVDIC—$NH_2$ (SEQ ID NO:24), N—Ac—CRAHAVDC—$NH_2$ (SEQ ID NO:28), N—Ac—CLRAHAVC—$NH_2$ (SEQ ID NO:30), N—Ac—CLRAHAVDC—$NH_2$ (SEQ ID NO:32), N—Ac—CSHAVC—$NH_2$ (SEQ ID NO:36), N—Ac—CFSHAVC—$NH_2$ (SEQ ID NO:85), N—Ac—CLFSHAVC—$NH_2$ (SEQ ID NO:86), N—Ac—CHAVSC—$NH_2$ (SEQ ID NO:38), N—Ac—CSHAVSC—$NH_2$ (SEQ ID NO:40), N—Ac—CSHAVSSC—$NH_2$ (SEQ ID NO:42), N—Ac—CHAVSSC—$NH_2$ (SEQ ID NO:44), N—Ac—KHAVD-$NH_2$ (SEQ ID NO:12), N—Ac—DHAVK—$NH_2$ (SEQ ID NO:14), N—Ac—KHAVE-$NH_2$ (SEQ ID NO:16), N—Ac-AHAVDI—$NH_2$ (SEQ ID NO:34), N—Ac—SHAVDSS—$NH_2$ (SEQ ID NO:77), N—Ac—KSHAVSSD-$NH_2$ (SEQ ID NO:48), N—Ac—CHAVC—S—$NH_2$ (SEQ ID NO:87), N—Ac—S—CHAVC—$NH_2$ (SEQ ID NO:88), N—Ac—CHAVC—SS—$NH_2$ (SEQ ID NO:89), N—Ac—S—CHAVC—S—$NH_2$ (SEQ ID NO:90), N—Ac—CHAVC-T-$NH_2$ (SEQ ID NO:91), N—Ac—CHAVC-E-$NH_2$ (SEQ ID NO:92), N—Ac—CHAVC-D-$NH_2$ (SEQ ID NO:93), N—Ac—CHAVYC—$NH_2$ (SEQ ID NO:94), $CH_3$—$SO_2$—HN—CHAVC—Y—$NH_2$ (SEQ ID NO:95), $CH_3$—$SO_2$—HN—CHAVC—$NH_2$ (SEQ ID NO:96), HC(O)—HN—CHAVC—$NH_2$ (SEQ ID NO:96), N—Ac—CHAVPen-$NH_2$ (SEQ ID NO:97), N—Ac-PenHAVC—$NH_2$ (SEQ ID NO:98), N—Ac—CHAVPC—$NH_{12}$ (SEQ ID NO:99) and derivatives thereof (e.g., in which terminal modifications are varied). In addition, a preferred modulating agent may comprise one or more additional CAR sequences, such as the sequence RGD, which is bound by integrins, as well as CAR sequences for occludin, N-CAM, OB-cadherin, cadherin-5, cadherin-6 and cadherin-8. As noted above, such additional sequence(s) may be separated from the HAV sequence via a linker. Alternatively, a separate modulator of integrin-mediated cell adhesion may be administered in conjunction with the modulating agent(s), either within the same pharmaceutical composition or separately.

Within the above methods, the modulating agent(s) are preferably administered systemically (usually by injection) or topically. A cyclic peptide may be linked to a targeting agent. As noted above, a modulating agent may further be linked to a targeting agent. For example, targeting to the bone marrow may be beneficial. A suitable dosage is sufficient to effect a statistically significant reduction in the population of B and/or T cells that express cadherin and/or an improvement in the clinical manifestation of the disease being treated. Typical dosages range as described above.

Within further aspects, the present invention provides methods and kits for preventing pregnancy in a mammal. In general, disruption of E-cadherin function prevents the adhesion of trophoblasts and their subsequent fusion to form syncitiotrophoblasts. In one embodiment, one or more modulating agents as described herein may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. Preferred modulating agents for use within such methods include those that comprise one or more cyclic peptides such as NAc—CHAVC—$NH_2$ (SEQ ID NO:96), CHAVC—Y—$NH_2$ (SEQ ID NO:84), N—Ac—CHAVDC—$NH_2$ (SEQ ID NO:20), N—Ac—CHAVDIC—$NH_2$ (SEQ ID NO:50), N—Ac—CHAVDINC—$NH_2$ (SEQ ID NO:51), N—Ac—CHAVDINGC—$NH_2$ (SEQ ID NO:76), N—Ac—CAHAVC—$NH_2$ (SEQ ID NO:22), N—Ac—CAHAVDC—$NH_2$ (SEQ ID NO:26), N—Ac—CAHAVDIC—$NH_2$ (SEQ ID NO:24), N—Ac—CRAHAVDC—$NH_2$ (SEQ ID NO:28), N—Ac—CLRAHAVC—$NH_2$ (SEQ ID NO:30), N—Ac—CLRAHAVDC—$NH_2$ (SEQ ID NO:32), N—Ac—CSHAVC—$NH_2$ (SEQ ID NO:36), N—Ac—CFSHAVC—$NH_2$ (SEQ ID NO:85), N—Ac—CLFSHAVC—$NH_2$ (SEQ ID NO:86), N—Ac—CHAVSC—$NH_2$ (SEQ ID NO:38), N—Ac—CSHAVSC—$NH_2$ (SEQ ID NO:40), N—Ac—CSHAVSSC—$NH_2$ (SEQ ID NO:42), N—Ac—CHAVSSC—$NH_2$ (SEQ ID NO:44), N—Ac—KHAVD-$NH_2$ (SEQ ID NO:12), N—Ac—DHAVK—$NH_2$ (SEQ ID NO:14), N—Ac—KHAVE-$NH_2$ (SEQ ID NO: 16), N—Ac-AHAVDI—$NH_2$ (SEQ ID NO:34), N—Ac—SHAVDSS—$NH_2$ (SEQ ID NO:77), N—Ac—KSHAVSSD-$NH_2$ (SEQ ID NO:48), N—Ac—CHAVC—S—$NH_2$ (SEQ ID NO:87), N—Ac—S—CHAVC—NH? (SEQ ID NO:88), N—Ac—CHAVC—SS—$NH_2$ (SEQ ID NO:89), N—Ac—S—CHAVC—S—$NH_2$ (SEQ ID NO:90), N—Ac—CHAVC-T-$NH_2$ (SEQ ID NO:91), N—Ac—CHAVC-E-$NH_2$ (SEQ ID NO:92), N—Ac—CHAVC-D-$NH_2$ (SEQ ID NO:93), N—Ac—CHAVYC—$NH_2$ (SEQ ID NO:94), $CH_3$—$SO_2$—HN—CHAVC—Y—$NH_2$ (SEQ ID NO:95), $CH_3$—$SO_2$—HN—CHAVC—$NH_2$ (SEQ ID NO:96), HC(O)—HN—CHAVC—$NH_2$ (SEQ ID NO:96), N—Ac—CHAVPen-$NH_2$ (SEQ ID NO:97), N—Ac-PenHAVC—$NH_2$ (SEQ ID NO:98), N—Ac—CHAVPC—$NH_2$ (SEQ ID NO:99) and derivatives thereof (e.g., in which terminal modifications are varied). In addition, a preferred modulating agent may comprise additional CAR sequences, such as the sequence RGD, which is bound by integrins. As noted above, such additional sequences may be separated from the HAV sequence via a linker. Alternatively, a separate modulator of integrin-mediated cell adhesion may be administered in conjunction with the modulating agent(s), either within the same pharmaceutical composition or separately.

Suitable methods for incorporation into a contraceptive device depend upon the type of device and are well known in the art. Such devices facilitate administration of the cyclic peptide(s) to the uterine region and may provide a sustained release of the cyclic peptide(s). In general, cyclic peptide(s) may be administered via a contraceptive device at a dosage ranging from 0.1 to 20 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more cyclic peptides.

Alternatively, a sustained release formulation of one or more cyclic peptides may be implanted, typically subdermally, in a mammal for the prevention of pregnancy. Such implantation may be performed using well known techniques. Preferably, the implanted formulation provides a dosage as described above, although the minimum effective dosage may be determined by those of ordinary skill in the art using, for example, an evaluation of hCG levels in the urine of women.

The present invention also provides methods for increasing vasopermeability in a mammal by administering one or more modulating agents or pharmaceutical compositions. Within blood vessels, endothelial cell adhesion (mediated by N-cadherin) results in decreased vascular permeability. Accordingly, modulating agents as described herein may be used to increase vascular permeability. Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. Particularly preferred modulating agents for use within such methods include those that comprise one or more cyclic peptides such as NAc—CHAVC—NH$_2$ (SEQ ID NO:96), CHAVC—Y—NH$_2$ (SEQ ID NO:84), N—Ac—CHAVDC—NH$_2$ (SEQ ID NO:20), N—Ac—CHAVDIC—NH$_2$ (SEQ ID NO:50), N—Ac—CHAVDINC—NH$_2$ (SEQ ID NO:51), N—Ac—CHAVDINGC—NH$_2$ (SEQ ID NO:76), N—Ac—CAHAVC—NH$_2$ (SEQ ID NO:22), N—Ac—CAHAVDC—NH$_2$ (SEQ ID NO:26), N—Ac—CAHAVDIC—NH$_2$ (SEQ ID NO:24), N—Ac—CRAHAVDC—NH$_2$ (SEQ ID NO:28), N—Ac—CLRAHAVC—NH$_2$ (SEQ ID NO:30), N—Ac—CLRAHAVDC—NH$_2$ (SEQ ID NO:32), N—Ac—CSHAVC—NH$_2$ (SEQ ID NO:36), N—Ac—CFSHAVC—NH$_2$ (SEQ ID NO:85), N—Ac—CLFSHAVC—NH$_2$ (SEQ ID NO:36), N—Ac—CHAVSC—NH$_2$ (SEQ ID NO:38), N—Ac—CSHAVSC—NH$_2$ (SEQ ID NO:40), N—Ac—CSHAVSSC—NH$_2$ (SEQ ID NO:42), N—Ac—CHAVSSC—NH$_2$ (SEQ ID NO:44), N—Ac—KHAVD-NH$_2$ (SEQ ID NO:12), N—Ac—DHAVK—NH$_2$ (SEQ ID NO:14), N—Ac—KHAVE-NH$_2$ (SEQ ID NO:16), N—Ac-AHAVDI—NH$_2$ (SEQ ID NO:34), N—Ac—SHAVDSS—NH$_2$ (SEQ ID NO:77), N—Ac—KSHAVSSD-NH$_2$ (SEQ ID NO:48), N—Ac—CHAVC—S—NH$_2$ (SEQ ID NO:87), N—Ac—S—CHAVC—NH$_2$ (SEQ ID NO:88), N—Ac—CHAVC—SS—NH$_2$ (SEQ ID NO:89), N—Ac—S—CHAVC—S—NH$_2$ (SEQ ID NO:90), N—Ac—CHAVC-T-NH$_2$ (SEQ ID NO:91), N—Ac—CHAVC-E-NH$_2$ (SEQ ID NO:92), N—Ac—CHAVC-D-NH$_2$ (SEQ ID NO:93), N—Ac—CHAVYC—NH$_2$ (SEQ ID NO:94), CH$_3$—SO$_2$—HN—CHAVC—Y—NH$_2$ (SEQ ID NO:95), CH$_3$—SO$_2$—HN—CHAVC—NH$_2$ (SEQ ID NO:96), HC(O)—HN—CHAVC—NH$_2$ (SEQ ID NO:96), N—Ac—CHAVPen-NH$_2$ (SEQ ID NO:97), N—Ac-PenHAVC—NH$_2$ (SEQ ID NO:98), N—Ac—CHAVPC—NH$_2$ (SEQ ID NO:99) and derivatives thereof (e.g., in which terminal modifications are varied). In addition, a preferred modulating agent may comprise an occludin CAR sequence LYHY (SEQ ID NO:55) and/or a CAR sequence for OB-cadherin or claudin. As noted above, such an additional sequence may be separated from the HAV sequence via a linker. Alternatively, a separate modulator of occludin mediated cell adhesion may be administered in conjunction with one or modulating agents, either within the same pharmaceutical composition or separately.

Within certain embodiments, preferred modulating agents for use within such methods include cyclic peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. For example, a modulating agent may comprise an HAV sequence with flanking E-cadherin-specific sequences and an HAV sequence with flanking N-cadherin-specific sequences. Alternatively, separate modulating agents capable of disrupting N- and E-cadherin mediated adhesion may be administered concurrently.

In one particularly preferred embodiment, a modulating agent is further capable of disrupting cell adhesion mediated by multiple adhesion molecules. Such an agent may additionally comprise an RGD sequence, a Dsc CAR sequence, a Dsg CAR sequence and/or the occludin CAR sequence LYHY (SEQ ID NO:55). Alternatively, a separate modulator of non-classical cadherin-mediated cell adhesion may be administered in conjunction with the modulating agent(s), either within the same pharmaceutical composition or separately. Fab fragments directed against any of the above CAR sequences may also be employed, either incorporated into a modulating agent or within a separate modulator that is administered concurrently.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within a further aspect, modulating agents as described herein may be used for controlled inhibition of synaptic stability, resulting in increased synaptic plasticity. Within this aspect, administration of one or more modulating agents may be advantageous for repair processes within the brain, as well as learning and memory, in which neural plasticity is a key early event in the remodeling of synapses. Cell adhesion molecules, particularly N-cadherin and E-cadherin, can function to stabilize synapses, and loss of this function is thought to be the initial step in the remodeling of the synapse that is associated with learning and memory (Doherty et al., *J. Neurobiology*, 26:437–446, 1995; Martin and Kandel, *Neuron*, 17:567–570, 1996; Fannon and Colman, *Neuron*, 17:423–434, 1996). Inhibition of cadherin function by administration of one or more modulating agents that inhibit cadherin function may stimulate learning and memory.

Preferred modulating agents for use within such methods include those that disrupt E-cadherin and/or N-cadherin mediated cell adhesion, and comprise one or more cyclic peptides such as NAc—CHAVC—NH$_2$ (SEQ ID NO:96), CHAVC—Y—NH$_2$ (SEQ ID NO:84), N—Ac—CHAVDC—NH$_2$ (SEQ ID NO:20), N—Ac—CHAVDIC—NH$_2$ (SEQ ID NO:50), N—Ac—CHAVDINC—NH$_2$ (SEQ ID NO:51), N—Ac—CHAVDINGC—NH$_2$ (SEQ ID NO:76), N—Ac—CAHAVC—NH$_2$ (SEQ ID NO:22), N—Ac—CAHAVDC—NH$_2$ (SEQ ID NO:26), N—Ac—CAHAVDIC—NH$_2$ (SEQ ID NO:24), N—Ac—CRAHAVDC—NH2 (SEQ ID NO:28), N—Ac—CLRAHAVC—NH$_2$ (SEQ ID NO:30), N—Ac—CLRAHAVDC—NH$_2$ (SEQ ID NO:32), N—Ac—CSHAVC—NH$_2$ (SEQ ID NO:36), N—Ac—CFSHAVC—NH2 (SEQ ID NO:85), N—Ac—CLFSHAVC—NH$_2$ (SEQ ID NO:86), N—Ac—CHAVSC—NH$_2$ (SEQ ID NO:38), N—Ac—CSHAVSC—NH$_2$ (SEQ ID NO:40), N—Ac—CSHAVSSC—NH$_2$ (SEQ ID NO:42), N—Ac—CHAVSSC—NH$_2$ (SEQ ID NO:44), N—Ac—KHAVD-NH$_2$ (SEQ ID NO:12), N—Ac—DHAVK—NH$_2$ (SEQ ID NO:14), N—Ac—KHAVE-NH$_2$ (SEQ ID NO:16), N—Ac-AHAVDI—NH$_2$ (SEQ ID NO:34), N—Ac—SHAVDSS—NH$_2$ (SEQ ID NO:77), N—Ac—KSHAVSSD-NH$_2$ (SEQ ID NO:48), N—Ac—CHAVC—S—NH$_2$ (SEQ ID NO:87), N—Ac—S—CHAVC—NH$_2$ (SEQ ID NO:88), N—Ac—CHAVC—SS—NH$_2$ (SEQ ID NO:89), N—Ac—S—CHAVC—S—NH$_2$ (SEQ ID NO:90), N—Ac—CHAVC-T-NH$_2$ (SEQ ID NO:91), N—Ac—CHAVC-E-NH$_2$ (SEQ ID NO:92), N—Ac—CHAVC-D-NH$_2$ (SEQ ID NO:93), N—Ac—CHAVYC—NH$_2$ (SEQ ID NO:94), CH$_3$—SO$_2$—HN—CHAVC—Y—NH$_2$ (SEQ ID NO:95), CH$_3$—SO$_2$—HN—CHAVC—NH$_2$ (SEQ ID NO:96), HC(O)—HN—CHAVC—NH$_2$ (SEQ ID NO:96), N—Ac—CHAVPen-NH$_2$ (SEQ ID NO:97), N—Ac-PenHAVC—NH$_2$ (SEQ ID NO:98), N—Ac—CHAVPC—NH$_2$ (SEQ ID NO:99) and derivatives thereof (e.g., in which terminal modifications are varied). In addition, a preferred modulating agent may comprise one or more non-classical cadherin CAR sequences, such as the sequence RGD, which is bound by integrins, the N-CAM CAR sequence KYSFNYDGSE (SEQ ID NO:53) and/or a cadherin-related neuronal receptor CAR sequence. As noted above, such additional sequence(s) may be separated from the HAV sequence via a linker.

Alternatively, a separate modulator of integrin and/or N-CAM mediated cell adhesion may be administered in conjunction with the modulating agent(s), either within the same pharmaceutical composition or separately. For such aspects, administration may be via encapsulation into a delivery vehicle such as a liposome, using standard techniques, and injection into, for example, the carotid artery. Alternatively, a modulating agent may be linked to a disrupter of the blood-brain barrier. In general dosages range as described above.

Other aspects of the present invention provide methods that employ antibodies raised against the modulating agents for diagnostic and assay purposes. Such polyclonal and monoclonal antibodies may be raised against a cyclic peptide using conventional techniques known to those of ordinary skill in the art. See, e.g., Harlow and Lane, *Antibodies: A Laboratory Manual*, Cold Spring Harbor Laboratory, 1988. In one such technique, an immunogen comprising the cyclic peptide is initially injected into any of a wide variety of mammals (e.g., mice, rats, rabbits, sheep or goats). Because of its small size, the cyclic peptide should be joined to a carrier protein, such as bovine serum albumin or keyhole limpet hemocyanin. Following one or more injections, the animals are bled periodically. Polyclonal antibodies specific for the cyclic peptide may then be purified from such antisera by, for example, affinity chromatography using the polypeptide coupled to a suitable solid support.

Monoclonal antibodies specific for the cyclic peptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the immunogen. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Cyclic peptides may also be used to generate monoclonal antibodies, as described above, that are specific for particular cadherins (e.g., antibodies that bind to E-cadherin, but do not bind significantly to N-cadherin, or vise versa). Such antibodies may generally be used for therapeutic, diagnostic and assay purposes.

Assays typically involve using an antibody to detect the presence or absence of a cadherin (free or on the surface of a cell), or proteolytic fragment containing the EC1 domain in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target cadherin, or a proteolytic fragment containing the EC1 domain, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody, and as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyinylchloride. The antibody may be immobilized on the solid support using a variety of techniques known to those in the art, which are amply described in the patent and scientific literature.

In certain embodiments, the assay for detection of a cadherin in a sample is a two-antibody sandwich assay. This assay may be performed by first contacting an antibody that has been immobilized on a solid support, commonly the well of a microtiter plate, with the biological sample, such that the cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme, dye, radionuclide, luminescent group, fluorescent group or biotin) capable of binding to a different site on the cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, cyclic peptides or antibodies thereto may be used to facilitate cell identification and sorting in vitro or imaging in vivo, permitting the selection of cells expressing different cadherins (or different cadherin levels). Preferably, the cyclic peptide(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a cyclic peptide or antibody linked to a fluorescent marker, such as fluorescein, is contacted with the cells, which are then analyzed by fluorescence activated cell sorting (FACS).

As noted above, in addition to diagnostic and assay purposes, antibodies as described herein may be used in vitro or in vivo to modulate cell adhesion. Within certain embodiments, antibodies may be used within methods in which enhanced cell adhesion is desired, as described above. For example, antibodies may be used within the above methods for enhancing and/or directing neurite outgrowth in vitro or in vivo. Antibodies may be used within the lumen of a tubular nerve guide or may be attached to a fiber nerve guide, suture or other solid support and used as described above for cyclic peptides. Antibody dosages are sufficient to enhance or direct neurite outgrowth, and will vary with the method of administration and the condition to be treated.

Antibodies may also be used as a "biological glue," as described above to bind multiple cadherin-expressing cells within a variety of contexts, such as to enhance wound healing and/or reduce scar tissue, and/or to facilitate cell adhesion in skin grafting or prosthetic implants. In general, the amount of matrix-linked antibody administered to a wound, graft or implant site varies with the severity of the wound and/or the nature of the wound, graft, or implant, but may vary as discussed above. Antibodies may also be linked to any of a variety of support materials, as described above, for use in tissue culture or bioreactors.

Within certain embodiments, antibodies (or, preferably, antigen-binding fragments thereof) may be used in situations where inhibition of cell adhesion is desired. Such antibodies or fragments may be used, for example, for treatment of demyelinating diseases, such as MS, or to inhibit interactions between tumor cells, as described above. The use of Fab fragments is generally preferred.

The following Examples are offered by way of illustration and not by way of limitation.

EXAMPLES

Example 1

Preparation of Representative Cyclic Peptides

This Example illustrates the solid phase synthesis of representative cyclic peptides.

Peptides were generally assembled on methylbenzhydrylamine resin (MBHA resin) for the C-terminal amide peptides. The traditional Merrifield resins were used for any C-terminal acid peptides. Bags of a polypropylene mesh material were filled with the resin and soaked in dichloromethane. The resin packets were washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane was added to activate the coupling reaction. The bottle was shaken for one hour to ensure completion of the reaction. The reaction mixture was discarded and the packets washed with DMF. The N-α-Boc was removed by acidolysis using a 55% TFA in dichloromethane for 30 minutes leaving the TFA salt of the α-amino group. The bags were washed and the synthesis completed by repeating the same procedure while substituting for the corresponding amino acid at the coupling step. Acetylation of the N-terminal was performed by reacting the peptide resins with a solution of acetic anhydride in dichloromethane in the presence of diisopropylethylamine. The peptide was then side-chain deprotected and cleaved from the resin at 0° C. with liquid HF in the presence of anisole as a carbocation scavenger.

The crude peptides were purified by reversed-phase high-performance liquid chromatography. Purified linear precursors of the cyclic peptides were solubilized in 75% acetic acid at a concentration of 2–10 mg/mL. A 10% solution of iodine in methanol was added dropwise until a persistent coloration was obtained. A 5% ascorbic acid solution in water was then added to the mixture until discoloration. The disulfide bridge containing compounds were then purified by HPLC and characterized by analytical HPLC and by mass spectral analysis.

N—Ac—CHAVC—NH$_2$ (SEQ ID NO:96) was synthesized on a 396–5000 Advanced ChemTech synthesizer using a Rink resin (4-(2',4'-Dimethoxyphenyl-Fmoc-aminomethyl)-phenoxy resin), which provided C-terminal amides using Fmoc chemistries. The Fmoc protecting group on the resin was removed with piperidine and coupling of the amino acids to the resin initiated. Two coupling reactions in NMP (N-methylpyrrolidinone) per amino acid were performed. The first coupling was carried out using DIC (diisopropylcarbodiimide) and the second coupling used HBTU (O-benzotriazole-N,N,N',N',-tetramethyluronium hexafluorophosphate) in the presence of DIPEA (diisopropylethylamine). Both couplings were done in the presence of HOBt (hydroxybenzotriazole) with the exception of histidine and the final cysteine. The trityl protecting group of the imidazole side chain of histidine is not stable in the presence of HOBt. Acetylation of the free amine on the N-terminus was carried out with acetic anhydride in NMP in the presence of DIPEA. The linear peptide was then cleaved from the resin with TFA in dichloromethane. This procedure also removed the trityl protecting group on the imidazole side chain of histidine. The crude linear peptide amide was then cyclized using chlorosilane-sulfoxide oxidation method to give the disulfide peptide. The crude cyclic peptide was purified using reverse-phase liquid chromatography. N—Ac—CHAVC—Y—NH$_2$ (SEQ ID NO:84) was synthesized using the same procedure, except that the cleavage cocktail (TFA, Dichloromethane) will also remove the OtBu protecting group of tyrosine.

Example 2

Disruption of the Ability of Mouse Cerebellar Neurons to Extend Neurites

Three cell adhesion molecules, N-cadherin, N-CAM and L1, are capable of regulating neurite outgrowth (Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell. Neurosci.* 8:99–111, 1994; Safell et al., *Neuron* 18:231–242, 1997). Neurons cultured on monolayers of 3T3 cells that have been transfected with cDNAs encoding N-cadherin, N-CAM or L1 extend longer neurites than neurons cultured on 3T3 cells not expressing these cell adhesion molecules. This Example illustrates the use of a representative cyclic peptide to inhibit neurite outgrowth.

Neurons were cultured on monolayers of 3T3 cells transfected with cDNA encoding N-cadherin essentially as described by Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell. Neurosci.* 8:99–111, 1994; Safell et al., *Neuron* 18:231–242, 1997. Briefly, monolayers of control 3T3 fibroblasts and 3T3 fibroblasts that express N-cadherin were established by overnight culture of 80,000 cells in individual wells of an 8-chamber well tissue culture slide. 3000 cerebellar neurons isolated from post-natal day 3 mouse brains were cultured for 18 hours on the various monolayers in control media (SATO/2%FCS), or media supplemented with various concentrations of the cyclic peptide N—Ac—CHAVC—NH$_2$ (SEQ ID NO:96) or a control peptide without the HAV sequence (N—Ac—CHGVC—NH$_2$; SEQ ID NO:11). The cultures were then fixed and stained for GAP43, which specifically binds to the neurons and their neurites. The length of the longest neurite on each GAP43 positive neuron was then measured by computer assisted morphometry.

Figure 22:
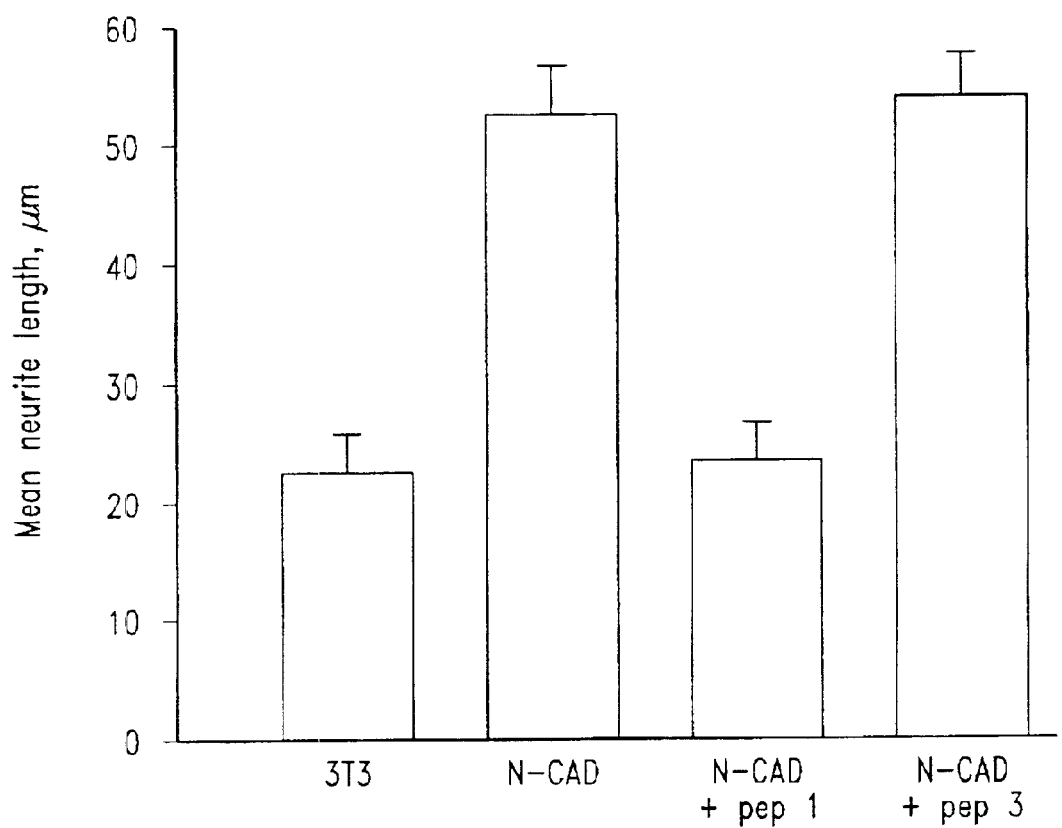
FIG. 22 is a bar graph showing the effect of N—Ac—CHAVC—NH₂ (SEQ ID NO:96) and N—Ac—CHGVC—NH₂ (SEQ ID NO:11) on N-cadherin-mediated neurite outgrowth. Mean neurite length is shown for cerebellar neurons cultured for 14 hours on monolayers of control 3T3 cells (unshaded), on N-cadherin expressing 3T3 cells (diagonal rising right), on N-cadherin expressing 3T3 cells in media supplemented with N—Ac—CHAVC—NH₂ (SEQ ID NO:96; diagonal cross hatch) and on N-cadherin expressing 3T3 cells in media supplemented with N—Ac—CHGVC—NH₂ (SEQ ID NO:11; diagonal rising left). The results show the mean length of the longest neurite measured in a single representative experiment, and the error bars show the s.e.m.

As shown in FIG. 22, culture for 18 hours with N—Ac—CHAVC—NH$_2$ (SEQ ID NO:96) at a concentration of 500 µg/mL inhibited neurite outgrowth on 3T3 cells expressing N-cadherin, whereas the cyclic peptide N—Ac—CHGVC—NH$_2$ (SEQ ID NO:11) (also at a concentration of 500 µg/ml) had no effect on this process. Furthermore, the cyclic peptide N—Ac—CHAVC—NH$_2$ (SEQ ID NO:96) (used at a concentration of 500 µg/ml) did not inhibit neurite outgrowth on 3T3 cells not expressing N-cadherin, N-CAM, or L1 (control cells), thus indicating that the peptide is not toxic and that it has no non-specific effects on neurite outgrowth (FIG. 22). These data also indicate that the peptide does not effect integrin function.

Figure 4:
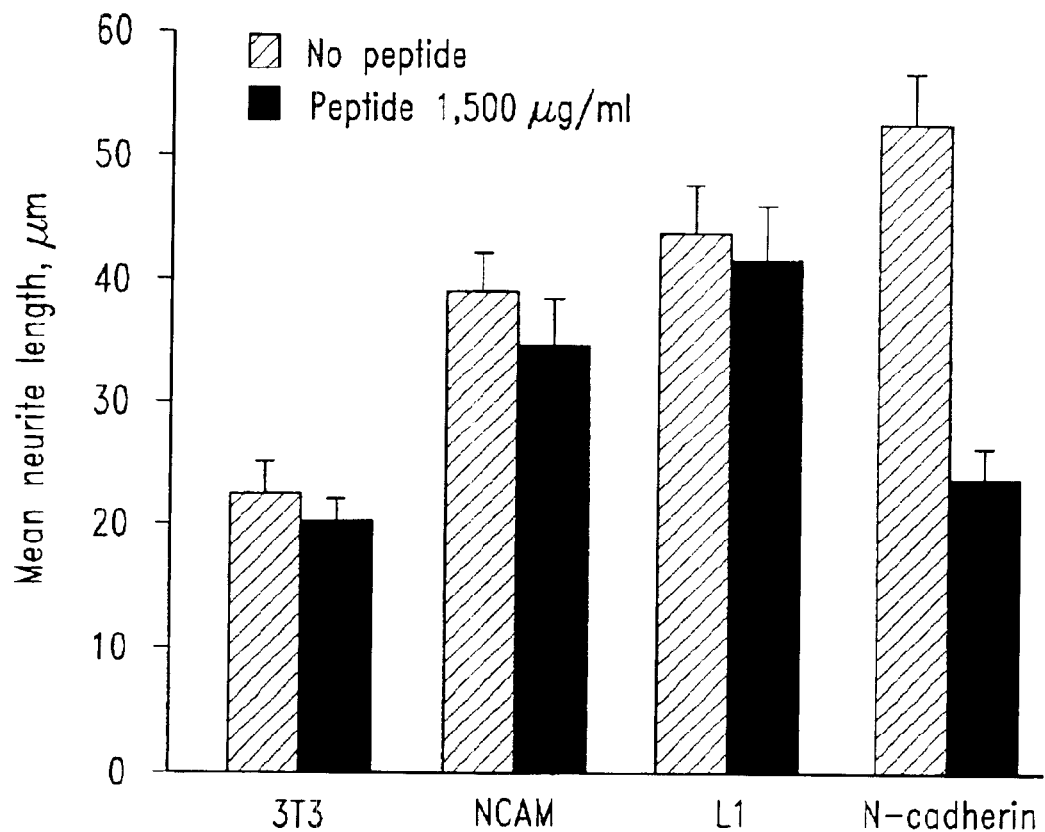
FIG. 4 is a histogram depicting the mean neurite length in microns for neurons grown in the presence (solid bars) or absence (cross-hatched bars) of 500 µg/mL of the representative cyclic peptide N—Ac—CHAVC—NH$_2$ (SEQ ID NO:96). In the first pair of bars, neurons were grown on a monolayer of untransfected 3T3 cells. In the remaining columns, the mean neurite length is shown for neurons cultured on 3T3 cells transfected with cDNA encoding N-CAM (second pair of bars), L1 (third pair of bars) or N-cadherin (fourth pair of bars).
Figure 23:
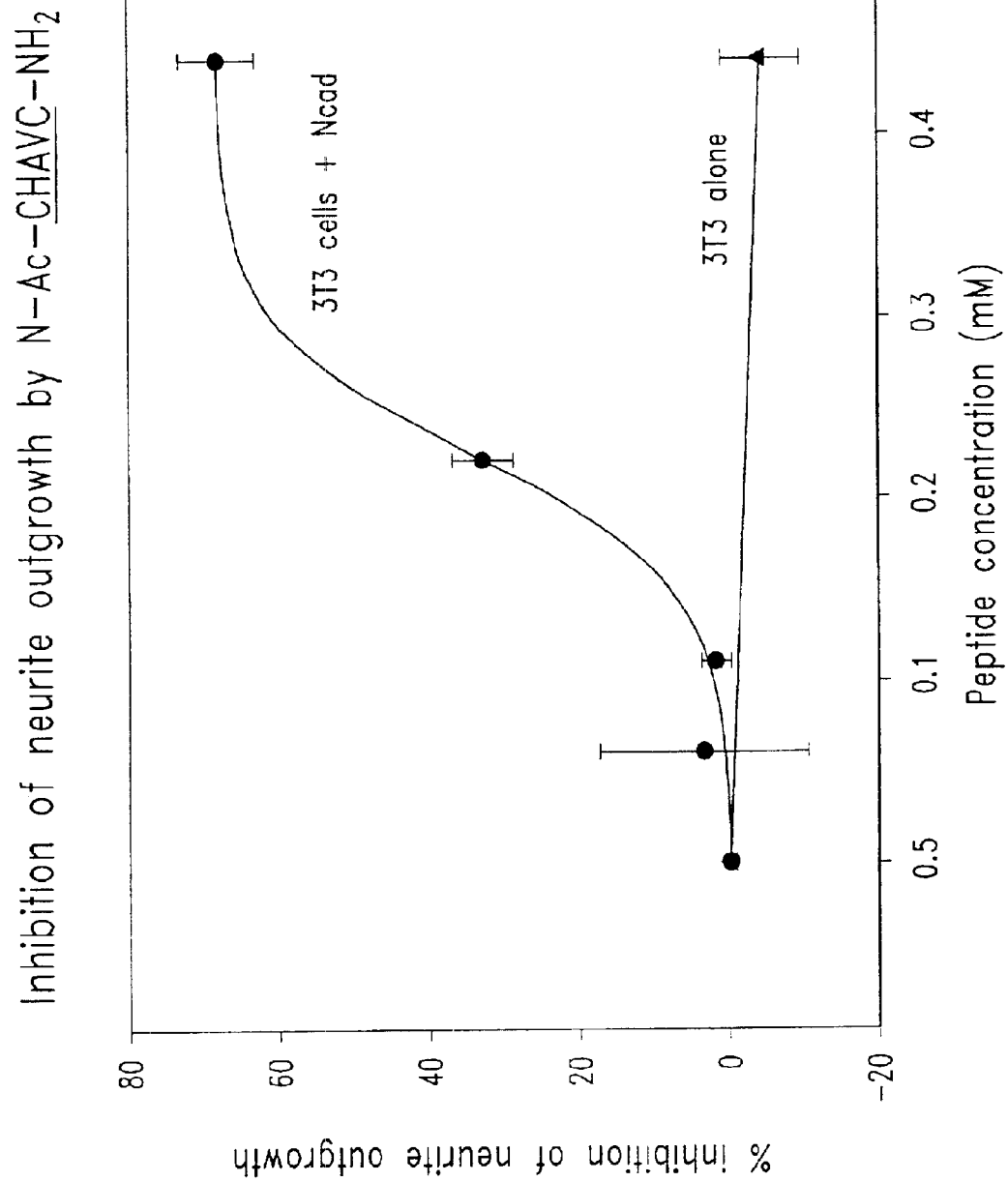
FIG. 23 is a graph showing dose-response curves that illustrate the inhibition of neurite outgrowth over both 3T3 cells and N-cadherin expressing 3T3 cells in the presence of increasing concentrations of N—Ac—CHAVC—NH₂ (SEQ ID NO:96). The peptide had no effect on the basal growth over 3T3 cells. The EC₅₀ value was determined to be 0.22 mM.

A dose-response study demonstrated that N—Ac—CHAVC—NH$_2$ (SEQ ID NO:96) significantly inhibited neurite outgrowth on 3T3 cells expressing N-cadherin at a concentration of 50 µg/mL, and completely inhibited neurite outgrowth on these cells at a concentration of 500 µg/mL (FIG. 23). Finally, N—Ac—CHAVC—NH$_2$ (SEQ ID NO:96) (used at a concentration of 500 µg/mL) did not inhibit neurite outgrowth on 3T3 cells expressing either N-CAM or L1 (FIG. 4). These results indicate that the peptide N—Ac—CHAVC—NH$_2$ (SEQ ID NO:96) specifically inhibits the function of N-cadherin. Collectively, the results obtained from these studies demonstrate that N—Ac—CHAVC—NH$_2$ (SEQ ID NO:96) is an effective inhibitor of neurite outgrowth by virtue of its ability to disrupt N-cadherin function.

Example 3

Disruption of Bovine Endothelial Cell Adhesion

This Example illustrates the use of representative cyclic peptides to disrupt adhesion of endothelial cells, which express N-cadherin.

Bovine pulmonary artery endothelial cells were harvested by sterile ablation and digestion in 0.1% collagenase (type II; Worthington Enzymes, Freehold, N.J.). Cells were maintained in Dulbecco's minimum essential medium (Clonetics, San Diego, Calif.) supplemented with 10% fetal calf serum (Atlantic Biologicals, Nor cross, GA) and 1% antibiotic-antimycotic at 37° C. in 7% CO$_2$ in air. Cultures were passaged weekly in trypsin-EDTA (Gibco, Grand Island, N.Y.) and seeded onto tissue culture plastic at 20,000 cells/cm$^2$ for all experiments. Endothelial cultures were used at 1 week in culture, which is approximately 3 days after culture confluency was established. The cells used in all protocols were between 4th passage and 10th passage. The cells were seeded onto coverslips and treated 30 minutes with N—Ac—CHAVC—NH$_2$ (SEQ ID NO:96) or N—Ac—CHGVC—NH$_2$ (SEQ ID NO:11) at 500 µg/ml and then fixed with 1% paraformaldehyde.

Figure 5A:
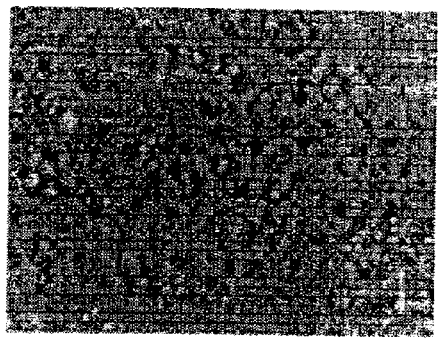
FIGS. 5A–5C are photographs showing monolayer cultures of bovine endothelial cells in the presence (FIG. 5A)
Figure 5B:
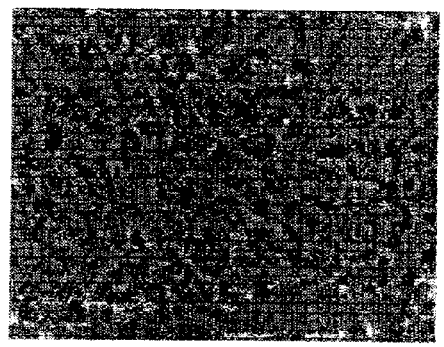
Figure 5C:
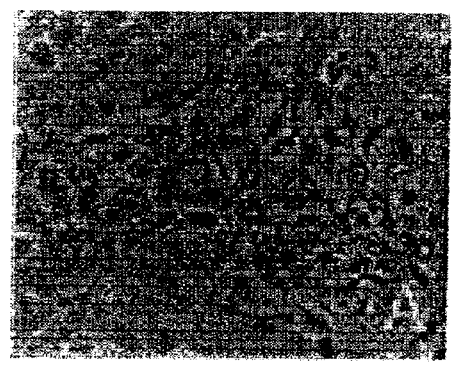

The peptide N—Ac—CHAVC—NH$_2$ (SEQ ID NO:96) disrupted the endothelial cell monolayer within 30 minutes after being added to the culture medium, whereas N—Ac—CHGVC—NH$_2$ (SEQ ID NO:11) had no affect on the cells (FIG. 5). Endothelial cell morphology was dramatically affected by N—Ac—CHAVC—NH$_2$ (SEQ ID NO:96), and the cells retracted from one another and became nonadherent. These data demonstrate that N—Ac—CHAVC—NH$_2$ (SEQ ID NO:96) is capable of inhibiting endothelial cell adhesion.

Figure 6A:
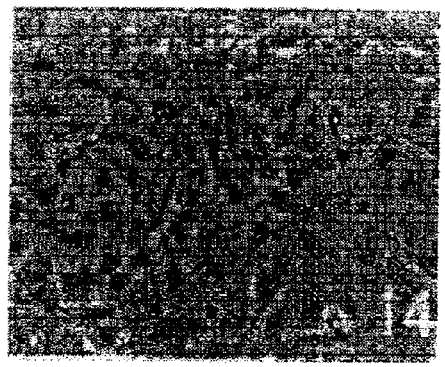
FIGS. 6A–6C are photographs showing monolayer cultures of bovine endothelial cells in the presence (FIG. 6A) and absence (FIG. 6C) of a representative cyclic peptide or in the presence of an inactive control peptide (FIG. 6B).
Figure 6B:
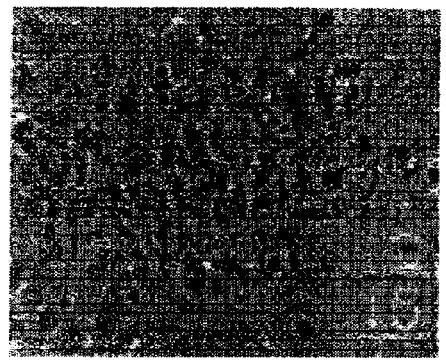
Figure 6C:
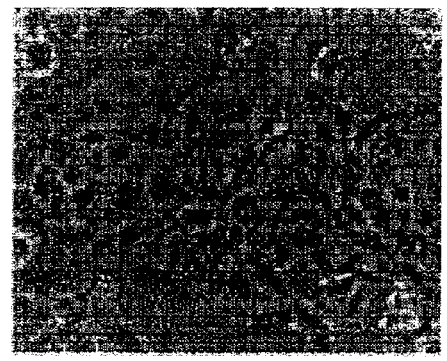
Figure 7A:
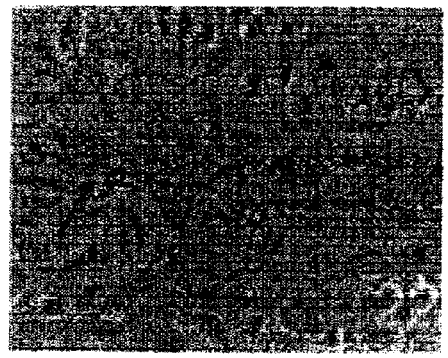
FIGS. 7A–7C are photographs showing monolayer cultures of bovine endothelial cells in the presence (FIG. 7A) and absence (FIG. 7C) of a representative cyclic peptide or in the presence of an inactive control peptide (FIG. 7B).
Figure 7B:
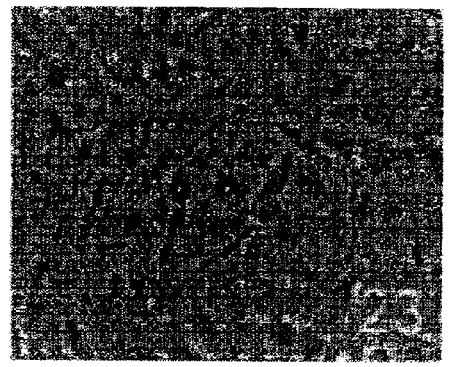
Figure 7C:
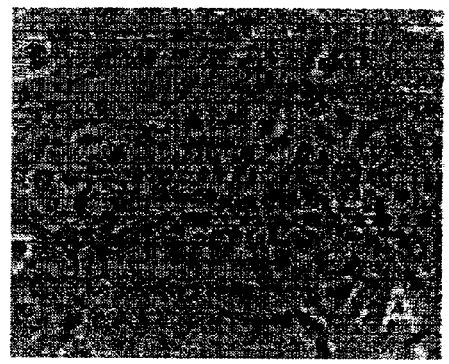
Figure 8A:
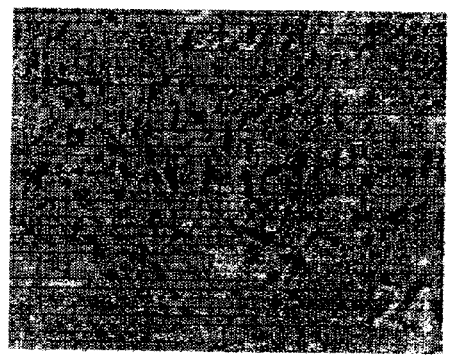
FIGS. 8A–8C are photographs showing monolayer cultures of bovine endothelial cells in the presence (FIG. 8A) and absence (FIG. 8C) of a representative cyclic peptide or in the presence of an inactive control peptide (FIG. 8B).
Figure 8B:
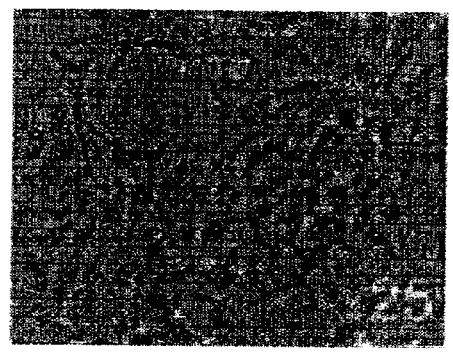
Figure 8C:
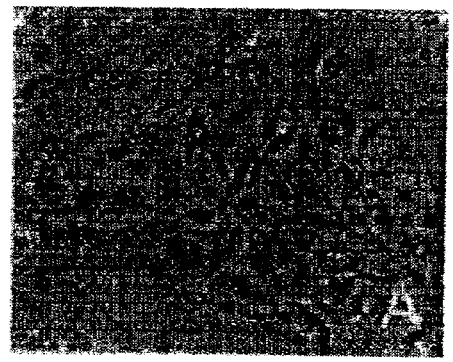

Under the same conditions, the cyclic peptides H—CHAVC—NH$_2$ (SEQ ID NO:96), N—Ac—CAHAVDIC—NH$_2$ (SEQ ID NO:24) (FIG. 6) and N—Ac—CHAVSC—NH$_2$ (SEQ ID NO:38) had no effect on endothelial cell morphology, indicating that not all cyclic HAV-containing peptides are capable of disrupting endothelial cell adhesion at a concentration of 500 µg/mL. It is not unexpected that the potencies of individual cyclic peptides will vary The cyclic peptide N—Ac—CAHAVDC—NH$_2$ (SEQ ID NO:26; FIG. 7) had a slight effect while N—Ac—CSHAVSSC—NH$_2$ (SEQ ID NO:42; FIG. 8) disrupted the endothelial cell monolayer and caused the cells to retract from one another.

Example 4

Disruption of Human Ovarian Cancer Cell Adhesion

This Example illustrates the use of a representative cyclic peptide to disrupt adhesion of human ovarian cancer cells.

The human ovarian cancer cell line SKOV3 (ATCC #HTB-77) expresses N-cadherin. SKOV3 cells were cultured in a modified MEM-based media containing 10% FCS. Cells were grown in T-250 culture flasks and maintained by periodic subculturing. Cyclic peptides were tested on cells grown in individual wells of 96-well culture dishes (surface area of each well was 0.32 cm$^2$). Cells were harvested from flasks and seeded at a density of 50,000 cells per well in 0.1 mL media containing the cyclic peptides at concentrations of 1, 0.1, or 0.01 mg/mL, or in the absence of cyclic peptide. Media control wells were also established. Cultures were evaluated periodically by microscopic examination under both bright field and phase contrast conditions. Cultures were maintained for 48 hours.

Figure 9A:
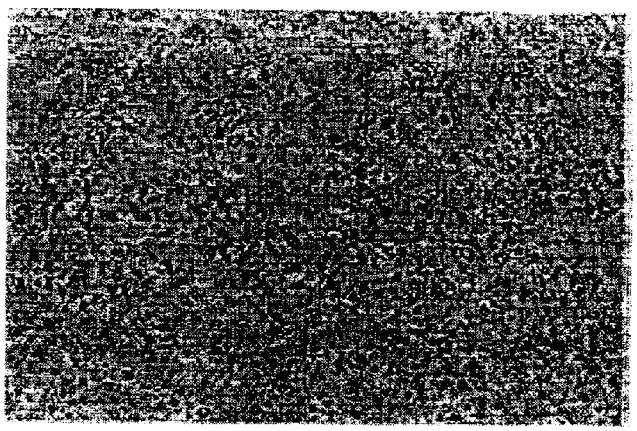
FIGS. 9A–9F are photographs showing monolayer cultures of human ovarian cancer cells (SKOV3) in the presence (FIGS. 9A and D–F) and absence (FIG. 9C) of a representative cyclic peptide or in the presence of an inactive control peptide (FIG. 9B).
Figure 9B:
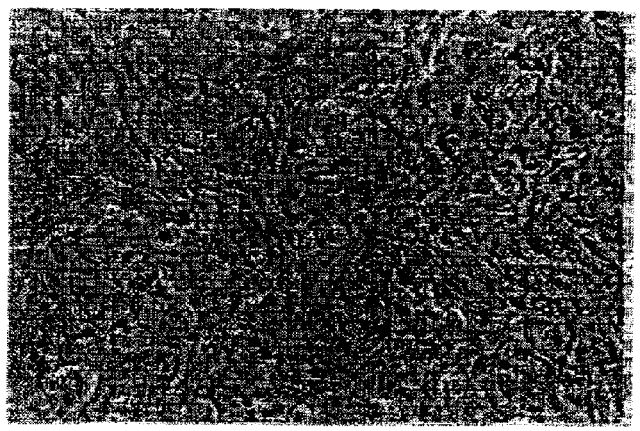
Figure 9C:
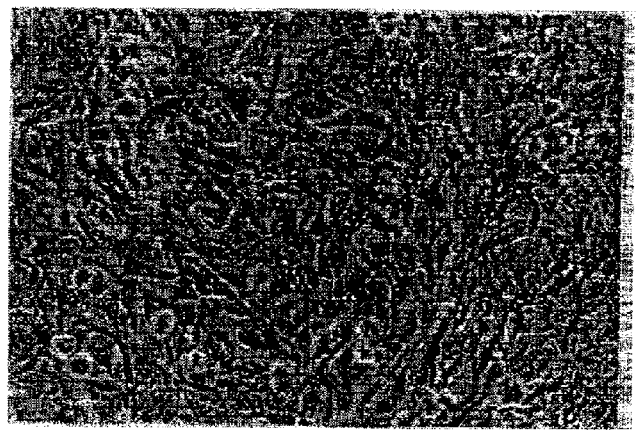
Figure 9D:
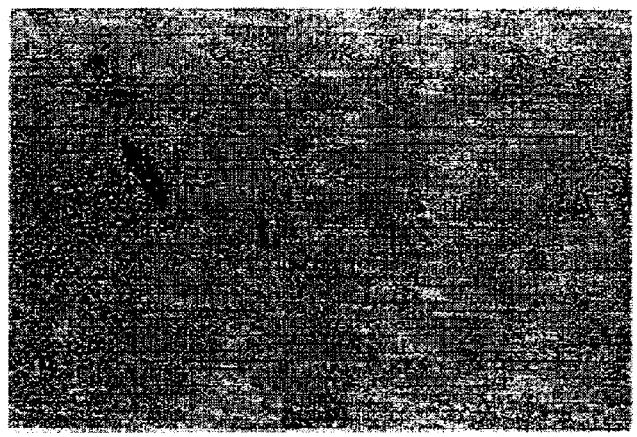
Figure 9E:
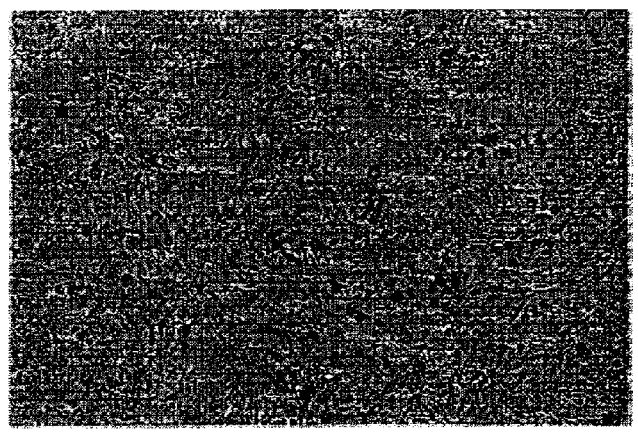
Figure 9F:
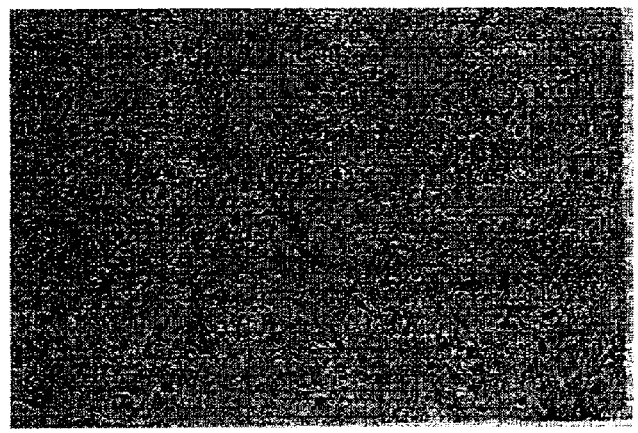
Figure 10A:
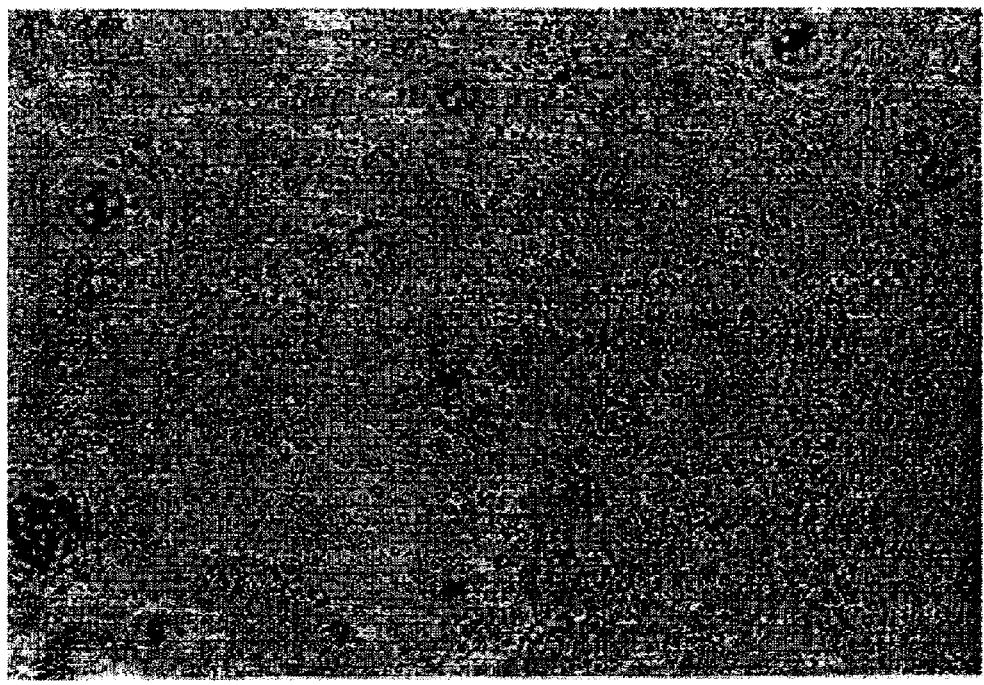
FIGS. 10A and 10B are photographs showing monolayer cultures of human ovarian cancer cells (SKOV3) 24 hours after exposure to 500 μg/mL of the representative cyclic peptide N—Ac—CHAVC—NH$_2$ (SEQ ID NO:96) (FIG. 10A) or the control peptide N—Ac—CHGVC—NH$_2$ (SEQ ID NO:11) (FIG. 10B). Note that the SKOV3 cells round-up when cultured in the presence of 0.5 mg/ml N—Ac—CHAVC—NH$_2$ (SEQ ID NO:96).
Figure 10B:
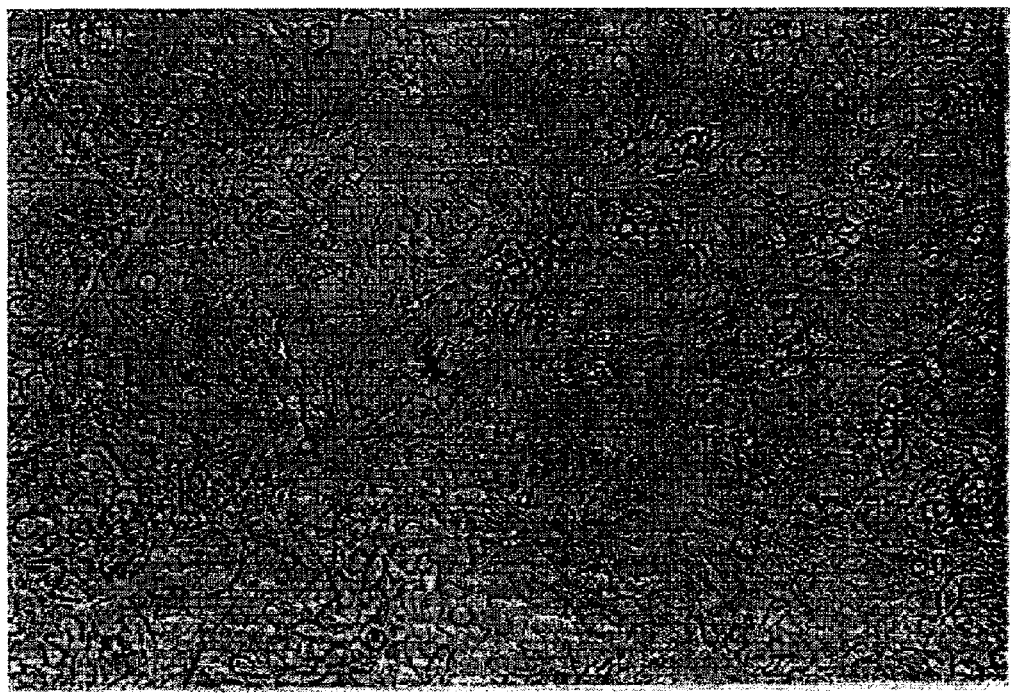

As shown in FIGS. 9A (compare to FIG. 9C) and 10A, the peptide N—Ac—CHAVC—NH$_2$ (SEQ ID NO:96) (final concentration of 1 mg/mL media) disrupted SKOV3 cell adhesion within 24 hours, whereas the control N—Ac—CHGVC—NH$_2$ (SEQ ID NO:11) had no affect on cell adhesion (FIGS. 9B and 10B). The effect of different amounts of N—Ac—CHAVC—NH$_2$ (SEQ ID NO:96) after 48 hours is shown in FIGS. 9D–F. In the presence of N—Ac—CHGVC—NH$_2$, (SEQ ID NO:1) (FIGS. 9B and 10B) the SKOV3 cells formed tightly adherent monolayers. In contrast, the SKOV3 cells did not spread onto the substrata, nor did they form tightly adherent monolayers in the presence of N—Ac—CHAVC—NH$_2$ (SEQ ID NO:96; FIGS. 9A, 9D and 10A). These data demonstrate that N—Ac—CHAVC—NH$_2$ (SEQ ID NO:96) is capable of inhibiting the function of human N-cadherin.

Figure 37A:
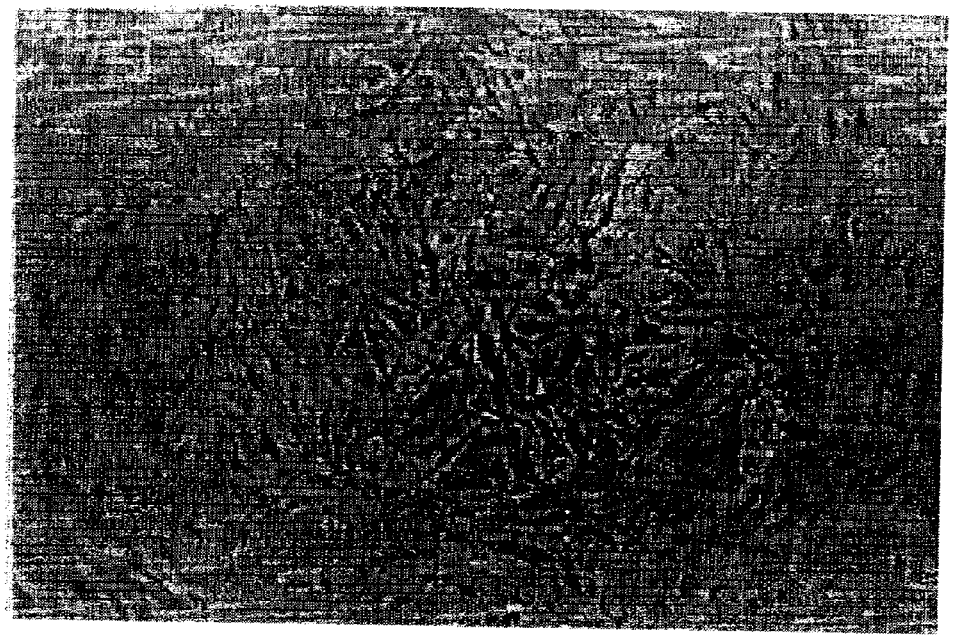
FIGS. 37A and 37B are photographs illustrating the effect of N—Ac—CHAVC—Y—NH$_2$ (SEQ ID NO:84) on SKOV3 cell adhesion. A confluent culture of SKOV3 cells was briefly trypsinated and counted using a hemacytometer. The cells were diluted to 5×10$^3$/mL in MEM (Gibco BRL) containing 10% FBS (Wisent). A 10 mg/mL solution of peptide was added directly to the media at a concentration of 1 mg/mL. The plate was incubated in a humidified chamber at 37° C. for 24 hours in 5% CO$_2$. Morphological changes were evaluated after 24 hours.
Figure 37B:
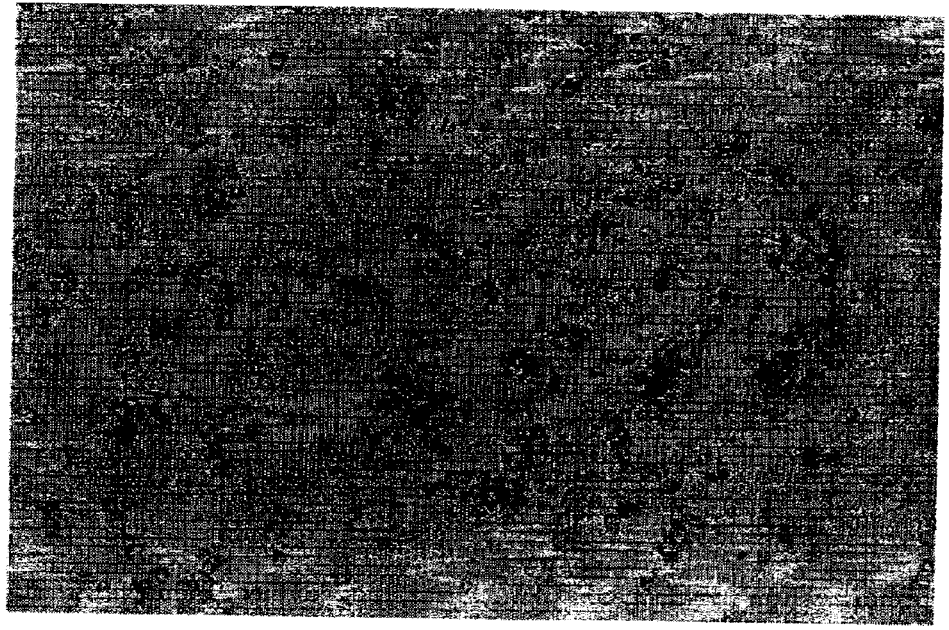
Figure 38A:
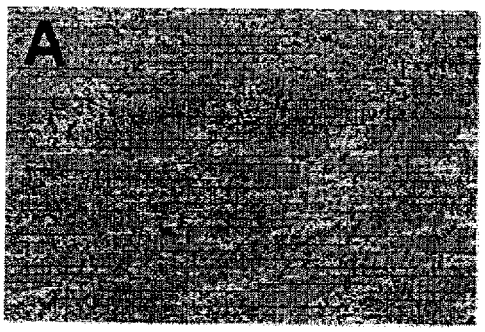
FIGS. 38A–38H are photographs illustrating the effect of the representative modulating agent N—Ac—CHAVC—NH$_2$ (SEQ ID NO:96) on apoptosis in human ovarian tumors grown in nude mice. The photographs show cross sections of tumors from mice treated with saline alone (FIGS. 38A, 38C, 38E and 38G) or with N—Ac—CHAVC—NH$_2$ (SEQ ID NO:96) (FIGS. 38B, 38D, 38F and 38H) once daily for 48 hours (FIGS. 38A–38B), 96 hours (FIGS. 38C–38D), 120 hours (FIGS. 38E–38F) or 168 hours (FIGS. 38G–38H), and sacrificed 24 hours after the last treatment. Cells stained brown are undergoing apoptosis. The magnification in each photograph was 10×.
Figure 38B:
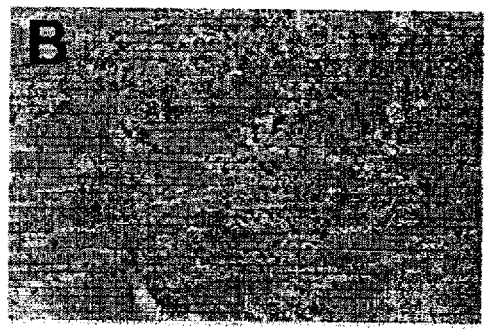
Figure 38C:
Figure 38D:
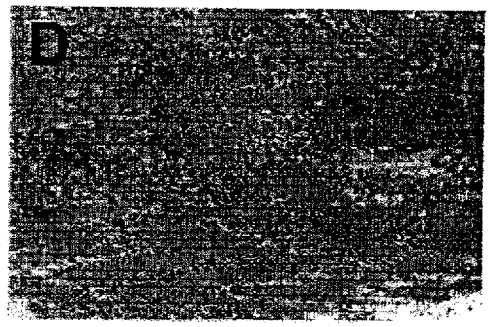
Figure 38E:
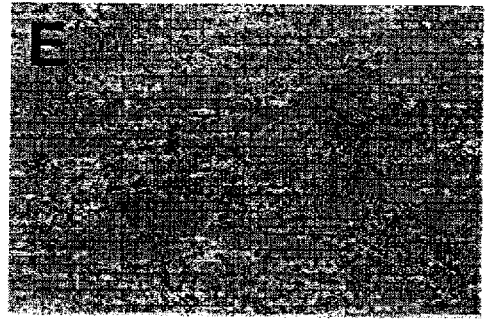
Figure 38F:
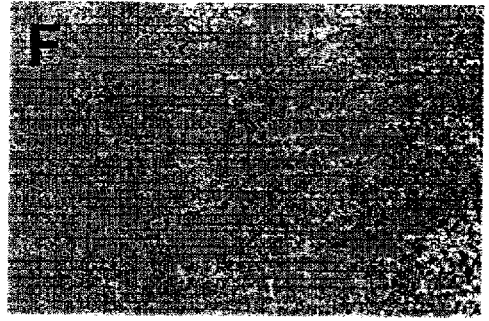
Figure 38G:
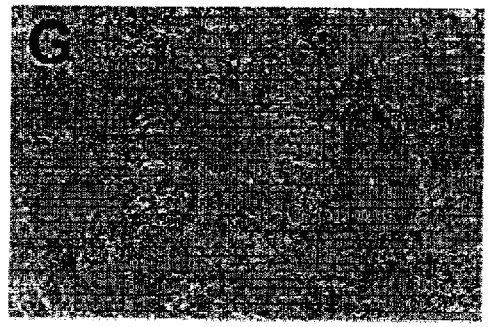
Figure 38H:
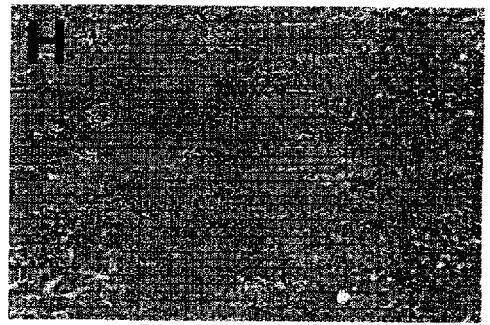
Figure 39A:
FIGS. 39A–39H are photographs illustrating the effect of the representative modulating agent N—Ac—CHAVC—NH$_2$ (SEQ ID NO:96) on apoptosis in human ovarian tumors grown in nude mice. The photographs show cross sections of tumors from mice treated with saline alone (FIGS. 39A, 39C, 39E and 39G) or with N—Ac—CHAVC—NH$_2$ (SEQ ID NO:96) (FIGS. 39B, 39D, 39F and 39H) once daily for 48 hours (FIGS. 39A–39B), 96 hours (FIGS. 39C–39D), 120 hours (FIGS. 39E–39F) or 168 hours (FIGS. 39G–39H), and sacrificed 24 hours after the last treatment. Cells stained brown are undergoing apoptosis. The magnification in each photograph was 40×.
Figure 39B:
Figure 39C:
Figure 39D:
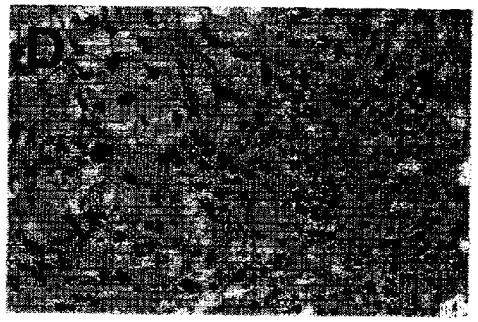
Figure 39E:
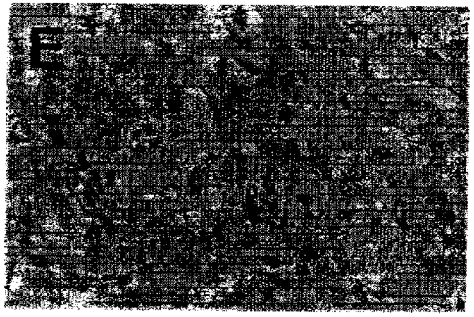
Figure 39F:
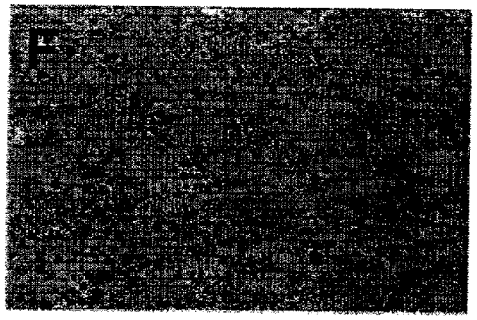
Figure 39G:
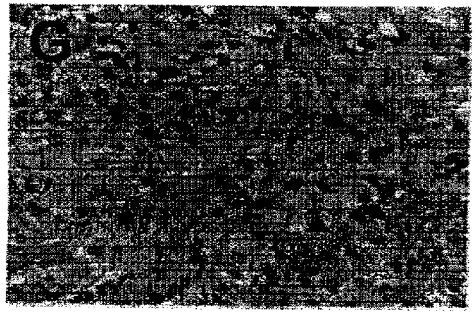
Figure 39H:
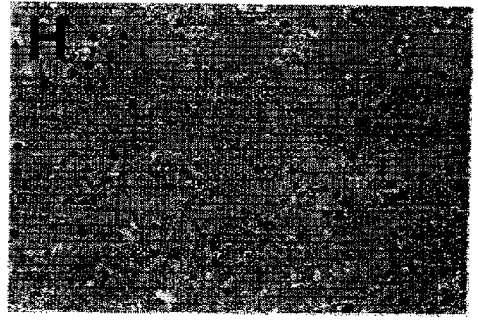

As shown in FIGS. 37A–37B, the cyclic peptide N—Ac—CHAVC—Y—NH$_2$ (SEQ ID NO:96) (final concentration of 1 mg/mL media) disrupted SKOV3 cell adhesion within 24 hours, whereas the control (vehicle alone (PBS)) had no effect on cell adhesion.

The cyclic peptides N—Ac—CAHAVDIC—NH$_2$ (SEQ ID NO:24), N—Ac—CAHAVDC—NH$_2$ (SEQ ID NO:26) and N—Ac—KHAVD-NH$_2$ (SEQ ID NO:12) were inactive in the SKOV3 cells, indicating that not all cyclic HAV-containing peptides are capable of disrupting epithelial cell adhesion at concentrations of 0.01–1 mg/mL It is not unexpected that the potencies of the cyclic peptides will vary.

Example 5

Disruption of Angiogenesis

Blood vessels are composed of adherent endothelial cells. This Example illustrates the use of a representative cyclic peptide to block angiogenesis (the growth of blood vessels from pre-existing blood vessels).

The chick chorioallantoic membrane assay was used to assess the effects of cyclic peptides on angiogenesis (Iruela-Arispe et al., *Molecular Biology of the Cell* 6:327–343, 1995). Cyclic peptides were embedded in a mesh composed of vitrogen at concentrations of 3, 17, and 33 µg/mesh. The meshes were then applied to 12-day-old chick embryonic chorioallantoic membranes. After 24 hours, the effects of the peptides on angiogenesis were assessed by computer assisted morphometric analysis.

The ability of representative cyclic peptides to inhibit angiogenesis is illustrated by the results presented in Table 2. For each concentration of cyclic peptide, the percent inhibition of angiogenesis (relative to the level of angiogenesis in the absence of cyclic peptide) is provided. Assays were performed in the presence (+) or absence (−) of 0.01 mM VEGF. For example, the cyclic peptide N—Ac—CHAVC—NH$_2$ (SEQ ID NO:96) inhibited angiogenesis by 46%, 51%, and 51% at concentrations of 3, 17, and 33 µg/mesh, respectively. The N-cadherin selective peptides N—Ac—CAHAVDIC—NH$_2$ (SEQ ID NO:24) and N—Ac—CAHAVDC—NH$_2$ (SEQ ID NO:26) also inhibited angiogenesis significantly. The E-cadherin selective cyclic peptides N—Ac—CHAVSC—NH$_2$ (SEQ ID NO:38) and N—Ac—CSHAVSSC—NH$_2$ (SEQ ID NO:42), as well as the scrambled peptide N—Ac—CVAHC—NH$_2$ (SEQ ID NO:18), were found to be relatively inactive in this assay.

TABLE 2

Percent Inhibition of Angiogenesis by Varying Concentrations of Cyclic Peptides

| Compound | Concentration, µg/mesh ± VEGF | | | | | |
|---|---|---|---|---|---|---|
| | 3(−) | 3(+) | 17(−) | 17(+) | 33(−) | 33(+) |
| H-CHAVC-NH$_2$ (SEQ ID NO: 96) | 11% | 27% | 13% | 34% | 17% | 35% |
| N—Ac-CHAVSC-NH$_2$ (SEQ ID NO: 38) | 11% | 17% | 12% | 16% | 17% | 19% |
| N—Ac-CVAHC-NH$_2$ (SEQ ID NO: 18) | −1% | 7% | 13% | 24% | 12% | 25% |
| N—Ac-CHAVC-NH$_2$ (SEQ ID NO: 96) | 12% | 46% | 22% | 51% | 28% | 51% |
| N—Ac-CAHAVDIC-NH$_2$ (SEQ ID NO: 24) | −1% | 21% | 15% | 37% | 33% | 49% |
| N—Ac-CAHAVDC-NH$_2$ (SEQ ID NO: 26) | 21% | 59% | 27% | 72% | 31% | 79% |
| N—Ac-CSHAVSSC-NH$_2$ (SEQ ID NO: 42) | 1% | −3% | −3% | 12% | 17% | 7% |

Example 6

Disruption of Normal Rat Kidney (NRK) Cell Adhesion

NRK cells express E-cadherin, and monolayer cultures of these cells exhibit a cobblestone morphology. This Example illustrates the ability of a representative cyclic peptide to disrupt NRK cell adhesion.

NRK cells (ATCC #1571-CRL) were plated at 10–20,000 cells per 35 mm tissue culture flasks containing DMEM with 10% FCS and sub-cultured periodically (Laird et al., *J. Cell Biol.* 131:1193–1203, 1995). Cells were harvested and replated in 35 mm tissue culture flasks containing 1 mm coverslips and incubated until 50–65% confluent (24–36 hours). At this time, coverslips were transferred to a 24-well plate, washed once with fresh DMEM and exposed to cyclic peptide solutions (N—Ac-CHAVC—NH$_2$ (SEQ ID NO:96) and N—Ac—CHGVC—NH$_2$ (SEQ ID NO:11)) at a concentration of 1 mg/mL for 24 hours. Fresh peptide solutions were then added and the cells were left for an additional 24 hours. Cells were fixed with 100% methanol for 10 minutes and then washed three times with PBS. Coverslips were blocked for 1 hour in 2% BSA/PBS and incubated for a further 1 hour in the presence of mouse anti-E-cadherin antibody (Transduction Labs, Lexington, Ky.; 1:250 dilution). Primary and secondary antibodies were diluted in 2% BSA/PBS. Following incubation in the primary antibody, coverslips were washed three times for 5 minutes each in PBS and incubated for 1 hour with donkey anti-mouse antibody conjugated to fluorescein (Jackson Immuno Research, West Grove, Pa.; diluted 1:200). Following a further wash in PBS (3×5 min) coverslips were mounted and viewed by confocal microscopy.

Figure 11A:
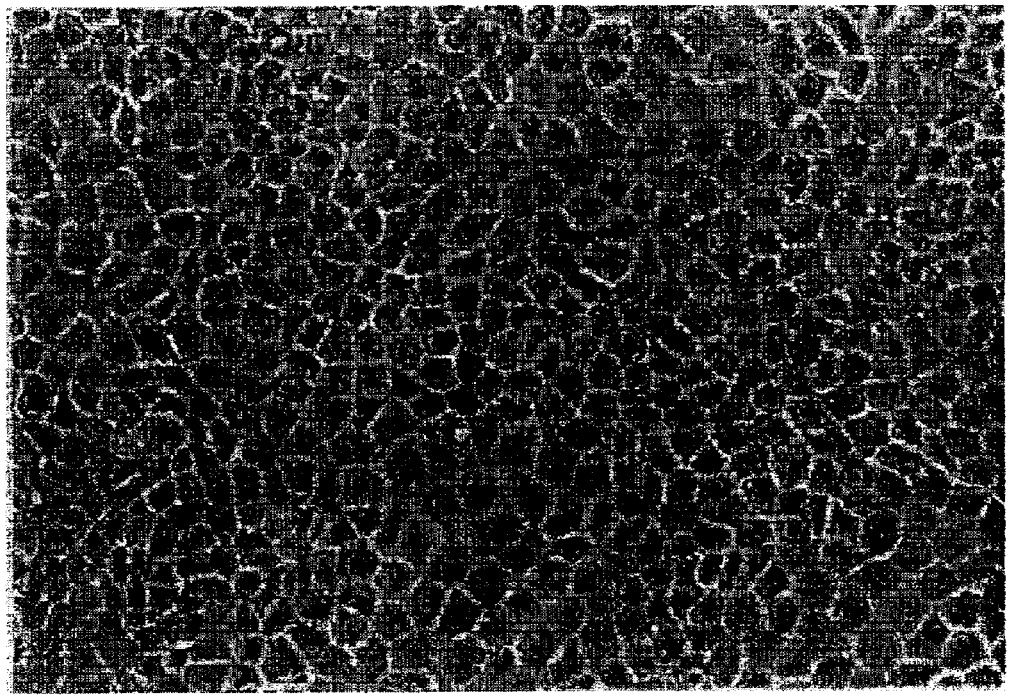
FIGS. 11A–11D are photographs of monolayer cultures of normal rat kidney (NRK) cells untreated (FIG. 11A) or after 48 hours of exposure to 1 mg/mL H—CHAVSC—OH (SEQ ID NO:38) (FIG. 11B), the control peptide N—Ac—CHGVC—NH$_2$ (SEQ ID NO:11), (FIG. 11C) or the representative cyclic peptide N—Ac—CHAVC—NH$_2$ (SEQ ID NO:96), (FIG. 11D). Note that NRK cells retract from one another when cultured in the presence of N—Ac—CHAVC—NH$_2$ (SEQ ID NO:96). Furthermore the NRK cells do not form cobblestone-like monolayers when exposed to this peptide.
Figure 11B:
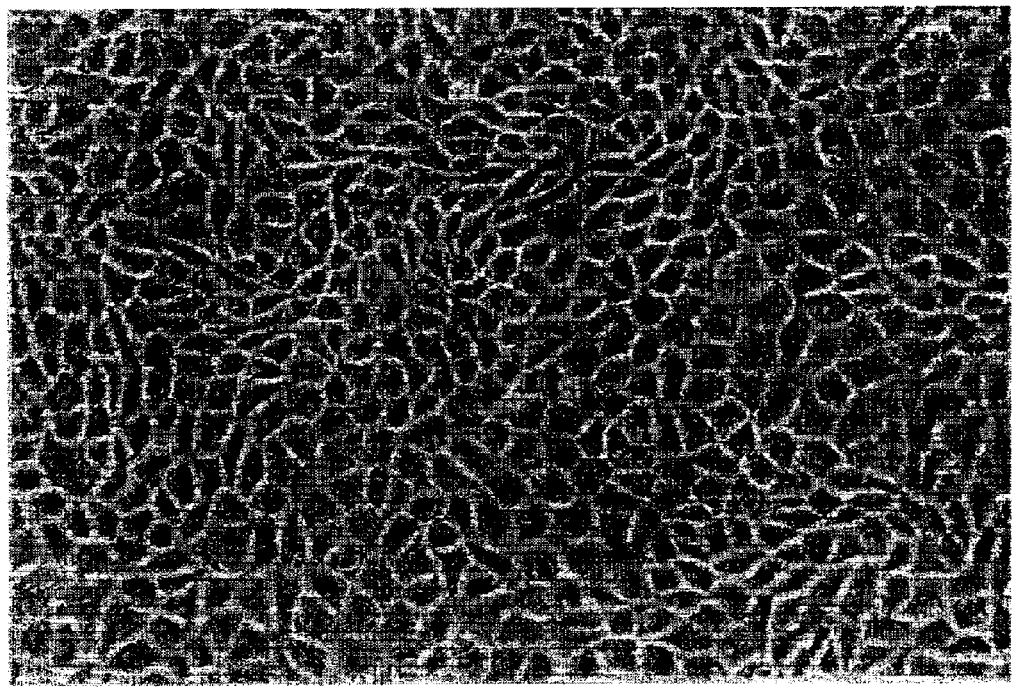
Figure 11C:
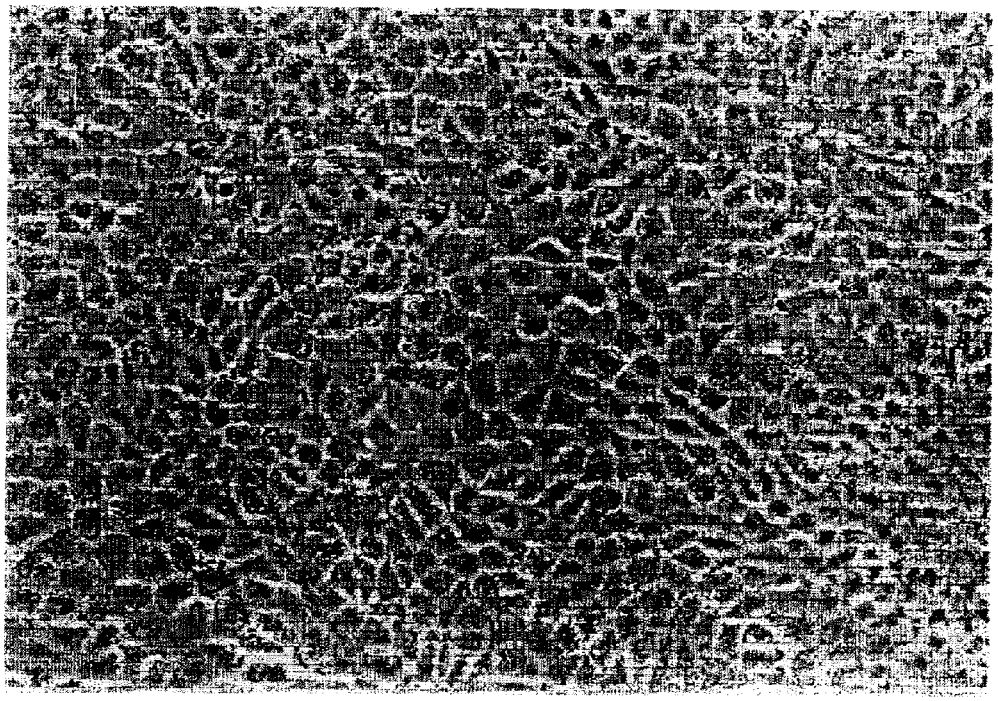
Figure 11D:
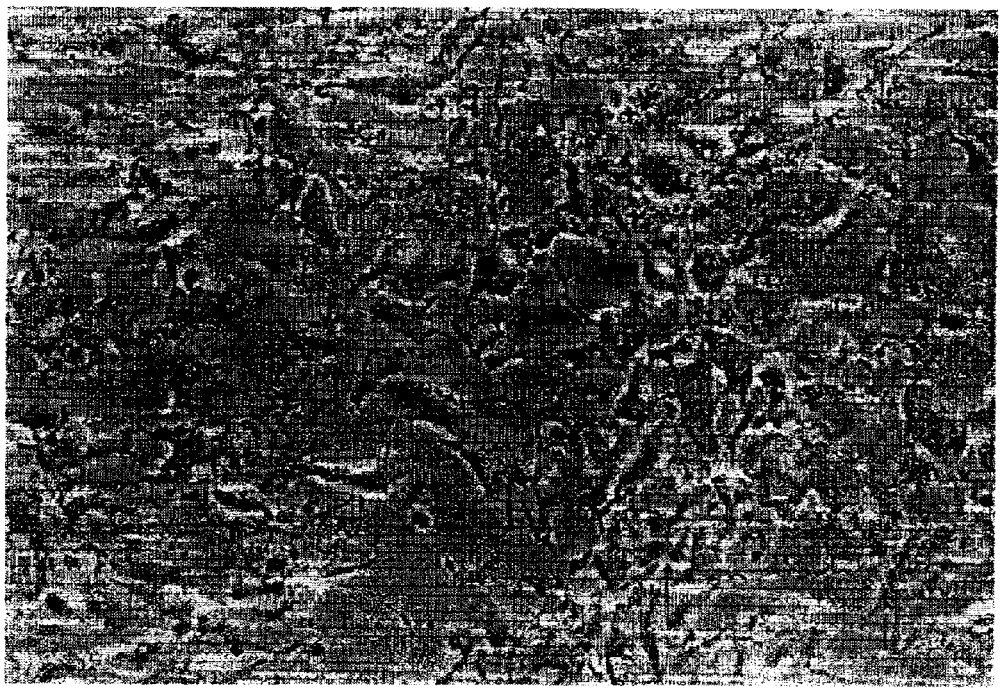
Figure 12A:
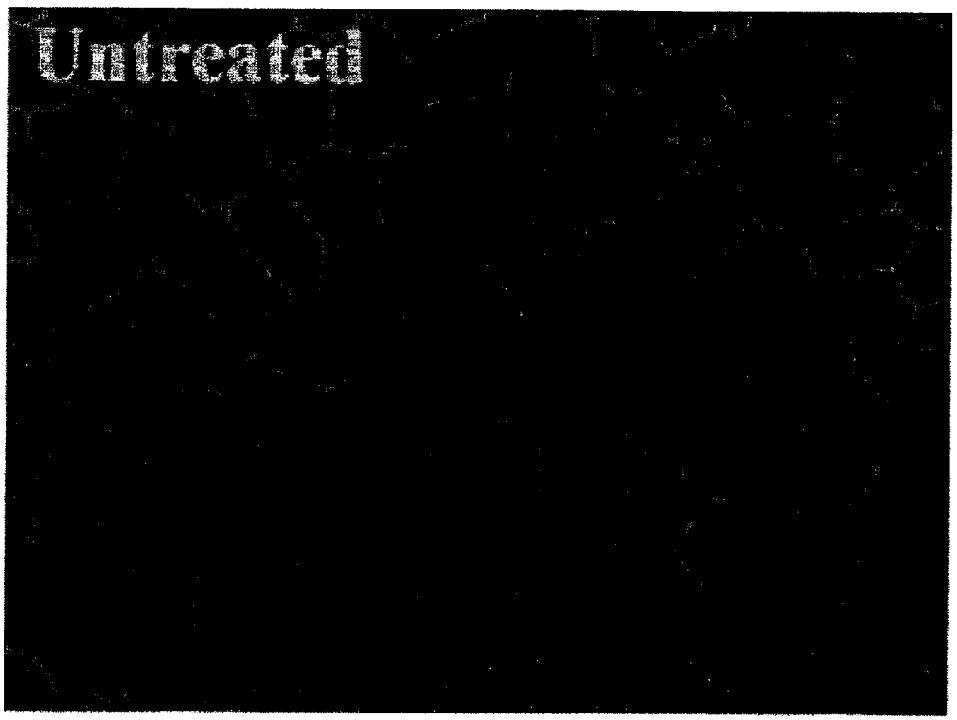
FIGS. 12A–12D are immunofluorescence photographs of the monolayer normal rat kidney (NRK) cultures shown in FIGS. 11A–D immunolabeled for E-cadherin.
Figure 12B:
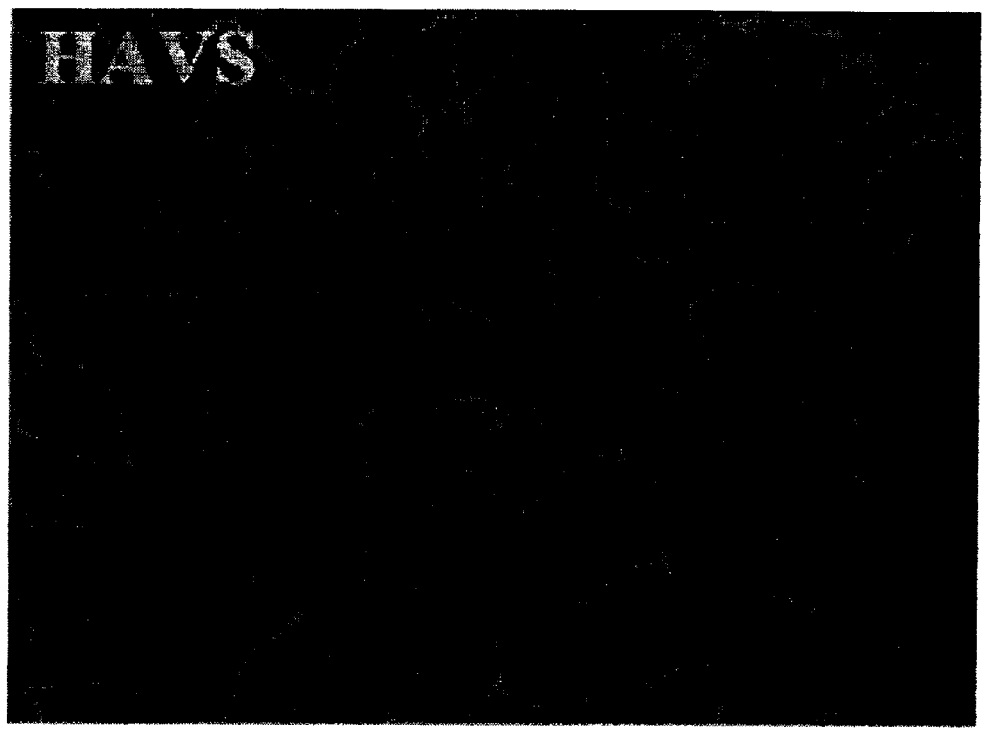
Figure 12C:
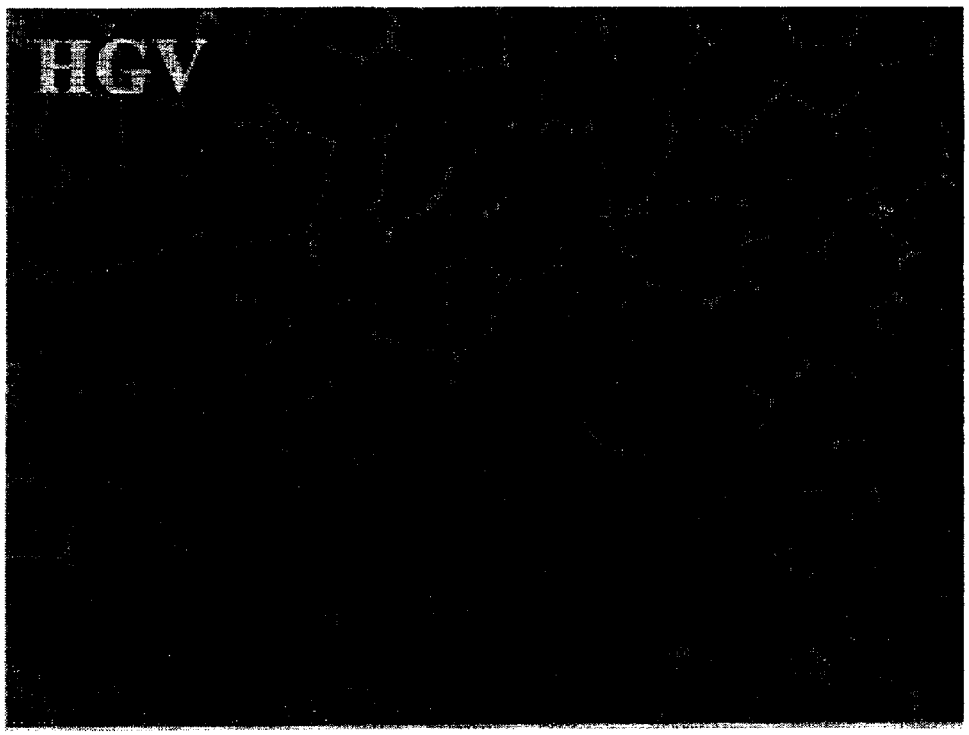
Figure 12D:
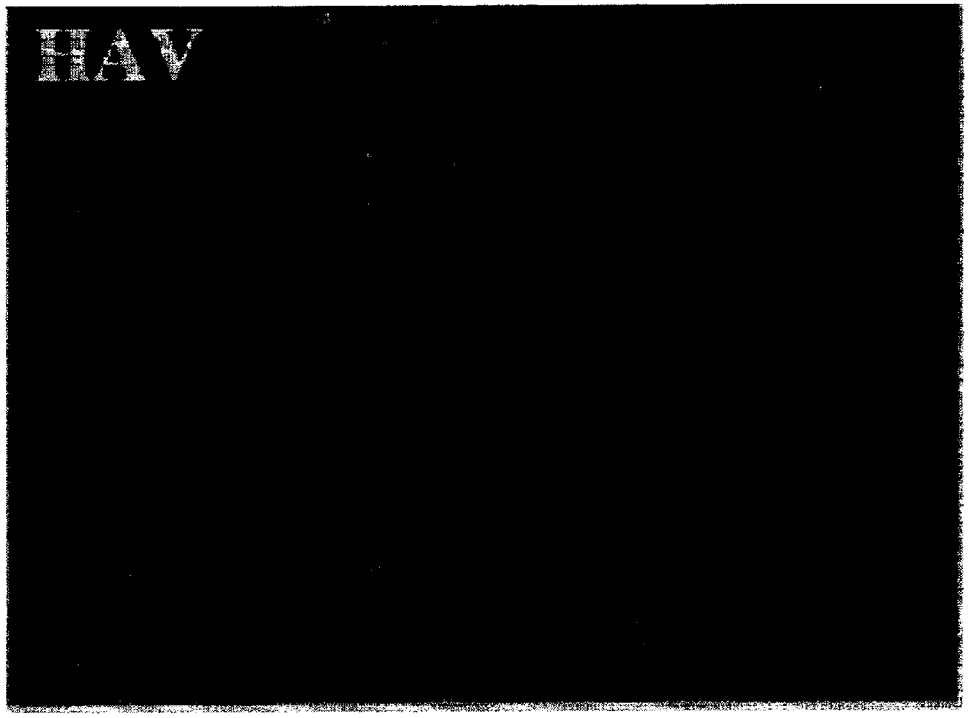

The peptide N—Ac—CHAVC—NH$_2$ (SEQ ID NO:96) disrupted NRK cell adhesion FIG. 11D, compare to 11A), whereas N—Ac—CHGVC—NH$_2$ (SEQ ID NO:11) had no affect on cell adhesion (FIG. 11C). In the presence of N—Ac—CHGVC—NH$_2$ (SEQ ID NO:11), the NRK cells formed tightly adherent monolayers with a cobblestone morphology. They also expressed E-cadherin, as judged by immunofluorescent staining protocols (Laird et al., *J. Cell Biol.* 131:1193–1203, 1995) (FIG. 12C). In contrast, the NRK cells which were treated with N—Ac—CHAVC—NH$_2$ (SEQ ID NO:96) did not adhere to one another and failed to form a contiguous monolayer (FIG. 11D). Furthermore, these cells expressed greatly reduced levels of E-cadherin (FIG. 12D). These data demonstrate that N—Ac—CHAVC—NH$_2$ (SEQ ID NO:96) is capable of disrupting NRK cell adhesion.

Example 7

Enhancement of Human Skin Permeability

The epithelial cells of the skin (known as keratinocytes) express E-cadherin. This Example illustrates the use of a representative cyclic peptide to enhance the permeability of human skin.

Abdominal skin from humans at autopsy within 24 hours of death was used in these assays. The effect of N—Ac—CHAVC—NH$_2$ (SEQ ID NO:96) and N—Ac—CHGVC—NH$_2$ (SEQ ID NO:11), used at a concentration of 500 μg/ml or 2.5 mg/ml, on the penetration of two fluorescent markers, Oregon Green 488 (charge -1, MW 386 daltons) and Rhodamine Green 3000 Dextran (no charge, MW 3000 daltons) through human skin was then evaluated utilizing a Franz Cell apparatus (Franz, *Curr. Prob. Dermatol.* 7:58–68, 1978; Franz, *J. Invest. Dermatol.* 64:190–195, 1975). The peptides and markers were dissolved in sterile phosphate buffer, pH 7.2, and phosphate buffer was used as the receptor fluid. 150 μl of solution containing 0.2 mg Oregon Green and 1.0 mg Rhodamine Green was used to evaluate 500 μg/ml peptide; 200 μl of solution containing 0.05 mg Oregon Green and 1.250 mg Rhodamine Green was used to evaluate 2.5 mg/ml peptide. The solution was placed on top of the epidermal side of the skin, and the penetration of the markers through the skin was assessed using a fluorescent spectrophotometric method (in a Perkin Elmer 650–105 Fluorescence Spectrophotometer, and comparing the reading to a standard curve) at 6, 12, 24, 36, and 48 hours after the start of the experiment. The fluorescent units were converted to a concentration unit of microgram/5 ml (volume of the receiver compartment) using a standard curve and regression analysis equations. The curve was linear for the concentrations tested for both markers ($r^2$=1 for OrG and 0.997 for RhG). For each peptide and marker combination, the experiment was performed in triplicate.

Figure 16:
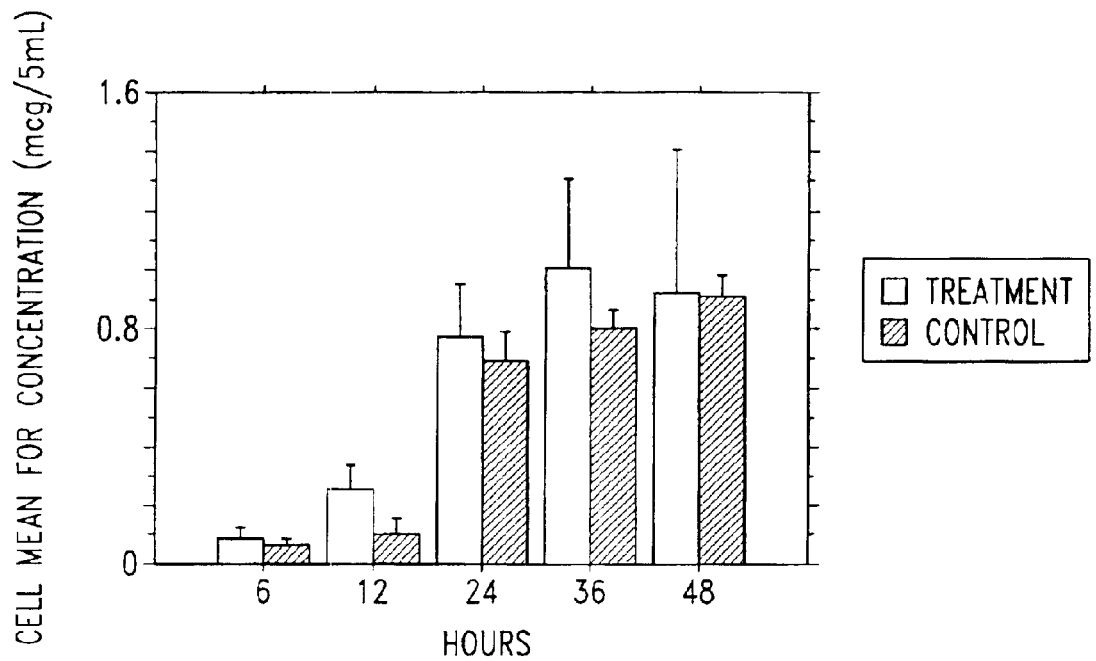
FIG. 16 is a histogram illustrating the effect of 500 μg/ml of a representative cyclic peptide (N—Ac—CHAVC—NH$_2$; SEQ ID NO:96; treatment bars) on the penetration of Oregon Green through the skin, as compared to the effect of the control peptide N—Ac—CHGVC—NH₂ (SEQ ID NO: 11; control bars). Penetration was determined by converting fluorescent units to a concentration unit of microgram/5 ml (volume of the receiver compartment) using a standard curve and regression analysis equations.
Figure 17:
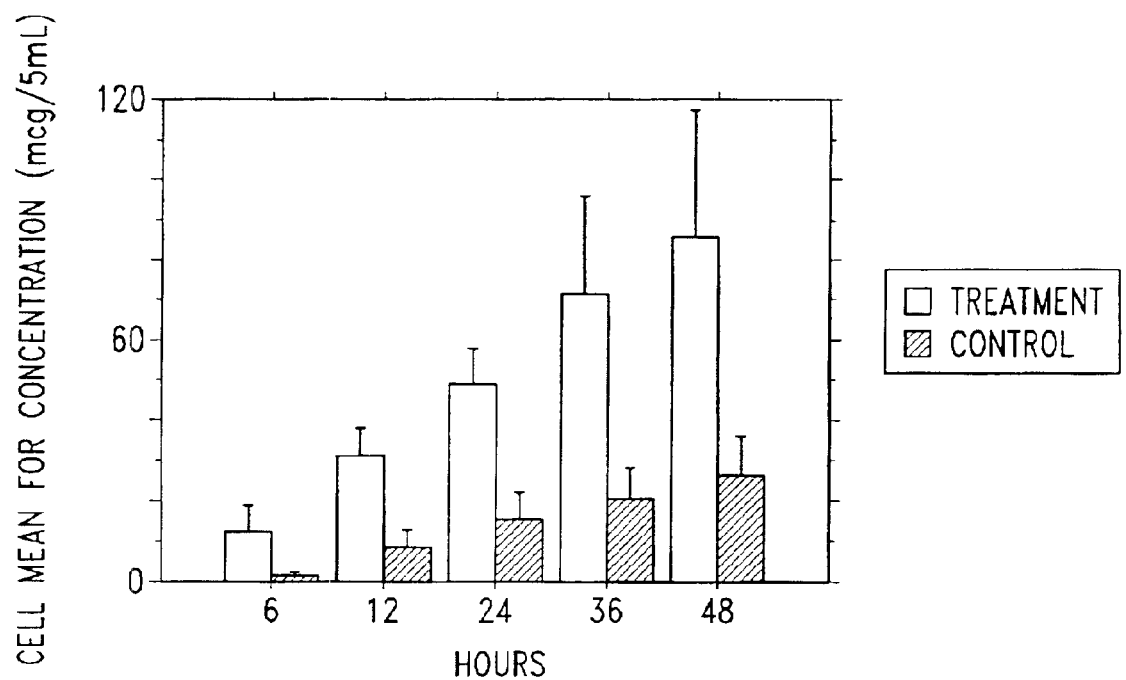
FIG. 17 is a histogram illustrating the effect of 500 μg/ml of a representative cyclic peptide (N—Ac—CHAVC—NH₂; SEQ ID NO:96; treatment bars) on the penetration of Rhodamine Green through the skin, as compared to the effect of the control peptide N—Ac—CHGVC—NH₂ (SEQ ID NO:11; control bars). Penetration was determined by converting fluorescent units to a concentration unit of microgram/5 ml (volume of the receiver compartment) using a standard curve and regression analysis equations.

At 500 μg/ml, N—Ac—CHAVC—NH$_2$ (SEQ ID NO:96; sample #1) slightly increased the penetration of Oregon Green through the skin, as compared to the effect of N—Ac—CHGVC—NH$_2$ (SEQ ID NO: 11; sample #3) on the penetration of this marker (Table 3 and FIG. 16). The penetration of Rhodamine Green through the skin was significantly increased in the presence of N—Ac—CHAVC—NH$_2$ (SEQ ID NO:96), in comparison to N—Ac—CHGVC—NH$_2$ (SEQ ID NO: 11) (Table 4 and FIG. 17).

Figure 18:
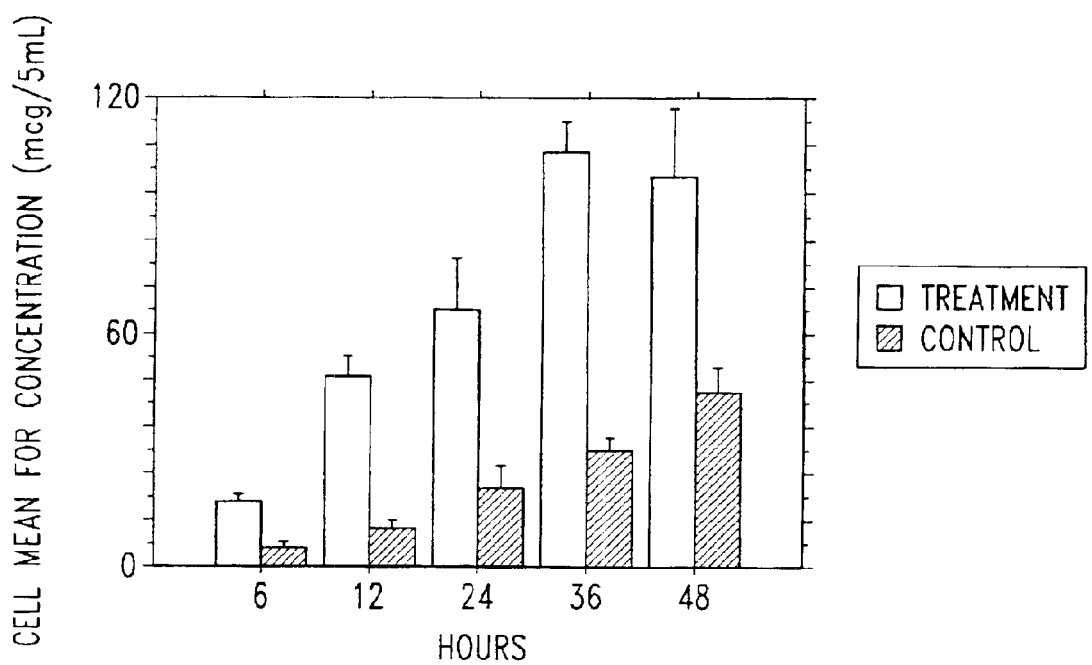
FIG. 18 is a histogram illustrating the effect of 2.5 mg/ml of a representative cyclic peptide (N—Ac—CHAVC—NH₂; SEQ ID NO:96; treatment bars) on the penetration of Oregon Green through the skin, as compared to the effect of the control peptide N—Ac—CHGVC—NH₂ (SEQ ID NO:11; control bars). Penetration was determined by converting fluorescent units to a concentration unit of microgram/5 ml (volume of the receiver compartment) using a standard curve and regression analysis equations.
Figure 19:
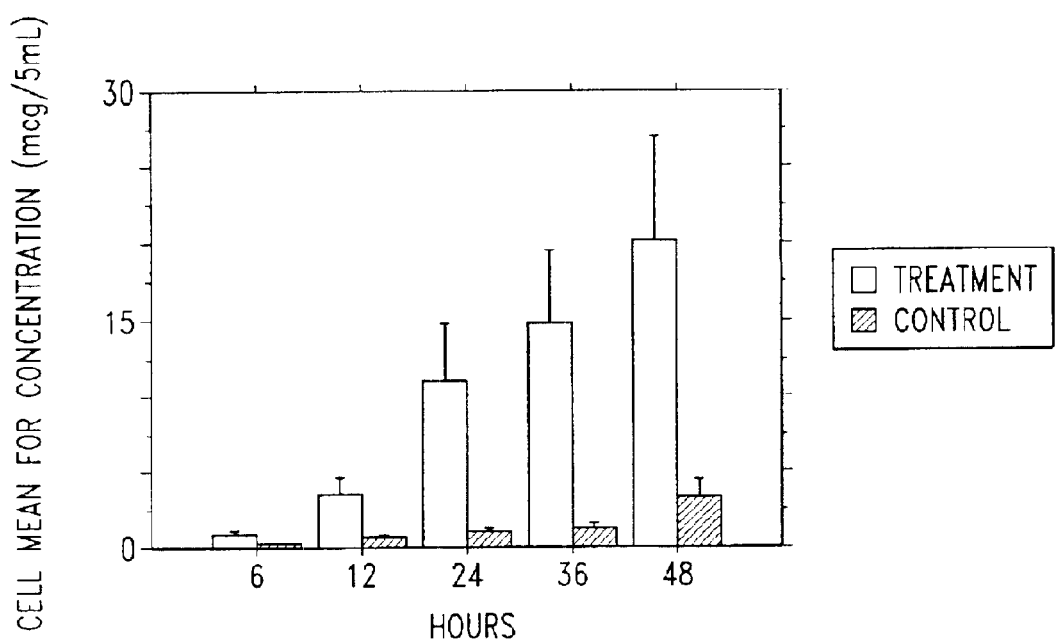
FIG. 19 is a histogram illustrating the effect of 2.5 mg/ml of a representative cyclic peptide (N—Ac—CHAVC—NH₂; SEQ ID NO:96; treatment bars) on the penetration of Rhodamine Green through the skin, as compared to the effect of the control peptide N—Ac—CHGVC—NH₂ (SEQ ID NO: 11; control bars). Penetration was determined by converting fluorescent units to a concentration unit of microgram/5 ml (volume of the receiver compartment) using a standard curve and regression analysis equations.
Figure 20:
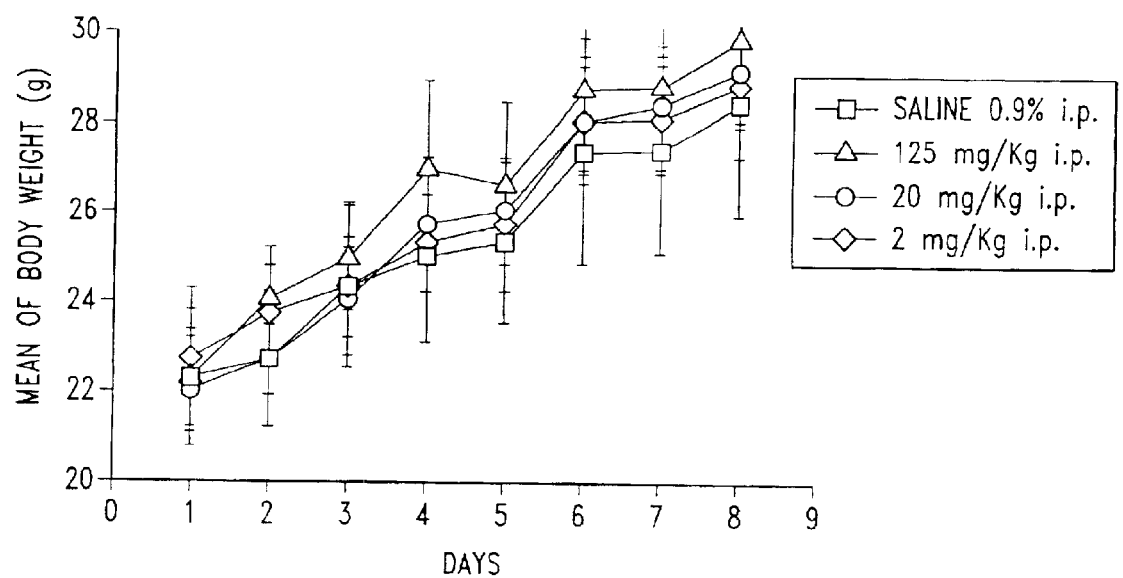
FIG. 20 is a graph illustrating the results of a study to assess the chronic toxicity of a representative cyclic peptide. The graph presents the mean body weight during the three-day treatment period (one intraperitoneal injection per day) and the four subsequent recovery days. Three different doses are illustrated, as indicated.

At 2.5 mg/ml, N—Ac—CHAVC—NH$_2$ (SEQ ID NO:96; sample #1) increased the penetration of Oregon Green through the skin, as compared to the effect of N—Ac—CHGVC—NH$_2$ (SEQ ID NO: 11; sample #3) on the penetration of this marker (Table 3 and FIG. 18). The penetration of Rhodamine Green through the skin was significantly increased in the presence of N—Ac—CHAVC—NH$_2$ (SEQ ID NO:96), in comparison to N—Ac—CHGVC—NH$_2$ (SEQ ID NO: 11) (Table 4 and FIG. 19).

TABLE 3

*Percutaneous absorption concentration (mg/5 ml) for Oregon Green ™ 488 as a function of time

| #Sample# | t = 6 hours | t = 12 hours | t = 24 hours | t = 36 hours | t = 48 hours |
|---|---|---|---|---|---|
| 500 μg/ml Peptide | | | | | |
| 1Sample#1 | 0.028 | 0.096 | 0.470 | 0.544 | 0.665 |
| 2Sample#1 | 0.167 | 0.322 | 1.096 | 1.56 | 1.725 |
| 3Sample#1 | 0.058 | 0.352 | 0.773 | 0.902 | 0.971 |
| Mean Sample#1 | 0.084 | 0.225 | 0.780 | 1.00 | 1.120 |
| 1Sample#3 | 0.098 | 0.200 | 0.709 | 0.769 | 0.923 |
| 2Sample#3 | 0.022 | 0.107 | 0.864 | 0.923 | 1.021 |
| 3Sample#3 | 0.045 | 0.088 | 0.522 | 0.714 | 0.764 |
| Mean Sample#3 | 0.055 | 0.132 | 0.698 | 0.802 | 0.902 |
| 2.5 mg/ml Peptide | | | | | |
| 1Sample#1 | 0.14 | 0.44 | 0.67 | 0.76 | 0.83 |
| 2Sample#1 | 0.11 | 0.32 | 0.33 | 0.88 | 0.56 |
| 3Sample#1 | 0.16 | 0.45 | 0.63 | 0.99 | 1.06 |
| Mean Sample#1 | 0.14 | 0.40 | 0.54 | 0.88 | 0.82 |
| 1Sample#3 | 0.04 | 0.11 | 0.12 | 0.23 | 0.36 |
| 2Sample#3 | 0.01 | 0.04 | 0.11 | 0.22 | 0.26 |
| 3Sample#3 | 0.06 | 0.08 | 0.26 | 0.29 | 0.46 |
| Mean Sample#3 | 0.04 | 0.07 | 0.16 | 0.25 | 0.36 |
| no dye | 0 | 0 | 0 | 0 | 0 |
| no dye | 0 | 0 | 0 | 0 | 0 |

*Defined as amount found in the receiver compartment (volume 5 = ml)

TABLE 4

*Percutaneous absorption concentration (mg/5ml) for
Dextran Rhodamine Green 3000 as a function of time

| #Sample# | t = 6 hours | t = 12 hours | t = 24 hours | t = 36 hours | t = 48 hours |
|---|---|---|---|---|---|
| 500 µg/ml Peptide | | | | | |
| 1Sample#1 | 0.4 | 3.0 | 16.174 | 21.044 | 25.747 |
| 2Sample#1 | 0.8 | 2.0 | 4.074 | 5.556 | 6.481 |
| 3Sample#1 | 1.2 | 5.556 | 13.158 | 17.565 | 27.826 |
| Mean Sample#1 | 0.8 | 3.52 | 11.15 | 14.72 | 20.02 |
| 1Sample#3 | 0.2 | 0.6 | 1.0 | 1.0 | 1.8 |
| 2Sample#3 | 0.3 | 1.0 | 1.4 | 1.6 | 5.370 |
| 3Sample#3 | 0.2 | 0.4 | 0.8 | 1.0 | 1.8 |
| Mean Sample#3 | 0.23 | 0.67 | 1.07 | 1.2 | 2.99 |
| 2.5 mg/ml Peptide | | | | | |
| 1Sample#1 | 24.52 | 45.35 | 66.28 | 120.0 | 146.79 |
| 2Sample#1 | 2.4 | 25.22 | 35.22 | 42.36 | 47.00 |
| 3Sample#1 | 11.05 | 23.83 | 44.85 | 51.50 | 60.1 |
| Mean Sample#1 | 12.66 | 31.47 | 48.78 | 71.28 | 133.56 |
| 1Sample#3 | 1.8 | 17.02 | 27.47 | 33.06 | 40.86 |
| 2Sample#3 | 0.2 | 2.0 | 5.56 | 5.79 | 8.25 |
| 3Sample#3 | 3.8 | 7.89 | 13.9 | 20.35 | 27.48 |
| Mean Sample#3 | 1.93 | 8.97 | 15.64 | 19.73 | 25.53 |
| no dye | 0 | 0 | 0 | 0 | 0 |
| no dye | 0 | 0 | 0 | 0 | 0 |

*Defined as amount found in the receiver compartment (volume = 5 ml)

Example 8

Disruption of Human Ovarian Cancer Cell Adhesion

This Example further illustrates the ability of representative cyclic peptides to disrupt human ovarian cancer cell adhesion.

Figure 13A:
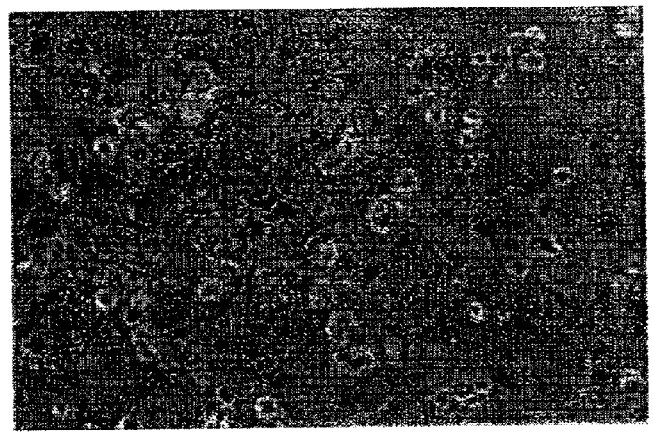
FIGS. 13A–13C are photographs showing monolayer cultures of human ovarian cancer cells (OVCAR3) in the presence of varying concentrations of a representative cyclic peptide.
Figure 13B:
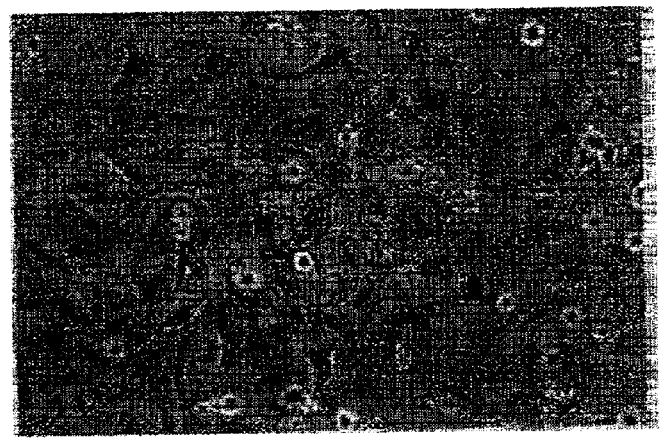
Figure 13C:
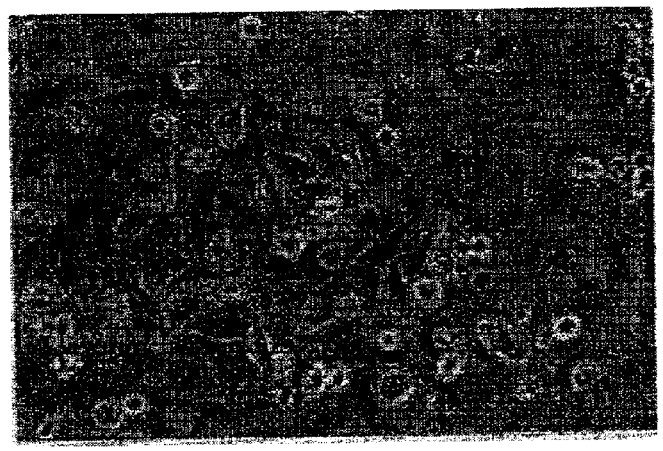

The human ovarian cancer cell line OVCAR-3, which expresses E-cadherin, was used in these experiments. Cells were cultured in RPMI supplemented with insulin and containing 20% FCS. Cells were grown in T-250 culture flasks and maintained by periodic subculturing. Cells were harvested from flasks and seeded in individual wells of 96-well culture dishes (surface area of each well was 0.32 cm$^2$) at a density of 50,000 cells per well in 0.1 ml media containing the cyclic peptides (at concentrations of 1, 0.1, or 0.01 mg/ml). Media control wells were also established. Cultures were evaluated periodically by microscopic examination under both bright field and phase contrast conditions, and were maintained for 48 hours. N—Ac—CHAVC—NH$_2$ (SEQ ID NO:96) was found to be inactive within this assay at these concentrations. However, the cyclic peptide N—Ac—CHAVSC—NH$_2$ (SEQ ID NO:38) disrupted OVCAR-3 adhesion (FIGS. 13A–C)). This data demonstrates that N—Ac—CHAVSC—NH$_2$ (SEQ ID NO:38) specifically affects cells that express E-cadherin.

Example 9

Disruption of Melanoma Cell Adhesion

This Example illustrates the ability of a representative cyclic peptide to disrupt melanoma cell adhesion.

Melanoma ME115 cells (kindly provided by Meenhard Herlyn, Wistar Institute, Philadelphia, Pa.) were plated on glass coverslips and cultured for 24 hours in 50% keratinocyte growth medium (Clonetics, San Diego, Calif.) and 50% L15. Fresh medium containing the cyclic peptides (final concentration 500 µg/mL media) N—Ac—CHAVC—NH$_2$ (SEQ ID NO:96) or N—Ac—CHGVC—NH$_2$ (SEQ ID NO:11) was then added. Following 24 hours of culture in the presence of the peptides, the medium was removed and fresh medium containing the peptides was added. The cells were fixed 24 hours later with cold methanol and stored in phosphate buffered saline (PBS).

Coverslips were blocked for 1 hour in 3% ovalbumin/PBS and incubated for a further 1 hour in the presence of rabbit pan-cadherin antibody (Sigma Chemical Co., St. Louis, Mo.) diluted 1:500. Primary and secondary antibodies were diluted in PBS containing 6% normal goat serum. Following incubation in the primary antibody, coverslips were washed 3 times for 5 minutes each in PBS and incubated for 1 hour in goat anti-rabbit immunoglobulin G conjugated to fluorescein (Kiekegard and Perry, South San Francisco, Calif.) diluted 1:100. Following a further wash in PBS (3×5 minutes) coverslips were mounted in Vectashield (Vector Labs, Burlingame, Calif.) and viewed with a Zeiss infinity corrected microscope.

Figure 14A:
FIGS. 14A and 14B are photographs showing cultures of human melanoma ME115 cells in the presence (FIG. 14B) and absence (FIG. 14A) of a representative cyclic peptide. The cells have been immunolabeled for cadherin.
Figure 14B:

Photographs, shown in FIG. 14, show an absence of cell membrane staining and the appearance of bright intracellular vesicular staining in cells treated with N—Ac—CHAVC—NH$_2$ (SEQ ID NO:96). In contrast, cells exposed to N—Ac—CHGVC—NH$_2$ (SEQ ID NO: 11) displayed cadherin staining all over the cell membrane. Occasionally, the staining concentrated at points of cell-cell contact. These results indicate that the representative cyclic peptide N—Ac—CHAVC—NH$_2$ (SEQ ID NO:96) disrupts melanoma cell adhesion.

Example 10

Disruption of Breast Cancer Cell Adhesion

This Example illustrates the ability of a representative cyclic peptide to disrupt human breast epithelial cell adhesion.

A1N4 human breast epithelial cells (kindly provided by Martha Stampfer, Lawrence Berkeley Laboratory, Berkeley, Calif.) were plated on glass coverslips and cultured in F12/DME containing 0.5% FCS and 10 ng/mL EGF for 24 hours. Fresh medium containing the cyclic peptides (final concentration 500 µg/mL media) N—Ac—CHAVC—NH$_2$ (SEQ ID NO:96) or N—Ac—CHGVC—NH$_2$ (SEQ ID NO:11) was then added. Following 24 hours of culture in the presence of the peptides, the medium was removed and fresh medium containing the peptides was added. The cells were fixed 24 hours later with cold methanol and stored in phosphate buffered saline (PBS).

Coverslips were blocked for 1 hour in 3% ovalbumin/PBS and incubated for a further 1 hour in the presence of 1 µg/mL mouse anti-E-cadherin antibody (Zymed, Gaithersburg, Md.). Primary and secondary antibodies were diluted in PBS containing 6% normal goat serum. Following incubation in the primary antibody, coverslips were washed 3 times for 5 minutes each in PBS and incubated for 1 hour with goat anti-mouse conjugated to fluorescein (Kiekegard and Perry, South San Francisco, Calif.) diluted 1:100. Following a further wash in PBS (3×5 minutes) coverslips were mounted in Vectashield (Vector Labs, Burlingame, Calif.) and viewed with a Zeiss infinity corrected microscope.

Figure 15A:
FIGS. 15A and 15B are photographs showing monolayer cultures of A1N4 human breast epithelial cells in the presence (FIG. 15B) and absence (FIG. 15A) of a representative cyclic peptide. The cells have been immunolabeled for E-cadherin.
Figure 15B:

Photographs, shown in FIGS. 15A and 15B, show reduced E-cadherin staining with a stitched appearance in cells treated with N—Ac—CHAVC—NH$_2$ (SEQ ID NO:96). In addition, holes are present in the monolayer where the cells have retracted from one another. In contrast, cells exposed to N—Ac—CHGVC—NH$_2$ (SEQ ID NO:11) displayed E-cadherin staining concentrated at points of cell-cell contact and formed a tightly adherent monolayer.

Example 11

Toxicity and Cell Proliferation Studies

This Example illustrates the initial work to evaluate the cytotoxic effects of representative cyclic peptides.

N—Ac—CHAVC—NH$_2$ (SEQ ID NO:96) and the control peptide N—Ac—CHGVC—NH$_2$ (SEQ ID NO:11) were evaluated for possible cytotoxic effects on human microvascular endothelial (HMVEC; Clonetics), human umbilical vein endothelial (HUVEC; ATCC #CRL-1730), IAFp2 (human fibroblast cell line; Institute Armand-Frapier, Montreal, Quebec), WI-38 (human fibroblast cell line; ATCC #CCL-75), MDA-MB231 (human breast cancer cell line; ATCC #HTB-26), and PC-3 (human prostate cancer cell line; ATCC #CRL-1435) cells utilizing the MTT assay (Plumb et al., *Cancer Res.* 49:4435–4440, 1989). Neither of the peptides was cytotoxic at concentrations up to and including 100 μM. Similarly, neither of the peptides was capable of inhibiting the proliferation of the above cell lines at concentrations up to 100 μM, as judged by $^3$H-thymidine incorporation assays.

In fact, none of the compounds tested thus far show any cytotoxicity at concentrations up to and including 100 μM (Table 5 and 6). However, N—Ac—CHAVSC—NH$_2$ (SEQ ID NO:38), N—Ac—CHGVSC—NH$_2$ (SEQ ID NO:39), N—Ac—CVAHC—NH$_2$ (SEQ ID NO:18), N—Ac—CVGHC—NH$_2$ (SEQ ID NO:19) and N—Ac—CSHAVSSC—NH$_2$ (SEQ ID NO:42) inhibited the proliferation of HUVEC at concentrations (IC$_{50}$ values) of 57 μM, 42 μM, 8 μM, 30 μM and 69 μM respectively, as judged by $^3$H-thymidine incorporation assays. N—Ac—CSHAVSSC—NH$_2$ (SEQ ID NO:42) also inhibited the proliferation of MDA-MB231 cells at a concentration of 76 μM and HMVEC cells at a concentration of 70 μM (Tables 5 and 6). N—Ac—CHAVSC—NH$_2$ (SEQ ID NO:38) inhibited the proliferation of MDA-MB231 cells at a concentration of 52 μM.

TABLE 5

Evaluation of Peptides for Cytotoxicity and Capacity to Inhibit Cell Proliferation of Normal Cells (IC$_{50}$ in μM)

| | | Normal Cells | | | | | | | |
|---|---|---|---|---|---|---|---|---|---|
| | | HMVEC | | HUVEC | | IAFp2 | | WI-38 | |
| Peptide | SEQ ID | Cell prol | Cytotox | Cell Prol | Cytotox | Cell Prol | Cytotox | Cell Prol | Cytotox |
| N—Ac-CHGVC-NH$_2$ (control for #1) | 11 | >100 μM | >100 μM | >100 μM | >100 μM | >100 μM | >100 μM | >100 μM | >100 μM |
| N—Ac-CHAVC-NH$_2$ (#1) | 96 | >100 μM | >100 μM | >100 μM | >100 μM | >100 μM | >100 μM | >100 μM | >100 μM |
| H-CHGVC-NH$_2$ (control for #2) | 11 | >100 μM | >100 μM | >100 μM | >100 μM | >100 μM | >100 μM | >100 μM | >100 μM |
| H-CHAVC-NH$_2$ (#2) | 96 | >100 μM | >100 μM | >100 μM | >100 μM | >100 μM | >100 μM | >100 μM | >100 μM |
| N—Ac-CHGVSC-NH$_2$ (control for #18) | 39 | >100 μM | >100 μM | >42 μM | >100 μM | >100 μM | >100 μM | >100 μM | >100 μM |
| N—Ac-CHAVSC-NH$_2$* (#18) | 38 | >100 μM | >100 μM | >57 μM | >100 μM | >100 μM | >100 μM | >100 μM | >100 μM |
| N—Ac-CSHGVC-NH (control for #16) | 37 | >100 μM | >100 μM | >100 μM | >100 μM | >100 μM | >100 μM | >100 μM | >100 μM |
| N—Ac-CSHAVC-NH$_2$ (#16) | 36 | >100 μM | >100 μM | >100 μM | >100 μM | >100 μM | >100 μM | >100 μM | >100 μM |
| N—Ac-CAHGVDC-NH$_2$ (control for #22) | 27 | >100 μM | >100 μM | >100 μM | >100 μM | >100 μM | >100 μM | >100 μM | >100 μM |
| N—Ac-CAHAVDC-NH$_2$ (#22) | 26 | >100 μM | >100 μM | >100 μM | >100 μM | >100 μM | >100 μM | >100 μM | >100 μM |
| N—Ac-KHGVD-NH$_2$ (control for #26) | 13 | >100 μM | >100 μM | >100 μM | >100 μM | >100 μM | >100 μM | >100 μM | >100 μM |
| N—Ac-KHAVD-NH$_2$ (#26) | 12 | >100 μM | >100 μM | >100 μM | >100 μM | >100 μM | >100 μM | >100 μM | >100 μM |
| H-CAHGVDC-NH$_2$ (control for #45) | 27 | >100 μM | >100 μM | >100 μM | >100 μM | >100 μM | >100 μM | >100 μM | >100 μM |
| H-CAHAVDC-NH$_2$ (#45) | 26 | >100 μM | >100 μM | >100 μM | >100 μM | >100 μM | >100 μM | >100 μM | >100 μM |
| H-CAHGVDIC-NH$_2$ (control for #47) | 25 | >100 μM | >100 μM | >100 μM | >100 μM | >100 μM | >100 μM | >100 μM | >100 μM |
| H-CAHAVDIC-NH$_2$ (#47) | 24 | >100 μM | >100 μM | >100 μM | >100 μM | >100 μM | >100 μM | >100 μM | >100 μM |
| N—Ac-CVGHC-NH$_2$ (control for #32) | 19 | >100 μM | >100 μM | >30 μM | >100 μM | >100 μM | >100 μM | >100 μM | >100 μM |

TABLE 5-continued

Evaluation of Peptides for Cytotoxicity and Capacity to Inhibit Cell Proliferation of Normal Cells (IC$_5$0 in μM)

| | | Normal Cells | | | | | | | |
|---|---|---|---|---|---|---|---|---|---|
| | | HMVEC | | HUVEC | | IAFp2 | | WI-38 | |
| Peptide | SEQ ID | Cell prol | Cytotox | Cell Prol | Cytotox | Cell Prol | Cytotox | Cell Prol | Cytotox |
| N—Ac-CVAHC-NH$_2$ (#32) | 18 | >100 μM | >100 μM | >8 μM | >100 μM | >100 μM | >100 μM | >100 μM | >100 μM |
| N—Ac-CAHGVDIC-NH$_2$ (control for #14) | 25 | >100 μM | >100 μM | >100 μM | >100 μM | >100 μM | >100 μM | >100 μM | >100 μM |
| N—Ac-CAHAVDIC-NH$_2$ (#14) | 24 | >100 μM | >100 μM | >100 μM | >100 μM | >100 μM | >100 μM | >100 μM | >100 μM |
| N—Ac-CSHGVSSC-NH$_2$ (control for #24) | 43 | >100 μM | >100 μM | >100 μM | >100 μM | >100 μM | >100 μM | >100 μM | >100 μM |
| N—Ac-CSHAVSSC-NH$_2$* (#24) | 42 | >70 μM | >100 μM | >69 μM | >100 μM | >100 μM | >100 μM | >100 μM | >100 μM |

*Incompletely soluble in RPMI at 1 mM

TABLE 6

Evaluation of Peptides for Cytotoxicity and Capacity to Inhibit Cell Proliferation of Tumoral Cells (IC$_5$0 in μM)

| | | Tumoral Cells | | | |
|---|---|---|---|---|---|
| | | MDA-MB231 | | PC-3 | |
| Peptide | SEQ ID | Cell Prol | Cytotox | Cell Prol | Cytotox |
| N—Ac-CHGVC-NH$_2$ (control for #1) | 11 | >100 μM | >100 μM | >100 μM | >100 μM |
| N—Ac-CHAVC-NH$_2$ (#1) | 96 | >100 μM | >100 μM | >100 μM | >100 μM |
| H-CHGVC-NH$_2$ (control for #2) | 11 | >100 μM | >100 μM | >100 μM | >100 μM |
| H-CHAVC-NH$_2$ (#2) | 96 | >100 μM | >100 μM | >100 μM | >100 μM |
| N—Ac-CHGVSC-NH$_2$ (control for #18) | 39 | >100 μM | >100 μM | >100 μM | >100 μM |
| N—Ac-CHAVSC-NH$_2$* (#18) | 38 | >52 μM | >100 μM | >100 μM | >100 μM |
| N—Ac-CSHGVC-NH$_2$ (control for #16) | 37 | >100 μM | >100 μM | >100 μM | >100 μM |
| N—Ac-CSHAVC-NH$_2$ (#16) | 36 | >100 μM | >100 μM | >100 μM | >100 μM |
| N—Ac-CAHGVDC-NH$_2$ (control for #22) | 27 | >100 μM | >100 μM | >100 μM | >100 μM |
| N—Ac-CAHAVDC-NH$_2$ (#22) | 26 | >100 μM | >100 μM | >100 μM | >100 μM |
| N—Ac-KHGVD-NH$_2$ (control for #26) | 13 | >100 μM | >100 μM | >100 μM | >100 μM |
| N—Ac-KHAVD-NH$_2$ (#26) | 12 | >100 μM | >100 μM | >100 μM | >100 μM |
| H-CAHGVDC-NH$_2$ (control for #45) | 27 | >100 μM | >100 μM | >100 μM | >100 μM |
| H-CAHAVDC-NH$_2$ (#45) | 26 | >100 μM | >100 μM | >100 μM | >100 μM |
| H-CAHGVDIC-NH$_2$ (control for #47) | 25 | >100 μM | >100 μM | >100 μM | >100 μM |
| H-CAHAVDIC-NH$_2$ (#47) | 24 | >100 μM | >100 μM | >100 μM | >100 μM |
| N—Ac-CVGHC-NH$_2$ (control for #32) | 19 | >100 μM | >100 μM | >100 μM | >100 μM |
| N—Ac-CVAHC-NH$_2$ (#32) | 18 | >100 μM | >100 μM | >100 μM | >100 μM |
| N—Ac-CAHGVDIC-NH$_2$ (control for #14) | 25 | >100 μM | >100 μM | >100 μM | >100 μM |
| N—Ac-CAHAVDIC-NH$_2$ (#14) | 24 | >100 μM | >100 μM | >100 μM | >100 μM |
| N—Ac-CSHGVSSC-NH$_2$ (control for #24) | 43 | >100 μM | >100 μM | >100 μM | >100 μM |
| N—Ac-CSHAVSSC-NH$_2$* (#24) | 42 | >76 μM | >100 μM | >100 μM | >100 μM |

*Incompletely soluble in RPMI at 1 mM

Example 12

Chronic Toxicity Study

This Example illustrates a toxicity study performed using a representative cyclic peptide.

Varying amounts of H—CHAVC—NH$_2$ (SEQ ID NO:96; 2 mg/kg, 20 mg/kg and 125 mg/kg) were injected into mice intraperitoneally every day for three days. During the recovery period (days 4–8), animals were observed for clinical symptoms. Body weight was measured (Table 22) and no significant differences occurred. In addition, no clinical symptoms were observed on the treatment or recovery days. Following the four day recovery period, autopsies were performed and no abnormalities were observed.

Example 13

Acute Toxicity Study

This Example illustrates further toxicity studies.

Mice were injected intraperitoneally for seven consecutive days with 20 mg/kg of N—Ac—CHAVC—NH$_2$ (SEQ ID NO:96) and sacrificed 24 hr after treatment. No gross or histopathological findings related to the treatment were found.

Mice were injected intraperitoneally with 125 mg/kg of N—Ac—CHAVC—NH$_2$ (SEQ ID NO:96) for three consecutive days and sacrificed on the fourth day. No gross or histopathological findings related to the treatment were found.

Rat were injected intravenously with 100 mg/kg of N—Ac—CHAVC—NH$_2$ (SEQ ID NO:96) with no gross or histopathological findings related to the treatment.

Mice were injected intravenously with either a saline control or 200 mg/kg of N—Ac—CHAVC—NH$_2$ (SEQ ID NO:96). Mice were sacrificed after 24 hours, or allowed a 14-day recovery period. In all cases, no animals died during the study, and no gross or histopathological findings related to the treatment were found.

Example 14

Stability of Cyclic Peptide in Blood

This Example illustrates the stability of a representative cyclic peptide in mouse whole blood.

Figure 21:
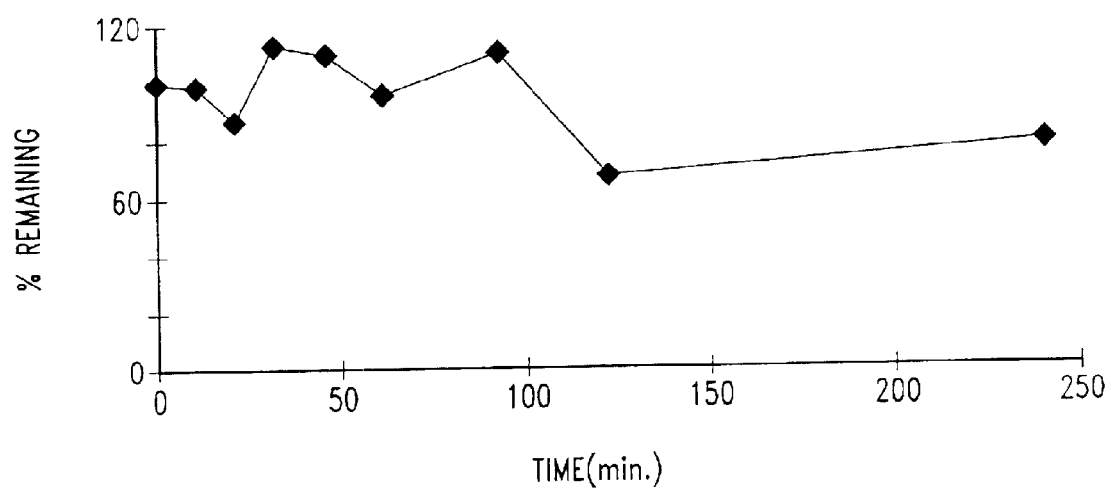
FIG. 21 is a graph illustrating the stability of a representative cyclic peptide in mouse whole blood. The percent of the cyclic peptide remaining in the blood was assayed at various time points, as indicated.

50 μl of a stock solution containing 12.5 μg/ml H—CHAVC—NH$_2$ (SEQ ID NO:96) was added to mouse whole blood and incubated at 37° C. Aliquots were removed at intervals up to 240 minutes, precipitated with acetonitrile, centrifuged and analyzed by HPLC. The results (Table 7 and FIG. 21) are expressed as % remaining at the various time points, and show generally good stability in blood.

TABLE 7

Stability of Representative Cyclic Peptide in Mouse Whole Blood

| Time (Min.) | Area 1 | Area 2 | Average | % Remaining |
|---|---|---|---|---|
| 0 | 341344 | 246905 | 294124.5 | 100.00 |
| 96 | 308924 | 273072 | 290998 | 98.94 |
| 20 | 289861 | 220056 | 254958.5 | 86.68 |
| 30 | 353019 | 310559 | 331789 | 112.81 |
| 45 | 376231 | 270860 | 323545.5 | 110.00 |
| 60 | 373695 | 188255 | 280975 | 95.53 |
| 90 | 435555 | 216709 | 326132 | 110.88 |
| 120 | 231694 | 168880 | 200287 | 68.10 |
| 240 | 221952 | 242148 | 232050 | 78.90 |

Example 15

Effect of Cyclic Peptide Modifications on N-cadherin Receptor Specificity

This Example illustrates the effect of sequences that flank the HAV seqenece, sequences external to the cyclic peptide ring and terminal modifications on specificaity for N-cadherin-mediated responses.

Cell Culture and Neurite Outgrowth Assays.

Co-cultures of cerebellar neurons on monolayers of control 3T3 cells and monolayers of transfected 3T3 cells that express physiological levels of chick N-cadherin or human L1 were established as previously described (Williams et al., *Neuron* 13:583–594, 1994). In brief, 80,000 3T3 cells (control and transfected) were plated into individual chambers of an eight-chamber tissue culture slide coated with polylysine and fibronectin and cultured in DMEM/10% FCS. After 24 hours, when confluent monolayers had formed, the medium was removed and 3000 cerebellar neurons isolated from post-natal day 2–3 rats were plated into each well in SATO media (Doherty et al., *Nature* 343:464–466, 1990) supplemented with 2% FCS. All of the test peptides were added immediately before the neurons as a 2× stock prepared in SATO/2% FCS. The co-cultures were maintained for 16–18 hours, at which time they were fixed and immunostained for GAP-43 which is present only in the neurons and delineates the neuritic processes. The mean length of the longest neurite per cell was measured for 150–200 neurons sampled in replicate cultures as previously described (Williams et al., *Neuron* 13:583–594, 1994). The percentage inhibition of neurite outgrowth at various peptide concentrations was calculated as the average of at least three independent experiments. Dose-response curves were evaluated and the EC$_{50}$ values determined.

Peptide Synthesis. Peptides were synthesized as described in Example 1. All peptides with the exception of N—Ac—CHAVDIC—NH$_2$ (SEQ ID NO:50) were prepared as a stock solution at a concentration of 5–10 mg/ml in distilled water, and stored in small aliquots at −70° C. until needed. For solubility reasons N—Ac—CHAVDIC—NH$_2$ (SEQ ID NO:50) was made up in tissue culture DMSO at a concentration of 20 mg/mL.

Effects of Cyclic HAV Peptides on N-cadherin Function. The ability of N—Ac—CHAVC—NH$_2$ (SEQ ID NO:96; compound 1) to inhibit neurite outgrowth was initially tested. This cyclic peptide has the cadherin CAR sequence (HAV) and no flanking amino acid residues. Neurons were cultured on confluent monolayers of control (untransfected) and N-cadherin expressing 3T3 cells for 16–18 hours. The cells were then fixed and the length of the longest neurite on 150–200 neurons was determined by standard assay, as described above. FIG. 22 gives the mean neurite length in a representative experiment where cerebellar neurons have been cultured over control and N-cadherin expressing cells. In the absence of peptide, the mean length of the longest neurite per cell was approximately double on the N-cadherin expressing cells, as compared to 3T3 cells. This response requires N-cadherin function in both the neuron and transfected fibroblast. FIG. 22 also illustrates inhibition of neurite outgrowth in neurons cultured over N-cadherin expressing cells in the presence of N—Ac—CHAVC—NH$_2$ (SEQ ID NO:96; compound 1, 500 μg/mL). In addition, the corresponding control peptide N—Ac—CHGVC—NH$_2$ (SEQ ID NO: 11; compound 2, 500 μg/mL) had no effect on neurite outgrowth over N-cadherin expressing monolayers (FIG. 22).

FIG. 23 gives the pooled data from a number of experiments where the neurons have been cultured over control and N-cadherin expressing cells in the presence of increasing concentrations of N—Ac—CHAVC—NH$_2$ (SEQ ID NO:96; compound 1). This compound has no significant effect on the N-cadherin response at concentrations up to 62 μg/ml. A significant inhibition (33.2+/−4.0%) of the response was seen at a peptide concentration of 125 μg/ml (mean +/−s.e.m, n=3 independent experiments), with a more complete inhibition at 250 μg/ml. Results pooled from four independent experiments demonstrated a 68.2+/−5.1% inhibition of the N-cadherin response when the peptide was present at 250 μg/ml (see Table 8). An $EC_{50}$ value of 0.22 mM was obtained from the dose-response curve. In contrast to the effects of the peptide on neurite outgrowth over N-cadherin expressing cells, it had no significant effect on neurite extension over control 3T3 cells (FIG. 23). This observation demonstrates that N—Ac—CHAVC—NH$_2$ (SEQ ID NO:96) is capable of acting as an antagonist and inhibiting cadherin function. Additionally, N—Ac—CHAVC—NH$_2$ (SEQ ID NO:96) does not inhibit integrin receptor function, as the latter is required for neurite extension over 3T3 cells. Compound 1 alone elicits a biological response of similar potency to the linear 10-mer N—Ac-LRAHAVDING-NH$_2$ (SEQ ID NO:79; % inhibition at 250 mg/mL, 68.8 +/−4.1). In contrast, compound 3, with a free amino group at the N-terminal region, was inactive (Table 8).

Figure 24:
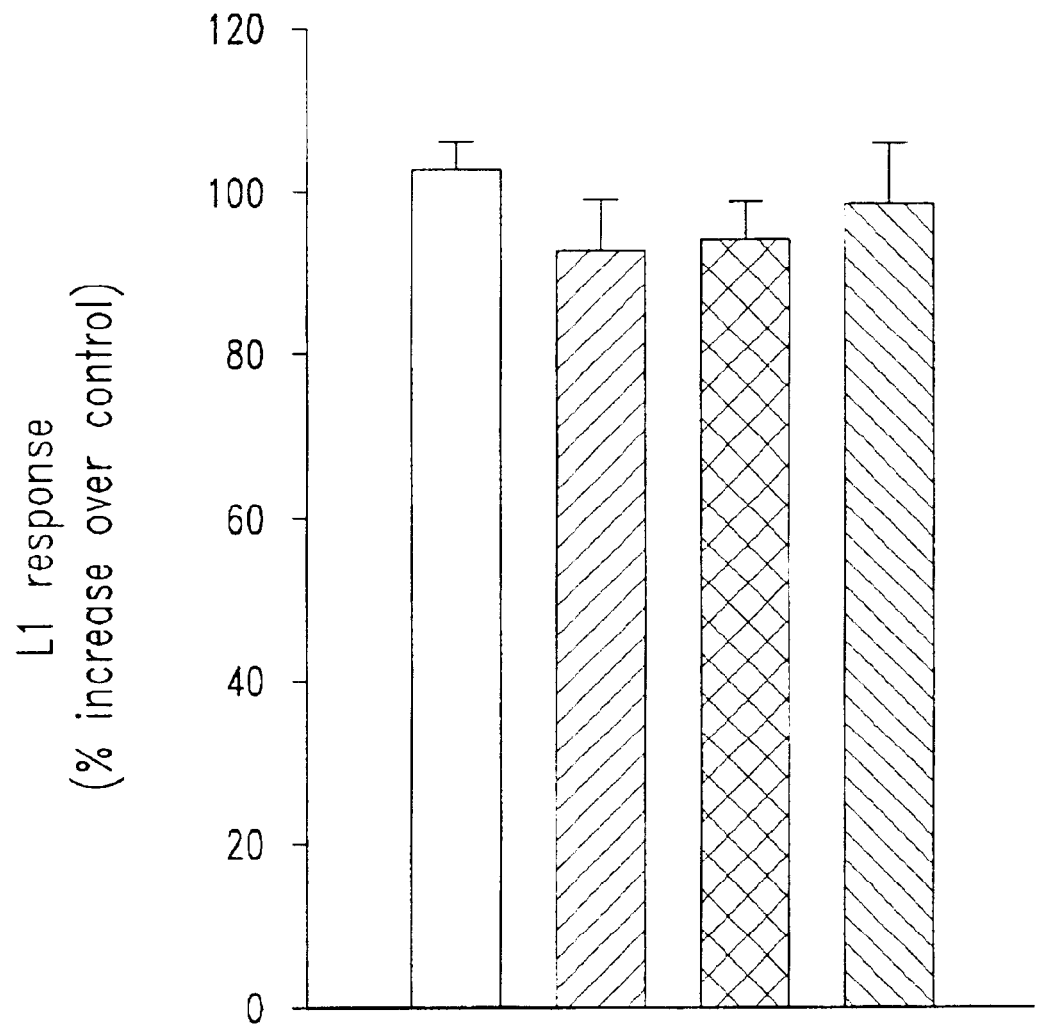
FIG. 24 is a bar graph illustrating the effects of the cyclic peptides N—Ac—CHAVDC—NH₂ (SEQ ID NO:20), N—Ac—CHAVDIC—NH₂ (SEQ ID NO:50) and N—Ac—CHAVDINC—NH₂ (SEQ ID NO:51) on L1 function. Cerebellar neurons were cultured on monolayers of control 3T3 cells and L1 expressing 3T3 cells for 16–18 hours in control media (unshaded) or control media supplemented with peptides N—Ac—CHAVDC—NH₂ (SEQ ID NO:20; diagonal rising right), N—Ac—CHAVDIC—NH₂ (SEQ ID NO:50; diagonal cross hatch) or N—Ac—CHAVDINC—NH₂ (SEQ ID NO:51; diagonal rising left) at a concentration of 100 μg/mL. The cultures were then fixed and neurite outgrowth determined by measuring the length of the longest neurite from a total of 150–200 neurons sampled in replicate cultures for each experimental condition. The results show L1 response, measured as a percentage increase in the mean length of the longest neurite relative to the 3T3 control value, for neurons grown in the absence or presence of the test peptide. The results are pooled from three independent experiments, and the bars show the s.e.m.

Peptides included in Table 8 are placed into one of three groups. The first group, comprising compounds 1 and 3 can be viewed as potential general or non-specific cadherin inhibitors. The second group, which includes compounds 23, 25, 27, 29, and 31, were designed as putative E-cadherin specific inhibitors by incorporation of flanking amino acids from the HAV region of native human E-cadherin. The remaining HAV-containing compounds were designed as putative N-cadherin inhibitors by virtue of their HAV flanking amino acids being derived from the native human N-cadherin sequence.

amino acid residues on the N-terminus of the CAR sequence in compound 5 (compound 11, N—Ac—CAHAVDC—NH$_2$, SEQ ID NO:26; compound 17, N—Ac—CRAHAVDC—NH$_2$; SEQ ID NO:28) completely eliminated inhibitory activity. Addition of a second amino acid on the C-terminus (Ile) to yield N—Ac—CHAVDIC—NH$_2$ (compound 33; SEQ ID NO:50) further increased activity from that found for compound 5 and addition of an amino acid to the N-terminus (compound 13, N—Ac—CAHAVDIC—NH$_2$; SEQ ID NO:24) reduced, but did not eliminate, the activity. Again removal of the N-terminus blocking group to yield H—CAHAVDIC—NH$_2$ (compound 11; SEQ ID NO:24) resulted in total loss of activity. Further extension of the C-terminus to yield N—Ac—CHAVDINC—NH$_2$ (compound 34; SEQ ID NO:51) resulted in only a slight loss in activity as exemplified by the small difference in the $EC_{50}$ values for these two compounds (Table 9). A further addition of a glycine residue (compound 35, N—Ac—CHAVDINGC—NH$_2$ (SEQ ID NO:76) completely abrogates activity. Furthermore, the most active N-cadherin antagonists (N—Ac—CHAVDIC—NH$_2$ (SEQ ID NO:50) $EC_{50}$=0.060 mM, N—Ac—CHAVDINC—NH$_2$ (SEQ ID NO:51), $EC_{50}$= 0.070 mM and N—Ac—CHAVDC—NH$_2$ (SEQ ID NO:20), $EC_{50}$=0.093 mM) did not interfere with the ability of neurons to extend neurites over 3T3 cells expressing L1 at concentrations that substantially inhibited the N-cadherin response (FIG. 24).

TABLE 8

Effects of Non-Specific, N-Cadherin Specific and E-Cadherin Specific Antagonists on N-Cadherin Dependent Neurite Outgrowth

| Test Peptide (250 μg/mL) | ID | % Inhibition | Control Peptide (250 μg/mL) | ID | Percent Inhibition |
|---|---|---|---|---|---|
| Non-Specific | | | | | |
| 1. N—Ac-CHAVC-NH$_2$ | 96 | 68.2 ± 5.1 (4) | 2. N—Ac-CHGVC-NH$_2$ | 11 | 4.8 ± 5.3 |
| 3. H-CHAVC-NH$_2$ | 96 | 1.7 ± 1.1 (3) | 4. H-CHGVC-NH$_2$ | 11 | 7.8 ± 7.1 |
| N-cadherin Specific | | | | | |
| 5. N—Ac-CHAVDC-NH$_2$ | 20 | 88.4 ± 3.7 (3) | 6. N—Ac-CHGVDC-NH$_2$ | 21 | −8.6 ± 5.8 |
| 7. N—Ac-CAHAVC-NH$_2$ | 22 | 58.5 ± 1.0 (3) | 8. N—Ac-CAHGVC-NH$_2$ | 23 | −6.4 ± 5.6 |
| 9. N—Ac-CAHAVDC-NH$_2$ | 26 | 13.3 ± 8.3 (3) | 10. N—Ac-CAHGVDC-NH$_2$ | 27 | 4.0 ± 6.9 |
| 11. H-CAHAVDC-NH$_2$ | 26 | 1.3 ± 13.0 (3) | 12. H-CAHGVDC-NH$_2$ | 27 | 5.7 ± 7.8 |
| 13. N—Ac-CAHAVDIC-NH$_2$ | 24 | 89.4 (2) | 14. N—Ac-CAHGVDIC-NH$_2$ | 25 | 4.8 ± 6.5 |
| 15. H-CAHAVDIC-NH$_2$ | 24 | −3.7 ± 2.9 (3) | 16. H-CAHGVDIC-NH$_2$ | 25 | 7.2 ± 8.1 |
| 17. N—Ac-CLRAHAVC-NH$_2$ | 30 | 9.9 ± 6.6 (3) | 18. N—Ac-CLRAHGVC-NH$_2$ | 31 | −0.5 ± 7.1 |
| 19. N—Ac-CRAHAVDC-NH$_2$ | 28 | −5.0 ± 4.9 (3) | 20. N—Ac-CRAHGVDC-NH$_2$ | 29 | −8.0 ± 6.0 |
| 21. N—Ac-CLRAHAVDC-NH$_2$ | 32 | 76.3 ± 6.6 (3) | 22. N—Ac-CLRAHGVDC-NH$_2$ | 33 | −6.8 ± 6.2 |
| E-cadherin Specific | | | | | |
| 23. N—Ac-CSHAVC-NH$_2$ | 36 | 11.0 ± 8.6 | 24. N—Ac-CSHGVC-NH$_2$ | 37 | 12.5 ± 7.5 |
| 25. N—Ac-CHAVSC-NH$_2$ | 38 | −2.5 ± 7.4 | 26. N—Ac-CHGVSC-NH$_2$ | 39 | −6.7 ± 5.8 |
| 27. N—Ac-CSHAVSC-NH$_2$ | 40 | 8.3 ± 7.3 | 28. N—Ac-CSHGVSC-NH$_2$ | 41 | 10.8 ± 7.6 |
| 29. N—Ac-CSHAVSSC-NH$_2$ | 42 | −12.6 ± 6.4 | 30. N—Ac-CSHGVSSC-NH$_2$ | 43 | −5.6 ± 5.9 |
| 31. N—Ac-CHAVSSC-NH$_2$ | 44 | 34.4 ± 11.3 (3) | 32. N—Ac-CHGVSSC-NH$_2$ | 45 | 14.8 ± 6.5 |

Placement of amino acids derived from the N-cadherin sequence on the N-terminus of the HAV sequence appears to either have little affect (compound 7, N—Ac—CAHAVC—NH$_2$; SEQ ID NO:22) or a detrimental affect (e.g., compound 17, N—Ac—CLRAHAVC—NH$_2$; SEQ ID NO:30) on activity. In contrast, addition of an aspartic acid residue on the C-terminus (compound 5, N—Ac—CHAVDC—NH$_2$; SEQ ID NO:20) dramatically increased the inhibitory activity of the peptides (Table 1). Addition of Structure/Activity Relationships for the Inhibition of Neurite Outgrowth with Cyclic HAV-Containing Peptides.

In order to further assess the effects of modifying the amino acids flanking the HAV sequence on receptor selectivity, a series of HAV-containing peptides were evaluated for their ability to inhibit neurite outgrowth. These peptides correspond to cyclized sequences derived from the human N-cadherin (RFHLRAHAVDINGN; SEQ ID NO:80) and E-cadherin (TLFSHAVSSNGN; SEQ ID NO:81) sequences immediately adjacent to the surrounding the active site (HAV).

Figure 25:
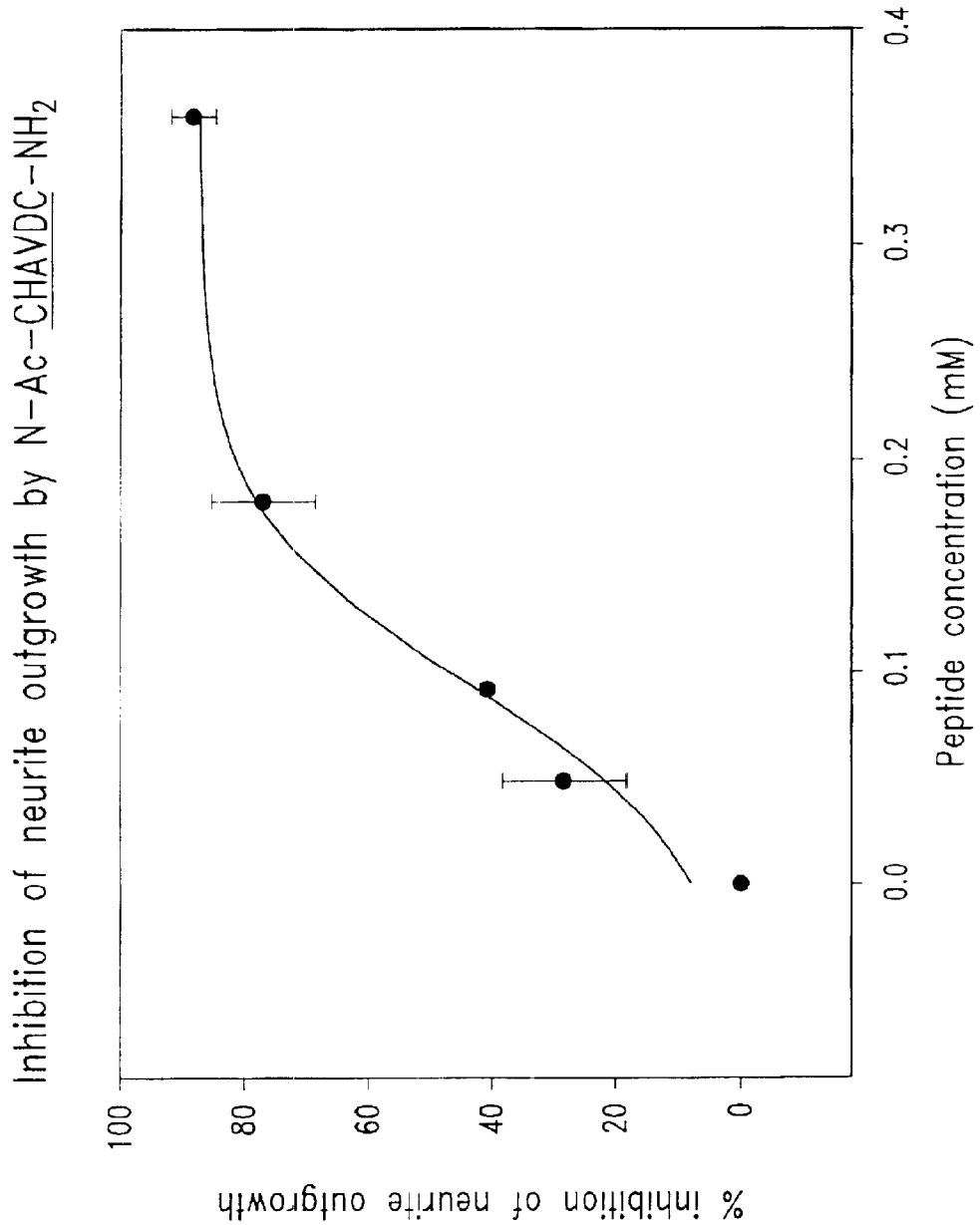
FIG. 25 is a graph dose-response curve that illustrates the inhibition of neurite outgrowth over N-cadherin expressing 3T3 cells in the presence of increasing concentrations of N—Ac—CHAVDC—NH₂ (SEQ ID NO:20).
Figure 26:
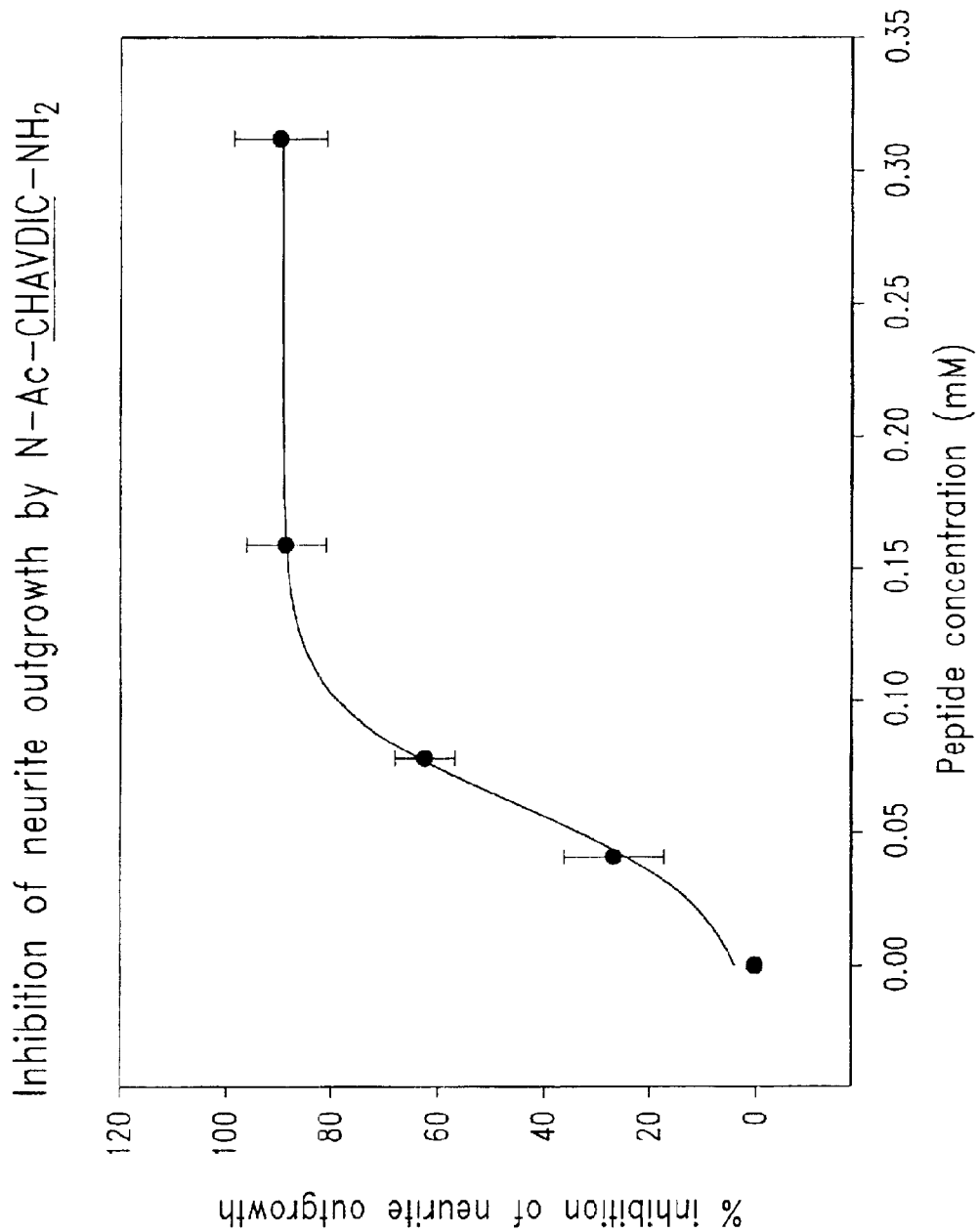
FIG. 26 is a graph dose-response curve that illustrates the inhibition of neurite outgrowth over N-cadherin expressing 3T3 cells in the presence of increasing concentrations of N—Ac—CHAVDIC—NH₂ (SEQ ID NO:50).
Figure 27:
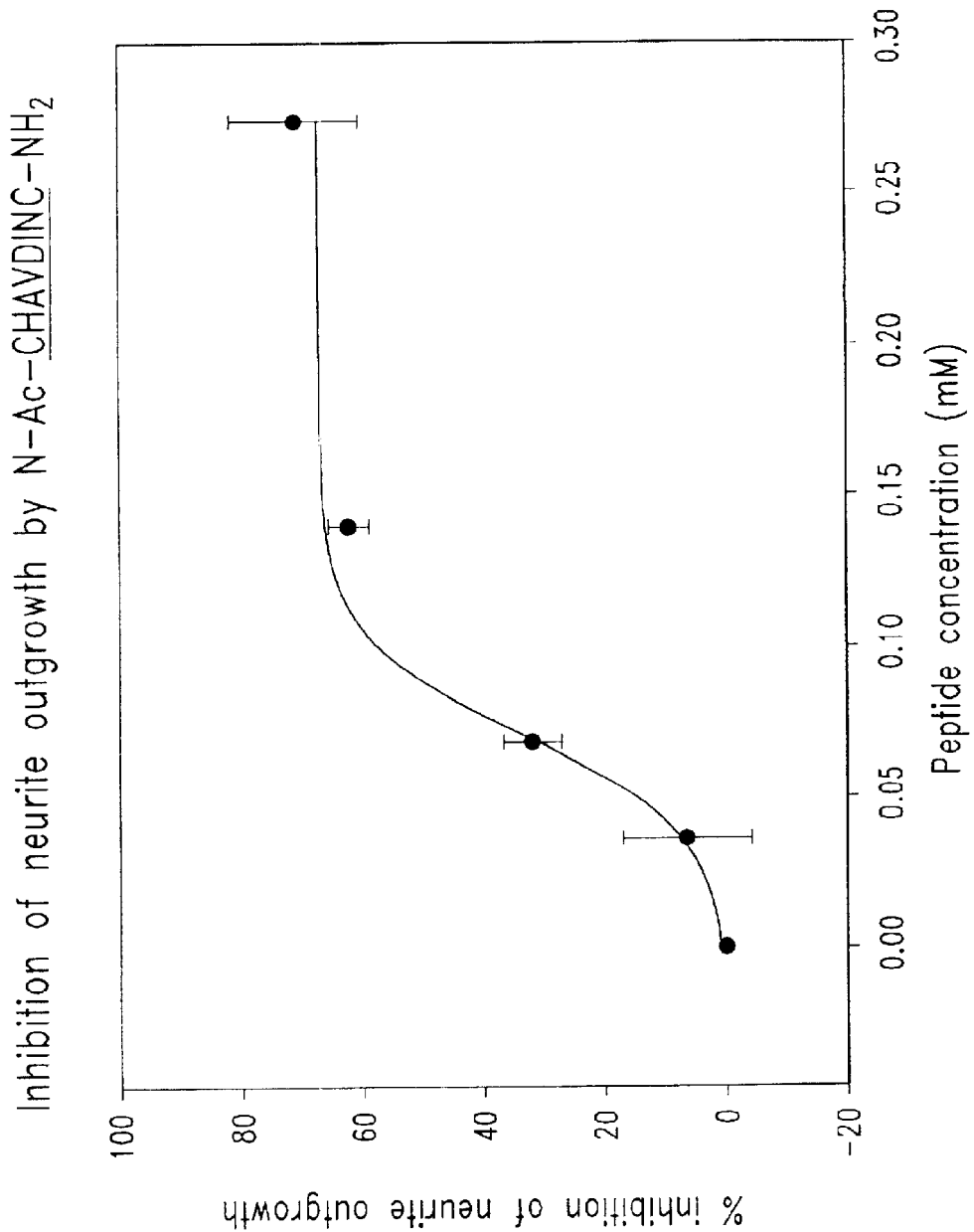
FIG. 27 is a graph dose-response curve that illustrates the inhibition of neurite outgrowth over N-cadherin expressing 3T3 cells in the presence of increasing concentrations of N—Ac—CHAVDINC—NH₂ (SEQ ID NO:51).

The results shown in Table 8 identify four "N-cadherin" peptides (N—Ac-CHAVDC—NH₂ (compound 5; SEQ ID NO:20), N—Ac—CAHAVC—NH₂ (compound 7; SEQ ID NO:22), N—Ac—CAHAVDIC—NH₂ (compound 13; SEQ ID NO:24) and N—Ac—CLRAHAVDC—NH₂ (compound 21; SEQ ID NO:32)) which are potent inhibitors of neurite outgrowth when used at a concentration of 250 μg/mL. All of these peptides except peptide N—Ac—CHAVDC—NH₂ (SEQ ID NO:20) lost activity at concentrations of 125 micrograms/mL or below. A dose response curve (FIG. 25) for N—Ac—CHAVDC—NH₂ (SEQ ID NO:20) indicated that significant activity remained at 33 μg/mL (% inhibition 28.5+/−10) and an EC₅₀ value of 0.093 mM was obtained. These results indicated that the aspartic acid on the carboxy terminus of the HAV motif was likely a key residue for N-cadherin receptor binding. To further explore the influence of the C-terminus residues on activity, N—Ac—CHAVDIC—NH₂ (compound 33; SEQ ID NO:50), N—Ac—CHAVDINC—NH₂ (compound 34; SEQ ID NO:51) and N—Ac—CHAVDINGC—NH₂ (compound 35; SEQ ID NO:76) were synthesized. Both N—Ac—CHAVDIC—NH₂ (SEQ ID NO:50) and N—Ac—CHAVDINC—NH₂ (SEQ ID NO:51) turned out to be potent inhibitors (Table 9) and dose response curves for these two compounds yield EC₅₀ values of 0.060 mM (FIG. 26) and 0.070 mM (FIG. 27), respectively. Also included in Table 9 are N—Ac—CHAVYC—NH₂ (SEQ ID NO:94) and N—Ac—CHAVPC—NH₂ (SEQ ID NO:99), which were found to be potent inhibitors.

TABLE 9

Effect of Additional C-terminal Residues on Neurite Outgrowth

| Test Peptide (125 μg/mL) | SEQ ID | % Inhibition | EC₅₀ (mM) |
| --- | --- | --- | --- |
| 5. N—Ac-CHAVDC-NH₂ | 20 | 77.1 ± 8.4 | 0.093 |
| 33. N—Ac-CHAVDIC-NH₂ | 50 | 88.3 ± 7.5 | 0.060 |
| 34. N—Ac-CHAVDINC-NH₂ | 51 | 62.0 ± 3.4 | 0.070 |
| 35. N—Ac-CHAVDINGC-NH₂ | 76 | 1.5 ± 2.2 | |
| N—Ac-CHAVYC-NH₂ | 94 | 64.9 ± 1.9 | 0.1283 |
| N—Ac-CHAVPC-NH₂ | 99 | 58.0 ± 4.3 | 0.1846 |

Interestingly, flanking of the HAV motif with amino acids found in human E-cadherin sequence resulted in either a complete (peptides 23, 25, 27 and 29) or substantial (peptide 31) reduction in inhibitory activity (Table 8). In addition, a series of corresponding control peptides, in which the HAV sequence had been replaced by HGV, were also tested in the screen. All sixteen control peptides failed to inhibit the N-cadherin response (see Table 8). Finally, if the N-terminal blocking group was removed these peptides lost activity (Table 8, compounds 3, 15).

Effects of HAV-Containing Peptides on the L1 Response. Other cell adhesion molecules, such as L1, can stimulate neurite outgrowth, and this response shares the same downstream signaling steps as the N-cadherin response. In order to ascertain the specificity of the most active N-cadherin antagonists (N—Ac—CHAVDC—NH₂ (compound 5; SEQ ID NO:20), N—Ac—CHAVDIC—NH₂ (compound 33; SEQ ID NO:50) and N—Ac—CHAVDINC—NH₂ (compound 34; SEQ ID NO:51)), cerebellar neurons were cultured over either control 3T3 cell monolayers, or monolayers of 3T3 cells stably transfected with cDNA encoding L1 in the presence and absence of each peptide. As previously reported, L1 stimulated neurite outgrowth from cerebellar neurons. This response was not inhibited by any of the above cyclic peptides at concentrations that prevented N-cadherin-mediated neurite outgrowth (FIG. 24 and Table 10).

TABLE 10

Specificity of Cadherin Antagonists

| Peptide (125 μg/ml) | % Inhibition of N-Cadherin Response | % Inhibition of L1 Response |
| --- | --- | --- |
| N—Ac-CHAVC-NH₂ (SEQ ID NO: 96) | 33.2 ± 4.0 | 41.6 ± 8.6 |
| N—Ac-CHAVDC-NH₂ (SEQ ID NO: 20) | 77.1 ± 8.4 | 9.6 ± 3.3 |
| N—Ac-CHAVDIC-NH₂ (SEQ ID NO: 50) | 88.3 ± 7.5 | 6.0 ± 4.7 |
| N—Ac-CHAVDINC-NH₂ (SEQ ID NO: 51) | 62.0 ± 3.4 | 1.7 ± 7.3 |

These results demonstrate that cyclic HAV peptides containing flanking amino acids found in N-cadherin are potent inhibitors of neurite outgrowth, whereas cyclic HAV-containing peptides containing flanking amino acids found in E-cadherin are inactive for such purposes. In addition, specificity for the N-cadherin receptor can be built into the peptides by adding flanking amino acids derived from native N-cadherin to the C-terminus, while addition of one or two amino acid residues on the N-terminus appears to be detrimental to activity (addition of a third amino acid on the N-terminus to give N—Ac—CLRAHAVDC—NH₂ (compound 21; SEQ ID NO:32) resulted in partial recovery of activity). Collectively, these results show that the information needed for "non-specific" cadherin binding resides in the HAV sequence, whereas the role of the surrounding amino acids is to either "constrain" the side chains of His and Val into a conformation required for "specific" cadherin (e.g., N-cadherin) recognition or to form additional interactions in the form of ionic bonds, hydrogen-bonds or hydrophobic interactions with the receptor.

Similar studies examined the effect of amino acids adjacent, but external, to the HAV-containing ring of a cyclic peptide on the potency of modulating agents as cadherin antagonists. The ability of several cyclic peptides (see Table 11) to inhibit neurite outgrowth was tested as described above. The most active of these was N—Ac—CHAVC—Y—NH₂ (SEQ ID NO:84), which was able to inhibit neurite outgrowth 89.9% at a concentration of 125 μg/mL. For comparison purposes, the inhibition of neurite outgrowth was also studied with N—Ac—CHAVYC—NH₂ (SEQ ID NO:94), which was also able to inhibit neurite outgrowth (64.9%) at 250 μg/mL. Dose response curves yielded EC₅₀ values of 0.08 and 0.12 mM for N—Ac—CHAVYC—NH₂ (SEQ ID NO:94) and N—Ac—CHAVC—Y—NH₂ (SEQ ID NO:84) respectively. These results indicate that, in some cases, removal of at least one amino acid from the cyclic structure may improve compound potency.

TABLE 11

Effects of Cadherin Antagonists on N-Cadherin Dependent Neurite Outgrowth

| Test Peptide (250 μg/ml) | Percent Inhibition |
| --- | --- |
| N—Ac-CHAVCS-NH₂ (87) | 6.9 ± 5.4 |
| N—Ac-CHAVCSS-NH₂ (89) | 37.8 ± 4.0 |
| N—Ac-SCHAVCS-NH₂ (90) | 15.7 ± 5.2 |
| N—Ac-CHAVCY-NH₂* (84) | 89.8 ± 6.8 |
| N—Ac-YCHAVC-NH₂ (10) | 10.6 ± 9.7 |
| N—Ac-CHAVCT-NH₂ (91) | 23.7 ± 6.6 |

TABLE 11-continued

Effects of Cadherin Antagonists on N-Cadherin Dependent Neurite Outgrowth

| Test Peptide (250 µg/ml) | Percent Inhibition |
|---|---|
| N—Ac-CHAVCD-NH₂ (93) | 3.3 ± 10.0 |
| N—Ac-CHAVCE-NH₂ (92) | 32.5 ± 5.2 |

*tested at 125 µg/ml

The effect of various terminal amino protecting groups on N-cadherin antagonist potency was similarly evaluated. The results are presented in Table 12. The use of hydrogen-bond acceptor groups such as N-acetyl, N-formyl or mesyl on the N-terminus was found to result in a substantial increase in potency as cadherin antagonists. The $EC_{50}$ (mM) for $CH_3$—$SO_2$—HN—CHAVC—$NH_2$ (SEQ ID NO:96) was 0.10, and for H—C(O)—HN—CHAVCS—$NH_2$ (SEQ ID NO:87) the $EC_{50}$ was 0.16

TABLE 12

Effects of N-Terminal Groups on Modulation of N-Cadherin Dependent Neurite Outgrowth

| Test Peptide (250 µg/ml) | Percent Inhibition |
|---|---|
| N—Ac-CHAVC-NH₂ (ID NO: 96) | 68.2 ± 5.1 |
| CH₃—SO₂—HN-CHAVC-NH₂ (ID NO: 96) | 74.7 ± 5 |
| H—C(O)—HN-CHAVCS-NH₂ (ID NO: 87) | 75.8 ± 5.6 |
| H-CHAVC-NH₂* (ID NO: 96) | 1.7 ± 1.1 |
| H-CAHAVDC-NH₂* (ID NO: 26) | 1.3 ± 13.0 |
| H-CAHAVDIC-NH₂* (ID NO: 24) | −3.7 ± 2.9 |

Example 16

Effect of Cyclic Peptide Modifications on E-cadherin Receptor Specificity

This Example illustrates the effect of sequences that flank the HAV sequence, sequences external to the cyclic peptide ring and terminal modifications on specificity for E-cadherin-mediated responses. In order to assess the effects of such modifications on receptor selectivity, a series of HAV-containing peptides were evaluated for their ability to disrupt adhesion of MDCK cells, as measured by a decrease in the electrical resistance across the monolayer. These peptides correspond to cyclized sequences derived from the human N-cadherin (RFHLRAHAVDINGN; SEQ ID NO:80) and E-cadherin (TLFSHAVSSNGN: SEQ ID NO:81) sequences immediately adjacent to and surrounding the active site (HAV).

Electrical Resistance Across MDCK Cells. Madin Darby canine kidney (MDCK) cells were plated in Millicells (Millipore, Bedford, Mass.), at a density of 300,000 cells per Millicell, and cultured in Dulbecco's Modified Eagle Medium (DMEM; Sigma, St. Louis, Mo.) containing 5% fetal calf serum (Sigma, St. Louis, Mo.) until monolayers formed. Monolayers were exposed to the modulating agent dissolved in medium. The electrical resistance was measured using the EVOM device (World Precision Instruments, Sarasota, Fla.). At the time of measurement, fresh medium, with or without the modulating agent, may be added to the Millicells.

Peptide Synthesis. Peptides were synthesized as described in Example 1. All peptides were prepared as a stock solution at a concentration of 5–10 mg/ml in distilled water, and stored in small aliquots at −80° C. until needed.

Table 13 shows $EC_{50}$ values obtained from the mean electrical resistance across MDCK cell monolayers cultured for 18 hours in medium alone (Control), or medium containing various cyclic peptides with different flanking sequences at a concentration of 0.5 mg/ml.

TABLE 13

Effects of Cyclic Peptides on Electrical Resistance across MDCK Cell Monolayer

| Test Peptide | Seq ID | $EC_{50}$ (mM) |
|---|---|---|
| Non-Specific | | |
| N—Ac-CHAVC-NH₂ | 96 | 0.27 |
| E-cadherin Specific | | |
| N—Ac-CSHAVC-NH₂ | 36 | 0.020 |
| N—Ac-CFSHAVC-NH₂ | 85 | 0.022 |
| N—Ac-CLFSHAVC-NH₂ | 86 | INACTIVE |
| N—Ac-CHAVSC-NH₂ | 38 | INACTIVE |
| N—Ac-CSHAVSC-NH₂ | 40 | INACTIVE |
| N—Ac-CSHAVSSC-NH₂ | 42 | INACTIVE |
| N—Ac-CHAVSSC-NH₂ | 44 | INACTIVE |
| N-cadherin Specific | | |
| N—Ac-CHAVDC-NH₂ | 20 | INACTIVE |
| N—Ac-CAHAVDIC-NH₂ | 24 | INACTIVE |
| N—Ac-CAHAVDC-NH₂ | 26 | INACTIVE |
| N—Ac-CHAVDINC-NH₂ | 51 | INACTIVE |

Effects of Cyclic HAV Peptides on E-cadherin Function: Peptides included in Table 13 are placed into one of three categories. The first category (N—Ac-CHAVC—$NH_2$ (SEQ ID NO:96)) can be viewed as general or non-specific cadherin inhibitors. N—Ac—CHAVC—$NH_2$ (SEQ ID NO:96) has the cadherin CAR sequence (HAV) and no flanking amino acid residues. An $EC_{50}$ value of 0.27 mM was obtained from the dose-response curve. This observation demonstrates that N—Ac—CHAVC—$NH_2$ (SEQ ID NO:96) is capable of acting as an E-cadherin antagonist and decreasing electrical resistance across a monolayer of MDCK cells.

The second group (N—Ac—CHAVDC—$NH_2$ (SEQ ID NO:20), N—Ac—CHAVDIC—$NH_2$ (SEQ ID NO:50), N—Ac—CAHAVDC—$NH_2$ (SEQ ID NO:26) and N—Ac—CHAVDINC—$NH_2$ (SEQ ID NO:51)) are N-cadherin specific, as shown from the neurite outgrowth assay. Flanking the HAV motif with amino acids found in the human N-cadherin sequence resulted in complete abrogation of E-cadherin specific activity.

The remaining HAV-containing compounds (N—Ac—CSHAVC—$NH_2$ (SEQ ID NO:36), N—Ac—CFSHAVC—$NH_2$ (SEQ ID NO:85), N—Ac—CLFSHAVC—$NH_2$ (SEQ ID NO:86), N—Ac—CHAVSC—$NH_2$ (SEQ ID NO:38), N—Ac—CSHAVSC—$NH_2$ (SEQ ID NO:40), N—Ac—CSHAVSSC—$NH_2$ (SEQ ID NO:42) and N—Ac—CHAVSSC—$NH_2$ (SEQ ID NO:44)) were designated as putative E-cadherin specific inhibitors by virtue of their HAV flanking amino acids being derived from the native human E-cadherin sequence. Placement of amino acids derived from the E-cadherin sequence on the C-terminus of the HAV sequence appears to have a detrimental affect on activity in this assay. In contrast, addition of a serine residue on the N-terminus dramatically increases the ability of the peptide to decrease the electrical resistance across a monolayer of MDCK cells (N—Ac—CSHAVC—$NH_2$; $EC_{50}$= 0.020 mM; SEQ ID NO:36). The addition of a second amino acid residue to the N-terminus did not appear to affect activity (N—Ac-CFSHAVC—$NH_2$; $EC_{50}$=00.022 mM;

SEQ ID NO:85). However, addition of a third amino acid to the N-terminus did result in loss of activity in this assay (N—Ac-CLFSHAVC—NH$_2$; SEQ ID NO:86.).

In similar studies, the effect of amino acids adjacent, but external, to the HAV-containing ring was examined. The results, presented in Table 14, indicate that all of the cyclic peptides except N—Ac—CHAVC-E-NH$_2$ (SEQ ID NO:92) could decrease electrical resistance across MDCK cells, with N—Ac—CHAVC—Y—NH$_2$ (SEQ ID NO:84) the most active. Additional amino acids on the C-terminus or the N-terminus did not eliminate activity, but also did not increase antagonist potency.

TABLE 14

Effects of Cyclic Peptides on Electrical Resistance across MDCK Cell Monolayer

| Test Peptide | Seq ID | EC$_{50}$ (mM) |
| --- | --- | --- |
| N—Ac-CHAVC-S-NH$_2$ | 87 | 0.49 |
| N—Ac—S-CHAVC-NH$_2$ | 88 | 0.49 |
| N—Ac-CHAVC-T-NH$_2$ | 91 | 0.48 |
| N—Ac-CHAVC-SS-NH$_2$ | 89 | 0.43 |
| N—Ac-CHAVC-D-NH$_2$ | 93 | 0.47 |
| N—Ac-CHAVC-Y-dNH$_2$ | 85 | 0.21 |
| N—Ac-CHAVC-E-NH$_2$ | 92 | INACTIVE |

In further studies, the effect of various terminal amino protecting groups on E-cadherin antagonist potency was evaluated. The results are presented in Table 15. The most active peptide was CH$_3$—SO$_2$—HN—CHAVCY—NH$_2$ (SEQ ID NO:95) with an EC$_{50}$ value of 0.14 mM. Interestingly, mesylation of the general inhibitor N—Ac—CHAVC—NH$_2$ (SEQ ID NO:96) to give CH$_3$—SO$_2$—HN—CHAVC—NH$_2$ (SEQ ID NO:96) resulted in a complete loss of activity. Formylation of N—Ac—CHAVC—NH$_2$ (SEQ ID NO:96) to give H—C(O)—HN—CHAVC—NH$_2$ (SEQ ID NO:96) also resulted in a decrease in potency.

TABLE 15

Effects of Cyclic Peptides on Electrical Resistance across MDCK Cell Monolayer

| Test Peptide | Seq ID | EC$_{50}$ (mM) |
| --- | --- | --- |
| CH$_3$—SO$_2$—HN-CHAVC-NH$_2$ | 96 | INACTIVE |
| CH$_3$—SO$_2$—HN-CHAVCY-NH$_2$ | 95 | 0.14 |
| H—C(O)—HN-CHAVC-NH$_2$ | 96 | 0.56 |

Example 17

Modulating Agent-Induced Reduction in Tumor Volume

This Example illustrates the use of a modulating agent for in vivo tumor reduction.

SKOV3 cells (ATCC) were grown to 70% confluence in Minimum Essential Medium (Life Technologies, Grand Island, N.Y.) supplemented with 10% Fetal Bovine Serum (Wisent, St. Bruno, Quebec) in a humidified atmosphere containing 5% CO$_2$. Cells were then dissociated with 0.02% PBS/EDTA. Total cell count and viable cell number was determined by trypan blue stain and a hemacytometer.

Approximately 1×10$^7$ cells were resuspended in 400 µl saline and injected in 6-week-old CD-1 nude mice (female, Charles River) subcutaneously. After 20 days of continuous tumor growth, tumor size was about 100 mm$^3$. The tumor-bearing animals were then injected intraperitoneally every day for 4 consecutive days with 20 mg/kg of the representative peptide modulating agent N—Ac—CHAVC—NH$_2$ (SEQ ID NO:96) and saline, for experimental and control respectively. Mice were sacrificed by cervical dislocation 4 days after final injection.

Figure 28A:
FIGS. 28A and 28B are photographs of human ovarian tumors grown in nude mice. Human ovarian cancer cells (SKOV3) were injected subcutaneously into nude mice. Tumors were grown to a size of 100 mm³. Animals were then injected intraperitoneally, on four consecutive days, with 20 mg/kg of the representative cyclic peptide N—Ac—CHAVC—NH₂ (FIG. 11B; SEQ ID NO:96) or saline (FIG. 28A). Mice were sacrificed, and tumor tissue was sectioned and stained with hematoxylin/eosin.
Figure 28B:
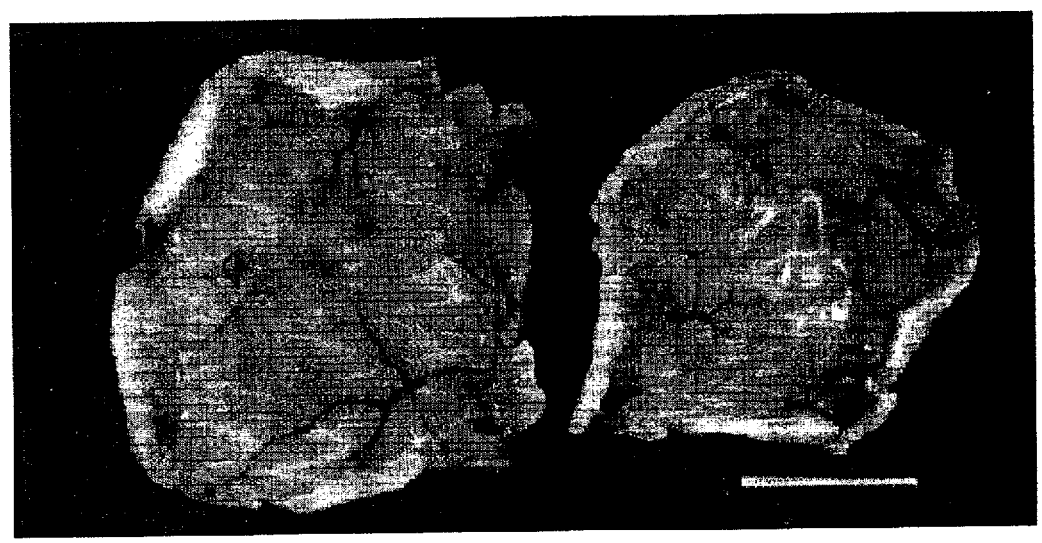

Tumor tissue was dissected and fixed in PBS with 4% paraformaldehyde for 48 hours. Specimens were then dehydrated in a series of alcohol incubations, and embedded in paraffin wax. Tissues were sectioned, rehydrated and stained with hematoxylin/eosin for morphological purposes. Representative sections obtained from treated and untreated mice are shown in FIGS. 28B and 28A, respectively.

Figure 29:
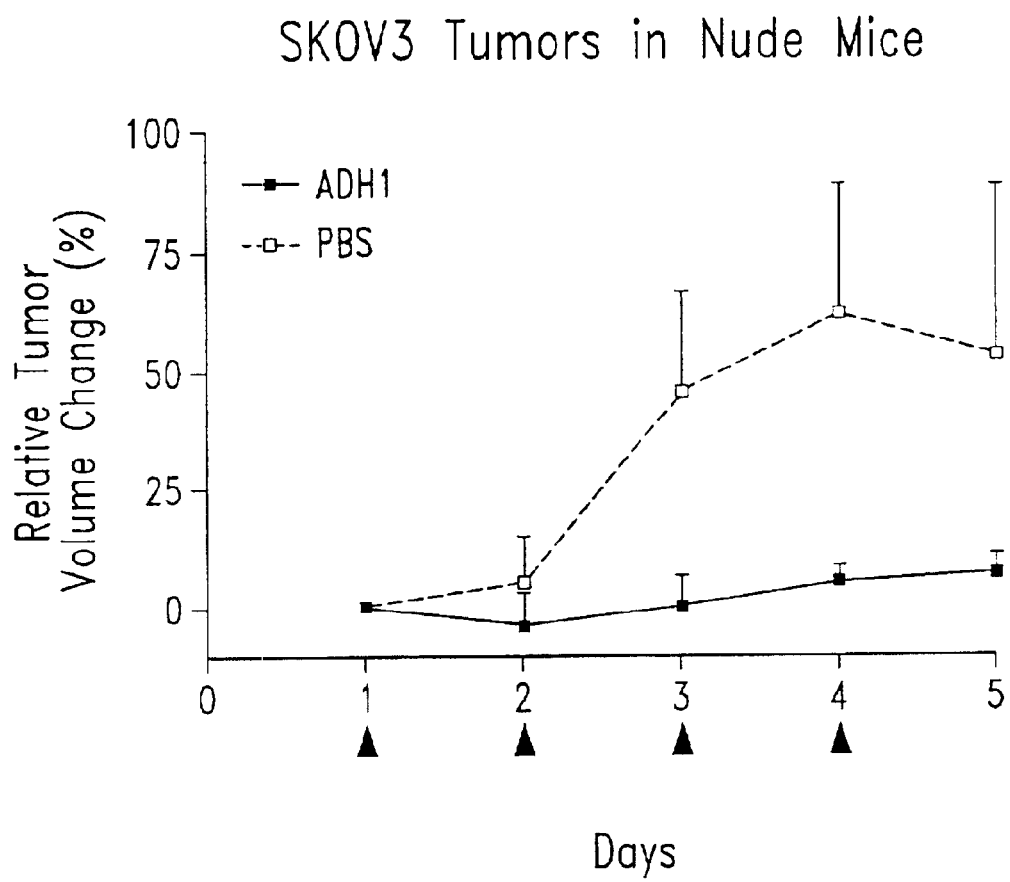
FIG. 29 is a graph showing the relative tumor volume change for human ovarian tumors in nude mice following intraperitoneal injection for four consecutive days as indicated, with 20 mg/kg of the representative cyclic peptide N—Ac—CHAVC—NH₂ (solid squares; SEQ ID NO:96) or saline (open squares).

FIG. 29 presents the results in graph form, showing the percent reduction in tumor volume over the four day treatment period. These data indicate that treatment with the cyclic peptide modulating agent prevents detectable tumor growth and results in a substantial decrease in tumor size, in comparison to the control.

Figure 30A:
FIGS. 30A and 30B are photographs of human ovarian tumors grown in nude mice. Animals were injected intraperitoneally, on four consecutive days, with 2 mg/kg of the representative cyclic peptide modulating agent N—Ac—CHAVC—NH₂ (FIG. 30A; SEQ ID NO:96) or saline (FIG. 30B). Mice were sacrificed 24 hours after the last injection, and tumor tissue was sectioned and stained with hematoxylin/eosin.
Figure 30B:

Within similar experiments, tumor-bearing nude mice as described above were injected intraperitoneally with 2 mg/kg of the representative peptide modulating agent N—Ac—CHAVC—NH$_2$ (SEQ ID NO:96) and saline, for experimental and control respectively. Injections were performed every day for 4 days. Mice were sacrificed 24 hours after the last injection. Tumor tissue was fixed, sectioned and stained as described above. Representative sections obtained from treated and untreated mice are shown in FIGS. 30A and 30B, respectively.

Figure 31:
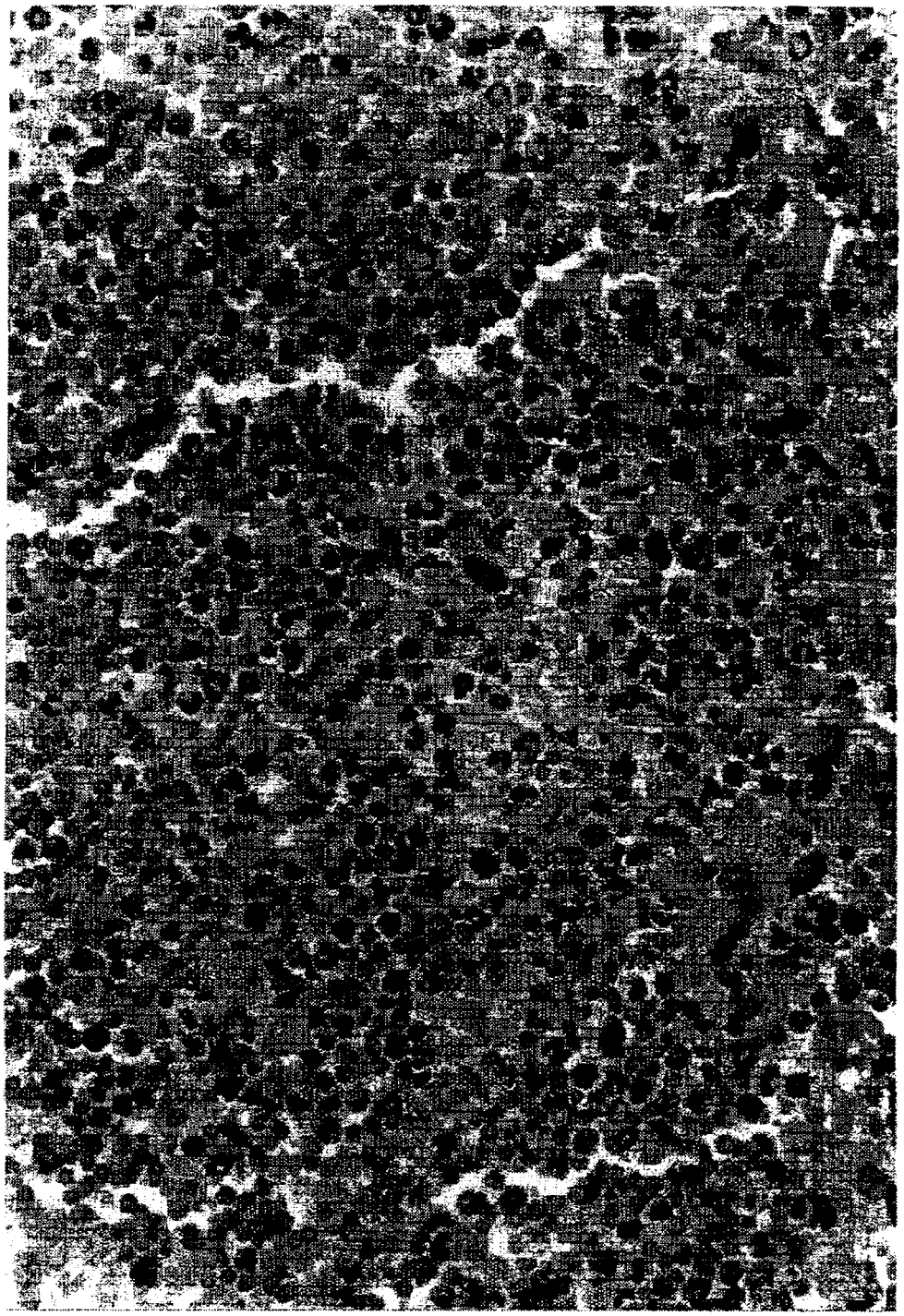
FIG. 31 is a photograph of a human ovarian tumor grown in a nude mouse, as described for FIG. 30A, showing leakage of red blood cells into the tumor mass.
Figure 32:
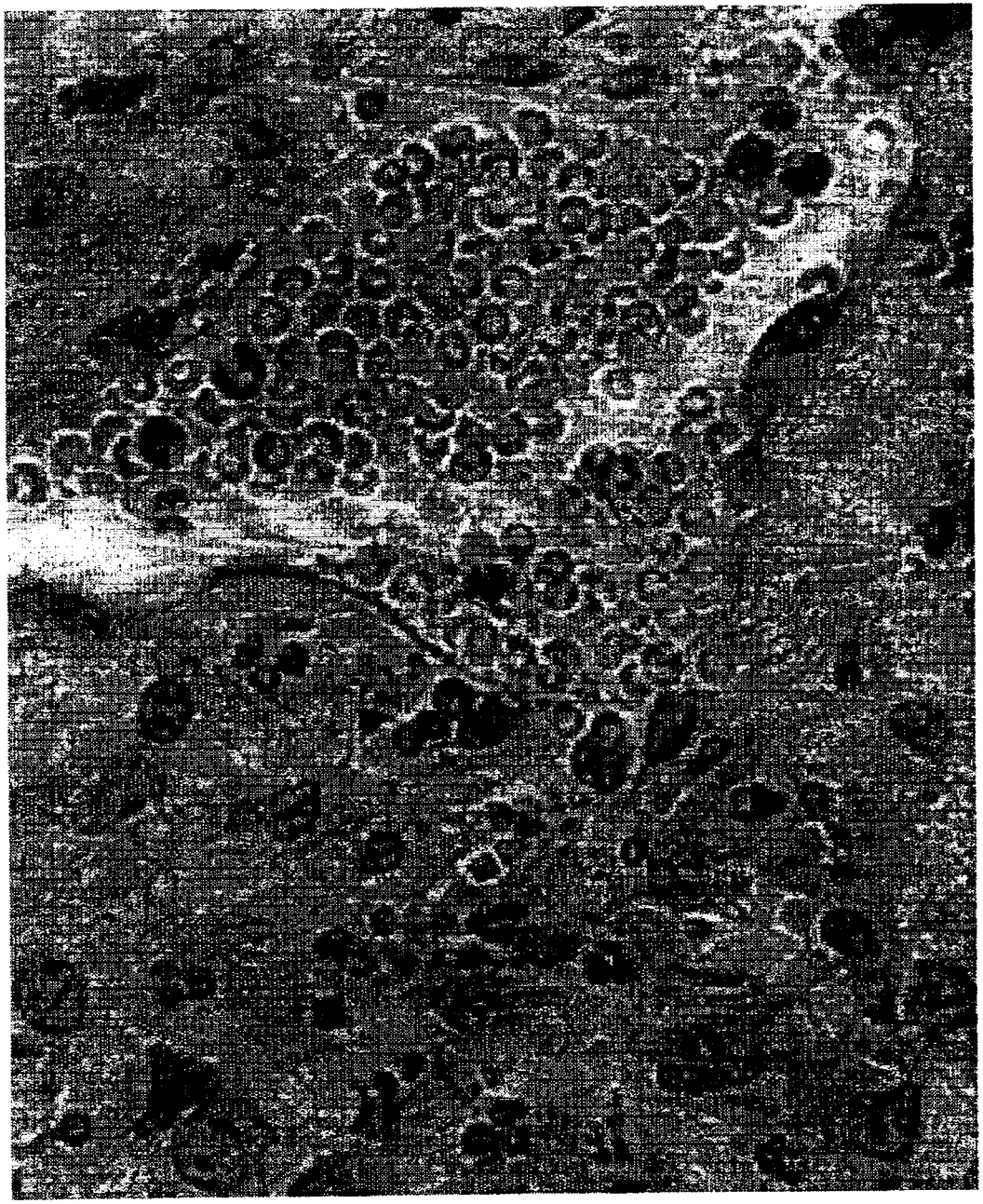
FIG. 32 is a photograph of a human ovarian tumor grown in a nude mouse, as described for FIG. 30A, showing a blood vessel that has been breached.

FIGS. 31 and 32 show close up images of the effect of the modulating agent on tumor blood vessels. In FIG. 31, red blood cells can be seen leaking into the tumor mass. FIG. 32 shows a blood vessel that has been breached and blood cells gathering and escaping at that point.

Figure 33:
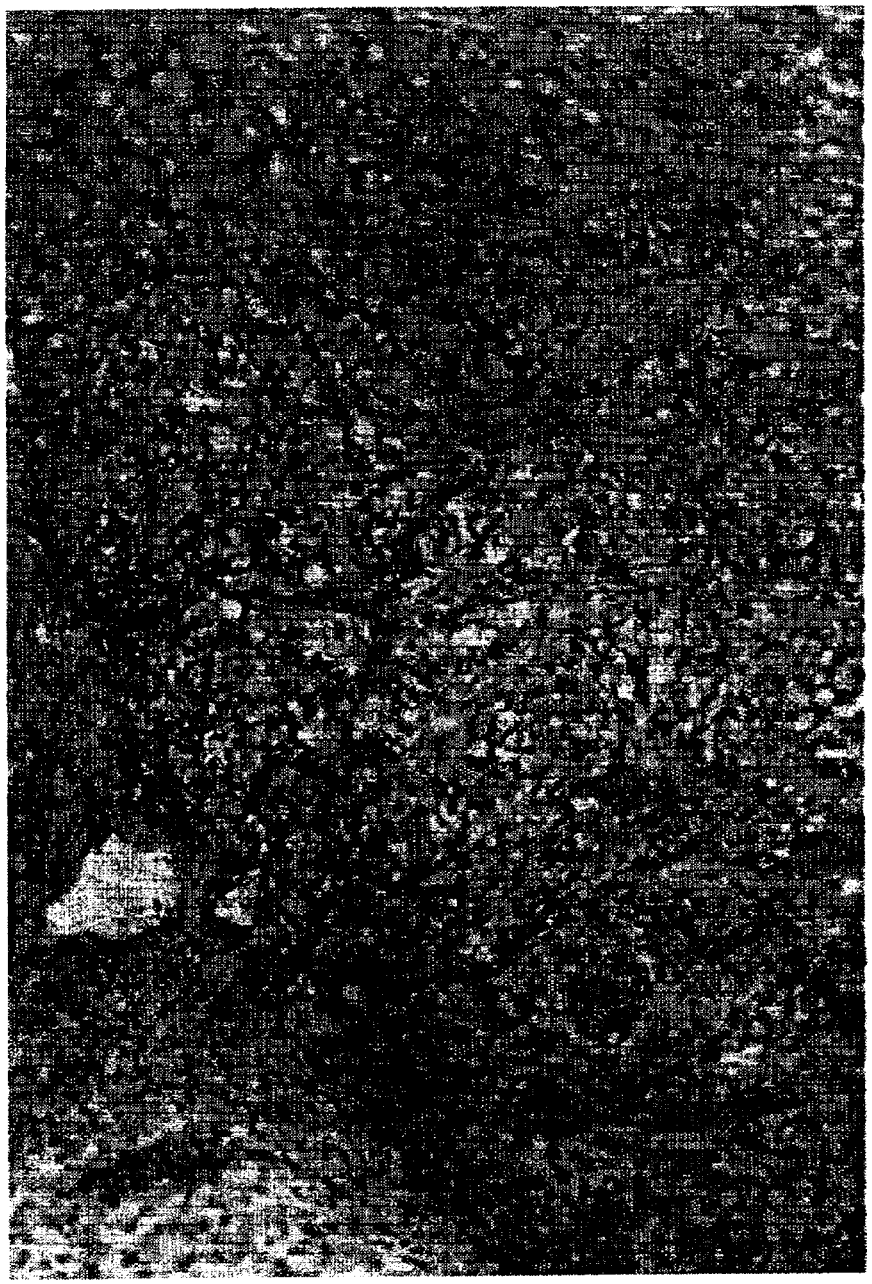
FIG. 33 is a photograph of a human ovarian tumor grown in a nude mouse, as described for FIG. 30B (i.e., untreated tumor), where the tumor section is stained for Von Willebrand Factor VIII.
Figure 34:
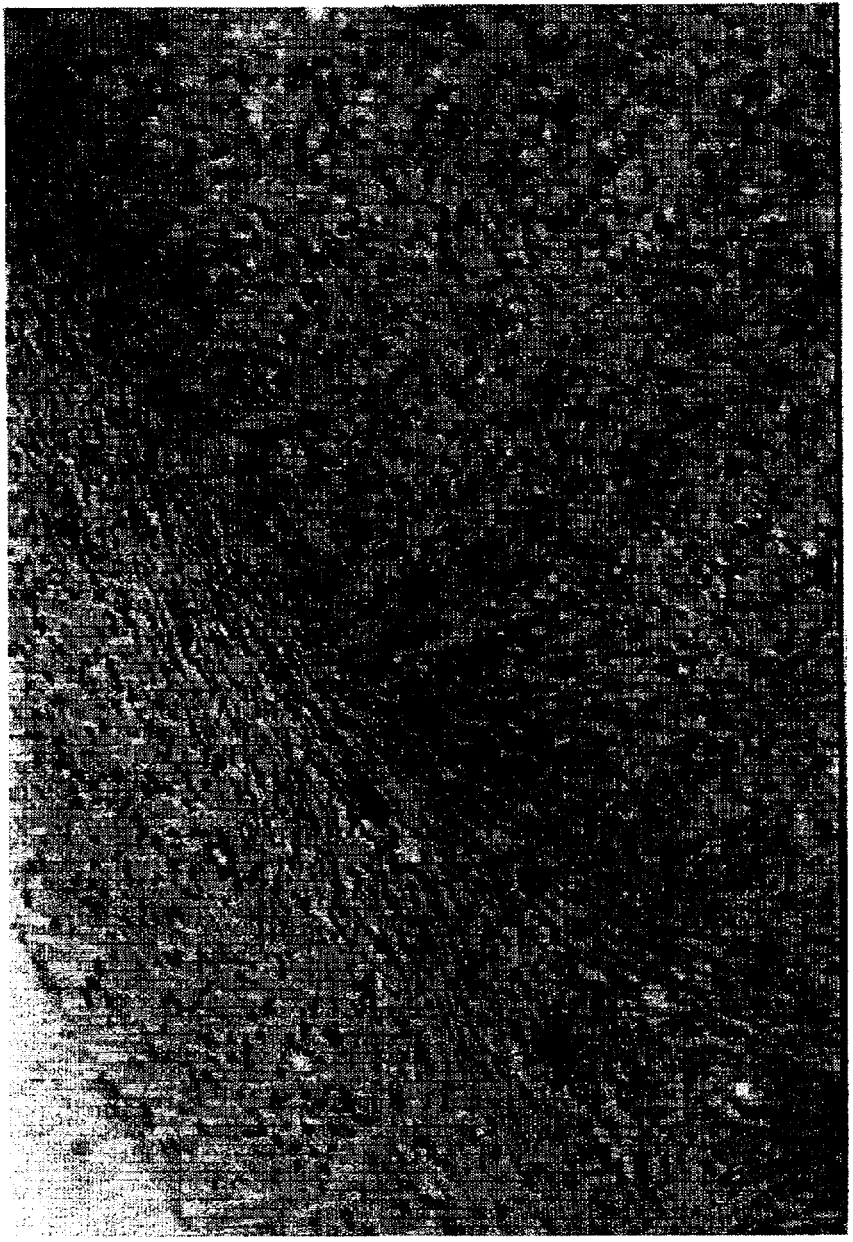
FIG. 34 is a photograph of a human ovarian tumor grown in a nude mouse, as described for FIG. 30A (i.e., tumor treated with the representative cyclic peptide modulating agent N—Ac—CHAVC—NH$_2$ (SEQ ID NO:96)), where the tumor section is stained for Von Willebrand Factor VIII.
Figure 35B:
FIGS. 35A–35D are photographs illustrating the ability of a representative cyclic peptide to induce apoptosis in cancer cells. SKOV3 human ovarian cancer cells containing either N—Ac—CHAVC—NH$_2$ (SEQ ID NO:96) or a control peptide (N—Ac—CHGVC—NH$_2$; SEQ ID NO:11) in MEM with 10% FBS were plated onto poly-L-lysine coated glass slides. The cells were cultured for 48 hours and fixed with 4% paraformaldehyde for 30 minutes at room temperature. The slides were then washed three times with PBS and assessed for cell death using the In situ cell death detection kit (Boehringer Mannheim; Laval, Quebec).
Figure 35D:
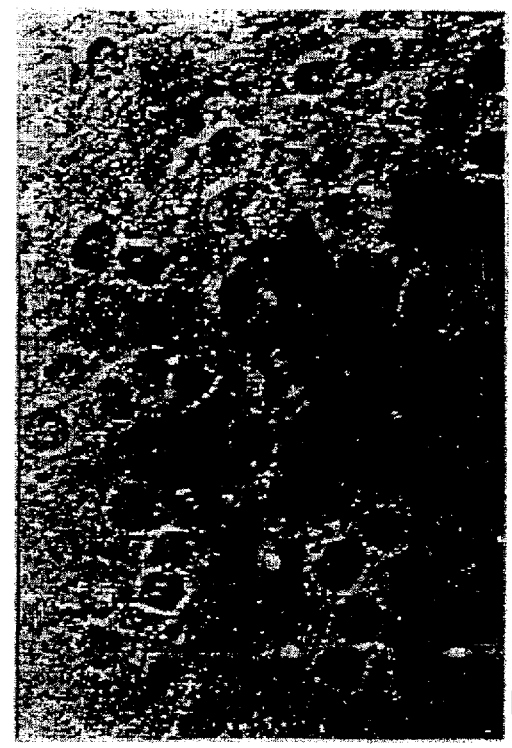
Figure 35A:
Figure 35C:
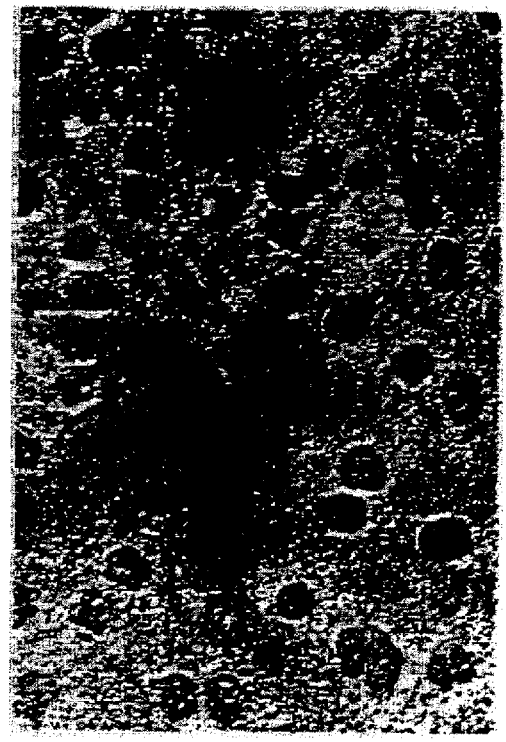

To further demonstrate the effect of the representative modulating agent N—Ac—CHAVC—NH$_2$ (SEQ ID NO:96) on tumor blood vessels, sections of the tumors described above were stained for Von Willebrand Factor VIII, a blood vessel-specific marker. An untreated tumor is shown in FIG. 33, and a treated tumor section is shown in FIG. 34. Taken together, these results clearly demonstrate that the representative modulating agent is capable of damaging tumor blood vessels and stopping tumor growth in vivo.

Figure 41:
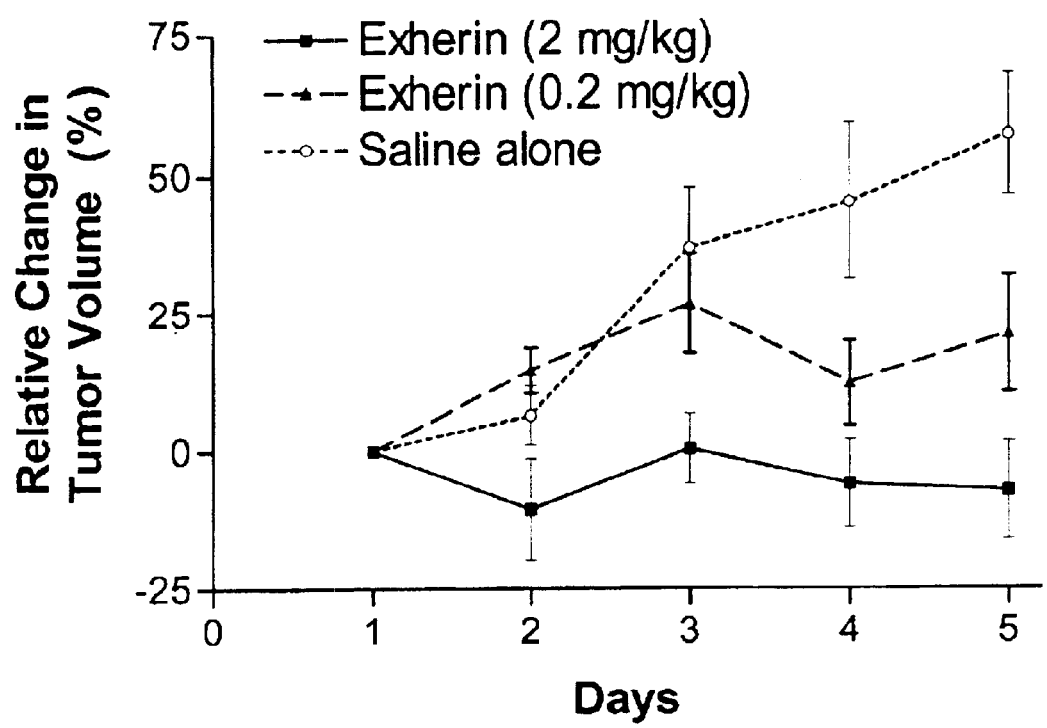
FIG. 41 is a graph illustrating the effect of the representative modulating agent N—Ac—CHAVC—NH$_2$ (SEQ ID NO:96) on tumor size of human ovarian tumors grown in nude mice. Mice were treated with 2 mg/kg peptide, 0.2 mg/kg peptide or saline alone, as indicated, over a period of 1–5 days. The relative change in tumor volume following each day of treatment is shown.

In a similar study, the effect of N—Ac—CHAVC—NH$_2$ (SEQ ID NO:96) on ovarian tumor growth was evaluated at 2 mg/kg and 0.2 mg/kg. Mice were treated as described above with saline alone, 2 mg/kg peptide or 0.2 mg/kg peptide once per day for 5 days. The percent change in tumor volume (relative to the tumor size at day 1) was determined. The results are presented in FIG. 41. Tumors treated with 0.2 mg/kg peptide grew at a slower rate than tumors treated with saline, and tumor treated with 2 mg/kg peptide showed a slight reduction in volume over the five day study.

Figure 42A:
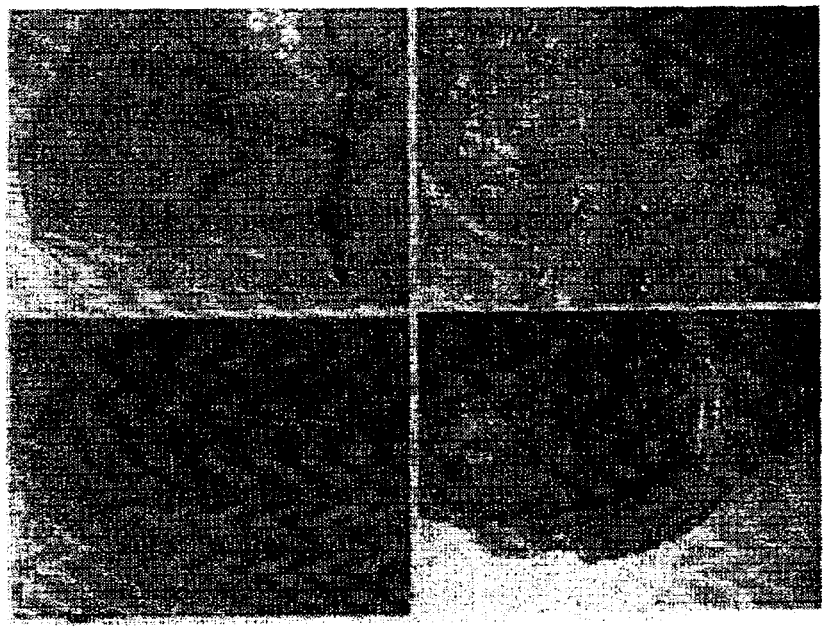
FIGS. 42A and 42B present photographs of breast cancer tumors grown in nude mice. After implanting tumor cells into the mammary fat pad, tumors were grown for 3–6 weeks. Mice were then injected once daily for four days with either 20 mg/kg of the representative modulating agent N—Ac—CHAVC—NH$_2$ (SEQ ID NO:96) (FIG. 42B) or saline as a control (FIG. 42A). Mice were sacrificed and tumors were photographed 24 hours after the last injection.
Figure 42B:

Breast cancer tumors were also grown in nude mice, as described above. After implanting tumor cells into the mammary fat pad, mice were injected once daily for four days with either the representative modulating agent N—Ac—CHAVC—NH$_2$ (SEQ ID NO:96) or saline as a control. Mice were sacrificed 24 hours after the last injection, and tumors were photographed. FIG. 42A shows photographs of four tumors from mice treated with saline. These tumors are well vascularized. FIG. 42B shows photographs of four tumors treated with peptide. These tumors are covered with pools of blood, and extensive rupturing of blood vessels can be seen on the surface of the tumors. The vascular effects of peptide treatment slow tumor growth.

Figure 43:
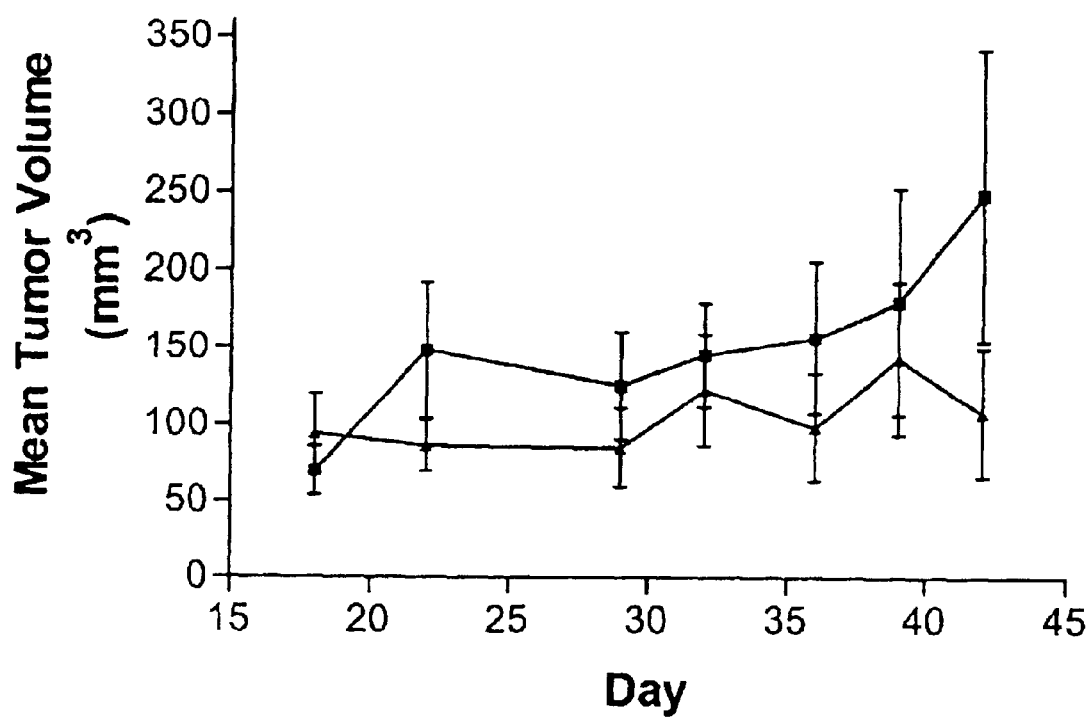
FIG. 43 is graph showing the mean tumor volume of breast tumors grown in nude mice. Tumor cells were implanted into the mammary fat pad and tumors were grown for 21 days. Mice were then injected once daily for four days with either 20 mg/kg of the representative modulating agent N—Ac—CHAVC—NH$_2$ (SEQ ID NO:96) or saline, as indicated. Mice were sacrificed and tumors were measured three weeks after the last injection.

FIG. 43 shows the effect of the modulating agent on tumor volume. MKL-F cells were injected into mammary fat pad, as described above, and the tumors were grown for 21 days before injection. Mice were then injected once daily for four days with either 20 mg/kg of the representative modulating agent N—Ac—CHAVC—NH2 (SEQ ID NO:96) or saline as a control. Mice were sacrificed 21 days after the last injection. Tumor volume was measured at day 18 following injection of cells, day 22 (following the first injection of modulating agent), and days 29, 32, 36, 39 and 42. Mean tumor volume for mice treated with modulating agent and saline alone is presented in FIG. 43.

Example 18

Disruption of Angiogenesis

Blood vessels are composed of adherent endothelial cells. This Example illustrates the use of a representative cyclic peptide to block angiogenesis (the growth of blood vessels from pre-existing blood vessels).

The chick chorioallantoic membrane assay was used to assess the effects of cyclic peptides on angiogenesis (Iruela-Arispe et al., *Molecular Biology of the Cell* 6:327–343, 1995). Cyclic peptides were embedded in a mesh composed of vitrogen at concentrations of 3, 17, and 33 μg/mesh. The meshes were then applied to 12-day-old chick embryonic chorioallantoic membranes. After 24 hours, the effects of the peptides on angiogenesis were assessed by computer assisted morphometric analysis.

The ability of representative cyclic peptides to inhibit angiogenesis is illustrated by the results presented in Table 16. For each concentration of cyclic peptide, the percent inhibition of angiogenesis (relative to the level of angiogenesis in the absence of cyclic peptide) is provided. Assays were performed in the presence (+) or absence (−) of 0.01 mM VEGF. For example, the cyclic peptide N—Ac—CHAVC—NH$_2$ (SEQ ID NO:96) inhibited angiogenesis by 46%, 51%, and 51% at concentrations of 3, 17, and 33 μg/mesh, respectively. The N-cadherin selective peptides N—Ac—CAHAVDIC—NH$_2$ (SEQ ID NO:18) and N—Ac—CAHAVDC—NH$_2$ (SEQ ID NO:19) also inhibited angiogenesis significantly. The E-cadherin selective cyclic peptides N—Ac—CHAVSC—NH$_2$ (SEQ ID NO:25) and N—Ac—CSHAVSSC—NH$_2$ (SEQ ID NO:27), as well as the scrambled peptide N—Ac—CVAHC—NH$_2$ (SEQ ID NO: 15), were found to be relatively inactive in this assay.

TABLE 16

| Compound | Concentration, μg/mesh ± VEGF | | | | | |
|---|---|---|---|---|---|---|
| | 3(−) | 3(+) | 17(−) | 17(+) | 33(−) | 33(+) |
| H-CHAVC-NH$_2$ (SEQ ID NO: 96) | 11% | 27% | 13% | 34% | 17% | 35% |
| N—Ac-CHAVSC-NH$_2$ (SEQ ID NO: 25) | 11% | 17% | 12% | 16% | 17% | 19% |
| N—Ac-CVAHC-NH$_2$ (SEQ ID NO: 15) | −1% | 7% | 13% | 24% | 12% | 25% |
| N—Ac-CHAVC-NH$_2$ (SEQ ID NO: 96) | 12% | 46% | 22% | 51% | 28% | 51% |
| N—Ac-CAHAVDIC-NH$_2$ (SEQ ID NO: 18) | −1% | 21% | 15% | 37% | 33% | 49% |
| N—Ac-CAHAVDC-NH$_2$ (SEQ ID NO: 19) | 21% | 59% | 27% | 72% | 31% | 79% |
| N—Ac-CSHAVSSC-NH$_2$ (SEQ ID NO: 27) | 1% | −3% | −3% | 12% | 17% | 7% |

TABLE 16-continued

Example 19

Induction of Apoptosis in Cancer Cells

This Example illustrates the use of a representative modulating agent for killing human ovarian cancer cells.

SKOV3 human ovarian cancer cells cultured in the presence of either N—Ac—CHAVC—NH$_2$ (SEQ ID NO:96) or a control peptide (N—Ac—CHGVC—NH$_2$; SEQ ID NO:11) in MEM with 10% FBS were plated onto poly-L-lysine coated glass slides. The cells were cultured for 24 or 48 hours and fixed with 4% paraformaldehyde for 30 minutes at room temperature. The slides were then washed three times with PBS and assessed for cell death. Cells were treated with 0.5 or 0.25 mg/mL of N—Ac—CHAVC—NH$_2$ (SEQ ID NO:96) or the control N—Ac—CHGVC—NH$_2$ (SEQ ID NO:11), as indicated. Cell death was measured as described by Gavrieli et al, *J. Cell. Biol.* 119:493–501, 1992 and using the In situ cell death detection kit (Boehringer Mannheim; Laval, Quebec).

Figure 36:
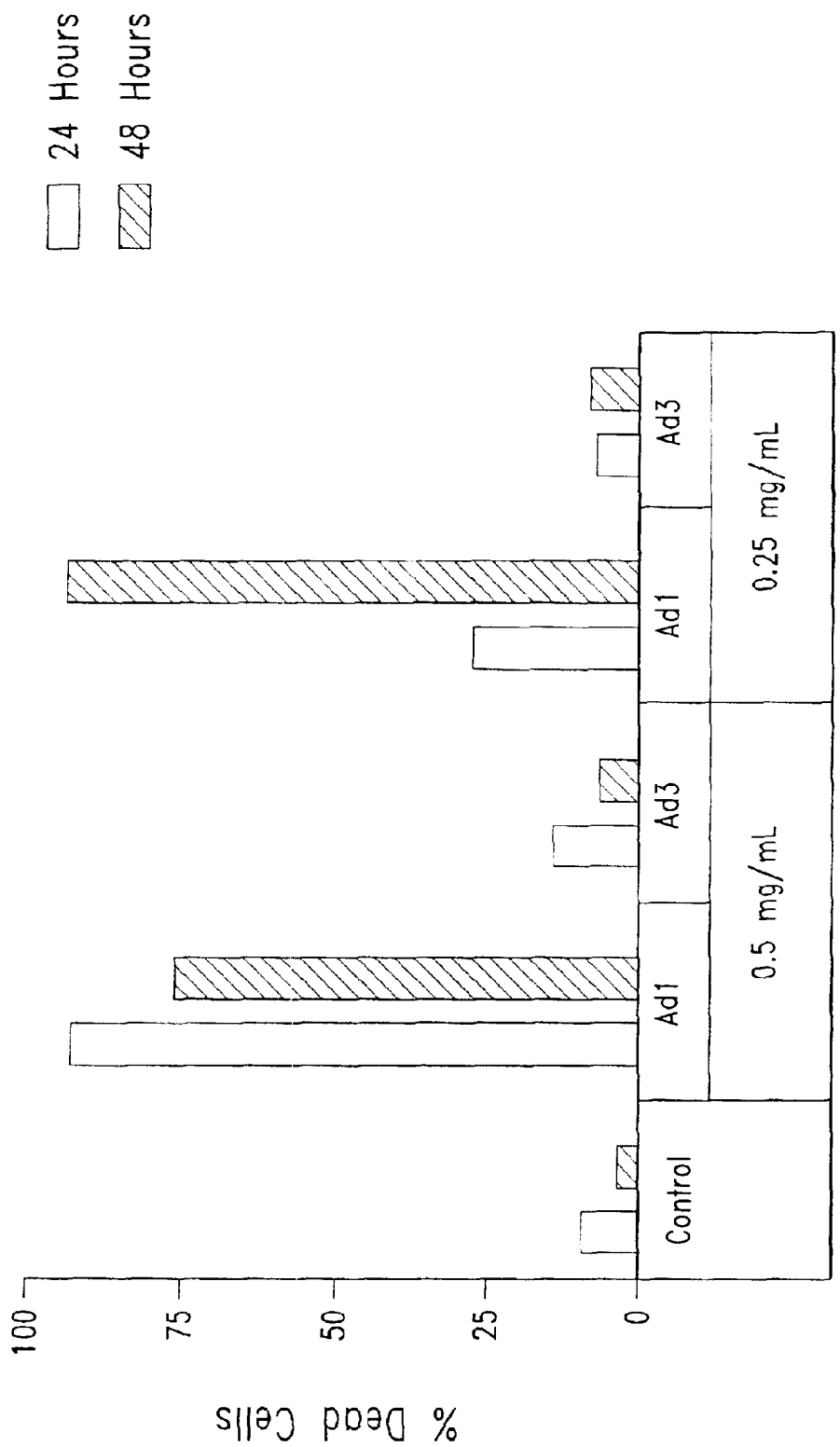
FIG. 36 is a histogram showing the percentage of dead cells following treatment with a representative cyclic peptide or a control peptide. SKOV human ovarian cancer cells containing either N—Ac—CHAVC—NH$_2$ (SEQ ID NO:96) or a control peptide (N—Ac—CHGVC—NH$_2$; SEQ ID NO:11) in MEM with 10% FBS were plated onto poly-L-lysine coated glass slides. The cells were cultured for 24 or 48 hours and fixed with 4% paraformaldehyde for 30 minutes at room temperature. The slides were then washed three times with PBS and assessed for cell death. Cells were treated with 0.5 or 0.25 mg/mL of N—Ac—CHAVC—NH$_2$ (SEQ ID NO:96) or the control N—Ac—CHGVC—NH$_2$ (SEQ ID NO:11). as indicated. Cell death was measured as described by Gavrieli et al, *J. Cell. Biol.* 119:493–501, 1992 and using the In situ cell death detection kit (Boehringer Mannheim; Laval, Quebec).

FIGS. 35A–35D show the results of such an assay, in which the cells were treated with the peptides for 48 hours. The fluorescent green nuclei evident in FIGS. 35C and 35D (cells treated with N—Ac—CHAVC—NH$_2$ (SEQ ID NO:96)) indicate that the cells are dead. In contrast, cells treated with the control peptide (FIGS. 35A and 35B) did not die. A bar graph further illustrating the ability of N—Ac—CHAVC—NH$_2$ (SEQ ID NO:96) to induce apoptosis is shown in FIG. 36. These observations indicate that this cyclic peptide can cause human ovarian cancer cell death.

Example 20

Induction of Apoptosis in Tumors

This Example illustrates the use of a representative modulating agent for inducing apoptosis in tumor cells and reducing tumor volume in vivo.

SKOV3 cells (ATCC) were grown to 70% confluence in Minimum Essential Medium (Life Technologies, Grand Island, N.Y.) supplemented with 10% Fetal Bovine Serum (Wisent, St. Bruno, Quebec) in a humidified atmosphere containing 5% CO$_2$. Cells were then dissociated with 0.02% PBS/EDTA. Total cell count and viable cell number was determined by trypan blue stain and a hemacytometer.

Approximately 1×10$^7$ cells were resuspended in 400 μl saline and injected in 6-week-old CD-1 nude mice (female, Charles River) subcutaneously. After 20 days of continuous tumor growth, tumor size was about 4.0 mm. The tumor-bearing animals were then injected intraperitoneally every day with 20 mg/kg of the representative peptide modulating agent N—Ac—CHAVC—NH$_2$ (SEQ ID NO:96) or saline, for 48 hours, 96 hours, 120 hours or 168 hours. Mice were sacrificed by cervical dislocation 24 hours after final injection.

Tumor tissue was dissected and fixed in PBS with 4% paraformaldehyde for 48 hours. Specimens were then dehydrated in a series of alcohol incubations, and embedded in paraffin wax. Apoptosis was assessed using the Apoptag kit (Intergen, Purchase N.Y.) according to the manufacturer's protocol, with slight modifications. More specifically, sections were deparaffinized and re-hydrated. After a five minute wash with PBS, the slides were treated with 20 μg/ml Proteinase K in PBS for 15 minutes at room temperature. This was followed by two washes with distilled water (2 minutes each wash). Endogenous peroxidase activity was blocked by incubation with 3% hydrogen peroxide (in PBS) for 5 minutes. Slides were washed twice with PBS (5 minutes/wash). Seventy-five μl of equilibration buffer (supplied with kit) was applied briefly (approximately 10 seconds) to the sections, and was followed by the application of working strength TdT (concentrated enzyme and dilution buffer solutions supplied with kit) and the enzymatic reaction allowed to proceed for 30 minutes at 37° C. The reaction was terminated by incubation in stop/wash buffer for 10 minutes (room temperature). The specimens were washed three times in PBS (1 minute/wash). Peroxidase-conjugated anti-digoxigenin antibody was added (65 μl of a diluted stock solution (supplied with kit)) to the slides, which were incubated overnight in a humidified chamber at 4° C. Subsequent visualization of apoptotic cells was achieved by washing (4×) the slides with PBS, followed by the application of the peroxidase substrate (DAB; diaminobenzidine tetrahydrochloride) for approximately 3–6 minutes at room temperature. The reaction was terminated by washing with distilled water, after which the slides were counterstained with hematoxylin. The specimens were then dehydrated through brief washes in ethanol, followed by washes in xylene, then mounted with Permount and cover-slipped.

Representative sections obtained from treated and untreated mice are shown in FIGS. 38A–38H (10× magnification) and 39A–39H (40× magnification). In these sections, cells stained brown are undergoing apoptosis. The tumors treated with N—Ac—CHAVC—NH$_2$ (SEQ ID NO:96) show an increase in apoptotic cells with longer treatment, as compared to tumors treated with saline.

Figure 40B:
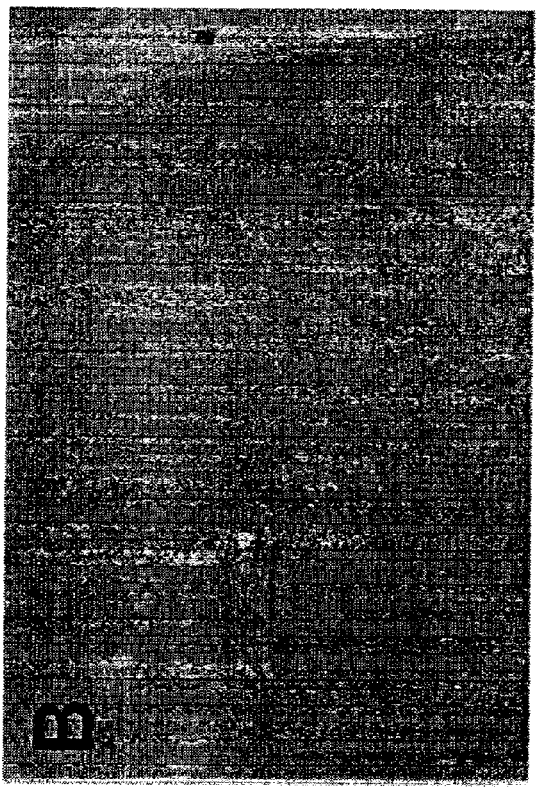
FIGS. 40A–40F are photographs illustrating the effect of the representative modulating agent N—Ac—CHAVC—NH$_2$ (SEQ ID NO:96) on apoptosis in human ovarian tumors grown in nude mice.
Figure 40A:
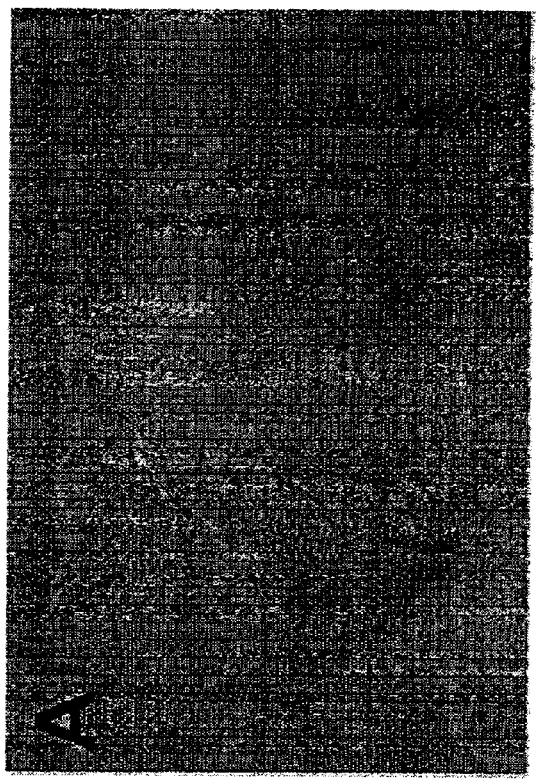
Figure 40D:
Figure 40C:
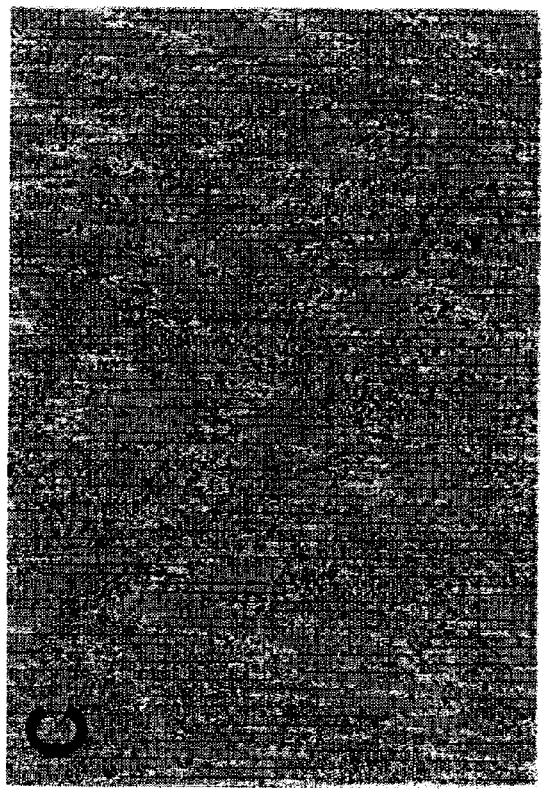
Figure 40F:
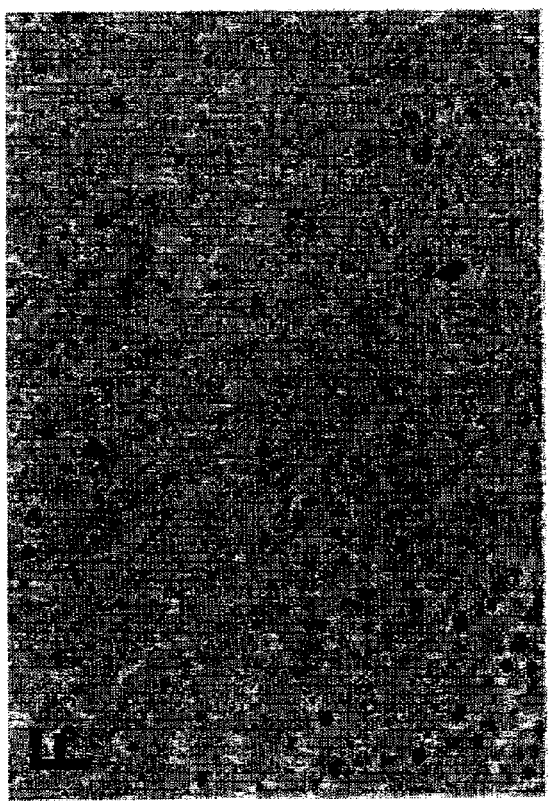
Figure 40E:

FIGS. 40B, 40D and 40F show tumor sections obtained from mice treated with N—Ac—CHAVC—NH$_2$ (SEQ ID NO:96) at 20 mg/kg once daily for four days and then sacrificed 11 days after the last treatment (FIGS. 40A, 40C and 40E show saline controls). The magnification in FIGS. 40A–40B was 4×, in FIGS. 40C–40D was 10× and in FIGS. 40E–40F was 40×). Tumors from mice treated with the peptide modulating agent showed an extensive area of apoptotic cells within the center of the tumor, as compared to the control tumors.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

---

What is claimed is:

1. A method for stimulating blood vessel regression, comprising administering to a mammal in need thereof a cell adhesion modulating agent comprising the sequence His-Ala-Val within a cyclic peptide ring, wherein the cyclic peptide modulates cadherin-mediated cell adhesion, and thereby stimulating blood vessel regression in the mammal, wherein the modulating agent has the formula:

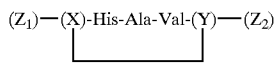

$$(Z_1)\text{—}(X)\text{-His-Ala-Val-}(Y)\text{—}(Z_2)$$

wherein $Z_1$ and $Z_2$ are independently selected from the group consisting of amino acid residues and combinations thereof in which the residues are linked by peptide bonds; wherein $Z_1$ and $Z_2$ independently range in size from 1 to 10 residues; and wherein X and Y are independently selected from the group consisting of amino acid residues, wherein a disulfide bond is formed between residues X and Y.

2. A method according to claim 1, wherein the mammal is afflicted with cancer, psoriasis, arthritis or age-related macular degeneration.

3. A method according to claim 1, wherein X has an N-terminal acetyl, formyl or mesyl group.

4. A method according to claim 1, wherein X and Y are cysteine residues.

5. A method according to claim 1, wherein the cyclic peptide comprises a sequence selected from the group consisting of: CHAVCS (SEQ ID NO:87), CHAVCSS (SEQ ID NO:89), SCHAVCS (SEQ ID NO:90), CHAVCY (SEQ ID NO:85), YCHAVC (SEQ ID NO:10), CHAVCT (SEQ ID NO:91), CHAVCD (SEQ ID NO:93) and CHAVCE (SEQ ID NO:92).

6. A method according to claim 5, wherein the cyclic peptide has an N-terminal acetyl group or $CH_3$—$SO_2$— group, and a C-terminal amide group.

7. A method according to claim 1, wherein the modulating agent comprises a cyclic peptide selected from the group consisting of N—Ac—CHAVYC—$NH_2$ (SEQ ID NO:94), N—Ac—CHAVPC—$NH_2$ (SEQ ID NO:99), N—Ac—CFSHAVC—$NH_2$ (SEQ ID NO:85), N—Ac—CLFSHAVC—$NH_2$ (SEQ ID NO:86), $CH_3$—$SO_2$—HN—CHAVC—$NH_2$ (SEQ ID NO:96), HC(O)-NH—CHAVC—$NH_2$ (SEQ ID NO:96), N—Ac—CHAVPen-$NH_2$ (SEQ ID NO:97) and N—Ac-PenHAVC—$NH_2$ (SEQ ID NO:98).

8. A method according to claim 1, wherein the modulating agent is linked to a targeting agent.

9. A method according to claim 1, wherein the modulating agent further comprises one or more of:

(a) a cell adhesion recognition sequence bound by an adhesion molecule other than a classical cadherin, wherein the cell adhesion recognition sequence is separated from any HAV sequence(s) by a linker, and/or (b) an antibody or antigen-binding fragment thereof that binds to a cell adhesion recognition sequence bound by an adhesion molecule other than a classical cadherin.

10. A method according to claim 9, wherein the cell adhesion recognition sequence comprises a sequence selected from the group consisting of NQK, NRN, NKD, EKD, ERD, DDK, EEY, EAQ, IYSY (SEQ ID NQ:58), TSSY (SEQ ID NO:59), VTAF (SEQ ID NO:60), VSAF (SEQ ID NO:61), RGD and LYHY (SEQ ID NO:55).

11. A method according to claim 1, wherein the modulating agent is present within a pharmaceutical composition comprising a pharmaceutically acceptable carrier.

12. A method according to claim 11, wherein the pharmaceutical composition further comprises a modulator of cell adhesion comprising one or more of:

(a) a cell adhesion recognition sequence bound by an adhesion molecule other than a classical cadherin; and/or (b) an antibody or antigen-binding fragment thereof that binds to a cell adhesion recognition sequence bound by an adhesion molecule other than a classical cadherin.

13. A method according to claim 12, wherein the cell adhesion recognition sequence comprises a sequence selected from the group consisting of NQK, NRN, MCD, EKD, ERD, DDK, EEY, EAQ, IYSY (SEQ ID NO:58), TSSY (SEQ ID NO:59), VTAF (SEQ ID NO:60), VSAF (SEQ ID NO:61), RGD and LYHY (SEQ ID NO:55).

* * * * *

UNITED STATES PATENT AND TRADEMARK OFFICE
CERTIFICATE OF CORRECTION

PATENT NO. : 6,967,238 B2 Page 1 of 1
APPLICATION NO. : 10/105008
DATED : November 22, 2005
INVENTOR(S) : Orest W. Blaschuk et al.

It is certified that error appears in the above-identified patent and that said Letters Patent is hereby corrected as shown below:

Title Page
References cited (56), page 2, column 2, other publications, "Fok-Seang et al., "An analysis of astrocytic cell lines with different abilities to promote axon growth," Brain Research 1689:207-223, 1995." should read as -- Fok-Seang et al., "An analysis of astrocytic cell lines with different abilities to promote axon growth," Brain Research 689:207-223, 1995. --

Column 132
Line 46, "MCD" should read as --NKD--.

Signed and Sealed this

First Day of August, 2006

JON W. DUDAS
*Director of the United States Patent and Trademark Office*